US011820825B2

(12) United States Patent
Logtenberg et al.

(10) Patent No.: US 11,820,825 B2
(45) Date of Patent: Nov. 21, 2023

(54) METHODS OF TREATING A SUBJECT HAVING AN EGFR-POSITIVE AND/OR ERBB-3-POSITIVE TUMOR

(71) Applicant: Merus N.V., Utrecht (NL)

(72) Inventors: Ton Logtenberg, Utrecht (NL); Mark Throsby, Utrecht (NL); Robertus Cornelis Roovers, Utrecht (NL)

(73) Assignee: Merus N.V., Utrecht (NL)

( * ) Notice: Subject to any disclaimer, the term of this patent is extended or adjusted under 35 U.S.C. 154(b) by 351 days.

(21) Appl. No.: 17/076,143

(22) Filed: Oct. 21, 2020

(65) Prior Publication Data

US 2021/0155698 A1    May 27, 2021

Related U.S. Application Data

(62) Division of application No. 15/121,619, filed as application No. PCT/NL2015/050124 on Feb. 27, 2015, now Pat. No. 10,844,127.

(30) Foreign Application Priority Data

Feb. 28, 2014  (EP) .................................. 14157351

(51) Int. Cl.
| A61K 39/395 | (2006.01) |
| C07K 16/28 | (2006.01) |
| C07K 16/32 | (2006.01) |

(52) U.S. Cl.
CPC .......... *C07K 16/2863* (2013.01); *C07K 16/32* (2013.01); *C07K 2317/31* (2013.01); *C07K 2317/565* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,801,687 A | 1/1989 | Ngo |
| 4,816,567 A | 3/1989 | Cabilly et al. |
| 5,151,504 A | 9/1992 | Croze |
| 5,731,168 A | 3/1998 | Carter et al. |
| 7,642,228 B2 | 1/2010 | Carter et al. |
| 7,705,103 B2 | 4/2010 | Sherman et al. |
| 8,349,574 B2 | 1/2013 | Bates et al. |
| 8,551,488 B2 | 10/2013 | Geuijen et al. |
| 8,592,562 B2 | 11/2013 | Kannan et al. |
| 8,628,774 B2 | 1/2014 | Gurney et al. |
| 9,220,775 B2 | 12/2015 | Chowdhury et al. |
| 9,248,181 B2 | 2/2016 | De Kruif et al. |
| 9,248,182 B2 | 2/2016 | De Kruif et al. |
| 9,358,286 B2 | 6/2016 | De Kruif et al. |
| 9,551,208 B2 | 1/2017 | Ma et al. |
| 9,758,805 B2 | 9/2017 | De Kruif et al. |
| 9,914,777 B2 | 3/2018 | Bakker et al. |
| 10,358,492 B2 | 7/2019 | Bakker et al. |
| 10,416,162 B2 | 9/2019 | Huang et al. |
| 10,844,127 B2 | 11/2020 | Logtenberg |
| 2003/0078385 A1 | 4/2003 | Arathoon et al. |
| 2004/0071696 A1 | 4/2004 | Adams et al. |
| 2006/0212956 A1 | 9/2006 | Crocker et al. |
| 2009/0181022 A1 | 7/2009 | Nielsen et al. |
| 2009/0182127 A1 | 7/2009 | Kjaergaard et al. |
| 2009/0191559 A1 | 7/2009 | Huang et al. |
| 2010/0015133 A1 | 1/2010 | Igawa et al. |
| 2010/0183615 A1 | 7/2010 | Kufer et al. |
| 2010/0286374 A1 | 11/2010 | Kannan et al. |
| 2011/0077163 A1 | 3/2011 | Doranz |
| 2011/0195454 A1 | 8/2011 | Mcwhirter et al. |
| 2012/0107234 A1 | 5/2012 | Pedersen et al. |
| 2012/0107306 A1 | 5/2012 | Elis et al. |
| 2012/0270801 A1 | 10/2012 | Frejd et al. |
| 2012/0328623 A1 | 12/2012 | Takahashi |
| 2013/0071859 A1 | 3/2013 | Bates et al. |
| 2013/0084297 A1 | 4/2013 | Daly et al. |
| 2013/0115208 A1 | 5/2013 | Ho et al. |
| 2013/0156779 A1 | 6/2013 | Clarke et al. |
| 2013/0185821 A1 | 7/2013 | Babb et al. |
| 2013/0251703 A1 | 9/2013 | Elis et al. |
| 2013/0259867 A1 | 10/2013 | Amler et al. |
| 2013/0336885 A1 | 12/2013 | Hongo et al. |

(Continued)

FOREIGN PATENT DOCUMENTS

| AU | 2014212081 A1 | 8/2015 |
| EP | 0120694 A2 | 10/1984 |

(Continued)

OTHER PUBLICATIONS

Almagro, J.C. and Fransson, J., "Humanization of Antibodies," Frontiers in Bioscience 13:1619-1633, Frontiers In Bioscience Publications, United States (Jan. 2008).
Armour, K.L., et al., "Differential Binding to Human FcgammaRIIa and FcgammaRIIb Receptors by Human IgG Wildtype and Mutant Antibodies," Molecular Immunology 40(9):585-593, Pergamon Press, England (2003).
Arteaga, C.L., et al., "Treatment of Her2-positive Breast Cancer: Current Status and Future Perspectives," Nature Reviews Clinical Oncology 9(1):16-32, Nature Publishing Group, England (Nov. 2011).

(Continued)

*Primary Examiner* — Mark Halvorson
(74) *Attorney, Agent, or Firm* — STERNE, KESSLER, GOLDSTEIN & FOX P.L.L.C.; Paul A Calvo

(57) ABSTRACT

The invention relates in one aspect to bispecific antibodies comprising a first antigen-binding site that binds EGFR and a second antigen-binding site that binds Erb B-3, wherein the antibody has a half maximal growth inhibitory concentration (IC50) of less than 200 pM for inhibiting EGFR and/or Erb B-3 ligand induced growth of Bx PC3 cells or Bx PC3-luc2 cells. Further described are method for producing the bispecific antibodies and means and methods for the treatment of subjects with the antibodies.

12 Claims, 46 Drawing Sheets

Specification includes a Sequence Listing.

(56) References Cited

U.S. PATENT DOCUMENTS

| | | |
|---|---|---|
| 2013/0336981 A1 | 12/2013 | De Kruif et al. |
| 2013/0344093 A1 | 12/2013 | Daly et al. |
| 2014/0056898 A1 | 2/2014 | Zhang et al. |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2014/0141019 A1 | 5/2014 | Kharrat et al. |
| 2014/0378664 A1 | 12/2014 | Suh et al. |
| 2015/0013996 A1 | 1/2015 | Davies et al. |
| 2015/0139996 A1 | 5/2015 | De Kruif et al. |
| 2015/0196637 A1 | 7/2015 | De Kruif et al. |
| 2016/0031984 A1 | 2/2016 | Reyes et al. |
| 2016/0229920 A1 | 8/2016 | Ward et al. |
| 2016/0367699 A1 | 12/2016 | Jackson et al. |
| 2017/0037145 A1 | 2/2017 | Geuijen et al. |
| 2017/0166653 A1 | 6/2017 | Garner et al. |
| 2020/0102393 A1 | 4/2020 | Throsby et al. |
| 2020/0291130 A1 | 9/2020 | Throsby et al. |

FOREIGN PATENT DOCUMENTS

| | | |
|---|---|---|
| EP | 0314161 A1 | 5/1989 |
| EP | 0481790 A2 | 4/1992 |
| EP | 0523949 A1 | 1/1993 |
| EP | 1870459 A1 | 12/2007 |
| EP | 2604625 A1 | 6/2013 |
| EP | 3600411 A1 | 2/2020 |
| EP | 3600413 A1 | 2/2020 |
| JP | H11500915 A | 1/1999 |
| JP | 2008531557 A | 8/2008 |
| JP | 2011508604 A | 3/2011 |
| JP | 2012509259 A | 4/2012 |
| JP | 2014508782 A | 4/2014 |
| JP | 2014511383 A | 5/2014 |
| JP | 2017507944 A | 3/2017 |
| WO | WO-9627011 A1 | 9/1996 |
| WO | WO-9850431 A2 | 11/1998 |
| WO | WO-0063403 A2 | 10/2000 |
| WO | WO-03004704 A2 | 1/2003 |
| WO | WO-03107218 A1 | 12/2003 |
| WO | WO-2004009618 A2 | 1/2004 |
| WO | WO-2004061104 A2 | 7/2004 |
| WO | WO-2005000894 A2 | 1/2005 |
| WO | WO-2005118635 A2 | 12/2005 |
| WO | WO-2006028936 A2 | 3/2006 |
| WO | WO-2006044908 A2 | 4/2006 |
| WO | WO-2006091209 A2 | 8/2006 |
| WO | WO-2006106905 A1 | 10/2006 |
| WO | WO-2007110205 A2 | 10/2007 |
| WO | WO-2007147901 A1 | 12/2007 |
| WO | WO-2008027236 A2 | 3/2008 |
| WO | WO-2008100624 A2 | 8/2008 |
| WO | WO-2008119353 A1 | 10/2008 |
| WO | WO-2008140493 A2 | 11/2008 |
| WO | WO-2009051974 A1 | 4/2009 |
| WO | WO-2009080251 A1 | 7/2009 |
| WO | WO-2009080252 A1 | 7/2009 |
| WO | WO-2009080253 A1 | 7/2009 |
| WO | WO-2009089004 A1 | 7/2009 |
| WO | WO-2009098596 A2 | 8/2009 |
| WO | WO-2009157771 A2 | 12/2009 |
| WO | WO-2010022736 A2 | 3/2010 |
| WO | WO-2010059315 A1 | 5/2010 |
| WO | WO-2010084197 A1 | 7/2010 |
| WO | WO-2010108127 A1 | 9/2010 |
| WO | WO-2010129304 A2 | 11/2010 |
| WO | WO-2010151792 A1 | 12/2010 |
| WO | WO-2011022727 A2 | 2/2011 |
| WO | WO-2011028952 A1 | 3/2011 |
| WO | WO-2011028953 A1 | 3/2011 |
| WO | WO-2011143545 A1 | 11/2011 |
| WO | WO-2012023053 A2 | 2/2012 |
| WO | WO-2012058768 A1 | 5/2012 |
| WO | WO-2012116317 A2 | 8/2012 |
| WO | WO-2012125573 A2 | 9/2012 |
| WO | WO-2012125864 A2 | 9/2012 |
| WO | WO-2012131555 A2 | 10/2012 |
| WO | WO-2013048883 A2 | 4/2013 |
| WO | WO-2013084151 A2 | 6/2013 |
| WO | WO-2013107218 A1 | 7/2013 |
| WO | WO-2013134686 A1 | 9/2013 |
| WO | WO-2013149159 A1 | 10/2013 |
| WO | WO-2013157953 A1 | 10/2013 |
| WO | WO-2013157954 A1 | 10/2013 |
| WO | WO-2014051433 A1 | 4/2014 |
| WO | WO-2014060365 A1 | 4/2014 |
| WO | WO-2014081954 A1 | 5/2014 |
| WO | WO-2014159580 A1 | 10/2014 |
| WO | WO-2014165855 A1 | 10/2014 |
| WO | WO-2015130172 A1 | 9/2015 |
| WO | WO-2015130173 A1 | 9/2015 |
| WO | WO-2016077734 A2 | 5/2016 |
| WO | WO-2016090024 A2 | 6/2016 |
| WO | WO-2017069628 A2 | 4/2017 |
| WO | WO-2018182422 A1 | 10/2018 |

OTHER PUBLICATIONS

Atwell, S., et al., "Stable Heterodimers from Remodeling the Domain Interface of a Homodimer Using a Phage Display Library," Journal of Molecular Biology 270(1):26-35, Elsevier, England (1997).

Baeuerle, P.A., et al, "Multiple Myeloma and Monoclonal Gammopathy of Undetermined Significance: Importance of Whole-body Versus Spinal Mr Imaging," Cancer Research 252(2):477-485, Radiology (Aug. 2009).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Balko, J.M., et al., "The Receptor Tyrosine Kinase Erbb3 Maintains the Balance Between Luminal and Basal Breast Epithelium," Proceedings of the National Academy of Sciences of the United States of America 109(1):221-226, National Academy of Sciences, United States (Jan. 2012).

Bargou, R., et al., "Tumor Regression in Cancer Patients by Very Low Doses of a T Cell-engaging Antibody," Science 321(5891):974-977, American Association for the Advancement of Science, United States (Aug. 2008).

Barthelemy P.A., et al., "Comprehensive Analysis of the Factors Contributing to the Stability and Solubility of Autonomous Human VH Domains," The Journal of Biological Chemistry 283, 3639-3654, American Society for Biochemistry and Molecular Biology (Feb. 2008).

Baselga, J., et al., "Pertuzumab Plus Trastuzumab Plus Docetaxel for Metastatic Breast Cancer," The New England Journal of Medicine 366(2):109-119, Massachusetts Medical Society, United States (Jan. 2012).

Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, England (Feb. 2000).

Berglund, L., et al., "The Epitope Space of the Human Proteome," Protein Science 17(4):606-613, Cold Spring Harbor Laboratory Press, United States (Apr. 2008).

Bluemel, C., et al., "Epitope Distance to the Target Cell Membrane and Antigen Size Determine the Potency of T Cell-mediated Lysis by BiTE Antibodies Specific for a Large Melanoma Surface Antigen," Cancer Immunology, Immunotherapy 59(8):1197-1209, Springer Verlag, Germany (Aug. 2010).

Bogan, A., et al., "Anatomy of Hot Spots in Protein Interfaces," Journal of Molecular Biology, vol. 280, pp. 1-9 (1998).

Bostrom, J., et al., "Variants of the Antibody Herceptin that Interact with HER2 and VEGF at the Antigen Binding Site," Science 323(5921):1610-1614, American Association for the Advancement of Science, United States (Mar. 2009).

(56) References Cited

OTHER PUBLICATIONS

Buday, L. et al., "Epidermal Growth Factor Regulates the Exchange Rate of Guanine Nucleotides on p21ras in Fibroblasts," Molecular and Cellular Biology, vol. 13{3}:1903-1910 {1993}.
Capelle, M., et al., "Spectroscopic Characterization of Antibodies Adsorbed to Aluminium Adjuvants: Correlation With Antibody Vaccine Immunogenicity," Vaccine 23(14):1686-1694, Elsevier Science, Netherlands (Feb. 2005).
Carmon, K.S., et al., "R-Spondins Function as Ligands of the Orphan Receptors LGR4 and LGR5 to Regulate Wnt/β-Catenin Signaling," Proceedings of the National Academy of Sciences 108(28):11452-11457, National Academy of Sciences, United States (2011).
Carter, P., "Bispecific Human IgG by Design," Journal of Immunological Methods 248(1-2):7-15, Elsevier, Netherlands (2001).
Carter, P., et al., "Toward the Production of Bispecific Antibody Fragments for Clinical Applications," Journal of Hematotherapy, vol. 4, pp. 463-470 (1995).
Cartron, G., et al., "Therapeutic Activity of Humanized Anti-cd20 Monoclonal Antibody and Polymorphism in IgG Fc Receptor FcgammaRIIIa Gene," Blood 99(3):754-758, American Society of Hematology, United States (2002).
Chames, P. and Baty, D., "Bispecific Antibodies for Cancer Therapy: The Light at the End of the Tunnel?," MAbs 1(6):539-547, Taylor & Francis, United States (Nov.-Dec. 2009).
Chatenoud, L., et al., "In Vivo Cell Activation Following OKT3 Administration. Systemic Cytokine Release and Modulation by Corticosteroids," Transplantation 49(4):697-702, Lippincott Williams & Wilkins, United States (Apr. 1990).
Choi Y, and Deane C.M., "Predicting Antibody Complementarity Determining Region Structures Without Classification," Molecular BioSystems 7:3327-3334, The royal society of chemistry (Sep. 2011).
Cochran J.R., et al., "Domain-level Antibody Epitope Mapping Through Yeast Surface Display of Epidermal Growth Factor Receptor Fragments," Journal of Immunology Methods 287(1-2):147-158, Elsevier, Netherland (Apr. 2004).
Corada, M., et al., "Monoclonal Antibodies Directed To Different Regions of Vascular Endothelial Cadherin Extracellular Domain Affect Adhesion and Clustering of the Protein and Modulate Endothelial Permeability," Blood 97(6):1679-1684, American Society of Hematology (Mar. 2001).
Cui, H., et al., "Chemically Programmed Bispecific Antibodies That Recruit and Activate T Cells," The Journal of Biological Chemistry 287(34):28206-28214, American Society for Biochemistry and Molecular Biology, United States (Aug. 2012).
Davies, J. and Riechmann, L., "Antibody VH Domains as Small Recognition Units," Biotechnology 13(5):475-479, Nature Publishing Group, United States (1995).
Davis, J.H., et al., "SEEDbodies: Fusion Proteins Based on Strand-exchange Engineered Domain (SEED) CH3 Heterodimers in an Fc Analogue Platform for Asymmetric Binders or Immunofusions and Bispecific Antibodies.," Protein Engineering, Design & Selection 23(4):195-202, Oxford University Press, England (2010).
De Genst, E., et al., "Antibody Repertoire Development in Camelids," Developmental and Comparative Immunology 30(1-2):187-198, Elsevier Science, United States (2006).
De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).
De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, England (Apr. 1995).
De Kruif, J., et al., "Generation of Stable Cell Clones Expressing Mixtures of Human Antibodies," Biotechnology and Bioengineering 106(5):741-750, Wiley, United States (Aug. 2010).
De Lau, W., et al., "Lgr5 Homologues Associate with Wnt Receptors and Mediate R-spondin Signalling," Nature 476(7360):293-297, Macmillan Publishers Limited, England (2011) (D14 as cited in Opposition of EP 2173379).
De Lau, W., et al., "The R-spondin/Lgr5/Rnf43 Module: Regulator of Wnt Signal Strength," Genes and Development 28(4):305-316, Cold Spring Harbor Laboratory Press, United States (2014) (D31 as cited in Opposition of EP 2173379.
De Vries, S.J., et al., "The HADDOCK Web Server for Data-driven Biomolecular Docking," Nature Protocols 5(5):883-897, Nature Publishing Group, England (May 2010).
De Wildt, et al., Analysis of Heavy and Light Chain Pairings Indicates that Receptor Editing Shapes the Human Antibody Repertoire, Journal of Molecular Biology, 285(3):895-901, Elsevier,England(1999).
Deisenhofer, J., "Crystallographic refinement and atomic models of a human Fc fragment and its complex with fragment B of protein A from *Staphylococcus aureus* at 2.9- and 2.8—A resolution," Biochemistry 20(9):2361-2370, American Chemical Society, United States (1981).
Demeule, B., et al., "Characterization of Protein Aggregation: the Case of a Therapeutic Immunoglobulin," Biochimica et Biophysica Acta 1774(1):146-153, Elsevier Publisher, Netherlands (Jan. 2007 ).
Demeule, B., et al., "Detection and Characterization of Protein Aggregates by Fluorescence Microscopy," International Journal of Pharmaceutics 329(1-2):37-45, Elsevier/North-Holland Biomedical Press, Netherlands (Feb. 2007 ).
Devash, Y., et al., "Vertical Transmission of Human Immunodeficiency Virus Is Correlated With the Absence of High-affinity/avidity Maternal Antibodies to the Gp120 Principal Neutralizing Domain," Proceedings of the National Academy of Sciences of the United States of America 87(9):3445-3449, National Academy of Sciences, United States (May 1990).
Di et al., "Ultra high content image analysis and phenotype profiling of 3D cultured microtissues," PLoS One. Oct. 7, 2014;9{10}:e109688 {2011}.
Dreier, T., et al., "Extremely Potent, Rapid and Costimulation-Independent Cytotoxic T-Cell Response against Lymphoma Cells Catalyzed By a Single-Chain Bispecific Antibody," International Journal of Cancer 100(6):690-697, Wiley-Liss, United States (2002).
Ellerson, J.R., et al., "Structure and Function of Immunoglobulin Domains. III. Isolation and Characterization of a Fragment Corresponding to the Cgamma2 Homology Region of Human Immunoglobin G1," Journal of Immunology 116(2):510-517, American Association of Immunologists, United States (Feb. 1976).
Ewer, M.S., et al., "Cardiotoxicity of Anticancer Treatments: What the Cardiologist Needs to Know," Nature Reviews Cardiology 7(10):564-575, Nature Publishing Group, England (Oct. 2010).
Farnan, D. and Moreno, G.T., "Multiproduct High-resolution Monoclonal Antibody Charge Variant Separations by pH Gradient Ion-exchange Chromatography," Analytical Chemistry 81(21):8846-8857, American Chemical Society, United States (2009).
Ferguson,K.M., "Structure-based View of Epidermal Growth Factor Receptor Regulation," AnnualReview of Biophysics 37:353-373, AnnualReviews, United States (2008).
Freeman D., et al., "Panitumumab and Cetuximab Epitope Mapping and in Vitro Activity," Journal of Clinical Oncology 26(15):14536-14536, American Society of Clinical Oncology (May 20, 2008).
Gale, N.W et al. "Grb2 Mediates the Egf-Dependent Activation of Guanine Nucleotide Exchange on Ras," Nature 363:88-92, Springer Nature Limited (May 1993).
Garrett, T.P., et al., "Crystal Structure of a Truncated Epidermal Growth Factor Receptor Extracellular Domain Bound to Transforming Growth Factor alpha," Cell 110(6):763-773, Cell Press, United States (Sep. 2002).
Geginat, J., et al., "Proliferation and Differentiation Potential of Human CD8+ Memory T-cell Subsets in Response to Antigen or Homeostatic Cytokines," Blood 101(11):4260-4266, American Society of Hematology, United States (Jun. 2003).
Giard D.J., et al., "In Vitro Cultivation of Human Tumors: Establishment of Cell Lines Derived From a Series of Solid tumors," Journal of National Cancer Institution 51:1417-1423 (Nov. 1973).

(56) References Cited

OTHER PUBLICATIONS

Greco, W.R., et al., "The Search for Synergy: a Critical Review From a Response Surface Perspective," Pharmacological Reviews 47(2):331-385, American Society for Pharmacology and Experimental Therapeutics, United States (Jun. 1995).
Griffiths, A.D., et al., "Human Anti-Self Antibodies with High Specificity from Phage Display Libraries," The EMBO Journal 12(2):725-734, Wiley Blackwell, England (Feb. 1993).
Gulli, L.F., et al., "Epidermal Growth Factor-induced Apoptosis in A431 Cells Can Be Reversed by Reducing the Tyrosine Kinase Activity," Cell Growth & Differentiation 7(2):173-178, The Association, United States (Feb. 1996).
Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).
Gussow, D. and Seemann, G., "Humanization of Monoclonal Antibodies," Methods in Enzymology 203:99-121, Elsevier Science, United States (1991).
Haagen, I.A., et al., "The Efficacy of CD3 X CD19 Bispecific Monoclonal Antibody (BsAB) in a Clonogenic Assay: The Effect of Repeated Addition of Bsab and Interleukin-2," Blood 85(11):3208-3212, American Society of Hematology, United States (Jun. 1995).
Han, Y., et al., "KLRL1, a Novel Killer Cell Lectinlike Receptor, Inhibits Natural Killer Cell Cytotoxicity," Blood 104(9):2858-2866, American Society of Hematology, United States (Nov. 2004).
Hao, H.X., et al., "ZNRF3 Promotes Wnt Receptor Turnover in an R-Spondin-Sensitive Manner," Nature 485(7397):195-200, Nature Publishing Group, England (2012).
Hendsch, Z.S., et al., "Preferential Heterodimer Formation via Undercompensated Electrostatic Interactions," Journal of the American Chemical Society 123(6):1264-1265, American Chemical Society, United States (Feb. 2001).
Horsten, H., et al., "Production of Non-Fucosylated Antibodies by Co-expression of Heterologous GDP-6-Deoxy-D-Lyxo-4-Hexulose Reductase," Glycobiology, 20(12):1607-1618, IRL Press at Oxford University Press, England, (Dec. 2010).
Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).
Ionescu, R.M., et al., "Contribution of Variable Domains to the Stability of Humanized IgG1 Monoclonal Antibodies," Journal of Pharmaceutical Sciences 97(4):1414-1426, Elsevier, United States (Apr. 2008).
Jain K.K., et al., "A Prospective Randomized Comparison of Epirubicin and Doxorubicin in Patients With Advanced Breast Cancer," Journal of Clinical Oncology 3(6):818-820, American Society of Clinical Oncology, United States (Jun. 1985).
Jorissen, R.N., et al., "Epidermal Growth Factor Receptor: Mechanisms of Activation and Signalling," Experimental Cell Research 284(1):31-53, Academic Press, United States (Mar. 2003).
Junttila, T.T., et al., "Ligand-Independent HER2/HER3/PI3K Complex Is Disrupted by Trastuzumab and Is Effectively Inhibited by the PI3K Inhibitor GDC-0941," Cancer Cell 15(5):429-440, Cell Press, United States (May 2009).
Junttila, T.T., et al., "Superior in Vivo Efficacy of Afucosylated Trastuzumab in the Treatment of HER2-amplified Breast Cancer," Cancer Research 70(11):4481-4489, American Association for Cancer Research, United States (Jun. 2010).
Kabat, E.A., et al., "Identical V Region Amino Acid Sequences and Segments of Sequences in Antibodies of Different Specificities. Relative Contributions of Vh and Vl Genes, Minigenes, and Complementarity-determining Regions to Binding of Antibody-combining Sites," Journal of Immunology 147(5):1709-1719, American Association of Immunologists, United States (Sep. 1991).

Kang J.C., et al., "Engineering Multivalent Antibodies to Target Heregulin-Induced HER3 Signaling in Breast Cancer Cells," Comparative Study 6(2):340-353, Landes Bioscience, United states (Apr. 2014).
Kipriyanov, S.M., et al., "Bispecific CD3 x CD19 Diabody for T Cell-Mediated Lysis of Malignant Human B Cells," International Journal of Cancer 77(5):763-772, Wiley-Liss, United States (1998).
Klimka, A., et al., "Human Anti-CD30 Recombinant Antibodies by Guided Phage Antibody Selection Using Cell Panning," British Journal of Cancer 83(2):252-260, Nature Publishing Group, England (Jul. 2000).
Kontermann, R.E., "Dual Targeting Strategies with Bispecific Antibodies," mAbs 4(2):182-197, Taylor and Francis, United States (2012).
Kruif, D.J., et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, England (Apr. 2009).
Kubota, T., et al., "Engineered therapeutic antibodies with improved effector functions," Cancer Science 100(9):1566-1572, Wiley Publishing on behalf of the Japanese Cancer Association, England (Sep. 2009).
Kulkarni-Kale, U., et al., "CEP: a Conformational Epitope Prediction Server," Nucleic Acids Research 33:W168-W171, Oxford University Press, England (Jul. 2005).
Kumar, R., et al., "The Second Pdz Domain of Inad Is a Type I Domain Involved in Binding to Eye Protein Kinase C. Mutational Analysis and Naturally Occurring Variants," Journal of Biological Chemistry 276(27):24971-24977, American Society for Biochemistry and Molecular Biology, United States (Jul. 2001).
Lakowicz, J.R., "Principles of Fluorescence Spectroscopy," 3rd Edition, Kluwer Academic/Plenum Publisher, 469 pages (2006).
Landgraf, R., et al., "HER2 Therapy. HER2 (ERBB2): Functional Diversity from Structurally Conserved Building Blocks," Breast Cancer Research 9(1):202, BioMed Central Ltd, England (2007).
Lanzavecchia, A. and Staerz, U.D., "Lysis of Nonnucleated Red Blood Cells by Cytotoxic T Lymphocytes," European Journal of Immunology 17(7):1073-1074, Wiley-VCH, Germany (Jul. 1987).
Le Gall, F., et al., "Effect of Linker Sequences Between the Antibody Variable Domains on the Formation, Stability and Biological Activity of a Bispecific Tandem Diabody," Protein Engineering, Design & Selection 17(4):357-366, Oxford University Press, England (Apr. 2004).
Ledon N., et al., "Comparative Analysis of Binding Affinities to Epidermal Growth Factor Receptor of Monoclonal Antibodies Nimotuzumab and Cetuximab Using Different Experimental Animal Models," Placenta 32: 531-534 (2011).
Lichtenberger, B.M., et aL., "Epidermal Egfr Controls Cutaneous Host Defense and Prevents Inflammation," Science Translational Medicine 5(199):14, (2013).
Liesveld, J.L., et al., "Expression of IgG Fc Receptors in Myeloid Leukemic Cell Lines. Effect of Colony-stimulating Factors and Cytokines," Journal of Immunology 140(5):1527-1533, American Association of Immunologists, United States (Mar. 1988).
Liu, C and Lee, A., "ADCC Enhancement Technologies for Next Generation Therapeutic Antibody," Trends in Bio/Pharmaceutical Industry, 9 pages, 2009.
Liu, H., et al., "Heterogeneity of Monoclonal Antibodies," Journal of Pharmaceutical Sciences 97(7):2426-2447, Wiley-Liss, United States (Jul. 2008).
Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).
Loffler, A., et al., "A Recombinant Bispecific Single-chain Antibody, CD19 x CD3, Induces Rapid and High Lymphoma-directed Cytotoxicity by Unstimulated T Lymphocytes," Blood 95(6):2098-2103, American Society of Hematology, United States (Mar. 2000).
Logtenberg, T., "Hub for Organoids", Poster Presentation, www.innovationforhealth.nl/index.php/page/getFileUID/id/82364b177dfed9754d785aafffb21363/cr_usedb/25, 29 pages, Mar. 22, 2016.

(56) References Cited

OTHER PUBLICATIONS

Mariuzza, R.A., et al., "The Structural Basis of Antigen-antibody Recognition," Annual Review of Biophysics and Biomolecular Structure 16:139-159, Annual Reviews, United States (1987).
Marks, J.D., et al., "By-passing Immunization. Human Antibodies from V-gene Libraries Displayed on Phage," Journal of Molecular Biology 222(3):581-597, Academic Press Limited, United States (Dec. 1991).
Marshall, A.S., et al., "Identification and Characterization of a Novel Human Myeloid Inhibitory C-type Lectin-like Receptor (MICL) That Is Predominantly Expressed on Granulocytes and Monocytes," The Journal of Biological Chemistry 279(15):14792-14802, American Society for Biochemistry and Molecular Biology, United States (Apr. 2004).
Marvin, J.S., et al., "Redesigning an Antibody Fragment for Faster Association With Its Antigen," Biochemistry 42(23):7077-7083, American Chemical Society, United States (Jun. 2003).
May C., et al., "Advances in Bispecific Biotherapeutics for the Treatment of Cancer," Biochemical Pharmacology 84:1105-1112 (2012).
Merchant, A.M., et al., "An Efficient Route to Human Bispecific IgG," Nature Biotechnology 16(7):677-681, Nature Publishing Group, United States (1998).
Merlino, GT. et al, "Amplification and Enhanced Expression of the Epidermal Growth Factor Receptor Gene in A431Human Carcinoma Cells," Science, vol. 224(4647): 417-419 (1984).
Merus, www.merus.nl, press release, 2 pages, dated Jan. 7, 2013.
Merus, www.merus.nl, press release, 3 pages, dated Jun. 17, 2013.
Meulemans, E.V., et al., "Selection of Phage-displayed Antibodies Specific for a Cytoskeletal Antigen by Competitive Elution With a Monoclonal Antibody," Journal of Molecular Biological 244(4):353-360 (1994).
Miller, S, "Protein-protein Recognition and the Association of Immunoglobulin Constant Domains," Journal of Molecular Biology 216(4):965-973, Elsevier Ltd (Dec. 1990).
Moore, P.A., et al., "Application of Dual Affinity Retargeting Molecules to Achieve Optimal Redirected T-cell killing of B-cell Lymphoma," Blood 117(17):4542-4551, American Society of Hematology, United States (Apr. 2011).
Moshaver, B., et al., "Identification of a Small Subpopulation of Candidate Leukemia-initiating Cells in the Side Population of Patients With Acute Myeloid Leukemia," Stem Cells 26(12):3059-3067, AlphaMed Press, United States (Dec. 2008).
Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, England (Apr. 1997).
Nissim, A., et al., "Antibody Fragments From a 'single Pot' Phage Display Library as Immunochemical Reagents," The EMBO Journal, 13(3):692-698, (Feb. 1994).
Nohaile, M.J., et al., "Altering dimerization specificity by changes in surface electrostatics," Proceedings of the National Academy of Sciences 98(6):3109-3114, National Academy of Sciences, United States (2001).
Non-Final Office Action dated May 10, 2016, in U.S. Appl. No. 14/974,581, De Kruif, C.A., et al., filed Dec. 18, 2015.
Norde, W.J., et al., "Myeloid Leukemic Progenitor Cells Can Be Specifically Targeted by Minor Histocompatibility Antigen LRH-1-reactive Cytotoxic T Cells," Blood 113(10):2312-2323, American Society of Hematology, United States (Mar. 2009 ).
Ocana, A., et al., "HER3 Overexpression and Survival In Solid Tumors: A Meta-Analysis," Journal of the National Cancer Institute 105(4):266-273, Oxford University Press, United States (Feb. 2013).
Office Action dated Apr. 10, 2015, in U.S. Appl. No. 13/866,747, De Kruif, C.A., et al., filed Apr. 19, 2013.
Office Action dated Apr. 10, 2015, in U.S. Appl. No. 14/081,848, De Kruif, C.A., et al., filed Nov. 15, 2013.
Office Action dated Apr. 10, 2015, in U.S. Appl. No. 14/395,330, De Kruif, C.A., et al., filed Oct. 17, 2014.
Office Action dated Apr. 13, 2015, in U.S. Appl. No. 13/866,756, De Kruif, C.A., et al., filed Apr. 19, 2013.
Office Action dated Feb. 12, 2016, in U.S. Appl. No. 14/081,848, De Kruif, C.A., et al., filed Nov. 15, 2013.
Office Action dated Jan. 25, 2017, in U.S. Appl. No. 14/974,581, De Kruif, C.A., et al., filed Dec. 18, 2015.
Office Action dated Nov. 1, 2016, in U.S. Appl. No. 15/205,629, Bakker, A.B.H., et al., filed Jul. 8, 2016.
Office Action dated Nov. 28, 2016, in U.S. Appl. No. 14/040,023, De Kruif, C.A., et al., filed Sep. 27, 2013.
Office Action dated Sep. 18, 2015, in U.S. Appl. No. 13/866,756, De Kruif, C.A., et al., filed Apr. 19, 2013.
Office Action dated Sep. 28, 2016, in U.S. Appl. No. 14/974,581, De Kruif, C.A., et al., filed Dec. 18, 2015.
Office Action dated Sep. 29, 2015, in U.S. Appl. No. 13/866,747, De Kruif, C.A., et al., filed Apr. 19, 2013.
Office Action dated Dec. 3, 2015, in U.S. Appl. No. 14/040,023, Bakker, A.B.H., et al., filed Sep. 27, 2013, 8 pages.
Offner, S., et al., "Induction of Regular Cytolytic T Cell Synapses by Bispecific Single-chain Antibody Constructs on MHC Class I-negative Tumor Cells," Molecular Immunology 43(6):763-771, Pergamon Press, England (Feb. 2006).
Oganesyan, V., et al., "Structural Characterization of a Human Fc Fragment Engineered for Lack of Effector Functions," Acta Crystallographica. Section D, Biological Crystallography 64(Pt 6):700-704, Wiley-Blackwell, United States (Jun. 2008).
Ogiso, H., et al., "Crystal Structure of the Complex of Human Epidermal Growth Factor and Receptor Extracellular Domains," Cell 110(6):775-787, Cell Press, United States (Sep. 2002).
Olayioye, M.A., et al., "TheErbb Signaling Network: Receptor Heterodimerization In Development and Cancer," EMBO Journal, Jul. 2000, vol. 19(13), pp. 3159-3167.
Papadea, C., et al., "Human Immunoglobulin G and Immunoglobulin G Subclasses: Biochemical, Genetic, and Clinical Aspects," Critical Reviews in Clinical Laboratory Sciences 27(1):27-58, Informa Healthcare, England (1989).
Pastore, S. et al., "Erk1/2 Regulates Epidermal Chemokine Expression and Skin Inflammation," Journal of Immunology 174:5047-5056 (2005).
Patel, D.K., "Clinical Use of Anti-epidermal Growth Factor Receptor Monoclonal Antibodies in Metastatic Colorectal Cancer," Pharmacotherapy 28(11):31S-41S (2008).
Peng, R., et al., "Bleomycin Induces Molecular Changes Directly Relevant to Idiopathic Pulmonary Fibrosis: A Modelor "Active," Disease, " Pios One, 8{4}: e59348, 15 pages {2013).
Peng, W., et al., "Blockade of the PD-1 Pathway Enhances the Efficacy of Adoptive Cell Therapy against Cancer," Oncoimmunology 2(2):e22691, Taylor & Francis, United States (Feb. 2013).
Prigent, S.,et al., "Identification of C-erbb-3 Binding Sites for Phosphatidylinositol 3'-kinase and Shc Using an Egf Receptor/c-erbb-3 Chimera," The EMBO Journal 13(12):2831-2841, National Center for Biotechnology Information (Jun. 1994).
Raffen, R., et al., "Reengineering Immunoglobulin Domain Interactions by Introduction of Charged Residues," Protein Engineering 11(4):303-309, Oxford University Press, England (Apr. 1998 ).
Reusch, U., et al., "Beyond mAbs with TandAbs," Innovations in Pharmaceutical Technology, 4 pages, (2011).
Ridgway, J.B., et al., "'Knobs-Into-Holes' Engineering of Antibody CH3 Domains for Heavy Chain Heterodimerization," Protein Engineering 9(7):617-621, Oxford University Press, England (1996).
Robertson, S.C., et al., "Rtk Mutations and Human Syndromes when Good Receptors Turn Bad," Trends in genetics 16(6):265-271 (Jun. 2000).
Robinson M.K., et al., "Targeting ErbB2 and ErbB3 with a bispecific single-chain FV Enhances targeting selectivity and induces a therapeutic effect in Vitro", British Journal of CA, Nature Publishing Group, GB 99(9):1415-1425, England, London (Oct. 2008).
Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).

(56) References Cited

OTHER PUBLICATIONS

Sandercock et al., "Identification of anti-tumour biologics using primary tumour models, 3-D phenotypic screening and image-based multi-parametric profiling." Mol Cancer. Jul. 31, 2015;14:147. PMID 26227951.

Sato, T., et al., "Long-term Expansion of Epithelial Organoids From Human Colon, Adenoma, Adenocarcinoma, and Barrett's Epithelium," Gastroenterology 141(5):1762-1772, W.B. Saunders, United States (Nov. 2011).

Schaefer, G., et al., "A Two-in-one Antibody Against Her3 and Egfr Has Superior Inhibitory Activity Compared With Monospecific Antibodies," Cancer cell 20(4):472-486, Cell Press, United States (Oct. 2011).

Schiffer, M., et al., "Analysis of Immunoglobulin Domain Interactions. Evidence for a Dominant Role of Salt Bridges," Journal of Molecular Biology 203(3):799-802, Elsevier, England (Oct. 1988).

Schmitz, K., and Ferguson K.M., "Interaction of Antibodies With Erbb Receptor Extracellular Regions," Experimental Cell Research 315(4):659-670, Academic Press, United states (Feb. 2009).

Schoeberl, B., et al., "An ErbB3 Antibody, MM-121, is Active in Cancers with Ligand-Dependent Activation," Cancer Research 70(6):2485-2494, American Association for Cancer Research, United States (Mar. 2010).

Selzer, T., et al., "Rational Design of Faster Associating and Tighter Binding Protein Complexes," Nature Structural & Molecular Biology 7(7):537-541, Nature Publishing Group, United States (Jul. 2000).

Sergina, N.V., et al., "Escape from HER-Family Tyrosine Kinase Inhibitor Therapy By The Kinase-Inactive HER3," Nature 445(7126):437-441, Nature Publishing Group, England (Jan. 2007).

Seshagiri, S., et al., "Recurrent R-spondin Fusions in Colon Cancer," Nature 488(7413):660-664, Nature Publishing Group, England (2012).

Shames, D.S., et al., "High Heregulin Expression Is Associated with Activated HER3 and May Define an Actionable Biomarker in Patients with Squamous Cell Carcinomas of the Head and Neck," PLoS One 8(2):e56765, Public Library of Science, United States (2013).

Sheinerman, F.B., et al., "Electrostatic Aspects of Protein-protein Interactions," Current Opinion in Structural Biology 10(2):153-159, Elsevier Science, England (Apr. 2000).

Sheridan, C., "Amgen Swallows Micromet to BiTE Into All Market," Nature Biotechnology 30(4):300-301, Nature America Publishing, United States (Apr. 2012).

Shields, R.L., et al., "High resolution mapping of the binding site on human IgG 1 for Fc gamma Ri, Fc gamma RII, Fc gamma RIII, and FcRn and design of IgG 1 variants with improved binding to the Fc gamma R," J Biol Chem., 276(9): 6591-6604, The American Society for Biochemistry and Molecular Biology, Inc., United States (2001).

Shiraiwa H., et al., "Engineering a Bispecific Antibody With a Common Light Chain: Identification and Optimization of an Anti-cd3 Epsilon and Anti-gpc3 Bispecific Antibody, Ery974," Methods 154:10-20, Academic Press (Feb. 2019).

Sinha, N., et al., "Differences in Electrostatic Properties at Antibody-antigen Binding Sites: Implications for Specificity and Cross-reactivity," Biophysical Journal 83(6):2946-2968, Cambridge, United States (Dec. 2002).

Sinha, N., et al., "Electrostatics in Protein Binding and Function," Current Protein and Peptide Science 3(6):601-614, Bentham Science Publishers, Netherlands (Dec. 2002).

Sluijter, B.J., et al., "4-1 BB-mediated Expansion Affords Superior Detection of in Vivo Primed Effector Memory CD8+ T Cells from Melanoma Sentinel Lymph Nodes," Clinical Immunology 137(2):221-233, Academic Press, United States (Nov. 2010).

Soltoff, S.P., et al., "ErbB3 is involved in activation of phosphatidylinositol 3-kinase by epidermal growth factor," Molecular and Cellular Biology 14(6):3550-3558, American Society for Microbiology, United States (Jun. 1994).

Spiess, C., et al., "Alternative Molecular Formats and Therapeutic Applications for Bispecific Antibodies," Molecular Immunology 67(2 Pt A):95-106, Pergamon Press, England (Oct. 2015).

Staerz, U.D., and Bevan, M.J., "Hybrid Hybridoma Producing a Bispecific Monoclonal Antibody that can Focus Effector T-cell Activity," Proceedings of the National Academy of Sciences USA 83(5):1453-1457, National Academy of Sciences, United States (1986).

Strelkauskas, A., et al., "Human Monoclonal Antibody: 2. Simultaneous Expression of IgG and IgM with Similar Binding Specificities by a Human Hybrid Clone," Hybridoma 6(5):479-488, Mary Ann Liebert, United states (Oct. 1987).

Suntharalingam, G., et al., "Cytokine Storm in a Phase 1 Trial of the Anti-CD28 Monoclonal Antibody TGN1412," The New England Journal of Medicine 355(10):1018-1028, Massachusetts Medical Society, United States (Sep. 2006).

Tanner, M., et al., "Characterization of a Novel Cell Line Established From a Patient With Herceptin-resistant Breast Cancer," Molecular Cancer Therapeutics 3(12):1585-1592, American Association for Cancer Research, United States (Dec. 2004).

Thery, J.C., et al., "Resistance to Human Epidermal Growth Factor Receptor Type 2-targeted Therapies," European Journal of Cancer 50(5):892-901, (Mar. 2014).

Uberall, I. et ai., "The status and role of ErbB receptors in human cancer," Exp Mol Pathol., vol. 84:79-89 (2008).

"UniProt Entry Q5QGZ9, UniProt, retrieved Jan. 21, 2015, from (http://www.uniprot.org/unirptoiQ5QGZ9)".

Van De Wetering, M., et al., "Prospective Derivation of a Living Organoid Biobank of Colorectal Cancer Patients," Cell, vol. 161:933-945, Science direct (Jun. 2015).

Van Rhenen, A., et al., "The Novel AML Stem Cell Associated Antigen CII-1 Aids in Discrimination Between Normal and Leukemic Stem Cells," Blood 110(7):2659-2666, American Society of Hematology, United States (Oct. 2007).

Wadhwa, D., et al., "Trastuzumab Mediated Cardiotoxicity in the Setting of Adjuvant Chemotherapy for Breast Cancer: a Retrospective Study," Breast Cancer Research and Treatment 117(2):357-364, Kluwer Academic, Netherlands (Sep. 2009).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Wehrman, T.S., et al., "A System for Quantifying Dynamic Protein Interactions Defines a Role for Herceptin in Modulating ErbB2 Interactions," Proceedings of the National Academy of Sciences of the United States of America 103(50):19063-19068, National Academy of Sciences, United States (Dec. 2006).

Weidle, UH. et al., "The Intriguing Options of Multispecific Antibody Formats for Treatment of Cancer," Cancer3enomics & Proteomics, vol. 10: 1-18 {2013).

Wilson, T.R., et al., "Widespread Potential for Growth-factor-driven Resistance to Anticancer Kinase Inhibitors," Nature 487(7408):505-509, Nature Publishing Group, England (Jul. 2012).

Yarden, Y. et al., "The EGFR family and its ligands in human cancer: signalling mechanisms and therapeutic opportunities," European Journal of Cancer 37(Supp4): S3-S8, ResearchGate GmbH (Sep. 2001).

Yarden, Y., et al., "The ERBB Network: At Last, Cancer Therapy Meets Systems Biology," Nature Reviews Cancer 12(8):553-563, Nature Publishing Group, England (Jul. 2012).

Yonesaka, K., et al., "Activation of ERBB2 Signaling Causes Resistance to the Egfr-Directed Therapeutic Antibody Cetuximab," Science Translational Medicine 3(99):99ra86, American Association for the Advancement of Science, United States (Sep. 2011).

Zebisch M and Jones EY, "Crystal structure of R-spondin 2 in complex with the ectodomains of its receptors LGR5 and ZNRF3." J Struct Biol. Aug. 2015;191(2):149-55.

Zebisch M and Jones EY, "ZNRF3/RNF43—A direct linkage of extracellular recognition and E3 ligase activity to modulate cell surface signalling." Prog Biophys Mol Biol. Sep. 2015; 118(3): 112-8.

Zeidler, R., et al., "Simultaneous Activation of T Cells and Accessory Cells by a New Class of Intact Bispecific Antibody Results in

(56) References Cited

OTHER PUBLICATIONS

Efficient Tumor Cell Killing," Journal of Immunology 163(3):1246-1252, American Association of Immunologists, United States (1999).
Zhang, H., et al., "ErbB Receptors: From Oncogenes to Targeted Cancer Therapies," Journal of Clinical Investigation 117(8):2051-2058, American Society for Clinical Investigation, United States (Aug. 2007).
Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).
Zhu, Z., et al., "Remodeling Domain Interfaces to Enhance Heterodimer Formation," Protein science 6(4):781-788, Cold Spring Harbor Laboratory Press, United States (Apr. 1997).
Adelaide, J., et al., "A Recurrent Chromosome Translocation Breakpoint in Breast and Pancreatic Cancer Cell Lines Targets the Neuregulin/NRG1 Gene," Genes Chromosome Cancer, 37(4), 333-345, Wiley-Liss, Inc., United States (2003).
Agus, D.B., et al., "Targeting ligand-activated ErbB2 signaling inhibits breast and prostate tumor growth," Cancer Cell, 2(2): 127-137, Cell Press, United States (2002).
Huhalov, A., et al., "MM-111, an ErbB2/ErbB3 Bispecific Antibody with Potent Activity in ErbB2-Overexpressing Cells, Positively Combines with Trastuzumab to Inhibit Growth of Breast Cancer Cells Driven by the ErbB2/ErbB3 Oncogenic Unit," American Association for Cancer Research, Proceedings of the Annual Meeting 51:845-846, American Association for Cancer Research, United States (Apr. 2010).
Appella, E., et al., "Structure and Function of Epidermal Growth Factor-Like Regions In Proteins," FEBS Letters 231(1):1-4, Wiley-Blackwell, United States (Apr. 1988).
Ardeshirpour, Y., et al., "In vivo assessment of HER2 receptor density in HER2-positive tumors by near-infrared imaging, using repeated injections of the fluorescent probe," Technology In Cancer Research & Treatment, 13(5):427-434, SAGE, United States (Oct. 2014).
Balko, J.M., et al., "Profiling of residual breast cancers after neoadjuvant chemotherapy identifies DUSP4 deficiency as a mechanism of drug resistance," Nature Medicine 18(7): 1052-1059, Nature Publishing Company, United Kingdom (Jul. 2012).
Bernard, A., et al., "A unique epitope on the CD2 molecule defined by the monoclonal antibody 9-1: epitope-specific modulation of the E-rosette receptor and effects on T-cell functions," Hum Immunol 17(4):388-405, Elsevier Inc., United States (1986).
Bettler., et al., "Binding site For Ige Of The Human Lymphocyte Low-Affinity Fc Epsilon Receptor (Fc Epsilon RII/CD23) is Confined to the Domain Homologous With Animal Lectins, " Proceedings of the National Academy of Sciences of the United States of America 86(18): 7118-7122, National Academy of Sciences, United States (Sep. 1989).
Birnbaum, D., et al., "Chromosome arm 8p and cancer: a fragile hypothesis," The Lancet Oncology, 4: 639-642, Lancet Publishing Group, United Kingdom (2003).
Blomquist, M.C., et al., "Vaccinia Virus 19-Kilodalton Protein: Relationship to Several Mammalian Proteins, Including Two Growth Factors," Proceedings of the National Academy of Sciences of the United States of America 81(23):7363-7367, National Academy of Sciences, United States (Dec. 1984).
Boyer, C.M., et al., "Relative Cytotoxic Activity of Immunotoxins Reactive With Different Epitopes on the Extracellular Domain of the C☐Erbb☐2 (Her☐2/Neu) Gene Product P185," International Journal of Cancer, 82(4): 525-531, John Wiley & Sons, Inc., United States (Aug. 1999).
Buday, L., et al., "Epidermal Growth Factor Regulates the Exchange Rate of Guanine Nucleotides on p21ras in Fibroblasts," Molecular and Cellular Biology 13(3):1903-1910, American Society for Microbiology, United States (1993).

Caldas, C., et al., "Humanization of the Anti-Cd18 Antibody 6.7: An Unexpected Effect of a Framework Residue in Binding to Antigen," Molecular Immunology 39(15):941-952, Pergamon Press, United Kingdom (May 2003).
Casset, F., et al., "A Peptide Mimetic of an Anti-CD4 Monoclonal Antibody By Rational Design," Biochemical and Biophysical Research Communications 307(1):198-205, Academic Press, United States (Jul. 2003).
Chandra, A., "The Role of ErbB3 Inhibitors as Cancer Therapeutics," Boston University, School of Medicine, pp. 1-78, thesis submitted in partial fulfillment of the requirements for the degree of Master of Science, Boston University, United States (May 2015).
Chang, H.J., et al., "Loop-sequence features and stability determinants in antibody variable domains by high-throughput experiments," Structure 22(1):9-21, Cell Press, United States (2014).
Chernomordik, V., et al., "Quantitative Analysis of Her2 Receptor Expression in Vivo By Near-Infrared Optical Imaging," Molecular Imaging, 9(4):192-200, SAGE Publications, United States (Aug. 2010).
Chien, N.C., et al., "Significant Structural and Functional Change of an Antigen-Binding Site by a Distant Amino Acid Substitution: Proposal of a Structural Mechanism," Proceedings of the National Academy of Sciences USA 86(14):5532-5536, National Academy of Sciences, United States (1989).
Chua, Y.L., et al., "The NRG1 gene is frequently silenced by methylation in breast cancers and is a strong candidate for the 8p tumor suppressor gene," Oncogene, 28(46): 4041-4052, Macmillan Publishers Limited, Germany (2009).
Clarke, M.F., et al., "Cancer stem cells—perspectives on current status and future directions: AACR Workshop on cancer stem cells," Cancer Research 66(19):9339-9344, American Association for Cancer Research, United States (2006).
Conforti, F., et al., "Dissecting Breast Cancer Complexity: Specific Biological Features and Vulnerabilities of Triple Positive Breast Cancer Tumors," Clinics of Oncology 2:1288, Remedy Publications, United States (May 2017).
Cooke, S.L., et al., High-resolution array CGH clarifies events occurring on 8p in carcinogenesis, BMC Cancer, 8(288): 1-15, BioMed Central Ltd., United Kingdom (2008).
Co-pending, U.S. Appl. No. 15/476,260, inventors Throsby, M., et al., filed Mar. 31, 2017 (Not Published).
Co-pending U.S. Appl. No. 61/635,935, inventors De Kruif, C.A., et al., filed Apr. 20, 2012 (Not Published).
Corona, S.P., et al., "CDK4/6 Inhibitors in HER2-positive Breast Cancer," Critical Reviews in Oncology/Hematology 118:208-214, Elsevier Ireland Ltd., Netherlands (2017).
Curley, M.D., et al., "Seribantumab, An Anti-ERBB3 Antibody, Delays the Onset of Resistance and Restores Sensitivity to Letrozole in an Estrogen Receptor-Positive Breast Cancer Model," Molecular Cancer Therapeutics 14(11): 2642-2652, American Association for Cancer Research Inc., United States (Nov. 2015).
Davis, C.G., "The Many Faces of Epidermal Growth Factor Repeats, " New Biologist 2(5):410-419, W.B. Saunders, United States (May 1990).
De Goeij, B.E., et al., "Efficient Payload Delivery by a Bispecific Antibody-Drug Conjugate Targeting HER2 and CD63," Molecular Cancer Therapeutics 5(11):2688-2697, American Association for Cancer Research, United States (Nov. 2016).
De Nardis, C., et al., "A new approach for generation bispecific antibodies based on a common light chain format and the stable architecture of human immunoglobulin G1," Journal of Biological Chemistry, 292(35): 14706-14717, The American Society for Biochemistry and Molecular Biology, Inc., United States (2017).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
Dhanasekaran, S.M., et al., "Transcriptome meta-analysis of lung cancer reveals recurrent aberrations in NRG1 and Hippo pathway genes," Nat. Commun 5:5893, Nature Publishing Group, United Kingdom (2014).

(56) References Cited

OTHER PUBLICATIONS

Dijoseph, J.F., et al., "Antibody-targeted Chemotherapy with CMC-544: A CD22-targeted Immunoconjugate of Calicheamicin for the Treatment of B-lymphoid Malignancies," Blood 103(5):1807-1814, American Society of Hematology, United States (2004).
Doolittle, R.F., et al., "Computer-Based Characterization ofEpidermal Growth Factor Precursor," Nature 307(5951):558-560, Nature Publishing Group, United Kingdom (Feb. 1984).
Duruisseaux, M., et al., "NRG1 fusion in a French cohort of invasive mucinous lung adenocarcinoma," Cancer Medicine, 5(12): 3579-3585, John Wiley & Sons Ltd., United States (2016).
Edwards, B.M., et al., "The Remarkable Flexibility of the Human Antibody Repertoire; Isolation of Over One Thousand Different Antibodies to a Single Protein, BLyS," Journal of Molecular Biology, 334(1):103-118, Academic Press Inc., United States (Nov. 2003).
Falls, D.L., "Neuregulins: functions, form, and signaling strategies," Exp. Cell Res, 284: 14-30, Elsevier, Netherlands (2003).
Fernandez-Cuesta, L., et al., "CD74-NRG1 Fusions in Lung Adenocarcinoma," Cancer Discovery, 4(4): 415-422, American Association for Cancer Research, United States (2014).
Fernandez-Cuesta, L., et al., "Molecular Pathways: Targeting NRG1 Fusions in Lung Cancer," Clinical Cancer Research, 21 (9): 1989-1994, American Association for Cancer Research, United States (2015).
Fu, W., et al., "Insights into HER2 signaling from step-by-step optimization of anti-HER2 antibodies," MAbs 6(4):978-90, Landes Bioscience, United States (2014).
Gaborit, N., et al., "Emerging anti-cancer antibodies and combination therapies targeting HER3/ERBB3," Human Vaccines and Immunotherapies, 12(3): 576-592, Taylor & Francis Group, United Kingdom (2015).
GenBank Accession No. NC_000017.10, *Homo sapiens* Chromosome 17, GRCh37.p13 Primary Assembly, 2013, 2 Pages.
GenBank Accession No. NC_018923.2, *Homo sapiens* Chromosome 12, Alternate Assembly CHM1_1.1, Whole Genome Shotgun Sequence, 2016.
GenBank Accession No. NC_018928.2, *Homo sapiens* Chromosome 17, Alternate Assembly CHM1_1.1, Whole Genome Shotgun Sequence, 2016.
GenBank Accession No. NP_001005862.1, Receptor Tyrosine-Protein Kinase erbB-2 Isoform b [*Homo sapiens*], 2018.
GenBank Accession No. NP_001005915.1, Receptor Tyrosine-Protein Kinase ErbB-3 isoform s Precursor [*Homo sapiens*], 2018.
GenBank Accession No. NP_001973.2, Receptor Tyrosine-Protein Kinase ErbB-3 isoform 1 precursor [*Homo sapiens*], 2018.
GenBank Accession No. NP_004439.2, Receptor Tyrosine-Protein Kinase ErbB-2 isoform a Precursor [*Homo sapiens*], 2018.
GenBank Accession No. NT_010783.15, *Homo sapiens* Chromosome 17 Genomic Scaffold, GRCh38.p12 Primary Assembly HSCHR17_CTG4, 2018.
GenBank Accession No. NT_029419.12, *Homo sapiens* Chromosome 12 Genomic Contig, GRCh37.p13 Primary Assembly, 2013.
Genbank, "*Homo sapiens* chromosome 12, GRCh37 .p13 Primary Assembly," Accession No. NC_000012.11 accessed at https:http://www.ncbi.nlm.nih.gov/nuccore/NC000012.11, 2013, 3 pages.
George, J., et al., "Differential effects of anti-beta$_2$-glycoprotein I antibodies on endothelial cells and on the manifestations of experimental antiphospholipid syndrome," Circulation 97:900-906, American Heart Association Inc., United States (1998).
Geuijen, C., et al., "Abstract LB-261: Mechanism of action of MCLA-128, a humanized bispecific IgG1 antibody targeting the HER2: HER3 heterodimer," Cancer Research; 1 061h Annual Meeting of The American Association for Cancer Research (AAACR), 75, Suppl. 15, pp. LB-261, Philadelphia, United States (2015).
Girlanda, S., et al., "MICA Expressed by Multiple Myeloma and Monoclonal Gammopathy of Undetermined Significance Plasma Cells Costimulates Pamidronate-activated Gammadelta Lymphocytes," Cancer Research, 65(16):7502-7508, American Association for Cancer Research, United States (Aug. 2005).
Giusti, A.M., et al., "Somatic diversification of S107 from an antiphosphocholine to an anti-DNA autoantibody is due to a single base change in its heavy chain variable region," Proceedings of the National Academy of Sciences 84(9):2926-2930, National Academy of Sciences, United States (1987).
Greenspan, N.S. and Di Cera, E., "Defining Epitopes: It's not as Easy as it Seems," Nature Biotechnology 17(10):936-937, Nature Publishing Group, United States (1999).
Hammond M.E.H., et al., "American Society of Clinical Oncology/College Of American Pathologists Guideline Recommendations for Immunohistochemical Testing of Estrogen and Progesterone Receptors in Breast Cancer," Journal of Clinical Oncology 28(16):2784-2795, Grune & Stratton, United States (Jun. 2010).
Hao, H.X., et al., "ZNRF3 Promotes Wnt Receptor Turnover in an R-Spondin-Sensitive Manner," Nature 485(7397):195-200, Nature Publishing Group, United Kingdom (2012), with Supplemental Information.
Harms B., et al., "Understanding the Role of Cross-arm Binding Efficiency in the Activity of Monoclonal and Multispecific Therapeutic Antibodies", Methods 65(1):95-104, Academic Press Inc., United States (Jan. 2014).
Hathaway, H.J., et al., "Detection of breast cancer cells using targeted magnetic nanoparticles and ultra-sensitive magnetic field sensors," Breast Cancer Research 13: R108, pp. 1-14, BioMed Central Ltd., United Kingdom (2011).
Hayes, N.V.L., and Gullick, W.J., "The Neuregulin Family of Genes and their Multiple Splice Variants in Breast Cancer," J. Mammary Gland Bioi Neoplasia, 13(205): 214, Springer, United States (2008).
Holm, P., et al., "Functional Mapping and Single Chain Construction of the Anti-cytokeratin 8 Monoclonal Antibody TS1," Molecular Immunology 44(6):1075-1084, Pergamon Press, United Kingdom (Feb. 2007).
Hommel, U., et al., "Human Epidermal Growth Factor. High ResolutionSolution Structure And Comparison With Human Transforming Growth Factor Alpha, "Journal of Molecular Biology 227(1):271-282, Elsevier, United Kingdom (Sep. 1992).
Huang W, et al., "Comparison of Central HER2 Testing With Quantitative Total HER2 Expression and HER2 Homodimer Measurements Using a Novel Proximity-Based Assay," American Journal of Clinical Pathology 134(2):303-311, Oxford University Press, United Kingdom (Aug. 2010).
International Search Report and Written Opinion for Application No. PCT/NL2018/050329, dated Sep. 17, 2018, European Patent Office, Netherlands, 10 pages.
International Search Report and Written Opinion for International Application No. PCT/NL2018/050205, dated Sep. 10, 2018, European Patent Office, Netherlands.
International Search Report and Written Opinion for Application No. PCT/NL2018/050204, dated Jun. 25, 2018, European Patent Office, Netherlands, 16 pages.
International Search Report for International Application No. PCT/NL2018/050206, dated Jun. 22, 2018, European Patent Office, Netherlands, 4 pages.
Jackson, C., et al., "Clinical Significance of HER-2 Splice Variants in Breast Cancer Progression and Drug Resistance," Int J Cell Biol 2013:973584, Hindawi Publishing Corporation, Egypt (2013).
Jelovac, D., et al., "HER2-Directed Therapy for Metastatic Breast Cancer," Oncology (Williston Park) 27(3):166-175, CMP Healthcare Media, United States (Mar. 2013).
Jiang, B., et al, "A Novel Peptide Isolated from a Phage Display Peptide Library with Trastuzumab Can Mimic Antigen Epitope of HER-2," The Journal of Biological Chemistry 280(6):4656-4662, The American Society for Biochemistry and Molecular Biology, United States (2005).
Jung, Y., et al., "VAMP2-NRG1 Fusion Gene is a Novel Oncogenic Driver of Non-Small- Cell Lung Adenocarcinoma," J Thor Oncol 10(7): 1107-1111, International Association for the Study of Lung Cancer, United States (2015).
Klein, C., et al., "Progress in Overcoming the Chain Association Issue in Bispecific Heterodimeric IgG Antibodies," MAbs 4(6):653-663, Taylor & Francis, United States (Nov.-Dec. 2012).
Kodack D.P., et al., "Combined Targeting of HER2 and VEGFR2 for Effective Treatment of HER2-amplified Breast Cancer Brain

(56) References Cited

OTHER PUBLICATIONS

Metastases," Proceedings of the National Academy of Sciences 109(45):E3119-E3127, National Academy of Science, United States (Nov. 2012).

Kol, A., et al., "HER3, Serious Partner in Crime: Therapeutic Approaches and Potential Biomarkers for Effect of HER3-targeting," Pharmacology & Therapeutics 143(1):1-11, Pergamon Press, United Kingdom (Jul. 2014).

Lazrek Y., et al., "Anti-HER3 Domain 1 and 3Antibodies Reduce TumorGrowth by Hindering HER2/HER3Dimerization and AKT-InducedMDM2. XIAP, and Fox01 Phosphorylation," Neoplasia 15(3):335-347, Neoplasia Press, Netherlands (Mar. 2013).

Le Clorennec, C., et al., "Neuregulin 1 Allosterically Enhances the Antitumor Effects of the Noncompeting Anti-HER3 Antibody 9 F7-F11 by Increasing Its Binding to HER3," Molecular Cancer Therapeutics, 16(7): 1312-1323, American Association for Cancer Research, United States (2017).

Lee H.J., et al., "Gemini Vitamin D Analog Suppresses Erbb2-positive mammary tumor growth via inhibition of ErbB2/AKT/ERK Signaling", Journal of Steroid Biochermistry and Molecular Biology, Elsevier Science LTD., Oxford, DB, 121(1-2):408-412, England (Jul. 2010).

Lee-Hoeflich, S.T., et al., "A Central Role for HER3 in HER2-Amplified Breast Cancer: Implications for Targeted Therapy," Cancer Research, 68(14): 5878-5887, American Association for Cancer Research, United States (2008).

Lumachi F., et al., "Endocrine Therapy of Breast Cancer," Current Medicinal Chemistry 18(4):513-522, Bentham Science Publishers, United Arab Emirates (2011).

Luo, H., et al., "Noninvasive Brain Cancer Imaging With a Bispecific Antibody Fragment, Generated via Click Chemistry," Proceedings of the National Academy of Sciences of the United States of America 112(41):12806-12811, National Academy of Sciences, United States (Oct. 2015).

Maccallum, R.M., et al., "Antibody-antigen Interactions: Contact Analysis and Binding Site Topography," Journal of Molecular Biology 262(5):732-745, Academic Press, United Kingdom (Oct. 1996).

Malm, M., et al., "Engineering of a Bispecific Affibody Molecule Towards HER2 and HER3 by Addition of an Albumin-Binding Domain Allows for Affinity Purification and in Vivo Half-Life Extension," Biotechnology Journal 9(9):1215-1222, Wiley-VCH Verlag, Germany (Sep. 2014).

Malm, M., et al., "Targeting HER3 Using Mono-and Bispecific Antibodies or Alternative Scaffolds," MABS 8(7):1195-1209, Taylor & Francis, United States (Oct. 2016).

Maussang ., et al., The Binding Mode of the Bispecific Anti-Her2xHer3 antibody MCLA-128 is Responsible for its Potent Inhibition of HRG-Driven Tumorigenesis, Research Poster Presentation Design, 2001, Apr. 1, 2017, Retrieved from the Internet: (URL: http://www.merus.nl/wordpress/wp-content/uploads/2017/04/MCLA- 128-poster-AACR2017-final-.pdf).

McDonagh, C.F., et al., "Antitumor Activity of a Novel Bispecific Antibody that Targets the ErbB2/ErbB3 Oncogenic Unit And Inhibits Heregulin-Induced Activation of ErbB3," Molecular Cancer Therapeutics 11(3):582-593, American Association for Cancer Research, United States (Mar. 2012).

Merten, H., et al., "Antibody-drug Conjugates for Tumor Targeting-novel Conjugation Chemistries and the Promise of Non-IgG Binding Proteins," Bioconjugate Chemistry 26(11):2176-2185, American Chemical Society, United States (Nov. 2015).

Momeny M., et al., "Heregulin-HER3-HER2 signaling promotes matrix metalloproteinase-dependent blood-brain-barrier transendothelial migration of human breast cancer cell lines," Oncotarget 6(6):3932-3946, Impact Journals LLC, United States (Feb. 2015).

Morrison M.M., et al., "ErbB3 Downregulation Enhances Luminal Breast Tumor Response to Antiestrogens," The Journal of clinical investigation 123(10):4329-4343, American Society for Clinical Investigation, United States (Oct. 2013).

Mullard, A., et al., "Maturing Antibody-drug Conjugate Pipeline Hits 30," Nature Reviews Drug Discovery 12(5):329-332, Nature Publishing Group, United Kingdom (May 2013).

Omenn, G.S., et al., "A new class of protein cancer biomarker candidates: differentially expressed splice variants of ERBB2 (HER2/neu) and ERBB1 (EGFR) in breast cancer cell lines," J Proteomics 107:103-12, Elsevier, Netherlands (2014).

Osborne K.C., et al., "Mechanisms of Endocrine Resistance in Breast Cancer," Annual review of medicine 62:233-247, Annual Reviews Inc, United States (2011).

Panke C., et al., "Quantification of Cell Surface Proteins with Bispecific Antibodies", Protein Engineering Design and Selection 26(10):645-654, Oxford University Press, United Kingdom (Aug. 2013).

Pedersen M.W., et al., "Targeting Three Distinct HER2 Domains with a Recombinant Antibody Mixture Overcomes Trastuzumab Resistance," Molecular Cancer Therapeutics 14(3):669-680, American Association for Cancer Research, United States (Jan. 2015).

Petterson, R.D., et al., "CD47 Signals T Cell Death," Journal of Immunolgy 15; 162 (12): 7031-7040, American Association of Immunologists, United States (Jun. 1999).

Pole, J.C.M., et al., High-resolution analysis of chromosome rearrangements on 8p in breast, colon and pancreatic cancer reveals a complex pattern of loss, gain and translocation, Oncogene, 25: 5693-5706, Nature Publishing Group, United Kingdom (2006).

Press, O.W., et al., "Ricin A—chain containing immunotoxins directed against different epitopes on the CD2 molecule differ in their ability to kill normal and malignant T cells," Journal of Immunology 141(12):4410-4417, The American Association of Immunologists Inc., United States (1988).

Regina, A., et al., "ANG4043, a Novel Brain-Penetrant peptide-mAb Conjugate, Is Efficacious Against HER2-positive Intracranial Tumors in Mice," Molecular Cancer Therapeutics 14(1):129-140, American Association for Cancer Research, Inc., United States (Jan. 2015).

Richards, D.A., et al., "A Phase 1 Study of Mm-111, a Bispecific HER2/HER3 Antibody Fusion Protein, Combined with Multiple Treatment Regimens in Patients with Advanced HER2-Positive Solid Tumors," Journal of Clinical Oncology 32(15):651, American Society of Clinical Oncology, United States (2014).

Riemer, A.B., et al., "Matching of Trastuzumab (Herceptin) Epitope Mimics Onto the Surface of Her-2/neu—a New Method of Epitope Definition," Molecular Immunology 42(9):1121-1124, Pergamon Press, United Kingdom (2005).

Rohrer, T., et al., "Consideration for the Safe and Effective Manufacturing of Antibody-drug conjugates," ADCReview.com, published on Jun. 21, 2013, retrieved from the Internet https://www.adcreview.com/articles/consideration-safe-effective-manufacturing-antibody-drug-conjugates/, 2020, 10 pages.

Roskoski, R., "The ErbB/HER Family of Protein-Tyrosine Kinases and Cancer," Pharmacological Research 79:34-74, Elsevier, Netherlands (Jan. 2014).

Rudikoff, S., et al., "Single Amino Acid Substitution Altering Antigen-binding Specificity," Proceedings of the National Academy of Sciences of the United States of America 79(6):1979-1983, National Academy of Sciences, United States (Mar. 1982).

Sanchez-Valdivieso, E.A., et al., "γ-Heregulin has no biological significance in primary breast cancer," British Journal of Cancer, 86(8): 1362-1366, Cancer Research UK, United Kingdom (2002).

Sandercock, A.M., et al., "Identification of anti-tumour biologics using primary tumour models, 3-D phenotypic screening and image-based multi-parametric profiling," Mol Cancer 14:147, BioMed Central Ltd., United Kingdom (2015).

Schlom, J., et al., "Therapeutic Advantage of High-affinity Anticarcinoma Radioimmunoconjugates," Cancer Research 52(5):1067-1072, American Association for Cancer Research, United States (Mar. 1992).

Schmidt, M., et al., "High-resolution insertion-site analysis by linear amplification—mediated PCR (LAM-PCR)," Nature Methods 4:1051-1057, Nature Publishing Group, United Kingdom (2007).

Sorkin, A., "Internalization of the Epidermal Growth Factor Receptor: Role In Signalling," Biochemical Society Transactions 29(Pt

(56) References Cited

OTHER PUBLICATIONS

4):480-484, Portland Press On The Behalf Of The Biochemical Society, United Kingdom (Aug. 2001).
Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (1991).
Troise, F., et al., "A novel ErbB2 epitope targeted by human antitumor immunoagents," FEBS Journal, 278: 1156-1166, John Wiley & Sons, United States (2011).
Geuijen, C.A.W., et al., "Unbiased Combinatorial Screening identifies a Bispecific IgG1 that potently inhibits HER3 signaling via HER2-Guided Ligand Bonding," Cancer Cell 33:922-936, Elsevier, Netherlands (2018), with Supplemental Information (26 pages).
Vajdos, F.F., et al., "Comprehensive Functional Maps of The Antigen-binding Site of an Anti-Erbb2 Antibody Obtained with Shotgun Scanning Mutagenesis," Journal of Molecular Biology 320(2):415-428, Academic Press, United Kingdom (Jul. 2002).
Volpi, C.C., et al., "The Landscape of D16her2 Splice Variant Expression Across Her2-positive Cancers," Sci. Rep. 9(1):3545, pp. 1-12, Nature Publishing Group, United Kingdom (2019).
Weinert, B.T., "Acetylation dynamics and stoichiometry in *Saccharomyces cerevisiae*," Molecular Systems Biology 10(1):716, Wiley-Blackwell, United States, 12 pages (2014).
Weinstein, E.J., et al., The oncogene heregulin induces apoptosos in breast wpithelial cells and tumors, Oncogene, 17: 2107-2113, Stockton Press, United Kingdom (1998).
Wick, M.J., et al., "Establishment and Characterization of a HER2-positive, TDM1-Resistant PDX Breast Model," Abstract C74 at AACR-NCI-EORTC International Conference: Molecular Targets and Cancer Therapeutics, Nov. 5-9, 2015, Molecular Cancer Therapeutics 14(12):Supplement 2, 4 pages (2015).
Wilson, T.R., et al., "Neuregulin-1-Mediated Autocrine Signaling Underlies Sensitivity to HER2 Kinase Inhibitors in a Subset of Human Cancer," Cancer Cells, 20(2): 158-172, Elsevier, Inc., Netherlands (2011).
Winkler, K., et al., "Changing the Antigen Binding Specificity by Single Point Mutations of an Anti-p24 (HIV-1) Antibody," The Journal of Immunology 165(8):4505-4514, The American Association of Immunologists, United States (2000).
Wolff A.C., et al., "Recommendations for Human Epidermal Growth Factor Receptor 2 Testing in Breast Cancer: American Society of Clinical Oncology/College of American Pathologists Clinical Practice Guideline Update," Journal of Clinical Oncology 31(31):3997-4013, Grune & Stratton, United States (Nov. 2013).
Woning, S.V.D., et al., "Quantification of ErbB3 Receptor Density on Human Breast Cancer Cells, Using a Stable Radio-Labeled Mutant of Nrg1beta," Biochemical and Biophysical Research Communications, 378(2):285-289, Elsevier, United States (Jan. 2009).
Wu, H., et al., "Humanization of a Murine Monoclonal Antibody by Simultaneous Optimization of Framework and CDR Residues," Journal of Molecular Biology 294(1):151-162, Elsevier, United Kingdom (Nov. 1999).
Xu, F., et al., "Antibody-Induced Growth Inhibition is Mediated Through Immunochemically and Functionally Distinct Epitopes on the Extracellular Domain of the c-erb-2 (HER-2/neu) Gene Product p185," International Journal of Cancer 53(3):401-408, Wiley-Liss, United States (1993).
Yu, H., et al., "Plasma Levels of Insulin-like Growth Factor-I and Lung Cancer Risk: A Case-control Analysis," Journal of the National Cancer Institute 91(2):151-156, Oxford University Press, United Kingdom (Jan. 1999).
Zhang B., et al., "Abstract 655: Combination of Mm-111, an Erbb2/erbb3 Bispecific Antibody, With Endocrine Therapies as an Effective Strategy for Treatment of Er+/her2+ Breast Cancer," Cancer Research 71(8):655-655, American Association for Cancer Research Inc., United States (Jul. 2011).
Zolot, R.S., et al., "Antibody-Drug Conjugates," Nature Reviews Drug Discovery 12(4):259-260, Nature Publishing Group, United Kingdom (Apr. 2013).

Office Action dated Jan. 22, 2020, in U.S. Appl. No. 15/121,619, Logtenberg, T.., et al., 371(c), filed Aug. 25, 2016, 27 pages.
Office Action dated Apr. 24, 2019, in U.S. Appl. No. 15/121,619, Logtenberg, T.., et al., 371(c), filed Aug. 25, 2016, 28 pages.
Office Action dated Jul. 19, 2018, in U.S. Appl. No. 15/121,619, Logtenberg, T.., et al., 371(c), filed Aug. 25, 2016, 27 pages.
Ahmed M. et al. Lack of in Vivo Antibody Dependent Cellular Cytotoxicity with Antibody containing gold particles/ Bioconjugate chemistry (2015): 26 812-816.
Bardelli, A et al., "Amplification of the MET receptor drives resistance to anti-EGFR therapies in colorectal cancer," Cancer Discovery 3(6):658-673, American Association for Cancer Research, United States (Jun. 2013) doi: 10.1158/2159-8290.CD-12-0558).
Birchmeier C., et al., "Met, Metastasis, Motility and More," Nature Reviews Molecular Cell Biology 4(12):915-925, Nature Publishing Group, England (Dec. 2003).
Castoldi, R., et al., "A Novel Bispecific EGFR/Met Antibody Blocks Tumor-promoting Phenotypic Effects Induced by Resistance to EGFR Inhibition and Has Potent Antitumor Activity," Oncogene, 32(50):5593-5601, Nature Publishing Group, England (Jul. 1, 2013).
Chen, C.T et al., "MET activation mediates resistance to lapatinib inhibition of HER2-amplified gastric cancer cells," Molecular Cancer Therapeutics 11(3):650-669, American Association for Cancer Research, Inc, United States (Mar. 2012).
Davidson E and Doranz BJ, "A high-throughput shotgun mutagenesis approach to mapping B-cell antibody epitopes." Immunology. Sep. 2014;143{1):13-20 {2014).
Desmyter, A., et al., "Antigen Specificity and High Affinity Binding Provided by One Single Loop of a Camel Single-domain Antibody," The Journal of Biological Chemistry 276(28):26285-26290, American Society for Biochemistry and Molecular Biology, United States (Jul. 2001).
Elliot, B.E et al. "The Role of Hepatocyte Growth Factor (Scatter Factor) InEpithelial-Mesenchymal Transition and Breast Cancer," Canadian Journal of Physiology and Pharmacology 80(2), 91-102, Canadian Science Publishing, Canada (Feb. 2002).
Fong, J.T., et al., "Alternative signaling pathways as potential therapeutic targets for overcoming EGFR and c-Met inhibitor resistance in non-small cell lung cancer," PLoS One 4;8(11):e78398, Public Library of Science, United States (Nov. 2013).
Hu, T., and Li, C., "Convergence between Wnt-—- catenin and EGFR signaling in cancer," Cancer 2010; 9(236):2-7.
International Preliminary Report on Patentability International Application No. PCT/NL2016/050726, European Patent Office, Netherlands dated Apr. 24, 2018.
International search report and written opinion for International Application No. PCT/NL2016/050726, European Patent Office, Netherlands dated Feb. 6, 2017.
Ji H. et al. Epidermal growth factor receptor variant III mutations in lung tumorigenesis and sensitivity to tyrosine kinase inhibitors. PNAS 2006 103(20):7817-7822.
Jin, H., et al., "Metmab, the One-Armed 5d5 Anti-C-Met Antibody, InhibitsOrthotopic Pancreatic Tumor Growth and Improves Survival," Cancer Research 68(11):4360-4368, American Association for Cancer Research, United States (Jun. 2008).
Kim, G.P., et al. "Targeting Colorectal Cancer with Human Anti-Egfr MonoclonocalAntibodies: Focus on Panitumumab," Biologics 2(2):223-228, Dove Medical Press, New Zealand (Jun. 2008).
Kim, K.A., et al., "Mitogenic Influence of Human R-Spondin1 on the Intestinal Epithelium," Science 309(5738):1256-1259, American Association for the Advancement of Science, United States (2005).
Kim, K.H., et al., "Progress of Antibody-Based Inhibitors of the Hgf-Cmet Axis in Cancer Therapy," Experimental & Molecular medicine 49(3):e307, Nature Publishing Group, United States (Mar. 2017).
Koide, A., et al., "The Fibronectin Type III Domain as a Scaffold for Novel Binding Proteins," Journal of Molecular Biology 284(4):1141-1151, Academic Press, United States (Dec. 1998).
Labrijn, A.F., et al., "Efficient Generation of Stable Bispecific IgG1 by Controlled Fab-arm Exchange," Proceedings of the National Academy of Sciences of the United States of America, 110(13):5145-5150, United States (Mar. 26, 2013).

(56) References Cited

OTHER PUBLICATIONS

Lee, D., et al., "Development of antibody-based c-Met inhibitors for targeted cancer therapy," Immuntargets and Therapy 9(4):34-44, Dove Medical Press, New Zealand (2015).

Li et al., "Structural basis for inhibition of the epidermal growth factor receptor by cetuximab.," Cancer Cell. Apr. 2005;7(4):301-11. pdb reference 1 YY9.

Lindmo et al., Determination of the immunoreactive fraction of radiolabeled monoclonal antibodies by linear extrapolation to binding at infinite antigen excess. J Immunol Methods. Aug. 3, 1984;72(1):77-89.

Ma, P.C., et al., "C-Met: Structure, Functions and Potential for Therapeutic Inhibition," Cancer and Metastasis Reviews 22:309-325, Kluwer Academic, Netherlands (Dec. 2003).

Marks, J.D., et al., "By-Passing Immunization: Building High Affinity Human Antibodies by Chain Shuffling," Biotechnology 10(7):779-783, Nature Publishing Company, United States (Jul. 1992).

Maulik, G., et al., Role of the hepatocyte growth factor receptor, c-Met, in oncogenesis and potential for therapeutic inhibition, Cytokine & Growth Factor Reviews 13(1):41-59, Elsevier Science, England (Feb. 2002).

Moores, S.L., et al., "A Novel Bispecific Antibody Targeting EGFR and cMet Is Effective against EGFR Inhibitor-Resistant Lung Tumors," Cancer Research, 76(13):3942-3953, United States (May 23, 2016).

Morgillo, F et al. Mechanisms of resistance to EGFRtargeted drugs: lung cancer. ESMO Open 2016 1:e000060. doi:10.1136/esmoopen-2016-000060.

Morita, H., et al., "Neonatal Lethality of LGR5 Null Mice Is Associated with Ankyloglossia and Gastrointestinal Distension," Molecular Cell Biology 24(22):9736-9743, American Society for Microbiology, United States (2004).

Mosmi, S., et al., "Role of MetMAb (OA-5D5) in c-MET Active Lung Malignancies," Expert Opinion on Biological Therapy, 11(12):1655-1662, Taylor & Francis, England (Dec. 1, 2011).

Musolino, A., et al., "Immunoglobulin G Fragment C Receptor Polymorphisms and Clinical Efficacy of Trastuzumab-based Therapy in Patients With Her-2/neu-positive Metastatic Breast Cancer," Journal of Clinical Oncology 26(11):1789-1796, American Society of Clinical Oncology, United States (2008).

Nakade, J. et al. "Triple Inhibition of Egfr, Met, and Vegf Suppresses Regrowth of Hgf-Triggered, Erlotinib-Resistant Lung Cancer Harboring an EGFR Mutation," Journal of Thoracic Oncology 9(6):775-783, Elsevier, United States (Jun. 2014).

Noh Jin Park., et al., "Measurement of Cetuximab and Panitumumab-Unbound Serum EGFR Extracellular Domain Using an Assay Based on Slow Off-Rate Modified Aptamer (SOMAmer) Reagents," PloS One, 8(8):e71703, Public Library of Science, United States (Aug. 21, 2013).

Online Mendelian Inheritance in Man (OMIM), "Epidermal growth factor receptor; EGFR," OMIM Entry: 131550, accessed at https://omim.org/, accessed on Sep. 29, 2020, 19 pages.

Online Mendelian Inheritance in Man (OMIM), "Oncogene MET hepatocyte growth factor receptor; HGFR," OMIM Entry: 164860, accessed at https://omim.org/, accessed on Sep. 29, 2020, 9 pages.

Organ S.L., et al., "An Overview of the C-Met Signaling Pathway," Therapeutic Advances in Medical Oncology 3(1 Suppl):S7-S19, Sage, England (2011).

Pan, D.S., et al., "Binding Characteristic of Fully Human Anti-EGFR Monoclonal Antibody to EGFR in Skin Tissues of Different Species of Animals," Chinese Journal of New Drugs Co. Ltd, 21(1):26-30, China (Jan. 2012).

Paul, I., et al., "Current Understanding on EGFR and Wnt/Beta-Catenin Signaling in Glioma and Their Possible Crosstalk," Genes & Cancer 2013; 4(11-12):427-446.

Peng et al., "Structures of Wnt-Antagonist ZNRF3 and Its Complex with R-Spondin 1 and Implications for Signaling," PLoS One. Dec. 12, 2013;8(12):e83110.

Peng, W.C., et al., "Structure of Stem Cell Growth Factor R-spondin 1 in Complex with the Ectodomain of its Receptor LGR5," Cell Reports 3(6):1885-1892, Cell Press, United States (2013) (D16 as cited in Opposition of EP 2173379).

Prigent SA et al. Identification of cErbB-3 binding sites for phosphatidylinositol 30-kinase and SHC using an EGF receptor/c-ErbB-3 chimera. EMBO J 1994;13:2831-41.

Rohrer, T., et al. Consideration for the Safe and Effective Manufacturing of Antibody-drug conjugates ADC, Journal of Antibody-drug Conjugates, 30(5):4,Published online2012, doi: 10.14229/jadc.2013.6.1.003.

Seidel, C. et al., "Role of hepatocyte growth factor and its receptorc-met in multiple myeloma," Medical Oncology 15:145-153, Springer Nature Switzerland AG (Sep. 1998).

Siegfried, J.M et al., "The clinical significance of hepatocyte growth factor for non-small cell lung cancer," The Annals of Thoracic Surgery 66(6):1915-1918, Elsevier, Netherlands (Dec. 1998).

International Search Report and Written Opinion for Application No. PCT/NL2018/050537, dated Jan. 30, 2019, European Patent Office, Rijswijk, Netherlands, 19 pages.

Surati, M., et al., "Role of MetMab (OA-5D5) in c-MET active lung malignancies," Expert Opinion on Biological Therapy 11(12):1655-1662, Taylor Francis, England (Dec. 2011).

Vecchione, L. et al., "EGFR-targeted therapy," Experimental cell research 317(19): 2765-2771, Academic Press, United States (Nov. 2011).

Xu, J.L. and Davis, M.M., "Diversity in the CDR3 Region of V(H) is Sufficient for Most Antibody Specificities," Immunity 13(1):37-45, Cell Press, United States (Jul. 2000).

Yano, S. et al. "Hepatocyte Growth Factor Induces Gefitinib Resistance of Lung Adenocarcinoma With Epidermal Growth Factor Receptor-activating Mutations," Cancer Research 68(22):9479-9487, American Association for Cancer Research, United States (Nov. 2008).

Zhang, Y.W et al., "MET kinase inhibitor SGX523 synergizes with epidermal growth factor receptor inhibitor erlotinib in a hepatocyte growth factor-dependent fashion to suppress carcinoma growth," Cancer Research, 70(17):6880-6890, American Association for Cancer Research, United States (Sep. 2010).

Krausova,M and Korinek, V., "Wnt Signaling In Adult Intestinal Stem Cells and Cancer," Cell signalling 26(3):570-579, Elsevier Science Ltd, England (Mar. 2014).

Yano, S., "Molecular Mechanism of EGFR-TKI Resistance," Japanese Journal of Lung Cancer 49(6):939-943, The Japan Lung Cancer Society (Oct. 2009).

FIG. 1
(SEQ ID NOS: 1 and 2)

```
GCTAGCacc atggggcccagcggcaccgccggcgccgccctgctggccctgctggcc
        A  S  T  M  G  P  S  G  T  A  G  A  A  L  L  A  L  L  A
Gccctgtgccccgccagccgggcc  ctggaggagaagaaggtgtgccagggcaccagcaac
 A  L  C  P  A  S  R  A    L  E  E  K  K  V  C  Q  G  T  S  N
aagctgacccagctgggcaccttcgaggaccacttcctgagcctgcagcggatgttcaac
 K  L  T  Q  L  G  T  F  E  D  H  F  L  S  L  Q  R  M  F  N
aactgcgaggtggtgctgggcaacctggagatcacctacgtgcagcggaactacgacctg
 N  C  E  V  V  L  G  N  L  E  I  T  Y  V  Q  R  N  Y  D  L
agcttcctgaagaccatccaggaggtggccggctacgtgctgatcgccctgaacaccgtg
 S  F  L  K  T  I  Q  E  V  A  G  Y  V  L  I  A  L  N  T  V
gagcggatccccctggagaacctgcagatcatccggggcaacatgtactacgagaacagc
 E  R  I  P  L  E  N  L  Q  I  I  R  G  N  M  Y  Y  E  N  S
tacgccctggccgtgctgagcaactacgacgccaacaagaccggcctgaaggagctgccc
 Y  A  L  A  V  L  S  N  Y  D  A  N  K  T  G  L  K  E  L  P
atgcggaacctgcaggagatcctgcacggcgccgtgcggttcagcaacaaccccgccctg
 M  R  N  L  Q  E  I  L  H  G  A  V  R  F  S  N  N  P  A  L
tgcaacgtggagagcatccagtggcgggacatcgtgagcagcgagttcctgagcaacatg
 C  N  V  E  S  I  Q  W  R  D  I  V  S  S  E  F  L  S  N  M
agcatggacttccagaaccacctgggcagctgccagaagtgcgaccccagctgccccaac
 S  M  D  F  Q  N  H  L  G  S  C  Q  K  C  D  P  S  C  P  N
ggcagctgctggggcgccggcgaggagaactgccagaagctgaccaagatcatctgcgcc
 G  S  C  W  G  A  G  E  E  N  C  Q  K  L  T  K  I  I  C  A
cagcagtgcagcggccggtgccggggcaagagccccagcgactgctgccacaaccagtgc
 Q  Q  C  S  G  R  C  R  G  K  S  P  S  D  C  C  H  N  Q  C
gccgccggctgcaccggcccccgggagagcgactgcctggtgtgccggaagttccgggac
 A  A  G  C  T  G  P  R  E  S  D  C  L  V  C  R  K  F  R  D
gaggccacctgcaaggacacctgcccccccctgatgctgtacaaccccaccacctaccag
 E  A  T  C  K  D  T  C  P  P  L  M  L  Y  N  P  T  T  Y  Q
atggacgtgaaccccgagggcaagtacagcttcggcgccacctgcgtgaagaagtgcccc
 M  D  V  N  P  E  G  K  Y  S  F  G  A  T  C  V  K  K  C  P
cggaactacgtggtgaccgaccacggcagctgcgtgcgggcctgcggcgccgacagctac
 R  N  Y  V  V  T  D  H  G  S  C  V  R  A  C  G  A  D  S  Y
gagatggaggaggacggcgtgcggaagtgcaagaagtgcgagggcccctgccggaaggtg
 E  M  E  E  D  G  V  R  K  C  K  K  C  E  G  P  C  R  K  V
tgcaacggcatcggcatcggcgagttcaaggacaccctgagcatcaacgccaccaacatc
 C  N  G  I  G  I  G  E  F  K  D  T  L  S  I  N  A  T  N  I
aagcacttcaagaactgcaccagcatcagcggcgacctgcacatcctgcccgtggccttc
 K  H  F  K  N  C  T  S  I  S  G  D  L  H  I  L  P  V  A  F
cggggcgacagcttcacccacaccccccccctggaccccaggagctggacatcctgaag
 R  G  D  S  F  T  H  T  P  P  L  D  P  Q  E  L  D  I  L  K
accgtgaaggagatcaccggcttcctgctgatccaggcctggcccgagaaccggaccgac
 T  V  K  E  I  T  G  F  L  L  I  Q  A  W  P  E  N  R  T  D
ctgcacgccttcgagaacctggagatcatccggggccggaccaagcagcacggccagttc
 L  H  A  F  E  N  L  E  I  I  R  G  R  T  K  Q  H  G  Q  F
agcctggccgtggtgagcctgaacatcaccagcctgggcctgcggagcctgaaggagatc
 S  L  A  V  V  S  L  N  I  T  S  L  G  L  R  S  L  K  E  I
```

FIG. 1, Cont'd

```
agcgacggcgacgtgatcatcagcggcaacaagaacctgtgctacgccaacaccatcaac
 S   D   G   D   V   I   I   S   G   N   K   N   L   C   Y   A   N   T   I   N
tggaagaagctgttcggcaccagcagccagaagaccaagatcatcagcaaccggggcgag
 W   K   K   L   F   G   T   S   S   Q   K   T   K   I   I   S   N   R   G   E
aacagctgcaaggccaccggccaggtgtgccacgccctgtgcagccccgagggctgctgg
 N   S   C   K   A   T   G   Q   V   C   H   A   L   C   S   P   E   G   C   W
ggccccgagcccgggactgcgtgagctgccagaacgtgagccggggccgggagtgcgtg
 G   P   E   P   R   D   C   V   S   C   Q   N   V   S   R   G   R   E   C   V
gacaagtgcaacatcctggagggcgagcccgggagttcgtggagaacagcgagtgcatc
 D   K   C   N   I   L   E   G   E   P   R   E   F   V   E   N   S   E   C   I
cagtgccaccccgagtgcctgccccaggtgatgaacatcacctgcaccggccggggcccc
 Q   C   H   P   E   C   L   P   Q   V   M   N   I   T   C   T   G   R   G   P
gacaactgcatccagtgcgcccactacatcgacggccccactgcgtgaagacctgcccc
 D   N   C   I   Q   C   A   H   Y   I   D   G   P   H   C   V   K   T   C   P
gccggcgtgatgggcgagaacaacaccctggtgtggaagtacgccgacgccggccacgtg
 A   G   V   M   G   E   N   N   T   L   V   W   K   Y   A   D   A   G   H   V
tgccacctgtgccaccccaactgcacctacggctgcaccggccccggcctggagggctgc
 C   H   L   C   H   P   N   C   T   Y   G   C   T   G   P   G   L   E   G   C
gcccggaacggccccaagatccccagcatcgccaccggcatgctgggcgccctgctgctg
 A   R   N   G   P   K   I   P   S   I   A   T   *G   M   L   G   A   L   L   L*
ctgctggtggtggccctgggcatcggcctgttcatgcggcggcggcacatcgtgcggaag
 *L   L   V   V   A   L   G   I   G   L   F   M*   R   R   R   H   I   V   R   K
cggaccctgcggcggctgctgcaggagcgggagctggtggagcccctgaccccccagcggc
 R   T   L   R   R   L   L   Q   E   R   E   L   V   E   P   L   T   P   S   G
gaggcccccaaccaggccctgctgcggatcctgaaggagaccgagttcaagaagatcaag
 E   A   P   N   Q   A   L   L   R   I   L   K   E   T   E   F   K   K   I   K
gtgctgggcagcggcgccttcggcaccgtgtacaagggcctgtggatccccgagggcgag
 V   L   G   S   G   A   F   G   T   V   Y   K   G   L   W   I   P   E   G   E
aaggtgaagatccccgtggccatcaaggagctgcgggaggccaccagccccaaggccaac
 K   V   K   I   P   V   A   I   K   E   L   R   E   A   T   S   P   K   A   N
aaggagatcctggacgaggcctacgtgatggccagcgtggacaaccccccacgtgtgccgg
 K   E   I   L   D   E   A   Y   V   M   A   S   V   D   N   P   H   V   C   R
ctgctgggcatctgcctgaccagcaccgtgcagctgatcacccagctgatgcccttcggc
 L   L   G   I   C   L   T   S   T   V   Q   L   I   T   Q   L   M   P   F   G
tgcctgctggactacgtgcgggagcacaaggacaacatcggcagccagtacctgctgaac
 C   L   L   D   Y   V   R   E   H   K   D   N   I   G   S   Q   Y   L   L   N
tggtgcgtgcagatcgccaagggcatgaactacctggaggaccggcggctggtgcaccgg
 W   C   V   Q   I   A   K   G   M   N   Y   L   E   D   R   R   L   V   H   R
gacctggccgcccggaacgtgctggtgaagacccccagcacgtgaagatcaccgacttc
 D   L   A   A   R   N   V   L   V   K   T   P   Q   H   V   K   I   T   D   F
ggcctggccaagctgctgggcgccgaggagaaggagtaccacgccgagggcggcaaggtg
 G   L   A   K   L   L   G   A   E   E   K   E   Y   H   A   E   G   G   K   V
cccatcaagtggatggccctggagagcatcctgcaccggatctacacccaccagagcgac
 P   I   K   W   M   A   L   E   S   I   L   H   R   I   Y   T   H   Q   S   D
gtgtggagctacggcgtgaccgtgtgggagctgatgaccttcggcagcaagccctacgac
 V   W   S   Y   G   V   T   V   W   E   L   M   T   F   G   S   K   P   Y   D
```

FIG. 1, Cont'd

```
ggcatccccgccagcgagatcagcagcatcctggagaagggcgagcggctgccccagccc
 G  I  P  A  S  E  I  S  S  I  L  E  K  G  E  R  L  P  Q  P
cccatctgcaccatcgacgtgtacatgatcatggtgaagtgctggatgatcgacgccgac
 P  I  C  T  I  D  V  Y  M  I  M  V  K  C  W  M  I  D  A  D
agccggcccaagttccggggagctgatcatcgagttcagcaagatggcccgggaccccag
 S  R  P  K  F  R  E  L  I  I  E  F  S  K  M  A  R  D  P  Q
cggtacctggtgatccagggcgacgagcggatgcacctgcccagccccaccgacagcaac
 R  Y  L  V  I  Q  G  D  E  R  M  H  L  P  S  P  T  D  S  N
ttctaccgggccctgatggacgaggaggacatggacgacgtggtggacgccgacgagtac
 F  Y  R  A  L  M  D  E  E  D  M  D  D  V  V  D  A  D  E  Y
ctgatccccagcagggcttcttcagcagccccagcaccagccggaccccctgctgagc
 L  I  P  Q  Q  G  F  F  S  S  P  S  T  S  R  T  P  L  L  S
agcctgagcgccaccagcaacaacagcaccgtggcctgcatcgaccggaacggcctgcag
 S  L  S  A  T  S  N  N  S  T  V  A  C  I  D  R  N  G  L  Q
agctgccccatcaaggaggacagcttcctgcagcggtacagcagcgaccccaccggcgcc
 S  C  P  I  K  E  D  S  F  L  Q  R  Y  S  S  D  P  T  G  A
ctgaccgaggacagcatcgacgacaccttcctgcccgtgcccgagtacatcaaccagagc
 L  T  E  D  S  I  D  D  T  F  L  P  V  P  E  Y  I  N  Q  S
gtgcccaagcggcccgccggcagcgtgcagaacccgtgtaccacaaccagcccctgaac
 V  P  K  R  P  A  G  S  V  Q  N  P  V  Y  H  N  Q  P  L  N
cccgcccccagccgggaccccactaccaggaccccacagcaccgccgtgggcaacccc
 P  A  P  S  R  D  P  H  Y  Q  D  P  H  S  T  A  V  G  N  P
gagtacctgaacaccgtgcagcccacctgcgtgaacagcaccttcgacagccccgccac
 E  Y  L  N  T  V  Q  P  T  C  V  N  S  T  F  D  S  P  A  H
tgggcccagaagggcagccaccagatcagcctggacaaccccgactaccagcaggacttc
 W  A  Q  K  G  S  H  Q  I  S  L  D  N  P  D  Y  Q  Q  D  F
ttccccaaggaggccaagcccaacggcatcttcaagggcagcaccgccgagaacgccgag
 F  P  K  E  A  K  P  N  G  I  F  K  G  S  T  A  E  N  A  E
tacctgcgggtggccccccagagcagcgagttcatcggcgcctgaGCGGCCGC
 Y  L  R  V  A  P  Q  S  S  E  F  I  G  A  -  A  A  A
```

FIG. 2

*EGFR HER3 swap varII ECD* (SEQ ID NO: 3)

LEEKKVCQGTSNKLTQLGTFEDHFLSLQRMFNNCEVVLGNLEITYVQRNYDLSFLKTIQEVAGYVLIALNTVERIPLEN
LQIIRGNMYYENSYALAVLSNYDANKTGLKELPMRNLQEILHGAVRFSNNPALCNVESIQWRDIVSSDFLSNMSMD
FQNHLCPPCHEVCKGRCWGPGSEDCQTLTKTICAPQCNGHCFGPNPNQCCHDECAGGCSGPQDTDCFACRHFN
DSGACVPRCPQPLVYNKLTFQLEPNPHTKYQYGGVCVASCPHNFVVDQTSCVRACPPDKMEVDKNGLKMCEPCG
GLCPKACEGIGIGEFKDSLSINATNIKHFKNCTSISGDLHILPVAFRGDSFTHTPPLDPQELDILKTVKEITGFLLIQAWP
ENRTDLHAFENLEIIRGRTKQHGQFSLAVVSLNITSLGLRSLKEISDGDVIISGNKNLCYANTINWKKLFGTSGQKTKIIS
NRGENSCKATGQVCHALCSPEGCWGPEPRDCVSCRNVSRGRECVDKCNLLEGEPREFVENSECIQCHPECLPQAM
NITCTGRGPDNCIQCAHYIDGPHCVKTCPAGVMGENNTLVWKYADAGHVCHLCHPNCTYGCTGPGLEGCPTNGP
KIPS

*EGFR HER3 swap varIII ECD* (SEQ ID NO: 4)

LEEKKVCQGTSNKLTQLGTFEDHFLSLQRMFNNCEVVLGNLEITYVQRNYDLSFLKTIQEVAGYVLIALNTVERIPLEN
LQIIRGNMYYENSYALAVLSNYDANKTGLKELPMRNLQEILHGAVRFSNNPALCNVESIQWRDIVSSDFLSNMSMD
FQNHLGSCQKCDPSCPNGSCWGAGEENCQKLTKIICAQQCSGRCRGKSPSDCCHNQCAAGCTGPRESDCLVCRKF
RDEATCKDTCPPLMLYNPTTYQMDVNPEGKYSFGATCVKKCPRNYVVTDHGSCVRACGADSYEMEEDGVRKCKK
CEGPCRKVCNGIGIGEFKDSLSINATNIKHFKNCTKILGNLDFLITGLNGDPWHKIPALDPEKLNVFRTVREITGYLNLQ
SWPPHMHNFSVFSNLTTIGGRSLYNRGFSLLIMKNLNVTSLGFRSLKEISAGRIYISANRQLCYHHSLNWTKVLGTSG
QKTKIISNRGENSCKATGQVCHALCSPEGCWGPEPRDCVSCRNVSRGRECVDKCNLLEGEPREFVENSECIQCHPE
CLPQAMNITCTGRGPDNCIQCAHYIDGPHCVKTCPAGVMGENNTLVWKYADAGHVCHLCHPNCTYGCTGPGLE
GCPTNGPKIPS

*EGFR HER3 swap varIV ECD* (SEQ ID NO: 5)

LEEKKVCQGTSNKLTQLGTFEDHFLSLQRMFNNCEVVLGNLEITYVQRNYDLSFLKTIQEVAGYVLIALNTVERIPLEN
LQIIRGNMYYENSYALAVLSNYDANKTGLKELPMRNLQEILHGAVRFSNNPALCNVESIQWRDIVSSDFLSNMSMD
FQNHLGSCQKCDPSCPNGSCWGAGEENCQKLTKIICAQQCSGRCRGKSPSDCCHNQCAAGCTGPRESDCLVCRKF
RDEATCKDTCPPLMLYNPTTYQMDVNPEGKYSFGATCVKKCPRNYVVTDHGSCVRACGADSYEMEEDGVRKCKK
CEGPCRKVCNGIGIGEFKDSLSINATNIKHFKNCTSISGDLHILPVAFRGDSFTHTPPLDPQELDILKTVKEITGFLLIQA
WPENRTDLHAFENLEIIRGRTKQHGQFSLAVVSLNITSLGLRSLKEISDGDVIISGNKNLCYANTINWKKLFGTSGQKT
KIISNRGENSCKATGQVCHALCSPEGCWGPEPRDCVSCRNVSRGRECVDKCNLLEGEPREFVECFSCHPECQPME
GTATCNGSGSDTCAQCAHFRDGPHCVSSCPHGVMGENNTLVWKYADAGHVCHLCHPNCTYGCTGPGLEGCPTN
GPKIPS

FIG. 3

|  |  | | Competition of phages with | | | |
|---|---|---|---|---|---|---|
|  |  |  | Domain I | Domain II | Domain III | Domain III |
| Cluster nr. | MF tested | no IgG | ICR10 | EGFR.1 | Cetuximab | MatuzuMab |
| 1 | 3998 | 2.494 | 2.227 | 2.343 | 0.101 | 0.671 |
| 2 | 4289 | 2.278 | 2.046 | 2.226 | 2.222 | 2.356 |
| 3 | 4000 | 2.597 | 1.736 | 2.604 | 2.533 | 0.345 |
| 4 | 4016 | 2.184 | 0.088 | 2.129 | 2.135 | 2.133 |
| 5 | 4029 | 1.898 | 2.193 | 1.256 | 1.235 | 1.938 |
| 6 | 4034 | 1.747 | 1.42 | 0.108 | 1.62 | 1.776 |
| 7 | 4035 | 1.594 | 0.951 | 1.554 | 1.079 | 1.309 |
| 8 | 4032 | 2.276 | 2.145 | 2.057 | 1.996 | 0.099 |
| 9 | 4284 | 2.04 | 2.212 | 1.776 | 2.08 | 1.226 |
| 10 | 4358 | 1.631 | 1.704 | 1.833 | 1.991 | 0.066 |
| 11 | 4280 | 2.549 | 2.302 | 2.135 | 1.141 | 0.613 |
| 12 | 4283 | 2.827 | 2.336 | 2.889 | 0.265 | 0.122 |
| 13 | 4281 | 2.107 | 2.195 | 1.968 | 1.589 | 1.255 |
| 14 | 4286 | 1.589 | 1.723 | 1.66 | 0.272 | 0.247 |
| 15 | 4285 | 2.176 | 2.332 | 1.599 | 2.369 | 2.285 |
| 16 | 4287 | 2.052 | 1.825 | 1.711 | 1.187 | 1.705 |
| 17 | 4359 | ND | ND | ND | ND | ND |

FIG. 11A

MF4280: heavy chain variable region sequence of an EGFR binding antibody

Complete VH sequence (SEQ ID NO: 7)

QVQLVQSGAEVKKPGASVKVSCKVSGYTLTELSMHWVRQAPGKGLEWMGGFDPEY
GKTFFAQNFQGRVTMTEDTSADTAYMELSSLRSEDTAVYYCATEGYYETTTYYYNLF
DSWGQGTLVTVSS

FR1 (SEQ ID NO: 8): QVQLVQSGAEVKKPGASVKVSCKVSGYTLT

CDR1 (SEQ ID NO: 9) : ELSMH

FR2 (SEQ ID NO: 10): WVRQAPGKGLEWMG

CDR2 (SEQ ID NO: 11): GFDPEYGKTFFAQNFQG

FR3 (SEQ ID NO: 12): RVTMTEDTSADTAYMELSSLRSEDTAVYYCAT

CDR3 (SEQ ID NO: 13): EGYYETTTYYYNLFDS

FR4 (SEQ ID NO: 14): WGQGTLVTVSS

Annotated nucleotide sequence (SEQ ID NOS: 6 and 7)

```
CAGGTGCAGCTG
  Q   V   Q   L
GTGCAGTCTGGGGCTGAGGTGAAGAAGCCTGGGGCCTCAGTGAAGGTCTCCTGCAAGGTT
  V   Q   S   G   A   E   V   K   K   P   G   A   S   V   K   V   S   C   K   V
TCCGGATACACCCTCACTGAATTATCCATGCACTGGGTGCGACAGGCTCCTGGTAAAGGG
  S   G   Y   T   L   T   E   L   S   M   H   W   V   R   Q   A   P   G   K   G
CTTGAATGGATGGGAGGCTTTGATCCTGAGTATGGTAAAACATTCTTCGCACAGAACTTC
  L   E   W   M   G   G   F   D   P   E   Y   G   K   T   F   F   A   Q   N   F
CAGGGCAGAGTCACCATGACCGAGGACACATCTGCAGACACAGCCTACATGGAGCTAAGC
  Q   G   R   V   T   M   T   E   D   T   S   A   D   T   A   Y   M   E   L   S
AGCCTGAGATCTGAGGACACGGCCGTGTATTACTGTGCAACAGAGGGGTATTATGAGACT
  S   L   R   S   E   D   T   A   V   Y   Y   C   A   T   E   G   Y   Y   E   T
ACTACTTATTACTACAACCTTTTTGACTCCTGGGGCCAGGGAACCCTGGTCACCGTCTCA
  T   T   Y   Y   Y   N   L   F   D   S   W   Q   G   T   L   V   T   V   S
AGC
  S
```

FIG. 11A, Cont'd

MF3998: heavy chain variable region sequence of an EGFR binding antibody

Complete VH sequence (SEQ ID NO: 16):

QVQLVQSGSELKKPGASVKVSCKASGYTFTNNAINWVRQAPGQGLEWMGWINTITG
DPTYAQGFTGRFVFSLDTSVSTAYLQISSLKAEDTGVYYCAREEFLEWLFFDYWGQG
TLVTVSS

FR1 (SEQ ID NO: 17):

QVQLVQSGSELKKPGASVKVSCKASGYTFT

CDR1 (SEQ ID NO: 18): NNAIN

FR2 (SEQ ID NO: 19): WVRQAPGQGLEWMG

CDR2 (SEQ ID NO: 20): WINTITGDPTYAQGFTG

FR3 (SEQ ID NO: 21):

RFVFSLDTSVSTAYLQISSLKAEDTGVYYCAR

CDR3 (SEQ ID NO: 22): EEFLEWLFFDY

FR4 (SEQ ID NO: 23): WGQGTLVTVSS

Annotated nucleotide sequence (SEQ ID NOS: 15 and 16)

```
CAGGTGCAGCTGGTGCAGTCTGGGTCTGAGTTGAAGAAG
  Q  V  Q  L  V  Q  S  G  S  E  L  K  K
CCTGGGGCCTCAGTGAAGGTTTCCTGCAAGGCTTCTGGATACACCTTCACTAACAATGCC
  P  G  A  S  V  K  V  S  C  K  A  S  G  Y  T  F  T  N  N  A
ATAAATTGGGTGCGACAGGCCCCTGGACAAGGGCTTGAGTGGATGGGATGGATCAACACC
  I  N  W  V  R  Q  A  P  G  Q  G  L  E  W  M  G  W  I  N  T
ATCACTGGGGACCCAACGTATGCCCAGGGCTTCACAGGACGGTTTGTCTTCTCCTTGGAC
  I  T  G  D  P  T  Y  A  Q  G  F  T  G  R  F  V  F  S  L  D
ACCTCTGTCAGCACGGCATATCTGCAGATCAGCAGCCTGAAGGCTGAGGACACTGGCGTG
  T  S  V  S  T  A  Y  L  Q  I  S  S  L  K  A  E  D  T  G  V
TATTACTGTGCGAGAGAGGAATTTTTGGAGTGGTTATTCTTTGACTACTGGGGCCAGGGA
  Y  Y  C  A  R  E  E  F  L  E  W  L  F  F  D  Y  W  G  Q  G
ACCCTGGTCACCGTCTCAAGC
  T  L  V  T  V  S  S
```

FIG. 11A, Cont'd

MF4010: heavy chain variable region sequence of an EGFR binding antibody

Complete VH sequence (SEQ ID NO: 25):

QVQLVQSGSELKKPGASVKVSCKASGYTFTNNAMNWVRQAPGQGLEWMGWINTIT
GDPSYAQGFTGRFVFSLDTSVNTAYLQISSLKAEDTAVYYCAREEFLEWLFFDYWGQ
GTLVTVSS

FR1 (SEQ ID NO: 26): QVQLVQSGSELKKPGASVKVSCKASGYTFT

CDR1 (SEQ ID NO: 27): NNAMN

FR2 (SEQ ID NO: 28): WVRQAPGQGLEWMG

CDR2 (SEQ ID NO: 29): WINTITGDPSYAQGFTG

FR3 (SEQ ID NO: 30): RFVFSLDTSVNTAYLQISSLKAEDTAVYYCAR

CDR3 (SEQ ID NO: 31): EEFLEWLFFDY

FR4 (SEQ ID NO: 32): WGQGTLVTVSS

Annotated nucleotide sequence (SEQ ID NOS: 24 and 25):

```
caggtgcagctggtgcagtctgggtctgagttgaagaagcct
 Q  V  Q  L  V  Q  S  G  S  E  L  K  K  P
ggggcctcagtgaaggtttcctgcaaggcttctggatacaccttcactaacaatgccatg
 G  A  S  V  K  V  S  C  K  A  S  G  Y  T  F  T  N  N  A  M
aattgggtgcgacaggcccctggacaagggcttgagtggatgggatggatcaacaccatc
 N  W  V  R  Q  A  P  G  Q  G  L  E  W  M  G  W  I  N  T  I
actggggacccatcgtatgcccagggcttcacaggacggtttgtcttctccctggacacc
 T  G  D  P  S  Y  A  Q  G  F  T  G  R  F  V  F  S  L  D  T
tctgtcaacacggcatatctgcagatcagcagcctgaaggctgaggacactgccgtatat
 S  V  N  T  A  Y  L  Q  I  S  S  L  K  A  E  D  T  A  V  Y
tactgtgcgagagaggaattttggagtggttattctttgactactggggccagggaacc
 Y  C  A  R  E  E  F  L  E  W  L  F  F  D  Y  W  G  Q  G  T
ctggtcaccgtctcaagcgtctccagt
 L  V  T  V  S  S  V  S  S
```

FIG. 11A, Cont'd

MF4003: heavy chain variable region sequence of an EGFR binding antibody

Complete VH sequence (SEQ ID NO: 34):

QVQLVQSGSELKKPGASVKVSCKASGYTFPSFAMNWLRQAPGQGLEWMGWITTNTGDPTYAQGFSGRFVFSLDTSVSTAYLQISSLKAEDTAVYYCARVYNWIRGFDYWGQGTLVTVSS

FR1 (SEQ ID NO: 35): QVQLVQSGSELKKPGASVKVSCKASGYTFP CDR1

(SEQ ID NO: 36): SFAMN

FR2 (SEQ ID NO: 37): WLRQAPGQGLEWMG

CDR2 (SEQ ID NO: 38): WITTNTGDPTYAQGFSG

FR3 (SEQ ID NO: 39): RFVFSLDTSVSTAYLQISSLKAEDTAVYYCAR

CDR3 (EQ ID NO: 40): VYNWIRGFDY

FR4 (SEQ ID NO: 41): WGQGTLVTVSS

Annotated nucleotide sequence (SEQ ID NOS: 33 and 34):

```
caggtgcagctggtgcaatctgggtctgagttgaagaagcct
  Q  V  Q  L  V  Q  S  G  S  E  L  K  K  P
ggggcctcagtgaaggtttcctgcaaggcttctggatacaccttccctagttttgctatg
  G  A  S  V  K  V  S  C  K  A  S  G  Y  T  F  P  S  F  A  M
aattggcttcgacaggcccctggacaagggcttgagtggatgggatggatcaccaccaac
  N  W  L  R  Q  A  P  G  Q  G  L  E  W  M  G  W  I  T  T  N
actggggacccaacgtatgcccaggcttctcaggacggtttgtgttctccctggacacc
  T  G  D  P  T  Y  A  Q  G  F  S  G  R  F  V  F  S  L  D  T
tctgtcagcacggcatatctgcagatcagcagcctaaaggctgaggacactgccgtgtat
  S  V  S  T  A  Y  L  Q  I  S  S  L  K  A  E  D  T  A  V  Y
tactgtgcgagagtttataactggataaggggatttgactactggggccagggaaccctg
  Y  C  A  R  V  Y  N  W  I  R  G  F  D  Y  W  G  Q  G  T  L
gtcaccgtctcaagcgtctccagt
  V  T  V  S  S  V  S
```

FIG. 11A, Cont'd

MF4289: heavy chain variable region sequence of an EGFR binding antibody:

Complete VH sequence (SEQ ID NO: 44):

QVQLVQSGSELKKPGASVKVSCKTSGYTFTDYAMTWVRQAPGQGLEWMGWITTNTGDPTYAPGFTGRFVFSLDTSVSTAYLQISSLKAEDTAVYYCARVYHWIRGFEFWGQGTLVTVSS

FR1 (SEQ ID NO: 45): QVQLVQSGSELKKPGASVKVSCKTSGYTFT

CDR1 (SEQ ID NO: 46): DYAMT

FR2 (SEQ ID NO: 47): WVRQAPGQGLEWMG

CDR2 (SEQ ID NO: 48): WITTNTGDPTYAPGFTG

FR3 (SEQ ID NO: 49): RFVFSLDTSVSTAYLQISSLKAEDTAVYYCAR

CDR3 (SEQ ID NO: 50): VYHWIRGFEF

FR4 (SEQ ID NO: 51): WGQGTLVTVSS

Annotated nucleotide sequence (SEQ ID NOS: 42 and 43):

```
ggcccagccggccatggcccaggtgcagctggtgcaatctgggtctgaattgaagaagcct
  A  Q  P  A  M  A  Q  V  Q  L  V  Q  S  G  S  E  L  K  K  P
ggggcctcagtgaaggtttcctgcaagacttctggatacaccttcactgactatgctatg
  G  A  S  V  K  V  S  C  K  T  S  G  Y  T  F  T  D  Y  A  M
acttgggtgcgacaggcccctggacaagggcttgaatggatgggatggatcaccaccaac
  T  W  V  R  Q  A  P  G  Q  G  L  E  W  M  G  W  I  T  T  N
actggggacccaacgtatgccccgggcttcacaggacggtttgtcttctccttggacacc
  T  G  D  P  T  Y  A  P  G  F  T  G  R  F  V  F  S  L  D  T
tctgtcagcacggcatatctgcagatcagcagcctaaaggccgaggacactgccgtatat
  S  V  S  T  A  Y  L  Q  I  S  S  L  K  A  E  D  T  A  V  Y
tactgtgcgagagtgtatcattggatacggggatttgagttttggggccagggaaccctg
  Y  C  A  R  V  Y  H  W  I  R  G  F  E  F  W  G  Q  G  T  L
gtcaccgtctcaagcgtctccagt
  V  T  V  S  S  V  S  S
```

FIG. 11A, Cont'd

MF3370: heavy chain variable region sequence of an EGFR binding antibody:

Complete VH sequence (SEQ ID NO: 53):

QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCAKDRHWHWWLDAFDY
WGQGTLVTVSS

FR1 (SEQ ID NO: 54): QVQLVQSGAEVKKPGASVKVSCKASGYTFT

CDR1 (SEQ ID NO: 55): SYGIS

FR2 (SEQ ID NO: 56): WVRQAPGQGLEWMG

CDR2 (SEQ ID NO: 57): WISAYNGNTNYAQKLQG

FR3 (SEQ ID NO: 58): RVTMTTDTSTSTAYMELRSLRSDDTAVYYCAK

CDR3 (SEQ ID NO: 59): DRHWHWWLDAFDY

FR4 (SEQ ID NO: 60): WGQGTLVTVSS

Annotated nucleotide sequence (SEQ ID NOS: 52 and 53):

```
caggttcagctggtgcagtctggagctgaggtgaagaagcct
  Q  V  Q  L  V  Q  S  G  A  E  V  K  K  P
ggggcctcagtgaaggtctcctgcaaggcttctggttacacctttaccagctatggtatc
  G  A  S  V  K  V  S  C  K  A  S  G  Y  T  F  T  S  Y  G  I
agctgggtgcgacaggcccctggacaagggcttgagtggatgggatggatcagcgcttac
  S  W  V  R  Q  A  P  G  Q  G  L  E  W  M  G  W  I  S  A  Y
aatggtaacacaaactatgcacagaagctccagggcagagtcaccatgaccacagacaca
  N  G  N  T  N  Y  A  Q  K  L  Q  G  R  V  T  M  T  T  D  T
tccacgagcacagcctacatggagctgaggagcctgagatctgacgacacggctgtgtat
  S  T  S  T  A  Y  M  E  L  R  S  L  R  S  D  D  T  A  V  Y
tactgtgcaaaagatcgtcattggcattggtggctggacgcctttgattattggggccaa
  Y  C  A  K  D  R  H  W  H  W  W  L  D  A  F  D  Y  W  G  Q
ggtaccctggtcaccgtctccagt
  G  T  L  V  T  V  S  S
```

FIG. 11A, Cont'd

MF4002: heavy chain variable region sequence of an EGFR binding antibody

Complete VH sequence (SEQ ID NO: 62):

QVQLVQSGSELKKPGSSVKVSCKASGYTFTNYAMNWVRQAPGQGLEWMGWITTNT
GDPTYAQGFTGRFVFSLDTSVSTAYLQISSLKAEDTAVYYCVRVYNWIRGFDYWGQG
TLVTVSS

FR1 (SEQ ID NO: 63): QVQLVQSGSELKKPGSSVKVSCKASGYTFT

CDR1 (SEQ ID NO: 64): NYAMN

FR2 (SEQ ID NO: 65): WVRQAPGQGLEWMG

CDR2 (SEQ ID NO: 66): WITTNTGDPTYAQGFTG

FR3 (SEQ ID NO: 67): RFVFSLDTSVSTAYLQISSLKAEDTAVYYCVR

CDR3 (SEQ ID NO: 68): VYNWIRGFDY

FR4 (SEQ ID NO: 69): WGQGTLVTVSS

Annotated nucleotide sequence (SEQ ID NO: 61 and 62):

```
caggtgcagctggtgcaatctgggtctgagttgaagaagcct
  Q  V  Q  L  V  Q  S  G  S  E  L  K  K  P
gggtcctcagtgaaggtttcctgcaaggcttctggatacaccttcactaactatgctatg
  G  S  S  V  K  V  S  C  K  A  S  G  Y  T  F  T  N  Y  A  M
aattgggtgcgacaggcccctggacaagggcttgagtggatgggatggatcaccaccaac
  N  W  V  R  Q  A  P  G  Q  G  L  E  W  M  G  W  I  T  T  N
actggggacccaacgtatgcccagggcttcacaggacgttttgtcttctccttggacacc
  T  G  D  P  T  Y  A  Q  G  F  T  G  R  F  V  F  S  L  D  T
tctgtcagtacggcatatctgcagatcagcagcctaaaggctgaggacactgccgtatat
  S  V  S  T  A  Y  L  Q  I  S  S  L  K  A  E  D  T  A  V  Y
tactgtgtgagagtgtataactggataaggggatttgactactggggccagggaaccctg
  Y  C  V  R  V  Y  N  W  I  R  G  F  D  Y  W  G  Q  G  T  L
gtcaccgtctcaagcgtctccagt
  V  T  V  S  S  V  S  S
```

FIG. 11A, Cont'd

MF3751: heavy chain variable region sequence of an EGFR binding antibody

Complete VH sequence (SEQ ID NO: 71):

QVQLVQSGAEVKKPGASVKVSCKASGYTFTGYYMHWVRQAPGQGLEWMGTINPSGGSTYYAQKFQGRVTMTRDTSTSTVYMELSSLRSEDTAVYYCARDRNWGWDFDYWGQGTLVTVSS

FR1 (SEQ ID NO: 72): QVQLVQSGAEVKKPGASVKVSCKASGYTFT

CDR1 (SEQ ID NO: 73): GYYMH

FR2 (SEQ ID NO: 74): WVRQAPGQGLEWMG

CDR2 (SEQ ID NO: 75): TINPSGGSTYYAQKFQG

FR3 (SEQ ID NO: 76): RVTMTRDTSTSTVYMELSSLRSEDTAVYYCAR

CDR3 (SEQ ID NO: 77): DRNWGWDFDY

FR4 (SEQ ID NO: 78): WGQGTLVTVSS

Annotated nucleotide sequence (SEQ ID NO: 70 and 71):

```
caggtgcagctg
 Q  V  Q  L
gtacagtctggggctgaggtgaagaagcctggggcctcagtgaaggtttcctgcaaggca
 V  Q  S  G  A  E  V  K  K  P  G  A  S  V  K  V  S  C  K  A
tctggatacaccttcaccggctactatatgcactgggtgcgacaggcccctggacaaggg
 S  G  Y  T  F  T  G  Y  Y  M  H  W  V  R  Q  A  P  G  Q  G
cttgagtggatgggaacaatcaaccctagtggtggtagcacatactacgcacagaagttc
 L  E  W  M  G  T  I  N  P  S  G  G  S  T  Y  Y  A  Q  K  F
cagggcagagtcaccatgaccagggacacgtccacgagcacagtctacatggagctgagc
 Q  G  R  V  T  M  T  R  D  T  S  T  S  T  V  Y  M  E  L  S
agcctgagatctgaggacacggccgtgtattactgtgcgagagatcggaactggggatgg
 S  L  R  S  E  D  T  A  V  Y  Y  C  A  R  D  R  N  W  G  W
Gactttgactactggggccagggaaccctggtcaccgtctccagt
 D  F  D  Y  W  G  Q  G  T  L  V  T  V  S  S
```

FIG. 11A, Cont'd

MF3752: heavy chain variable region sequence of an EGFR binding antibody

Complete VH sequence (SEQ ID NO: 80):

EVQLVESGPEVKKPGASVKVSCKASGYTFTSYYMHWVRQAPGQGLEWMGTINPSGG
STYYAQKFQGRVTLTRDTSTSTVYMVLSSLRSEDTAVYYCARDRNWGWDFDYWGQG
TLVTVSS

FR1 (SEQ ID NO: 81): EVQLVESGPEVKKPGASVKVSCKASGYTFT

CDR1 (SEQ ID NO: 82): SYYMH

FR2 (SEQ ID NO: 83): WVRQAPGQGLEWMG

CDR2 (SEQ ID NO: 84): TINPSGGSTYYAQKFQG

FR3 (SEQ ID NO: 85): RVTLTRDTSTSTVYMVLSSLRSEDTAVYYCAR

CDR3 (SEQ ID NO: 86): DRNWGWDFDY

FR4 (SEQ ID NO: 87): WGQGTLVTVSS

Annotated nucleotide sequence (SEQ ID NOS: 79 and 80):

```
  gaggtgcagctggtggagtctgggcctgaggtgaagaagcct
   E  V  Q  L  V  E  S  G  P  E  V  K  K  P
  ggggcctcagtgaaggtttcctgcaaggcatctggatacaccttcaccagctactatatg
   G  A  S  V  K  V  S  C  K  A  S  G  Y  T  F  T  S  Y  Y  M
  cactgggtgcgacaggcccctggacaagggcttgagtggatgggaacaatcaaccctagt
   H  W  V  R  Q  A  P  G  Q  G  L  E  W  M  G  T  I  N  P  S
  ggtggtagcacatactacgcacagaagttccagggcagagtcaccctgaccagggacacg
   G  G  S  T  Y  Y  A  Q  K  F  Q  G  R  V  T  L  T  R  D  T
  tccacgagcacagtctacatggtgctgagcagcctgagatctgaggacacggccgtgtat
   S  T  S  T  V  Y  M  V  L  S  S  L  R  S  E  D  T  A  V  Y
  tactgtgcgagagatcggaactggggatgggactttgactactggggccagggaaccctg
   Y  C  A  R  D  R  N  W  G  W  D  F  D  Y  W  G  Q  G  T  L
  gtcaccgtctcaagcgtctccagt
   V  T  V  S  S  V  S  S
```

FIG. 11B

MF3178: heavy chain variable region sequence of an erbB-3 binding antibody

Nucleic acid sequence (underlined sequence encodes end of leader peptide) (SEQ ID NO: 88):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCTGTGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence (SEQ ID NO: 89):

QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDHGSRHFWSYWGFDYWGQGTLVTVSS

CDR1 (SEQ ID NO: 90): GYYMH

CDR2 (SEQ ID NO: 91): WINPNSGGTNYAQKFQG

CDR3 (SEQ ID NO: 92): DHGSRHFWSYWGFDY

FIG. 11B, Cont'd

MF3176: heavy chain variable region sequence of an erbB-3 binding antibody

Nucleic acid sequence (underlined sequence encodes end of leader peptide) (SEQ ID NO: 93):

```
  1 GGCCCAGCCG GCCATGGCCG AGGTGCAGCT GTTGGAGTCT GGGGGAGGCT TGGTACAGCC
 61 TGGGGGGTCC CTGAGACTCT CCTGTGCAGC CTCTGGATTC ACCTTTAGCA GCTATGCCAT
121 GAGCTGGGTC CGCCAGGCTC CAGGGAAGGG GCTGGAGTGG GTCTCAGCTA TTAGTGGTAG
181 TGGTGGTAGC ACATACTACG CAGACTCCGT GAAGGGCCGG TTCACCATCT CCAGAGACAA
241 TTCCAAGAAC ACGCTGTATC TGCAAATGAA CAGCCTGAGA GCCGAGGACA CGGCTGTGTA
301 TTACTGTGCA AGAGATTGGT GGTACCCGCC GTACTACTGG GGCTTTGATT ATTGGGGCCA
361 AGGTACCCTG GTCACCGTCT CCAGT
```

Amino acid sequence (SEQ ID NO: 94):

EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCARDWWYPPYYWGFDYWG
QGTLVTVSS

CDR1 (SEQ ID NO: 95):    SYAMS

CDR2 (SEQ ID NO: 96):    AISGSGGSTYYADSVKG

CDR3 (SEQ ID NO: 97):    DWWYPPYYWGFDY

FIG. 11B, Cont'd

MF3163: heavy chain variable region sequence of an erbB-3 binding antibody

Nucleic acid sequence (underlined sequence encodes end of leader peptide) (SEQ ID NO: 98):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AAAGATTCTT ACTCTCGTCA TTTCTACTCT TGGTGGGCCT TTGATTATTG
361 GGGCCAAGGT ACCCTGGTCA CCGTCTCCAG T
```

Amino acid sequence (SEQ ID NO: 99):

QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAKDSYSRHFYSWWAFDYWGQGTLVTVSS

| | |
|---|---|
| CDR1 (SEQ ID NO: 100): | GYYMH |
| CDR2 (SEQ ID NO: 101): | WINPNSGGTNYAQKFQG |
| CDR3 (SEQ ID NO: 102): | DSYSRHFYSWWAFDY |

FIG. 11B, Cont'd

MF3307: heavy chain variable region sequence of an erbB-3 binding antibody

Nucleic acid sequence (underlined sequence encodes end of leader peptide) (SEQ ID NO: 108):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AGAGGTTCTC GTAAACGTCT GTCTAACTAC TTCAACGCCT TTGATTATTG
361 GGGCCAAGGT ACCCTGGTCA CCGTCTCCAG T
```

Amino acid sequence (SEQ ID NO: 109):

QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGSRKRLSNYFNAFDYWGQGTLVTVSS

| | |
|---|---|
| CDR1 (SEQ ID NO: 110): | GYYMH |
| CDR2 (SEQ ID NO: 111): | WINPNSGGTNYAQKFQG |
| CDR3 (SEQ ID NO: 112): | GSRKRLSNYFNAFDY |

FIG. 11B, Cont'd

```
                                                    CDR1              CDR2
        1         10        20        30            40        50        60
MF3178  QVQLVQSGAEVKKPGASVKVSCKASGYTFT  GYYMH  WVRQAPGQGLEWMG  WINPNSGGTNYAQKFQG
MF6055  .........D....................  .....  .........A....  ....S.......K....
MF6056  .........D...........T........  .....  .........A....  ....S.......K....
MF6057  .........D...........T........  .....  .........A....  ....Q............
MF6058  .........D...........T........  .....  .........A....  ....Q.......K....
MF6059  ..............................  .....  ..............  ....G..S.........
MF6060  .........D....................  .....  .........A....  ....Q.......K....
MF6061  ..............................  .....  ..............  ....Q...........K.
MF6062  ..............................  .....  ..............  ....G..S.........
MF6063  ..............................  .....  ..............  ....Q.......K....
MF6064  ..............................  .....  ............K.  ....Q............
MF6065  ..............................  S....  ..............  ....QG.S.........
MF6066  ..............................  .....  ..............  ....Q..S.........
MF6067  ..............................  .....  ..............  ....Q............
MF6068  ..............................  .....  ..............  ....Q............
MF6069  ..............................  .....  ..............  ....Q............
MF6070  ..............................  S....  ..............  ....SG.S.........
MF6071  ..............................  .....  ..............  ....S..S.........
MF6072  ..............................  .....  ..............  ....S............
MF6073  ..............................  .....  ..............  ....S............
MF6074  ..............................  .....  ..............  ....S............
```

```
                                             CDR3
        70        80        90        100       110       120      SEQ ID NO:
MF3178  RVTMTRDTSISTAYMELSRLRSDDTAVYYCAR  DHGSRHFWSYWGFDY  WGQGTLVTVSS   89
MF6055  ......E..T....................T.....  ...............  ...........  114
MF6056  ..S...E..T.....Q..........T.....      ...............  ...........  116
MF6057  ...............Q................      ...............  ...........  118
MF6058  ..S...E..T.....Q..........T.....      ...............  ...........  120
MF6059  ................................      ...............  ...........  122
MF6060  ......E..T................T.....      ...............  ...........  124
MF6061  .........T......................      ...............  ...........  126
MF6062  .........T......................      ...............  ...........  128
MF6063  .........T......................      ...............  ...........  130
MF6064  .........T......................      ...............  ...........  132
MF6065  .........T..V..........E........      ...............  ...........  134
MF6066  .........T......S...E...........      ...............  ...........  136
MF6067  .........T..V.....S.............      ...............  ...........  138
MF6068  .........T......................      ...............  ...........  140
MF6069  ................................      ...............  ...........  142
MF6070  .........T..V..........E........      ...............  ...........  144
MF6071  .........T......S...E...........      ...............  ...........  146
MF6072  .........T..V.....S.............      ...............  ...........  148
MF6073  .........T......................      ...............  ...........  150
MF6074  ................................      ...............  ...........  152
```

FIG. 11B, Cont'd

DNA sequences of MF3178 variants (without sequence encoding leader peptide)

>MF6055_VH (SEQ ID NO: 113)

caggtgcagctggtgcagtctggggctgacgtgaagaagcctggggcctcagtgaaggtctcctgcaagg cttctggatacaccttcaccggctactatatgcactgggtgcgacaggcccctggacaagctcttgagtg gatgggatggatcaaccct tctagtggtggcacaaactatgcaaagaagtttcagggcagggtcacgatg accagggagacgtccacaagcacagcctacatggagctgagcaggctgagatctgacgacacggctacgt attactgtgcaagagatcatggttctcgtcatttctggtcttactggggctttgattattggggccaagg taccc tggtc accgt ctcca gt

>MF6056_VH (SEQ ID NO:115)

caggtgcagctggtgcagtctggggctgacgtgaagaagcctggggcctcagtgaaggtcacgtgcaagg cttctggatacaccttcaccggctactatatgcactgggtgcgacaggcccctggacaagctcttgagtg gatgggatggatcaaccct tctagtggtggcacaaactatgcaaagaagtttcagggcagggtctctatg accagggagacgtccacaagcacagcctacatgcagctgagcaggctgagatctgacgacacggctacgt attactgtgcaagagatcatggttctcgtcatttctggtcttactggggctttgattattggggccaagg taccctggtcaccgtctccagt

>MF6057_VH (SEQ ID NO: 117)

caggtgcagctggtgcagtctggggctgatgtgaagaagcctggggcctcagtgaaggtcacgtgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccatcagcacagcctacatgcagctgagcaggctgagatctgacgacacggctgtgt attactgtgcaagagatcatggttctcgtcatttctggtcttactggggctttgattattggggccaagg taccctggtcaccgtctccagt

FIG. 11B, Cont'd

>MF6058_VH (SEQ ID NO:118)

caggtgcagctggtgcagtctggggctgacgtgaagaagcctggggcctcagtgaaggtcacgtgcaagg
cttctggatacaccttcaccggctactatatgcactgggtgcgacaggcccctggacaagctcttgagtg
gatgggatggatcaaccctcaaagtggtggcacaaactatgcaaagaagtttcagggcagggtctctatg
accagggagacgtccacaagcacagcctacatgcagctgagcaggctgagatctgacgacacggctacgt
attactgtgcaagagatcatggttctcgtcatttctggtcttactggggctttgattattggggccaagg
taccctggtcaccgtctccagt

>MF6059_VH (SEQ ID NO: 119)

caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctggcagtggttctacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactggggctttgattattggggccaagg
taccctggtcaccgtctccagt

>MF6060_VH (SEQ ID NO: 123)

caggtgcagctggtgcagtctggggctgacgtgaagaagcctggggcctcagtgaaggtctcctgcaagg
cttctggatacaccttcaccggctactatatgcactgggtgcgacaggcccctggacaagctcttgagtg
gatgggatggatcaaccctcaaagtggtggcacaaactatgcaaagaagtttcagggcagggtcacgatg
accagggagacgtccacaagcacagcctacatggagctgagcaggctgagatctgacgacacggctacgt
attactgtgcaagagatcatggttctcgtcatttctggtcttactggggctttgattattggggccaagg
taccctggtcaccgtctccagt

FIG. 11B, Cont'd

>MF6061_VH (SEQ ID NO: 125)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttaagggcagggtcacgatg accagggacacgtccaccagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6062_VH (SEQ ID NO: 127)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctggcagtggttctacaaactatgcacagaagtttcagggcagggtcacgatg accagggacacgtccacaagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6063_VH (SEQ ID NO: 128)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcaaagaagtttcagggcagggtcacgatg accagggacacgtccaccagcacagcctacatggagctgagcaggctgagatctgacgacacggctgtgt attactgtgcaagagatcatggttctcgtcatttctggtcttactggggctttgattattggggccaagg taccctggtcaccgtctccagt

FIG. 11B, Cont'd

>MF6064_VH (SEQ ID NO: 131)

caggtgcagctggtgcagtctggggctgaggtgaagaagcctggggcctcagtgaaggtctcctgcaagg cttctggatacaccttcaccggctactatatgcactgggtgcgacaggcccctggaaagggg cttgagtg gatgggatggatcaaccctcagagtggtggcacaaactatgcacagaagtttcagggcagggtcacgatg accagggacacgtccacgagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6065_VH (SEQ ID NO: 133)

caggtgcagctggtgcagtctggggctgaggtgaagaagcctggggcctcagtgaaggtctcctgcaagg cttctggatacaccttcacctcttactatatgcactgggtgcgacaggcccctggacaagggcttgagtg gatgggatggatcaaccctcaggggggttctacaaactatgcacagaagtttcagggcagggtcacgatg accagggacacgtccaccagcacagtgtacatggagctgagcaggctgagatctgaggacacggctgtgt attactgtgcaagagatcatggttctcgtcatttctggtcttactggggctttgattattggggccaagg taccctggtcaccgtctccagt

>MF6066_VH (SEQ ID NO: 135)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggttctacaaactatgcacagaagtttcagggcagggtcacgatg accagggacacgtccaccagcacagcctacatggagctgagctctctgagatctgaggacacggctgtgt attactgtgcaagagatcatggttctcgtcatttctggtcttactggggctttgattattggggccaagg taccctggtcaccgtctccagt

FIG. 11B, Cont'd

>MF6067_VH (SEQ ID NO: 137)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccaccagcacagtctacatggagctgagctctctgagatctgacgacacggctgtgt attactgtgcaagagatcatggttctcgtcatttctggtcttactggggctttgattattggggccaagg taccctggtcaccgtctccagt

>MF6068_VH (SEQ ID NO: 139)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccaccagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6069_VH (SEQ ID NO: 141)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaaccctcagagtggtggcacaaactatgcacagaagtttcagggcagggtcacgatg accagggacacgtccatcagcacagcctacatggagctgagcaggctgagatctgacgacacggctgtgt attactgtgcaagagatcatggttctcgtcatttctggtcttactggggctttgattattggggccaagg taccctggtcaccgtctccagt

FIG. 11B, Cont'd

>MF6070_VH (SEQ ID NO: 143)

caggtgcagctggtgcagtctggggctgaggtgaagaagcctggggcctcagtgaaggtctcctgcaagg cttctggatacaccttcacctcttactatatgcactgggtgcgacaggcccctggacaagggcttgagtg gatgggatggatcaacccttctgggggttctacaaactatgcacagaagtttcagggcagggtcacgatg accagggacacgtccaccagcacagtgtacatggagctgagcaggctgagatctgaggacacggctgtgt attactgtgcaagagatcatggttctcgtcatttctggtcttactggggctttgattattggggccaagg taccctggtcaccgtctccagt

>MF6071_VH (SEQ ID NO: 145)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaacccttctagtggttctacaaactatgcacagaagtttcagggcagggtcacgatg accagggacacgtccaccagcacagcctacatggagctgagctctctgagatctgaggacacggctgtgt attactgtgcaagagatcatggttctcgtcatttctggtcttactggggctttgattattggggccaagg taccctggtcaccgtctccagt

>MF6072_VH (SEQ ID NO: 147)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaacccttctagtggtggcacaaactatgcacagaagtttcagggcagggtcacgatg accagggacacgtccaccagcacagtctacatggagctgagctctctgagatctgacgacacggctgtgt attactgtgcaagagatcatggttctcgtcatttctggtcttactggggctttgattattggggccaagg taccctggtcaccgtctccagt

FIG. 11B, Cont'd

>MF6073_VH (SEQ ID NO: 149)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaacccttctagtggtggcacaaactatgcacagaagtttcagggcagggtcacgatg accagggacacgtccaccagcacagcctacatggagctgagcaggctgagatctgacgacacggctgtgt attactgtgcaagagatcatggttctcgtcatttctggtcttactggggctttgattattggggccaagg taccctggtcaccgtctccagt

>MF6074_VH (SEQ ID NO: 151)

caggtgcagctggtgcagtctggggctgaggtgaagaagcctggggcctcagtgaaggtctcctgcaagg cttctggatacaccttcaccggctactatatgcactgggtgcgacaggcccctggacaagggcttgagtg gatgggatggatcaacccttctagtggtggcacaaactatgcacagaagtttcagggcagggtcacgatg accagggacacgtccatcagcacagcctacatggagctgagcaggctgagatctgacgacacggctgtgt attactgtgcaagagatcatggttctcgtcatttctggtcttactggggctttgattattggggccaagg taccctggtcaccgtctccagt

FIG. 11B, Cont'd

Nucleic acid alignment (*without* end of leader sequence)

```
MF3178  CAGGTGCAGCTGGTGCAGTCTGGGGCTGAGGTGAAGAAGCCTGGGGCCTCAGTGAAGGTCTCCTGCAAG
MF6058  ..............................C...........................A.G......
MF6061  ....................................................................
MF6065  ....................................................................
                                             CDR1
MF3178  GCTTCTGGATACACCTTCACC GGCTACTATATGCAC TGGGTGCGACAGGCCCCTGGACAAGGGCTTG
MF6058  ..................... ..............  ...........................CT....
MF6061  ..................... ..............  ..............................
MF6065  ..................... TCT...........  ..............................
                                             CDR2
MF3178  AGTGGATGGGA TGGATCAACCCTAACAGTGGTGGCACAAACTATGCACAGAAGTTTCAGGGC AGGGT
MF6058  ........... ........C.A.....................A................. .....
MF6061  ........... ........C.G.....................A................. .....
MF6065  ........... ........C.GG.G...TCT.............................. .....

MF3178  CACGATGACCAGGGACACGTCCATCAGCACAGCCTACATGGAGCTGAGCAGGCTGAGATCTGACGACAC
MF6058  .T.T.........G.......CA............C................................
MF6061  ....................C...............................................
MF6065  ....................C........TG....................................G.....
                                             CDR3
MF3178  GGCTGTGTATTACTGTGCAAGA GATCATGGTTCTCGTCATTTCTGGTCTTACTGGGGCTTTGATTAT
MF6058  ....AC................ ..............................................
MF6061  ...................... ..............................................
MF6065  ...................... ..............................................

MF3178  TGGGGCCAAGGTACCCTGGTCACCGTCTCCAGT (Nucleotides 20 - 391 of SEQ ID NO: 88)
MF6058  ................................. (SEQ ID NO: 119)
MF6061  ................................. (SEQ ID NO: 125)
MF6065  ................................. (SEQ ID NO: 133)
```

FIG. 11C a) Common Light Chain (SEQ ID NO: 153)

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIKRTVAAPSVFIFP
PSDEQLKSGTASVVCLLNNFYPREAKVQWKVDNALQSGNSQESVTEQDSKDSTYSLS
STLTLSKADYEKHKVYACEVTHQGLSSPVTKSFNRGEC

FIG. 11D heavy chain for EGFR binding (SEQ ID NO: 154)

QVQLVQSGAEVKKPGASVKVSCKVSGYTLTELSMHWVRQAPGKGLEWMGGFDPEY
GKTFFAQNFQGRVTMTEDTSADTAYMELSSLRSEDTAVYYCATEGYYETTTYYYNLF
DSWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTDPPSREEMTKNQVSLTCEVKGFYPSDIAVEWESNGQPEN
NYKTTPPVLDSDGSFFLYSKLTVDKSRWQQGNVFSCSVMHEALHNHYTQKSLSLSPG heavy chain for erbB-3 binding (SEQ ID NO: 155)

QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTKPPSREEMTKNQVSLKCLVKGFYPSDIAVEWESNGQPEN
NYKTTPPVLDSDGSFFLYSKLTVDKSRWQQGNVFSCSVMHEALHNHYTQKSLSLSPG

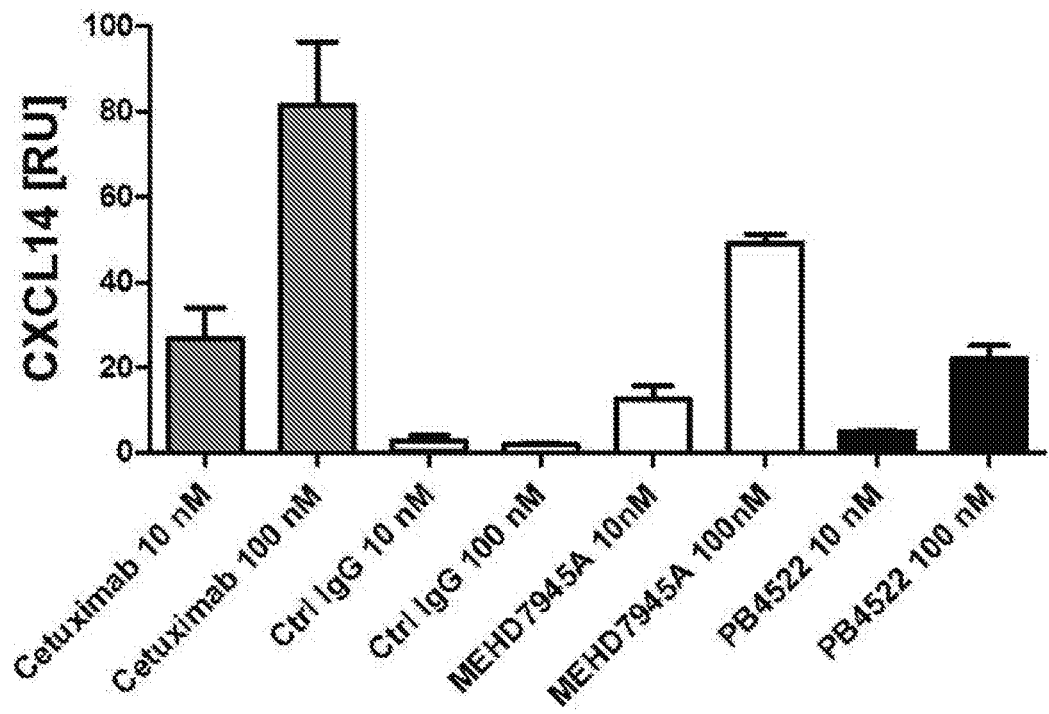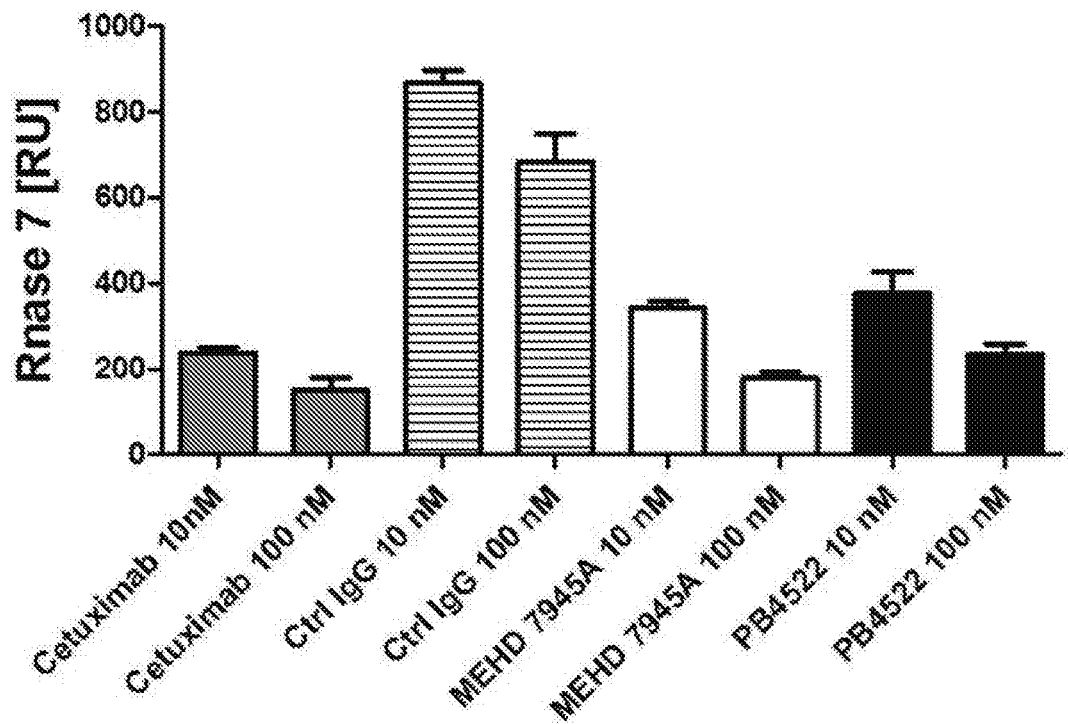
FIG. 12

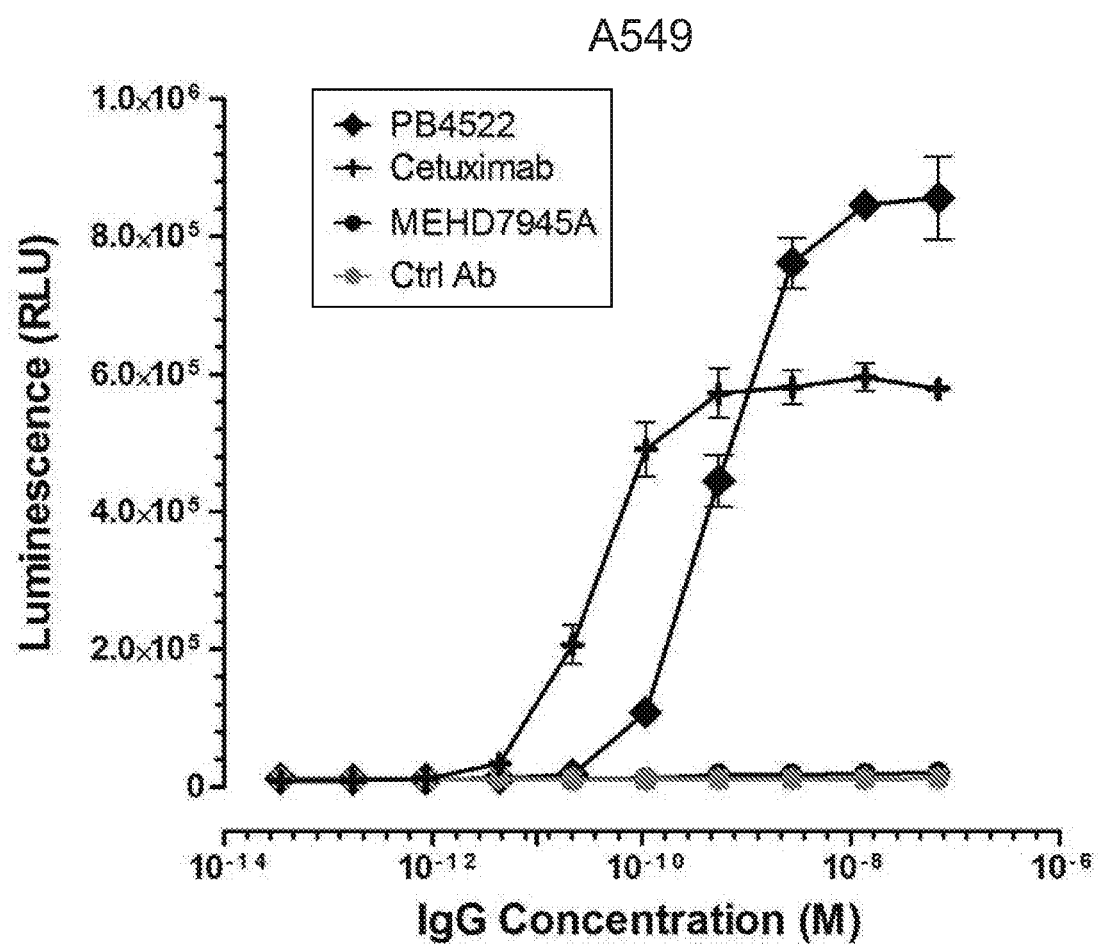
FIG. 13, Cont'd

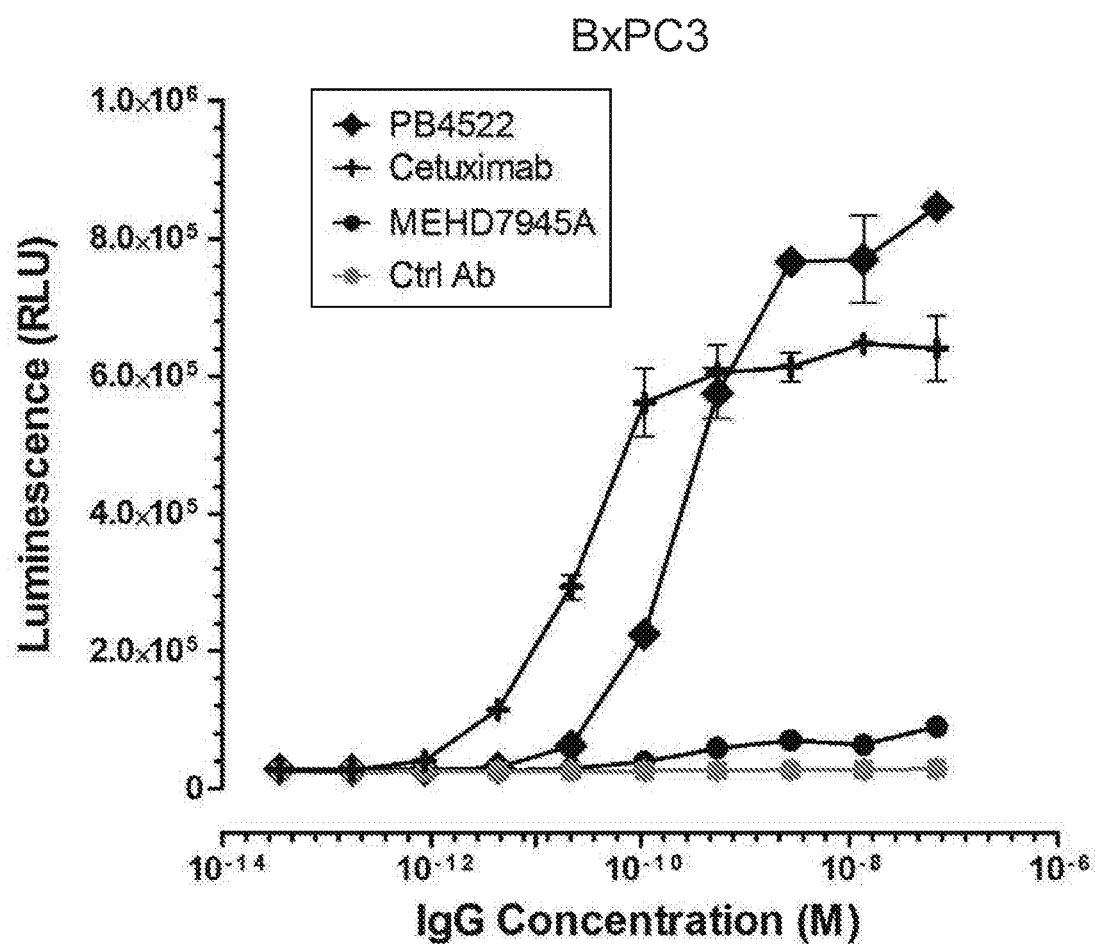
FIG. 13, Cont'd

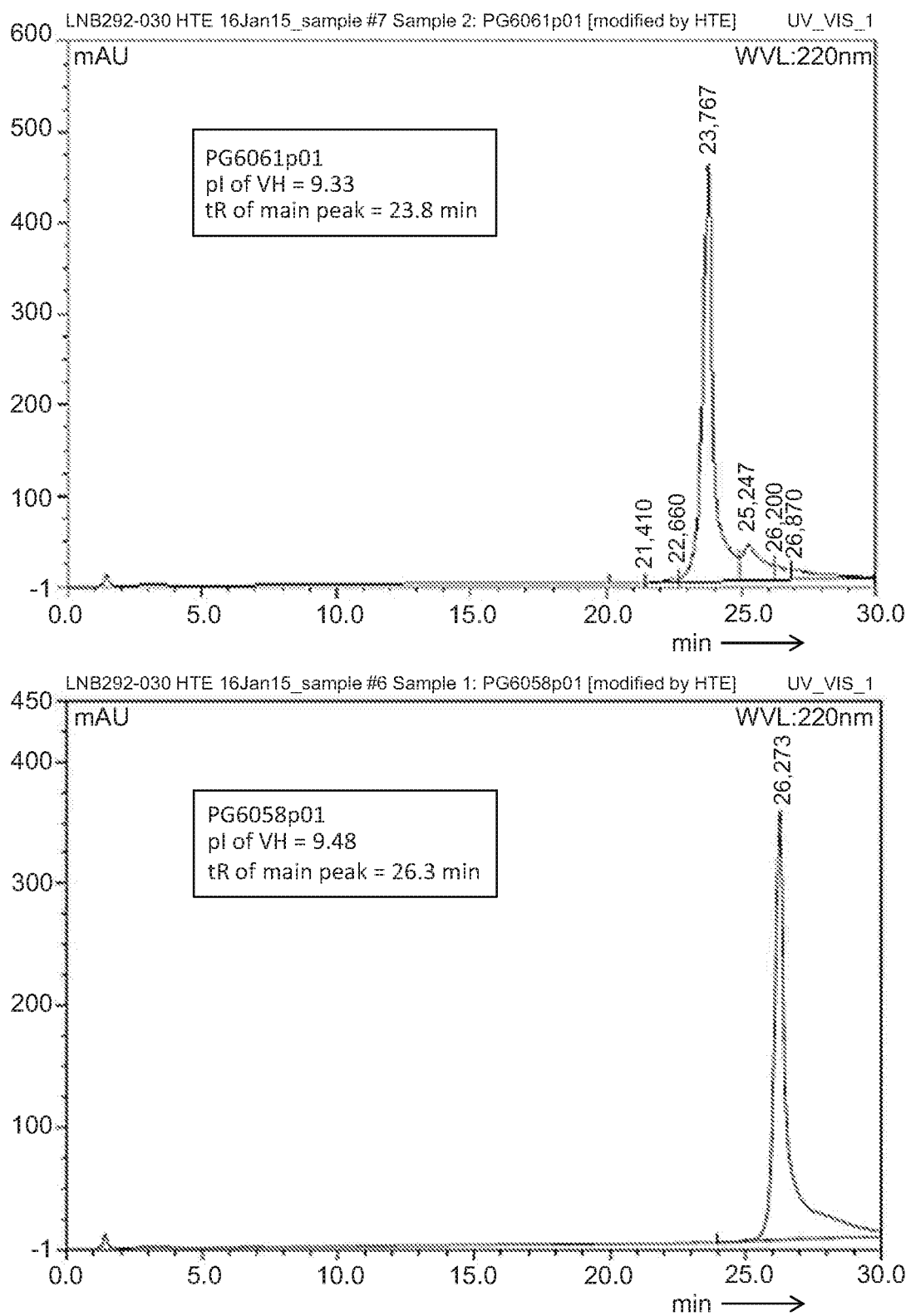
FIG. 15, Cont'd

METHODS OF TREATING A SUBJECT HAVING AN EGFR-POSITIVE AND/OR ERBB-3-POSITIVE TUMOR

CROSS-REFERENCE TO RELATED APPLICATIONS

This application is a division of U.S. application Ser. No. 15/121,619, filed Aug. 25, 2016, now U.S. Pat. No. 10,844,127, which is a national stage entry under 35 U.S.C. § 371 of PCT/NL2015/050124, filed Feb. 27, 2015. Each application is incorporated by reference herein in its entirety.

REFERENCE TO SEQUENCE LISTING SUBMITTED ELECTRONICALLY

The content of the electronically submitted sequence listing (Name: "4096_0090002_Seqlisting_ST25.txt"; Size: 184,951 bytes; and Date of Creation: Apr. 28, 2023) is herein incorporated by reference in its entirety.

The invention relates to the field of antibodies. In particular it relates to the field of therapeutic (human) antibodies for the treatment of diseases involving aberrant cells. More in particular it relates to antibodies that bind EGFR and ErbB-3 and their use in the binding of EGFR and ErbB-3 positive cells, particularly tumor cells.

The epidermal growth factor (EGF) receptor (EGFR) is the prototype cell-surface receptor for members of the epidermal growth factor family (EGF-family) of extracellular protein ligands. EGFR is also known as the ErbB-1 receptor. The receptor has been given various names in the past (EGFR; ERBB; ERBB1; HER1; PIG61; mENA). In the present invention the names ErbB-1, EGFR or HER1 in humans will be used interchangeably. EGFR is a member of the ErbB family of receptors, a subfamily of four closely related receptor tyrosine kinases: ErbB-1 (EGFR), ErbB-2 (HER2/c-neu; Her2), ErbB-3 (Her 3) and ErbB-4 (Her 4).

EGFR exists on the cell surface and is activated by binding of its specific ligands, including epidermal growth factor and transforming growth factor a (TGFα). Upon activation by its growth factor ligands, the receptor undergoes a transition from an inactive mostly monomeric form to an active homo-dimer. In addition to forming homo-dimers after ligand binding, EGFR may pair with another member of the ErbB receptor family, such as ErbB2, to create an activated hetero-dimer. There is also evidence to suggest that dimers form in the absence of ligand-binding and clusters of activated EGFRs form after ligand binding.

EGFR dimerization stimulates its intrinsic intracellular protein-tyrosine kinase (PTK) activity. This activity induces several signal transduction cascades that lead to cell proliferation and differentiation. The kinase domain of EGFR can cross-phosphorylate tyrosine residues of other receptors it is complexed with, and can itself be activated in that manner.

Mutations involving EGFR have been identified in several types of cancer, and it is the target of an expanding class of anticancer therapies. These include EGFR targeted small molecules as gefitinib and erlotinib for lung cancer, and antibodies as cetuximab and panitumab for colon cancer and head and neck cancer.

Cetuximab and panitumumab are monoclonal antibodies that inhibit the receptor. Other monoclonals in clinical development are zalutumumab, nimotuzumab, and matuzumab. The monoclonal antibodies aim to block the extracellular ligand-induced receptor activation, mostly by blocking ligand binding to the receptor. With the binding site blocked, signal-inducing molecules cannot attach effectively and thereby also not activate downstream signaling. However, ligand-induced receptor activation may also be inhibited by stabilization of the inactive receptor conformation (matuzumab).

Although there is some success with the EGFR targeted antibody therapy, most are associated with the development of treatment resistance over time. One of the ways in which EGFR positive tumors can escape the targeted therapy is by signaling through another receptor(dimer). For instance, increased signaling by EGFR/ErbB-3 (HER1/HER3) dimers due to increased HER3 expression or heregulin expression is associated with EGFR related drug resistance in lung cancers and head and neck cancers. Apart from the induction of treatment resistance, some side effects of EGFR-targeting antibodies have been observed. One example is the development of a skin rash, associated with efficient EGFR inhibition. When extreme, such rashes can lead to a reduction in treatment cycles and/or premature termination of treatment.

ErbB-3 does not have inherent kinase inactivity. Therefore, effective inhibition of ErbB-3 receptor signaling cannot be achieved with small molecule tyrosine kinase inhibitors (TKI's). Recently a monoclonal antibody termed MEHD7945A was found to show promise in a pre-clinical setting of EGFR positive tumors. MEHD7945A is a monoclonal antibody with two identical antigen-binding sites. MEHD7945A has the unique property that it has two identical antigen-binding arms that each individually have the capacity to bind either EGFR or ErbB-3, but not to other receptors. Once an antigen is bound, the antigen-binding site is blocked for the other antigen. Therefore, MEHD7945A (called a 'two in one' antibody) can be regarded both as an EGFR-targeting antibody, as well as a HER3 targeting antibody.

SUMMARY OF THE INVENTION

The invention provides a bispecific antibody comprising a first antigen-binding site that binds EGFR and a second antigen-binding site that binds ErbB-3 and wherein the antibody has a half maximal growth inhibitory concentration (IC50) of less than 200 pM for inhibiting EGFR and/or ErbB-3 ligand induced growth of BxPC3 cells (ATCC CRL-1687) or BxPC3-luc2 cells (Perkin Elmer 125058).

Further provided is an antibody that comprises an antigen-binding site that binds EGFR, wherein the antibody comprises an immunoglobulin heavy chain with a heavy chain variable region that binds EGFR and that comprises the amino acid sequence of VH chain MF3998; MF4280; MF4002; MF4003; MF4010; MF4289; MF3370; MF3751; MF3752 as depicted in FIG. 11A, preferably wherein the immunoglobulin light chain variable region comprises the amino acid sequence of FIG. 11C The invention further provides an antibody that comprises an antigen-binding site that binds ErbB-3, comprising an immunoglobulin heavy chain with a heavy chain variable region that binds ErbB-3 and that comprises the amino acid sequence of VH chain MF3178; MF3176; MF3163; MF3307, MF6055-MF6074, preferably MF3178, MF3176, MF3163, MF6058, MF6061 or MF6065 as depicted in FIG. 11B, preferably wherein the immunoglobulin light chain variable region comprises the amino acid sequence of FIG. 11C.

An antibody of the invention is, unless otherwise specifically specified, preferably a bispecific antibody.

The invention further provides a pharmaceutical composition comprising an antibody according to the invention.

Also provided is an antibody of the invention that further comprises a label, preferably a label for in vivo imaging.

The invention further provides a method for the treatment of a subject having a EGFR, ErbB-3 or EGFR/ErbB-3 positive tumor or at risk of having said tumor comprising administering to the subject a bispecific antibody according to the invention. Also provided is a bispecific antibody according to the invention for use in the treatment of a subject having or at risk of having an EGFR, ErbB-3 or EGFR/ErbB-3 positive tumor.

DETAILED DESCRIPTION OF THE INVENTION

As used herein, the term "antigen-binding site" refers to a site on an antibody which is capable of binding to antigen. The unmodified antigen-binding site is typically formed by and present in the variable domain of the antibody. In one embodiment an antibody variable domain of the invention comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

Antigen binding by an antibody is typically mediated through the complementarity determining regions (CDR's) of the antibody and the specific three-dimensional structure of both the antigen and the variable domain allowing these two structures to bind together with precision (an interaction similar to a lock and key), as opposed to random, non-specific sticking of antibodies. As an antibody typically recognizes only part of an antigen (called the epitope), and as such epitope may be present in other, but preferably non-human, compounds as well, antibodies according to the present invention that bind EGFR and/or ErbB-3 may recognize other proteins as well, but preferably not other human proteins, if such other compounds contain the same epitope. Hence, the term "binding" does not exclude binding of the antibodies to another protein or protein(s) that contain the same epitope. Such other protein(s) is preferably not a human protein. Instead, cross-reactivity is allowed. An EGFR antigen-binding site and an ErbB-3 antigen-binding site as defined in the present invention typically do not bind to other proteins on the membrane of cells in a post-natal, preferably adult human. An antibody according to the present invention is typically capable of binding EGFR and ErbB-3 with a binding affinity (i.e. equilibrium dissociation constant KD) of at least $1 \times 10e-6$ M, as outlined in more detail below.

As used herein, antigen-binding refers to the typical binding capacity of an antibody to its antigen. An antibody comprising an antigen-binding site that binds to EGFR, binds to EGFR and, under otherwise identical conditions, at least 100-fold lower to the homologous receptors ErbB-2 and ErbB-4 of the same species. An antibody comprising an antigen-binding site that binds to ErbB-3, binds to ErbB-3 and, under otherwise identical conditions, not to the homologous receptors ErbB-2 and ErbB-4 of the same species. Considering that the ErbB-family is a family of cell surface receptors, the binding is typically assessed on cells that express the receptor(s). Binding of an antibody to an antigen can be assessed in various ways.

The term "interferes with binding" as used herein means that the antibody is directed to an epitope on ErbB-3 and the antibody competes with ligand for binding to ErbB-3. The antibody may diminish ligand binding, displace ligand when this is already bound to ErbB-3 or it may, for instance through steric hindrance, at least partially prevent that ligand can bind to ErbB-3. One way to measure binding of an antigen binding site is to incubate the antibody with the antigen (preferably cells expressing the antigen), removing unbound antibody (preferably by a wash stop) and detecting bound antibody by means of a labeled antibody that binds to the bound antibody constant domain. The measurement is preferably compared with a positive and negative reference. In case of cells the negative reference is a cell that does not express the antigen.

The term "antibody" as used herein means a proteinaceous molecule preferably belonging to the immunoglobulin class of proteins, containing one or more variable domains that bind an epitope on an antigen, where such domains are derived from or share sequence homology with the variable domain of an antibody. Antibodies of the invention preferably comprise two variable domains. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least $1 \times 10e-6$ M, more preferably $1 \times 10e-7$ M, more preferably higher than $1 \times 10e-9$ M. Typically, antibodies for therapeutic applications have affinities of up to $1 \times 10e-10$ M or higher. Antibodies such as bispecific antibodies of the present invention comprise the constant domains (Fc part) of a natural antibody. An antibody of the invention is typically a bispecific full length antibody, preferably of the human IgG subclass. Preferably, the antibodies of the present invention are of the human IgG1 subclass. Such antibodies of the invention have good ADCC properties, have favorable half life upon in vivo administration to humans and CH3 engineering technology exists that can provide for modified heavy chains that preferentially form hetero-dimers over homo-dimers upon co-expression in clonal cells For instance, ADCC activity of an antibody can be improved when the antibody itself has a low ADCC activity, by slightly modifying the constant region of the antibody (Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489)

An antibody of the invention is preferably a "full length" antibody. The term 'full length' according to the invention is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. An antibody binds to antigen via the variable domains contained in the Fab portion, and after binding can interact with molecules and cells of the immune system through the constant domains, mostly through the Fe portion. The terms 'variable domain', 'VH/VL pair', 'VH/VL' are used herein interchangeably. Full length antibodies according to the invention encompass antibodies wherein mutations may be present that provide desired characteristics. Such mutations should not be deletions of substantial portions of any of the regions. However, antibodies wherein one or several amino acid residues are deleted, without essentially altering the binding characteristics of the resulting antibody are embraced within the term "full length antibody". For instance, an IgG antibody can have 1-20 amino acid residue insertions, deletions or a combination thereof in the constant region.

Full length IgG antibodies are preferred because of their favorable half life and the need to stay as close to fully autologous (human) molecules for reasons of immunogenicity. An antibody of the invention is preferably a bispecific IgG antibody, preferably a bispecific full length IgG1 antibody. IgG1 is favored based on its long circulatory half life in man. It is preferred that the bispecific IgG antibody according to the invention is a human IgG1.

The term 'bispecific' (bs) means that one part of the antibody (as defined above) binds to one epitope on an antigen whereas the second part binds to a different epitope on the antigen, or on a different antigen. The different epitope is typically present on a different antigen. According to the present invention, said first and second antigens are in fact two different proteins. A preferred bispecific antibody is an antibody that comprises parts of two different monoclonal antibodies and consequently binds to two different types of antigen. One arm of the bispecific antibody typically contains a variable domain of one antibody and the other arm contains a variable domain of another antibody. The heavy chain variable regions of the bispecific antibody of the invention are different from each other, whereas the light chain variable regions are preferably the same in the bispecific antibodies of the invention, i.e. the bispecific antibodies of the invention are preferably composed of two parental antibodies that have the same light chain (i.e. common light chain antibodies). A bispecific antibody wherein the different heavy chain variable regions are associated with the same, or a common, light chain is also referred to as a bispecific antibody with a common light chain. Further provided is therefore a bispecific antibody according to the invention, wherein both arms comprise a common light chain.

Preferred bispecific antibodies can be obtained by co-expression of two different heavy chains and a common light chain in a single cell. When wildtype CH3 domains are used, co-expression of two different heavy chains and a common light chain will result in three different species, AA, AB and BB. To increase the percentage of the desired bispecific product (AB) CH3 engineering can be employed, or in other words, one can use heavy chains with compatible hetero-dimerization domains as defined hereunder.

The term 'compatible hetero-dimerization domains' as used herein refers to protein domains that are engineered such that engineered domain A' will preferentially form hetero-dimers with engineered domain B' and vice versa, whereas homo-dimerization between A'-A' and B'-B' is disfavoured.

The term "common light chain" according to the invention refers to light chains which may be identical or have some amino acid sequence differences while the binding specificity of the full-length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms "common light chain", 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998, Nissim et al. 1994). Preferably, the common light chain has a germline sequence. A preferred germline sequence is a light chain variable region that is frequently used in the human repertoire and has good thermodynamic stability, yield and solubility. A preferred germline light chain is based on O12, preferably it is the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org). Further provided is therefore a bispecific antibody according to the invention, wherein said common light chain is a germline light chain, preferably a rearranged germline human kappa light chain comprising the IgVK1-39 gene segment, most preferably the rearranged germline human kappa light chain IgVK1-39*01/IGJK1*01. The terms rearranged germline human kappa light chain IgVκ1-39*01/IGJκ1*01, IGKV1-39/IGKJ1, huVκ1-39 light chain or in short huVκ1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain of the present invention can also be a light chain as specified herein above, having 1-5 amino acid insertions, deletions, substitutions or a combination thereof.

Also contemplated are antibodies wherein a VH is capable of specifically recognizing a first antigen and the VL, paired with the VH in a immunoglobulin variable domain, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer et al (Cancer Cell 20, 472-486, October 2011), are different from bispecific antibodies of the invention and are further referred to as "two-in-one antibodies". Such "two-in-one" antibodies have identical arms and are not antibodies of the present invention.

EGFR is a member of a family of four receptor tyrosine kinases (RTKs), named Her- or cErbB-1, -2, -3 and -4. The EGFR has an extracellular domain (ECD) that is composed of four sub-domains, two of which are involved in ligand binding and one of which is involved in homo-dimerisation and hetero-dimerisation[1,2] (for review, see Ref. 3). The reference numbers used in this section refer to the numbering of the references in the list headed "References cited in the specification". EGFR integrates extracellular signals from a variety of ligands to yield diverse intracellular responses.[4,5] The major signal transduction pathway activated by EGFR is composed of the Ras-mitogen-activated protein kinase (MAPK) mitogenic signalling cascade. Activation of this pathway is initiated by the recruitment of Grb2 to tyrosine phosphorylated EGFR.[6,7] This leads to activation of Ras through the Grb2-bound Ras-guanine nucleotide exchange factor Son of Sevenless (SOS). In addition, the PI3-kinase-Akt signal transduction pathway is also activated by EGFR, although this activation is much stronger in case there is co-expression of Her3.[8,9] The EGFR is implicated in several human epithelial malignancies, notably cancers of the breast, bladder, non-small cell lung cancer lung, colon, ovarian head and neck and brain.[10] Activating mutations in the gene have been found, as well as over-expression of the receptor and of its ligands, giving rise to autocrine activation loops (for review, see Ref. 11). This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients.[12] Database accession numbers for the human EGFR protein and the gene encoding it are (GenBank NM_005228.3). The accession number is primarily given to provide a further method of identification of EGFR protein as a target, the actual sequence of the EGFR protein bound by an antibody may vary, for instance because of a mutation in the encoding gene such as those occurring in some cancers or the like. Where reference herein is made to EGFR, the reference refers to human EGFR unless otherwise stated. The antigen-binding site that binds EGFR, binds EGFR and a variety of variants thereof such as those expressed on some EGFR positive tumors.

The term 'ErbB-3' as used herein refers to the protein that in humans is encoded by the ERBB3 gene. Alternative names for the gene or protein are HER3; LCCS2; MDA-BF-1; c-ErbB-3; c-ErbB3; ErbB3-S; p180-ErbB3; p45-sErbB3; and p85-sErbB3. Where reference is made herein to ErbB-3, the reference refers to human ErbB-3. An antibody comprising an antigen-binding site that binds ErbB-3, binds human ErbB-3. The ErbB-3 antigen-binding site may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11, NC_018923.2, NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive tumor cells. The antigen-binding site that binds ErbB-3 preferably binds domain III of ErbB-3. In a preferred embodiment the affinity (KD) of an antigen-binding site for an ErbB-3 positive cell is lower than or equal to 2.0 nM, more preferably lower than or equal to 1.5 nM, more preferably lower than or equal to 1.39 nM, more preferably lower than or equal to 0.99 nM. In a preferred embodiment, an antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein. In one preferred embodiment, the affinity (KD) of an antigen-binding site for ErbB-3 on SK-BR-3 cells is lower than or equal to 2.0 nM, more preferably lower than or equal to 1.5 nM, more preferably lower than or equal to 1.39 nM, preferably lower than or equal to 0.99 nM. In one embodiment, said affinity (KD) is within the range of 1.39-0.59 nM. In one preferred embodiment, the affinity (KD) an antigen-binding site for ErbB-3 on BT-474 cells is lower than or equal to 2.0 nM, more preferably lower than or equal to 1.5 nM, more preferably lower than or equal to 1.0 nM, more preferably lower than 0.5 nM, more preferably lower than or equal to 0.31 nM, more preferably lower than or equal to 0.23 nM. In one embodiment, said affinity (KD) is within the range of 0.31-0.15 nM. The above-mentioned affinities are preferably as measured using steady state cell affinity measurements, wherein cells are incubated at 4° C. using radioactively labeled antibody, where after cell-bound radioactivity is measured, as described in the Examples.

An antigen-binding site that binds at least one amino acid of domain III of ErbB-3 preferably binds an amino acid selected from the group consisting of R426 and surface-exposed amino acid residues that are located within 11.2 Å from R426 in the native ErbB-3 protein. The amino acid residue numbering is that of Protein Data Bank (PDB) ID #4P59. As shown in the Examples, antibodies binding this region of domain III of ErbB-3 exhibit particularly good binding characteristics and they are capable of counteracting an activity of ErbB-3 on ErbB-3 positive cells. The term "surface-exposed amino acid residues that are located within 11.2 Å from R426 in the native ErbB-3 protein" refers to amino acid residues that are in the tertiary structure of the ErbB-3 protein spationally positioned within 11.2 Å from R426 and that are at least in part exposed to the outside of the protein, so that they can be reached by antibodies. Preferably, said amino acid residues that are located within 11.2 Å from R426 in the native ErbB-3 protein are selected from the group consisting of L423, Y424, N425, G427, G452, R453, Y455, E480, R481, L482, D483 and K485 (see for instance FIG. 16 and Table 8). In one preferred embodiment, a bispecific antibody according to the invention is provided, wherein said antibody comprises an antigen-binding site that binds at least R426 of domain III of ErbB-3. Preferably, said antibody comprises an antigen-binding site that binds at least R426 of domain III of ErbB-3.

The invention further provides a bispecific antibody comprising an antigen-binding site that binds at least R426 of domain III of ErbB-3. Preferably, said antibody comprises an antigen-binding site that binds at least R426 of domain III of ErbB-3. Preferably said antibody further comprises a variable region as depicted in FIG. 11B. In a preferred embodiment the antibody further comprises a binding site for EGFR. The variable region preferably comprises a sequence as depicted in FIG. 11a.

A bispecific antibody of the invention preferably has improved ADCC activity. One technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to the invention, which is afucosylated. Alternatively, or additionally, multiple other strategies can be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIb. A bispecific antibody of the invention is preferably afucosylated in order to enhance ADCC activity. A bispecific antibody of the invention preferably comprises a reduced amount of fucosylation of the N-linked carbohydrate structure in the Fc region, when compared to the same antibody produced in a normal CHO cell.

The invention provides a bispecific antibody comprising a first antigen-binding site that binds EGFR and a second antigen-binding site that binds ErbB-3, wherein the antibody has a half maximal growth inhibitory concentration (IC50)

of less than 200 pM for inhibiting EGFR and/or ErbB-3 ligand induced growth of BxPC3 cells (ATCC CRL-1687) or BxPC3-luc2 cells (Perkin Elmer 125058). Said antibody preferably has an IC50 for inhibiting EGFR and/or ErbB-3 ligand induced growth of BxPC3 cells (ATCC CRL 1687) or BxPC3-luc2 cells (Perkin Elmer 125058) of less than 100 pM, preferably less than 50 pM, more preferably less than 20 pM. An antibody of the invention preferably has an IC50 of more than 1 pM for inhibiting EGFR and/or ErbB-3 ligand induced growth of BxPC3 cells (ATCC CRL 1687) or BxPC3-luc2 cells (Perkin Elmer 125058).

The invention further provides a bispecific comprising a first antigen-binding site that binds EGFR and a second antigen-binding site that binds ErbB-3, wherein the antibody has a half maximal growth inhibitory concentration (IC50) for inhibiting EGFR and/or ErbB-3 ligand induced growth of BxPC3 cells (ATCC CRL-1687) or BxPC3-luc2 cells (Perkin Elmer 125058) that is lower than the IC50 of the antibody MEHD7945A for inhibiting growth of these cells under otherwise the same conditions. The anti-EGFR/anti-HER3 antibody MEHD7945A is described in WO2010/108127. Preferably the IC50 for inhibiting EGFR and/or ErbB-3 ligand induced growth of BxPC3 cells or BxPC3-luc2 cells of an antibody of the invention is lower than 90% of the IC50 of MEHD7945A for inhibiting growth of these cells under otherwise the same conditions, preferably lower than 80%, more preferably lower than 60%, more preferably lower than 50%, more preferably lower than 40%, more preferably lower than 30%, more preferably lower than 20%, more preferably lower than 10% of the IC50 of the antibody MEHD7945A. An antibody of the invention preferably has an IC50 for inhibiting EGFR and/or ErbB-3 ligand induced growth of BxPC3 cells (ATCC CRL 1687) or BxPC3-luc2 cells (Perkin Elmer 125058) of more than 1% of the IC50 of the antibody MEH D7945A for inhibiting growth of these cells under otherwise the same conditions. An antibody of the invention preferably has the indicated IC50 for inhibiting EGFR and ErbB-3 ligand induced growth of BxPC3 cells (ATCC CRL 1687) or BxPC3-luc2 cells (Perkin Elmer 125058).

An antibody that is effective at relatively low concentrations of the antibody is preferred in the present invention. Such an antibody can be provided in lower amounts and/or with a lower frequency of administration making the utility of the antibody more economic. An antibody that is effective at relatively low concentrations of the antibody more effectively inhibits proliferation of tumor cells in vivo, particularly at lower concentrations. Such an antibody also has a better therapeutic window, and can be administered less frequently or with longer administration intervals.

EGFR and ErbB-3 each can bind a number of ligands and stimulate growth of BxPC3 cells or BxPC3-luc2 cells. In the presence of a ligand for one or both receptors the growth of BxPC3 or BxPC3-luc2 cells is stimulated. EGFR and/or ErbB-3 ligand-induced growth of BxPC3 cells can be measured by comparing the growth of the cells in the absence and presence of the ligand. The preferred EGFR ligand for measuring EGFR ligand-induced growth of BxPC3 or BxPC3-luc2 cells is EGF. The preferred ErbB-3 ligand for measuring ErbB-3 ligand-induced growth of BxPC3 or BxPC3-luc2 cells is NRG1. The ligand-induced growth is preferably measured using saturating amounts of ligand. In a preferred embodiment EGF is used in an amount of 100 ng/ml of culture medium. NRG1 is preferably used in 10 ng/ml of culture medium. It is preferred that the half maximal growth inhibitory concentration (IC50) is measured on EGFR and ErbB-3 ligand induced BxPC3 or BxPC3-luc2 cells. It is preferred that EGF is the EGFR-ligand in this assay and that NRG1 is the ErbB-3 ligand. A suitable test for the IC50 assay is described in the examples.

In the presence of excess ErbB-2, ErbB-2/ErbB-3 hetero-dimers may provide a growth signal to the expressing cell in the absence of detectable ligand for the ErbB-3 chain in the hetero-dimer. This ErbB-3 receptor function is herein referred as a ligand-independent receptor function of ErbB-3. The ErbB-2/ErbB-3 hetero-dimer also provide a growth signal to the expressing cell in the presence an ErbB-3 ligand. This ErbB-3 receptor function is herein referred to as a ligand-induced receptor function of ErbB-3.

EGF and NRG1 are preferably the EGF and NRG1 of R&D systems, cat. nr. 396-HB and 236-EG as described in the examples.

An antibody of the invention comprising an antigen-binding site that binds ErbB-3 preferably can reduce a ligand-induced receptor function of ErbB-3 on a ErbB-3 positive cell. The antibody is capable of reducing ErbB-3 signaling via dimerization with EGFR. The antibody is capable of reducing ErbB-3 signaling via ErbB-2. The ErbB-3 positive cell is preferably also positive for ErbB-2. The ErbB-3 positive cell is preferably also positive for EGFR. The ligand-induced receptor function of ErbB-3 is preferably ErbB-3 ligand-induced growth of an ErbB-2 and ErbB-3 positive cell. In a preferred embodiment the ErbB-2 and ErbB-3 positive cell comprises at least 50.000 ErbB-2 receptors on the cell surface. In a preferred embodiment at least 100.000 ErbB-2 receptors. In a preferred embodiment the ErbB-2 and ErbB-3 positive cell comprises no more than 1.000.000 ErbB-2 receptors on the cell surface. In a preferred embodiment the ErbB-2 and ErbB-3 positive cell comprises more than 1.000.000 ErbB-2 receptors on the cell surface. In a preferred embodiment said ErbB-2 and ErbB-3 positive cell is an BxPC3 cell (ATCC CRL-1687), a or BxPC3-luc2 cell (Perkin Elmer 125058); an MCF-7 cell (ATCC® HTB-22™), an SKBR3 cell (ATCC® HTB-30™) an NCI-87 cell (ATCC® CRL-5822™) or an A431 cell (ATCC® CRL-1555™). Preferably said ErbB-2 and ErbB-3 positive cell is also EGFR positive. Said ErbB-2 and ErbB-3 positive cell is preferably a BxPC3 or BxPC3-luc2 cell as indicated herein above.

As used herein the ligand-induced receptor function is reduced by at least 20%, preferably at least 30, 40, 50 60, or at least 70% in a particularly preferred embodiment the ligand-induced receptor function is reduced by 80, more preferably by 90%. The reduction is preferably determined by determining a ligand-induced receptor function in the presence of a bispecific antibody of the invention, and comparing it with the same function in the absence of the antibody, under otherwise identical conditions. The conditions comprise at least the presence of an ErbB-3 ligand. The amount of ligand present is preferably an amount that induces half of the maximum growth of an ErbB-2 and ErbB-3 positive cell line. The ErbB-2 and ErbB-3 positive cell line for this test is preferably the BxPC3 or BxPC3-luc2 cell as indicated herein above. The test and/or the ligand for determining ErbB-3 ligand-induced receptor function is preferably a test for ErbB-3 ligand induced growth reduction as specified in the examples.

An antibody of the invention comprising an antigen-binding site that binds ErbB-3, preferably interferes with binding of an ErbB-3 ligand to ErbB-3. Such antibodies are more effective in reducing ligand induced growth of BxPC3 or BxPC3-luc2 cells particularly in the context of an antibody that also comprises an antigen-binding site that binds EGFR.

The term "ErbB-3 ligand" as used herein refers to polypeptides which bind and activate ErbB-3. Examples of ErbB-3 ligands include, but are not limited to neuregulin 1 (NRG1) and neuregulin 2 (NRG2) (for review Olayioye M A et al.; EMBO J (2000) Vol 19: pp 3159-3167). The term includes biologically active fragments and/or variants of a naturally occurring polypeptide.

The term "EGFR ligand" as used herein refers to polypeptides which bind and activate EGFR. Examples of EGFR ligands include, but are not limited to EGF, TGF-α, HB-EGF, amphiregulin, betacellulin and epiregulin (for review Olayioye M A et al.; EMBO J (2000) Vol 19: pp 3159-3167). The term includes biologically active fragments and/or variants of a naturally occurring polypeptide The first antigen-binding site of an antibody of the invention preferably binds domain I or domain III of EGFR. Preferably said antibody binds domain III of EGFR. The antibody preferably inhibits EGF induced proliferation of BxPC3 or BxPC3-luc2 cells.

A bispecific antibody of the invention preferably comprises antibody-dependent cell-mediated cytotoxicity (ADCC). An antibody that has a low intrinsic ADCC activity can be provided with additional ADCC activity. The antibody can be engineered to enhance the ADCC activity (for review, see Cancer Sci. 2009 September; 100(9):1566-72. Engineered therapeutic antibodies with improved effector functions. Kubota T, Niwa R, Satoh M, Akinaga S, Shitara K, Hanai N). Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are co-incubated with the antibody-labeled target cells. Target cell lysis is subsequently measured by release of intracellular label by a scintillation counter or spectrophotometry. A preferred test is detailed in the examples. A bispecific antibody of the invention is preferably afucosylated. A bispecific antibody of the invention preferably comprises a reduced amount of fucosylation of the N-linked carbohydrate structure in the Fc region, when compared to the same antibody produced in a normal CHO cell.

A bispecific antibody of the present invention is preferably used in humans. To this end an antibody of the invention is preferably a human or humanized antibody.

Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention is preferably a human constant region. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR regions. The variable region of an EGFR binding VH, an ErbB-3 binding VH, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope. Deimmunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A bispecific antibody according to the invention preferably comprises a constant region of a human antibody. According to differences in their heavy chain constant domains, antibodies are grouped into five classes, or isotypes: IgG, IgA, IgM, IgD, and IgE. Those classes or isotypes comprise at least one of said heavy chains that is named with a corresponding Greek letter. In a preferred embodiment the invention provides an antibody according to the invention wherein said constant region is selected from the group of IgG, IgA, IgM, IgD, and IgE constant regions, more preferably said constant region comprises an IgG constant region, more preferably an IgG1 constant region, preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region.

The invention in one embodiment provides an antibody comprising a variable domain that binds EGFR, wherein said antibody comprises at least the CDR3 sequence of an EGFR specific heavy chain variable region selected from the group consisting of MF3998; MF4280; MF4002; MF4003; MF4010; MF4289; MF3370; MF3751; MF3752 as depicted in FIG. 11A, or wherein said antibody comprises a heavy chain CDR3 sequence that differs in at most three, preferably in at most two, preferably in no more than one amino acid from a CDR3 sequence of a VH selected from the group consisting of MF3998; MF4280; MF4002; MF4003; MF4010; MF4289; MF3370; MF3751; MF3752 as depicted in FIG. 11A. Said antibody preferably comprises at least the CDR3 sequence of MF3998; MF4280; MF4003; MF4010; MF4289; or MF3370 as depicted in FIG. 11A.

Said antibody preferably comprises at least the CDR1, CDR2 and CDR3 sequences of an EGFR specific heavy chain variable region selected from the group consisting of MF3998; MF4280; MF4002; MF4003; MF4010; MF4289; MF3370; MF3751; MF3752 as depicted in FIG. 11A, or heavy chain CDR1, CDR2 and CDR3 sequences that differ in at most three, preferably in at most two, preferably in at most one amino acid from the CDR1, CDR2 and CDR3 sequences of EGFR specific heavy chain variable region selected from the group consisting of MF3998; MF4280; MF4002; MF4003; MF4010; MF4289; MF3370; MF3751; MF3752 as depicted in FIG. 11A. Said antibody preferably comprises at least the CDR1, CDR2 and CDR3 sequences of MF3998; MF4280; MF4003; MF4010; MF4289; or MF3370 as depicted in FIG. 11A.

The invention also provides an antibody comprising a variable domain that binds ErbB-3, wherein said antibody comprises at least the CDR3 sequence of an ErbB-3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 1113, or wherein said antibody comprises a heavy chain CDR3 sequence that differs in at most three, preferably in at most two, preferably in no more than one amino acid from a CDR3 sequence of a VH selected from the group consisting of MF3178, MF3176, MF3163, MF3307, MF6055-MF6074, preferably MF3178, MF3176, MF3163, MF6058, MF6061 or MF6065 as depicted in FIG. 11B. Said antibody preferably comprises at least the CDR3 sequence of MF3178, MF3176 or MF3163, most preferably at least the CDR3 sequence of MF3178. Said antibody preferably comprises at least the CDR1, CDR2 and CDR3 sequences of an ErbB 3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 11B, or heavy chain CDR1, CDR2 and CDR3 sequences that differ in at most three, preferably in at most two, preferably in at most one amino acid from the CDR1, CDR2 and CDR3 sequences of MF3178, MF3176, MF3163, MF3307, MF6055-MF6074, preferably MF3178, MF3176, MF3163, MF6058, MF6061 or MF6065. Said antibody preferably comprises at least the CDR1, CDR2 and CDR3 sequences of MF3178, MF3176 or MF3163, most preferably at least the CDR1, CDR2 and CDR3 sequence of MF3178.

The invention in one embodiment provides a bispecific antibody comprising a first antigen-binding site that binds EGFR and a second antigen-binding site that binds ErbB-3, wherein said first antigen-binding site comprises at least the CDR3 sequence of an EGFR specific heavy chain variable region selected from the group consisting of MF3998; MF4280; MF4002; MF4003: MF4010; MF4289; MF3370; MF3751; MF3752 as depicted in FIG. 11A, or a heavy chain CDR3 sequence that differs in at most three, preferably in at most two, preferably in no more than one amino acid from a CDR3 sequence of a VH selected from the group consisting of MF3998; MF4280; MF4002; MF4003; MF4010; MF4289; MF3370; MF3751; MF3752 as depicted in FIG. 11A, and wherein said second antigen-binding site comprises at least the CDR3 sequence of an ErbB 3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 16B or FIG. 16E, or a heavy chain CDR3 sequence that differs in at most three, preferably in at most two, preferably in no more than one amino acid from a CDR3 sequence of a VH selected from the group consisting of M F3178, M F3176, M F3163, M F3307, M F6055-M F6074, preferably M F3178, MF3176, MF3163, MF6058, MF6061 or MF6065 as depicted in FIG. 11B. Said first antigen-binding site preferably comprises at least the CDR3 sequence of MF3998; MF4280; MF4003; MF4010; MF4289; or MF3370 as depicted in FIG. 11A and said second antigen-binding site preferably comprises at least the CDR3 sequence of MF3178, MF3176 or MF3163, most preferably at least the CDR3 sequence of MF3178 of FIG. 11B. Said first antigen-binding site preferably comprises at least the CDR1, CDR2 and CDR3 sequences of an EGFR specific heavy chain variable region selected from the group consisting of MF3998; MF4280; MF4003; MF4010; MF4289; or MF3370 as depicted in FIG. 11A, or heavy chain CDR1, CDR2 and CDR3 sequences that differ in at most three, preferably in at most two, preferably in at most one amino acid from the CDR1, CDR2 and CDR3 sequences of MF3998; MF4280; MF4003; MF4010; MF4289; or MF3370 as depicted in FIG. 11A, and said second antigen-binding site preferably comprises at least the CDR1, CDR2 and CDR3 sequences of an ErbB 3 specific heavy chain variable region selected from the group consisting of MF3178, MF3176, MF3163, MF3307, MF6055-MF6074, preferably MF3178, MF3176, MF3163, MF6058, MF6061 or MF6065 as depicted in FIG. 11B, or heavy chain CDR1, CDR2 and CDR3 sequences that differ in at most three, preferably in at most two, preferably in at most one amino acid from the CDR1, CDR2 and CDR3 sequences of MF3178, MF3176, MF3163, MF3307, MF6055-MF6074, preferably MF3178, MF3176, MF3163, MF6058, MF6061 or MF6065. Said first antigen-binding site preferably comprises at least the CDR1, CDR2 and CDR3 sequences of MF3998; MF4280; MF4003; MF4010; MF4289; or MF3370 as depicted in FIG. 11A, and said second antigen-binding site preferably comprises at least the CDR1, CDR2 and CDR3 sequences of MF3178, MF3176 or MF3163, most preferably at least the CDR1, CDR2 and CDR3 sequence of MF3178.

A preferred embodiment provides a bispecific antibody comprising a first antigen-binding site that binds EGFR and a second antigen-binding site that binds ErbB-3, wherein said first antigen-binding site comprises at least the CDR3 sequence of MF3998 as depicted in FIG. 11A, or a CDR3 sequence that differs in at most three, preferably in at most two, preferably in no more than one amino acid from the CDR3 sequence of MF3998 as depicted in FIG. 11A, and wherein said second antigen-binding site comprises at least the CDR3 sequence of M F3178, or a CDR3 sequence that differs in at most three, preferably in at most two, preferably in no more than one amino acid from the CDR3 sequence of MF3178.

The invention in one embodiment provides a bispecific antibody comprising a first antigen-binding site that binds EGFR and a second antigen-binding site that binds ErbB-3, wherein said first antigen-binding site comprises at least the CDR1, CDR2 and CDR3 sequences of MF3998, or CDR1, CDR2 and CDR3 sequences that differ in at most three, preferably in at most two, preferably in at most one amino acid from the CDR1, CDR2 and CDR3 sequences of MF3958, and wherein said second antigen-binding site comprises at least the CDR1, CDR2 and CDR3 sequence of MF3178, or CDR1, CDR2 and CDR3 sequences that differ in at most three, preferably in at most two, preferably in at most one amino acid from the CDR1, CDR2 and CDR3 sequences of MF3178.

The invention in one embodiment provides a bispecific antibody comprising a first antigen-binding site that binds EGFR and a second antigen-binding site that binds ErbB-3, wherein said first antigen-binding site comprises at least the CDR3 sequence of MF3998 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3998 and wherein said second antigen-binding site comprises at least the CDR1, CDR2 and CDR3 sequence of MF3178.

The invention in one embodiment provides a bispecific antibody comprising a first antigen-binding site that binds EGFR and a second antigen-binding site that binds ErbB-3, wherein said first antigen-binding site comprises at least the CDR3 sequence of MF4280 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF4280 and wherein said second antigen-binding site comprises at least the CDR1, CDR2 and CDR3 sequence of MF3178.

CDR sequences are for instance varied for optimization purposes, preferably in order to improve binding efficacy or the stability of the antibody. Optimization is for instance performed by mutagenesis procedures where after the stability and/or binding affinity of the resulting antibodies are preferably tested and an improved EGFR or ErbB 3-specific CDR sequence is preferably selected. A skilled person is well capable of generating antibody variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

The invention in one embodiment provides an antibody comprising a variable domain that binds EGFR, wherein the VH chain of said variable domain comprises the amino acid sequence of VH chain MF3998; MF4280; MF4002; MF4003; MF4010; MF4289; MF3370; MF3751; MF3752 as depicted in FIG. 11A; or comprises the amino acid sequence of VH chain MF3998; MF4280; MF4002; MF4003; MF4010; MF4289; MF3370; MF3751; MF3752 depicted in FIG. 11A having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11A. Said antibody preferably comprises a variable domain that binds EGFR, wherein the VH chain of said variable domain comprises the amino acid sequence of VH chain MF3998; MF4280; MF4003; MF4010; MF4289; or MF3370 as depicted in FIG. 11A; or comprises the amino acid sequence of VH chain MF3998; MF4280; MF4003; MF4010; MF4289; or MF3370 as depicted in FIG. 11A having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11A. An antibody comprising a variable domain that binds EGFR, preferably further comprises a variable domain that binds ErbB-3. The antibody comprising a variable domain that binds EGFR is preferably a bispecific antibody that preferably further comprises a variable domain that binds ErbB-3. The VH chain of the variable domain that binds Erb-B3 preferably comprises the amino acid sequence of VH chain MF3178; MF3176; MF3163; MF3307, MF6055-MF6074, preferably MF3178, MF3176, MF3163, MF6058, MF6061 or MF6065 as depicted in FIG. 11B; or comprises the amino acid sequence of VH MF3178; MF3176; MF3163; MF3307, MF6055-MF6074, preferably MF3178, MF3176, MF3163, MF6058, MF6061 or MF6065 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. The VH chain of the variable domain that binds Erb-B3 preferably comprises the amino acid sequence of MF3178, MF3176 or MF3163; or comprises the amino acid sequence of MF3178, MF3176 or MF3163 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the respective VH chain sequence of FIG. 11A. In a preferred embodiment the VH chain of the variable domain that binds ErbB-3 comprises the amino acid sequence of MF3178; or comprises the amino acid sequence of MF3178 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence.

Preferably, the mentioned amino acid insertions, deletions and substitutions in a VH or VL as specified herein are not present in the CDR3 region. The mentioned amino acid insertions, deletions and substitutions are also preferably not present in the CDR1 and CDR2 regions. The mentioned amino acid insertions, deletions and substitutions are also preferably not present in the FR4 region.

The invention further provides an antibody comprising a variable domain that binds ErbB-3, wherein the VH chain of said variable region comprises the amino acid sequence of VH chain MF3178; MF3176; MF3163 or MF3307 as depicted in FIG. 11B, or comprises the amino acid sequence of VH MF3178; MF3176; MF3163; MF3307; MF6055-MF6074, preferably MF3178, MF3176, MF3163, MF6058, MF6061 or MF6065 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. The VH chain of the variable domain that binds ErbB3 preferably comprises the amino acid sequence of VH chain MF3178, MF3176 or MF3163; or comprises the amino acid sequence of VH chain MF3178, MF3176 or MF3163 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. In a preferred embodiment the VH chain of the variable domain that binds ErbB-3 comprises the amino acid sequence of VH chain MF3178 depicted in FIG. 11B; or comprises the amino acid sequence of VH chain MF3178 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence. The antibody preferably further comprises a variable domain that binds EGFR. The VH chain of the variable domain that binds EGFR preferably comprises an amino acid sequence of VH chain of FIG. 11A.

Further provided is an antibody according to the invention, wherein said antibody comprises an EGFR specific heavy chain variable region sequence selected from the group consisting of the heavy chain variable region sequences of MF3998; MF4280; MF4002; MF4003; MF4010; MF4289; MF3370; MF3751; MF3752 as depicted in FIG. 11A, or wherein said antibody comprises a heavy chain variable region sequence that differs in at most 15 amino acids from the heavy chain variable region sequences of MF3998; MF4280; MF4002; MF4003; MF4010; MF4289; MF3370; MF3751; MF3752 as depicted in FIG. 11A.

Further provided is an antibody according to the invention, wherein said antibody comprises an ErbB 3 specific heavy chain variable region sequence selected from the group consisting of the heavy chain variable region sequences of MF3178, MF3176, MF3163, MF3307, MF6055-MF6074, preferably MF3178, M F3176, M F3163, M F6058, M F6061 or M F6065 as depicted in FIG. 11B, or wherein said antibody comprises a heavy chain variable region sequence that differs in at most 15 amino acids from the heavy chain variable region sequences of MF3178, MF3176, MF3163, MF3307, MF6055-MF6074, preferably MF3178, MF3176, MF3163, MF6058, MF6061 or MF6065.

The invention further provides an antibody comprising two variable domains that each bind EGFR wherein a VH of the variable domains comprises the amino acid sequence of the VH chain MF3998; MF4280; MF4002; MF4003; MF4010; MF4289; MF3370; MF3751; MF3752 as depicted in FIG. 11A; or comprises the amino acid sequence of the VH chain MF3998; MF4280; MF4002; MF4003; MF4010; MF4289; MF3370; MF3751; MF3752 as depicted in FIG. 11A, wherein said VH-chain has at most 15, preferably 1, 2, 3, 4, 5, 6, 7, 8, 9 or 10 and preferably has 1, 2, 3, 4 or 5 amino acid insertions, deletions, substitutions or a combination thereof with respect to the VH chain sequence of FIG. 11A. Said VH preferably comprises the amino acid sequence of the VH chain MF3998; MF4280; MF4003; MF4010; MF4289; or MF3370 as depicted in FIG. 11A; or the amino acid sequence of the VH chain MF3998; MF4280; MF4003; MF4010; MF4289; or MF3370 as depicted in FIG. 11A, having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11A. The variable domains of the antibody preferably comprise identical VH chains, preferably having a sequence as depicted in FIG. 11A. An antibody with variable domains with identical VH chains is not a bispecific antibody. VH chains are identical for the present invention if they comprise the same VH chain sequence as depicted in FIG. 11, or the same VH chain sequence but for 1, 2, 3, 4 or 5 amino acid insertions, deletions, substitutions or a combination thereof with respect to the VH chain sequence of FIG. 11A.

The invention further provides an antibody comprising two variable domains that each bind ErbB3 wherein a VH of the variable domains comprises the amino acid sequence of VH chain MF3178; MF3176; MF3163 or MF3307 as depicted in FIG. 11B; or comprises the amino acid sequence of VH chain MF3178; MF3176; MF3163 or MF3307 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. Said VH preferably comprises the amino acid sequence of VH chain MF3178, MF3176 or MF3163; or comprises the amino acid sequence of VH chain MF3178, MF3176 or MF3163 depicted in FIG. 11B having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. Said VH preferably comprises the amino acid sequence of VH chain MF3178; or comprises the amino acid sequence of VH chain MF3178 depicted in FIG. 1113 having at most 15, preferably 1, 2, 3, 4, 5, 6, 7, 8, 9 or 10 and preferably having 1, 2, 3, 4 or 5 amino acid insertions, deletions, substitutions or a combination thereof with respect to the VH chain sequence of FIG. 11B. The variable domains of the antibody preferably comprise identical VH chains, preferably having a sequence as depicted in FIG. 11B. An antibody with variable domains with identical VH chains is not a bispecific antibody. The VH chains are identical if they comprise the same VH chain sequence as depicted in FIG. 11B, or the same VH chain sequence but for 1, 2, 3, 4 or 5 amino acid insertions, deletions, substitutions or a combination thereof with respect to the VH chain sequence of FIG. 11B.

The invention preferably provides an antibody comprising a variable domain that binds EGFR and a variable domain that binds ErbB-3,
wherein the VH chain of the variable domain that binds EGFR comprises
 the amino acid sequence of VH chain MF3998 as depicted in FIG. 11; or
 the amino acid sequence of VH chain MF3998 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ErbB-3 comprises
 the amino acid sequence of VH chain MF3178 as depicted in FIG. 11; or
 the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3,
wherein the VH chain of the variable domain that binds EGFR comprises
 the amino acid sequence of VH chain MF4280 as depicted in FIG. 11; or
 the amino acid sequence of VH chain MF4280 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and
wherein the VH chain of the variable domain that binds ErbB-3 comprises
 the amino acid sequence of VH chain MF3178 as depicted in FIG. 11; or
 the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3, wherein the VH chain of the variable domain that binds EGFR comprises the amino acid sequence of VH chain MF4003 as depicted in FIG. 11; or the amino acid sequence of VH chain MF4003 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3178 as depicted in FIG. 11; or the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3,
wherein the VH chain of the variable domain that binds EGFR comprises the amino acid sequence of VH chain MF4010 as depicted in FIG. 11; or the amino acid sequence of VH chain MF4010 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3178 as depicted in FIG. 11; or the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3,
wherein the VH chain of the variable domain that binds EGFR comprises the amino acid sequence of VH chain MF4289 as depicted in FIG. 11; or the amino acid sequence of VH chain MF4289 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3178 as depicted in FIG. 11; or the amino acid sequence of VH chain MF3178 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH.

The invention preferably provides an antibody comprising a variable domain that binds EGFR and a variable domain that binds ErbB-3,
wherein the VH chain of the variable domain that binds EGFR comprises the amino acid sequence of VH chain MF3370 as depicted in FIG. 11; or the amino acid sequence of VH chain MF3370 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH; and wherein the VH chain of the variable domain that binds ErbB-3 comprises the amino acid sequence of VH chain MF3163 as depicted in FIG. 11; or the amino acid sequence of VH chain MF3163 as depicted in FIG. 11 having at most 15, preferably 1, 2, 3, 4, 5, 6, 7, 8, 9 or 10 and preferably having 1, 2, 3, 4 or 5 amino acid insertions, deletions, substitutions or a combination thereof with respect said VH. This antibody binds to human EGFR and murine EGFR and can be used to study target effects in mice.

When compared to the sequence in FIG. 11, the behavior of a VH chain typically starts to become noticeably different when it has more than 15 amino acid changes with respect to the amino acid sequence of a VH chain as depicted in FIG. 11. A VH chain having at most 15, preferably 1, 2, 3, 4, 5, 6, 7, 8, 9 or 10 amino acid insertions, deletions, substitutions or a combination thereof with respect to the VH chain depicted in FIG. 11, preferably has 1, 2, 3, 4 or 5 amino acid insertions, deletions, substitutions or a combination thereof with respect to the VH chain depicted in FIG. 11, preferably 1, 2, 3 or 4 insertions, deletions, substitutions or a combination thereof, preferably 1, 2 or 3 insertions, deletions, substitutions or a combination thereof, more preferably 1 or 2 insertions, deletions, substitutions or a combination thereof, and preferably 1 insertion, deletion, substitution or a combination thereof with respect to the VH chain depicted in FIG. 11. The one or more amino acid insertions, deletions, substitutions or a combination thereof are preferably not in the CDR1, CDR2 and CDR3 region of the VH chain. They are also preferably not present in the Fr4 region. An amino acid substitution is preferably a conservative amino acid substitution.

In a preferred embodiment the invention provides an antibody that has a heavy chain comprising an amino acid sequence as depicted in FIG. 11D, or an amino acid sequence of FIG. 11D having at most 15, preferably 1, 2, 3, 4, 5, 6, 7, 8, 9 or 10 and preferably having 1, 2, 3, 4 or 5 amino acid insertions, deletions, substitutions or a combination thereof with respect to the sequence of FIG. 11D. In a preferred embodiment the antibody has two heavy chains each comprising an amino acid sequence as depicted in FIG. 11*l*), or an amino acid sequence of FIG. 11D having at most 15, preferably 1, 2, 3, 4, 5, 6, 7, 8, 9 or 10 and preferably having 1, 2, 3, 4 or 5 amino acid insertions, deletions, substitutions or a combination thereof with respect to the sequence of FIG. 11D. The at most 15, preferably 1, 2, 3, 4, 5, 6, 7, 8, 9 or 10 and preferably 1, 2, 3 4 or 5 amino acid substitutions are preferably conservative amino acid substitutions. The insertions, deletions, substitutions or a combination thereof are preferably not in the CDR3 region of the VH chain, preferably not in the CDR1, CDR2 and CDR3 region of the VH chain and preferably not in the FR4 region.

Rational methods have evolved toward minimizing the content of non-human residues in the human context. Various methods are available to successfully graft the antigen-binding property of an antibody onto another antibody. The binding properties of antibodies rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein. The invention therefore further provides a human or humanized bispecific antibody comprising a first antigen-binding site that binds EGFR and a second antigen-binding site that binds ErbB-3, wherein the variable domain comprising the EGFR binding site comprises a VH CDR3 sequence as depicted in FIG. 11A, and wherein the variable domain comprising the ErbB-3 binding site comprises a VH CDR3 region as depicted in FIG. 11B. The VH variable region comprising the EGFR binding site preferably comprises the sequence of the CDR1 region, CDR2 region and the CDR3 region of a VH chain in FIG. 11A. The VH variable region comprising the ErbB-3 binding site preferably comprises the sequence of the CDR1 region, CDR2 region and the CDR3 region of a VH chain in FIG. 11B. CDR grafting may also be used to produce a VH chain with the CDR regions of a VH of FIG. 11, but having a different framework. The different framework may be of another human VH, or of a different mammal.

The mentioned at most 15, preferably 1, 2, 3, 4, 5, 6, 7, 8, 9 or 10 and preferably 1, 2, 3, 4 or 5 amino acid substitutions are preferably conservative amino acid substitutions, the insertions, deletions, substitutions or a combination thereof are preferably not in the CDR3 region of the VH chain, preferably not in the CDR1, CDR2 or CDR3 region of the VH chain and preferably not in the FR4 region.

The light chain of a variable domain comprising a variable heavy chain sequence as depicted in FIG. 11, is preferably a germline light chain of or based on O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two different light chains. The ratio of bispecific antibody that is produced by the cell can be further improved by stimulating the pairing of two different heavy chains with each other over the pairing of two identical heavy chains. The art describes various ways in which such heterodimerization of heavy chains can be achieved. One way is to generate 'knob into hole' bispecific antibodies. See US Patent Application 20030078385 (Arathoon et al. Genentech). Another method is by using charge engineering as described in Gunasekaran (JBC 2010, vol 285, pp 19637-19646). Another and preferred method is described in U.S. provisional application 61/635,935, which has been followed up by U.S. regular application Ser. No. 13/866,747 and PCT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the stop of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that binds EGFR and that contains a 1st CH3 domain, and h) a second nucleic acid molecule encoding a heavy chain comprising an antigen-binding site that binds ErbB-3 and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it is the rearranged germline human kappa light chain IgVκ1 39*01I/IGJκ1*01, as described above. Means for preferential pairing of said $1^{st}$ and said $2^{nd}$ CH3 domain are preferably the corresponding mutations in the CH3 domain of the heavy chain coding regions. The preferred mutations to produce essentially only bispecific antibodies are the amino acid substitutions L351K and T366K (numbering according to Kabat) in the first CH3 domain and the amino acid substitutions L351D and L368E in the second CH3 domain, or vice versa. Further provided is therefore a method according to the invention for producing a bispecific antibody, wherein said first CH3 domain comprises the amino acid substitutions L351K and T366K (numbering according to Kabat) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH3 domain comprises the amino acid substitutions L351D and L368E (numbering according to Kabat) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

In one embodiment the invention provides a nucleic acid molecule encoding an antibody heavy chain variable region according to the invention. The nucleic acid molecule (typically an in vitro, isolated or recombinant nucleic acid molecule) preferably encodes a heavy chain variable region as depicted in FIG. 11A or FIG. 11B, or a heavy chain variable region as depicted in FIG. 11A or FIG. 11B having 1, 2, 3, 4 or 5 amino acid insertions, deletions, substitutions or combination thereof. In a preferred embodiment the nucleic acid molecule comprises a sequence as depicted in FIG. 11. In another preferred embodiment the nucleic acid molecule encodes the same amino acid sequence as the nucleic acid depicted in FIG. 11 but has a different sequence because it encodes one or more different codons. The invention further provides a nucleic acid sequence encoding a heavy chain of FIG. 11D.

A nucleic acid molecule as used in the invention is typically but not exclusively a ribonucleic acid (RNA) or a deoxyribonucleic acid (DNA). Alternative nucleic acids are available for a person skilled in the art. A nucleic acid according to the invention is for instance comprised in a cell. When said nucleic acid is expressed in said cell, said cell can produce an antibody according to the invention. Therefore, the invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a Chinese hamster ovary (CHO) cell, an NS0 cell or a PER-C6™ cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIG. 11. Preferably said nucleic acid molecule comprises a sequence as depicted in FIG. 11a or 11b.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

The invention further provides a pharmaceutical composition comprising an antibody according to the invention. The pharmaceutical composition preferably comprises a preferably pharmaceutically acceptable excipient or carrier. In a preferred embodiment the pharmaceutical composition comprises 5-50 mM Histidine, 100-300 mM Trehalose, 0.1-03 g/L PolySorbate20 or a combination thereof. The pH is preferably set at pH=5.5-6.5. In a preferred embodiment the pharmaceutical composition comprises 25 mM Histidine, 220 mM Trehalose, 0.2 g/L PolySorbate20 or a combination thereof. The pH is preferably set at pH=5.5-6.5, most preferably at pH=6.

An antibody of the invention preferably further comprises a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebraska).

The invention further provides a method for the treatment of a subject having an EGFR, ErbB-3 or EGFR/ErbB-3 positive tumor or at risk of having said tumor comprising administering to the subject an antibody or pharmaceutical composition according to the invention. Before start of said treatment, the method preferably comprises determining whether said subject has, or is at risk of, such EGFR, ErbB-3 or EGFR/ErbB-3 positive tumor. The invention further provides an antibody or pharmaceutical composition of the invention for use in the treatment of a subject having or at risk of having an EGFR, ErbB-3 or EGFR/ErbB-3 positive tumor.

To establish whether a tumor is positive for EGFR the skilled person can for instance determine the EGFR amplification and/or staining immune-histochemistry. At least 10% of the tumor cells in a biopt should be positive. The biopt can also contain 20%, 30% 40% 50% 60% 70% or more positive cells. To establish whether a tumor is positive for HER3 the skilled person can for instance determine the H E R3 amplification and/or staining in immunohistochemistry. At least 10% tumor cells in a biopt should be positive. The biopt can also contain 20%, 30% 40% 50% 60% 70% or more positive cells.

The tumor is preferably an EGFR, ErbB-3 or EGFR/ErbB-3 positive cancer. Preferably said positive cancer is a breast cancer, such as early-stage breast cancer. However, the invention can be applied to a wide range of EGFR, ErbB-3 or EGFR/ErbB-3 positive cancers, like breast cancer, colon cancer, pancreatic cancer, gastric cancer, ovarian cancer, colorectal cancer, head- and neck cancer, lung cancer including non-small cell lung cancer, bladder cancer and the like. The subject is preferably a human subject. The subject is preferably a subject eligible for antibody therapy using an EGFR specific antibody such as cetuximab. In a preferred embodiment the subject comprises a tumor, preferably an EGFR/ErbB-3 positive cancer, preferably a tumor/cancer with an EGFR monoclonal antibody resistant phenotype.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regime of cetuximab. The dosage can also be lower.

A bispecific antibody according to the invention preferably induces less skin toxicity as compared to cetuximab under otherwise similar conditions of course. A bispecific antibody according to the invention preferably produces less proinflammatory chemokines, preferably of CXCL14 as compared to cetuximab under otherwise similar conditions of course. A bispecific antibody according to the invention preferably induces less impairment of antimicrobial RNAses, preferably Rnase 7, as compared to cetuximab under otherwise similar conditions of course.

The present invention describes among others antibodies that target the EGFR and ErbB-3 receptors and result in potent proliferation inhibition of cancer cell lines in vitro and tumor growth inhibition in vivo. A diverse panel of human and Fab binding arms specific for either EGFR or ErbB-3 were identified. These were produced as bispecific antibodies by cloning them into complementary expression vectors that contain mutations in the CH3 region that drives hetero-dimerization of heavy chains. Many bispecific antibodies were produced at small scale and tested in binding and functional assays on cancer cell lines. Various bispecific antibodies were selected and tested in an orthotopic xenograft model using the BxPC3-luc2 cell line. This cell line expresses both the EGFR and ErbB-3 receptors and is partially dependent on the presence of an EGFR ligand and an ErbB-3 ligand for growth. BxPC3 models are a robust and stringent screening model. An antibody of the invention, particularly a bispecific antibody of the invention can combine low toxicity profiles with high efficacy. An antibody of the invention can be useful in various types and lines of EGFR-targeted therapies. An antibody of the invention can have an increased therapeutic window when compared to an antibody that binds the same antigen(s) with both arms. A bispecific antibody of the invention can exhibit better growth inhibitory effects in vitro, in vivo or a combination thereof when compared to the MEHD7945A antibody.

Preferred embodiments of the invention provide uses of antibodies according to the invention under heregulin stress conditions. Heregulin is a growth factor that is involved in growth of ErbB-3 positive tumor cells. Typically, when the tumor cells express high levels of heregulin (referred to as heregulin stress), currently known therapies like trastuzumab, pertuzumab and lapatinib are no longer capable of inhibiting tumor growth. This phenomenon is called heregulin resistance. Surprisingly, however, an antibody according to the invention is also capable of counteracting growth of tumor cells that express high levels of heregulin. As used herein, an expression level of heregulin is considered high if a cell has a heregulin expression level that is at least 60%, preferably at least 70%, more preferably at least 80%, more preferably at least 85%, more preferably at least 90% or 95% of the heregulin expression level of BXPC3 or MCF7 cells. Heregulin expression levels are for instance measured using qPCR with tumor RNA (such as for instance described in Shames et al. PLOS ONE, February 2013, Vol. 8, Issue 2, pp 1-10 and in Yonesaka et al., Sci. transl. Med., Vol. 3, Issue 99 (2011); pp 1-11), or using protein detection methods, like for instance ELISA, preferably using blood, plasma or serum samples (such as for instance described in Yonesaka et al., Sci. transl. Med., Vol. 3, Issue 99 (2011); pp 1-11).

Also provided is a method for counteracting the formation of a metastasis in a subject having a EGFR, ErbB-3 or EGFR/ErbB-3 positive tumor, wherein said EGFR, ErbB-3 or EGFR/ErbB-3 positive tumor has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds EGFR and a second antigen-binding site that binds ErbB-3. Also provided is a bispecific antibody comprising a first antigen-binding site that binds EGFR and a second antigen-binding site that binds ErbB-3 for use in the treatment or prevention of focal adhesion of a EGFR, ErbB-3 or EGFR/ErbB-3 positive tumor cell, or for use in the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of focal adhesion of a EGFR, ErbB-3 or EGFR/ErbB-3 positive tumor cell, or for the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Said EGFR, ErbB-3 or EGFR/ErbB-3 positive tumor is preferably breast cancer, colon cancer, pancreatic cancer, gastric cancer, ovarian cancer, colorectal cancer, head- and neck cancer, lung cancer including non-small cell lung cancer, bladder cancer and the like. Most preferably, said tumor is breast cancer. Further provided is therefore a bispecific antibody according to the invention comprising a first antigen-binding site that binds EGFR and a second antigen-binding site that binds ErbB-3 for use in the treatment or prevention of focal adhesion, or the formation of metastases, of breast cancer, colon cancer, pancreatic cancer, gastric cancer, ovarian cancer, colorectal cancer, head- and neck cancer, lung cancer including non-small cell lung cancer, bladder cancer and the like, preferably breast cancer cells, wherein said cells have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the present invention is typically capable of reducing a ligand-induced receptor function, preferably ligand induced growth, of ErbB 3 on a ErbB 2 and ErbB 3 positive cell. Said antibody according to the invention preferably comprises an antigen-binding site that binds domain III of ErbB-3. The affinity (KD) of said ErbB-3 antigen-binding site for an ErbB-3 positive cell is preferably lower than or equal to 2.0 nM, more preferably lower than or equal to 1.39 nM, more preferably lower than or equal to 0.99 nM.

In one preferred embodiment, said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

One preferred embodiment provides a use of an antibody according to the invention for the preparation of a medicament for the treatment of an EGFR, ErbB-3 or EGFR/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said EGFR, ErbB-3 or EGFR/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore an antibody according to the invention for use in the treatment of a subject having or at risk of having breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, preferably breast cancer, wherein cells of said cancer have a heregulin expression level that is at least 60%, preferably at least 70%, more preferably at least 80%, more preferably at least 85%, more preferably at least 90% or 95% of the heregulin expression level of BXPC3 or MCF7 cells.

High heregulin levels are typically present during the formation of metastases (i.e. the migration, invasion, growth and/or differentiation of tumor cells or tumor initiating cells). Typically, tumor initiating cells are identified based on stem cell markers such as CD44. These processes can therefore barely be counteracted with currently known therapies like trastuzumab and pertuzumab. Since an antibody according to the invention is capable of counteracting growth and/or differentiation of tumor cells or tumor initiating cells that express high levels of heregulin, such antibody according to the invention is also particularly suitable for counteracting the formation of metastases. Further provided is therefore a method for counteracting the formation of a metastasis in a subject having a EGFR, ErbB-3 or EGFR/ErbB-3 positive tumor, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds EGFR and a second antigen-binding site that binds ErbB-3. Also provided is a bispecific antibody comprising a first antigen-binding site that binds EGFR and a second antigen-binding site that binds ErbB-3 for use in the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of the formation of metastases, wherein said EGFR, ErbB-3 or EGFR/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Said EGFR, ErbB-3 or EGFR/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore a bispecific antibody according to the invention comprising a first antigen-binding site that binds EGFR and a second antigen-binding site that binds ErbB-3 for use in the treatment or prevention of the formation of metastases of breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma cells, preferably breast cancer cells, wherein said cells have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the present invention is typically capable of reducing a ligand-induced receptor function, preferably ligand induced growth, of ErbB-3 on a EGFR and ErbB-3 positive cell. Said antibody according to the invention preferably comprises a first antigen-binding site that binds domain I of EGFR and a second antigen-binding site that binds domain III of ErbB-3. The affinity of said second antigen-binding site for an ErbB-3 positive cell is preferably lower than or equal to 2.0 nM, more preferably lower than or equal to 1.39 nM, more preferably lower than or equal to 0.99 nM.

In one embodiment, said bispecific antibody is for use in the treatment of a subject under heregulin stress conditions, as explained in more detail herein above.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1. In terms of functional activity a bispecific antibody of the invention can demonstrate superior potency compared to MEHD7945A in vitro and in vivo.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 1: Annotated sequence of the chimeric cynomolgus-human EGFR encoding construct. Restriction sites used for re-cloning (Nhe1-Not1) are indicated in capitals. The start of the mature peptide is underlined and indicated in bold. The trans-membrane region is in bold and italics.

FIG. 2: Amino acid sequences of the extra-cellular domain (ECD) of EGFR 'swap-domain variants': the human EGFR ECD was used as backbone and specific domains were swapped for the human HER3 sequence. HER3-derived sequences are indicated. These sequences were cloned in frame with a c-Myc derived epitope tag and the trans-membrane region of the platelet-derived growth factor receptor (PDGFR).

FIG. 3: Epitope mapping of anti-EGFR Fab's (MF number; selected from the 'immune' phage libraries) expressed on phage by competition for binding with known, literature-derived antibodies. Representative OD values obtained after testing of phage binding to immobilized EGFR in ELISA in the presence (or absence) of the indicated antibodies ND: not determined. The domain specificity of the control antibodies is indicated.

FIGS. 11A-11D: Nucleic acid and amino acid sequences of VH-chains, common light chain and heavy chains of antibodies of the invention. FIG. 11A depicts heavy chain variable regions that bind EGFR. Where in this Figure a leader sequence is indicated this is not part of the VH chain or antibody, but is typically cleaved of during processing of the protein in the cell that produces the protein. The VH chain sequence of a heavy chain indicated with the capitals MG followed by a number in the text is indicated herein by the same number preceded with the letters VH. FIG. 11B further specifies the amino acid sequences of heavy chain variable region sequences of an erbB-3 binding antibodies MF6055-MF6074. The variable heavy chain sequences are variants of heavy chain variable region MF3178. Dots indicate the same amino acid as in MF3178 at that position. The CDR regions are separated by a space and indicated in bold. FIG. 11C depicts light chain variable region sequences. FIG. 11D depicts heavy chain sequences for EGFR and erbB-3 binding."

FIG. 12: CXCL14 and Rnase7 expression in primary keratinocytes stimulated with different IgGs. Expression was measured by Q-PCR in the presence of two antibody concentrations.

FIG. 16A HER3 crystal structure (PDB #4P59) showing epitope residue Arg 426 in gray spheres and all surface exposed residues within an 11.2 Å radius from Arg 426 in black spheres, FIG. 16B Solvent exposed surface of epitope region with Arg 426 and distant residues shown in gray and all surface exposed residues within a 11.2 Å radius from Arg 426 shown in black, FIG. 16C Residues in the epitope region Arg 426 in light gray and surrounding residues (all labeled) in dark gray. Figures and analyses were made with Yasara (www.vasara.org).

EXAMPLES

Figure 4:
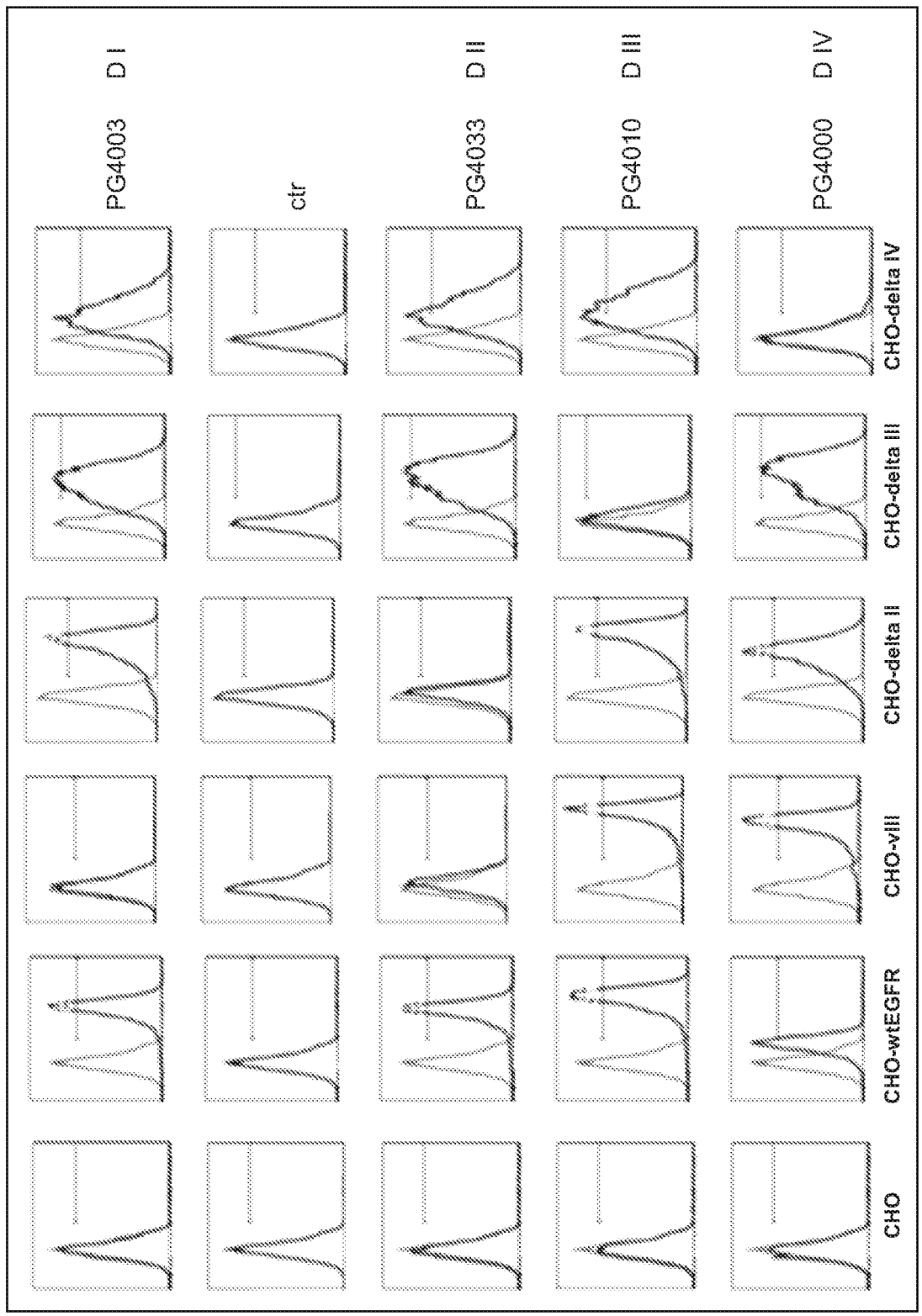
FIG. 4: example of epitope mapping of selected anti-EGFR common light chain (cLC) IgG (PG numbers) by FACS staining using EGFR swap domain mutants. Antibodies were tested for binding to CHO cells stably expressing the indicated EGFR swap mutants (domains in the wtEGFR sequence that were swapped for the corresponding domain of HER3). Light line: negative control (irrelevant antibody) staining; dark line: antibody staining. vIII: EGFR variant III, lacking domain I and most of domain II). Ctr: negative control staining (irrelevant primary antibody added). The determined domain specificity is indicated on the right of the Figure.

Cell Lines:

BxPC-3-luc2 (Perkin Elmer 125058), CHO-K1 (DSMZ ACC110), 293F (Invitrogen R790-07), A549 ATCC @ CCL-185™ Homo sapiens lung Carcinoma, BxPC-3 ATCC @ CRL-1687™ Homo sapiens pancreas adenocarcinoma, and A431 cells DSMZ ACC 91 were purchased and routinely maintained in growth media supplemented with 10% fetal heat inactivated bovine serum (FBS). 293F Freestyle cells were obtained from Invitrogen and routinely maintained in 293 FreeStyle medium. BxPc-3-luc2 (Bioware® Ultra Light Producing) cell line is a luciferase expressing cell line which was stably transfected with firefly luciferase gene (luc2). The cell line was established by transducing lentivirus (pGL4 luc2) containing luciferase 2 gene under the control of human ubiquitin C promoter. The cell line is commonly referred to as BxPc-3-luc2, it is a human cell pancreas adenocarcinoma cell line derived from BxPC-3 ATCC (CRL-1687™). Bioluminescence In Vitro: Approximately 370 photons/sec/cell. Exact number will vary depending on imaging and culturing conditions.

Cloning of the cDNA Encoding Cynomolgus EGFR and EGFR Swap-Domain Constructs

A construct encoding a chimeric receptor comprising the extra-cellular domain (ECD) of cynomolgus EGFR fused to the human trans-membrane domain and intra-cellular tail was copied from a published patent application by Micromet (US 2010/0183615 A1). The sequence is depicted in FIG. 1. This cDNA was synthetically made by GeneArt and was cloned in the vector pMK-RQ, flanked by the restriction sites Nhe1 and Not1. The cDNA was liberated from this vector using these two enzymes and then cloned into the mammalian expression vector pCDNA3.1. The cDNA was fully sequenced to make sure it matched the designed construct and no mutations were found.

For epitope mapping purposes, constructs were generated in which the different domains in the extra-cellular domain (ECD) of EGFR (L1, CR1, L2 and CR2, also named domains I-IV: [1]) were swapped for the corresponding domains of HER3: FIG. 2. These were then cloned into an expression vector for transient expression in (antigen-negative) CHO cells, in frame with an extra-cellular cMyc-derived epitope tag and the trans-membrane region of the platelet-derived growth factor receptor. Constructs were designed, synthesised by GeneArt and subsequently cloned into pDisplay as Sfi1-Sal1 fragments. All constructs were sequenced, shown to be correct and tested for expression. Only the domain I swap variant (HER3 domain I with HER1 domains II-V) was shown not to give rise to detectable amounts of protein on the surface of transfected cells (not shown).

The reference numbers used in the Examples refer to the numbering of the references in the list headed "References cited in the Examples".

Immunisations of MeMo with rhEGFR-Fc Fusion Protein and A431 Cells Over-Expressing the Antigen Mice that are transgenic for a rearranged human VL and a divers set of unrearranged human VH, DH and JH gene segments operably linked to murine constant region genes (MeMo®; see also WO2009/157771) were immunized with EGFR-Fc protein (R&D Systems, cat nr. 344-ER) emulsified with TitermaxGold adjuvant (TMG, Sigma Aldrich, cat. nr. T2684) at an interval of 14 days. MeMo produces common light chain (cLC) antibodies upon exposure to an antigen, i.e.: all antibodies coming out of Memo carry essentially the same light chain yet are diversified in their heavy chains. At day 0 and 14 mice were vaccinated subcutaneously (s.c.) to minimize the TMG induced discomfort of the mice. At all later time points mice were immunized via the intra-peritoneal (i.p.) route to insure the antigen is efficiently taken up and presented in the spleen. At day 35, the anti-EGFR serum titer was determined by FACS using the EGFR over-expressing cell line A431. Mice that developed at day 35 a serum titer >$\frac{1}{1,000}$ received a final i.p. boost with EGFR-Fc protein dissolved in PBS at day 42 followed by collection of spleen and lymph node three days later. Mice with too low EGFR serum titer at day 35 received an additional i.p. boost of EGFR-Fc in TMG at day 49.

Subsequently, serum titers were determined at day 56 by ELISA. Those mice that at day 56 had a serum titer above the acceptance criteria received a final i.p. boost with EGFR-Fc protein dissolved in PBS at day 63 followed by collection of spleen and lymph node. Mice were injected with 20 μg EGFR-Fc protein dissolved in 125 μl TMG or 200 μl PBS.

Two MeMo mice immunized with EGFR-Fc received also a boost with A431 cells. This was because these mice had developed a low a-EGFR-Fc IgG serum titer that was primarily directed against the Fc-tail. To specifically boost the EGFR response were these mice boosted with a single i.p. injection of 2E+6 A431 cells in 200 μl PBS at day 49.

All mice were shown to have mounted a significant response directed to the extracellular domain of EGFR, as witnessed by their reactivity with CHO cells stably expressing full length human EGFR and with A431 cells over-expressing EGFR in FACS.

Generation of 'Immune' Phage Antibody Libraries from Immunised Mice

After immunisation, RNA was extracted from lymphoid tissues (lymph nodes, spleen) and the polyclonal pool of VH-encoding cDNA's was amplified using VH family specific primers as previously described (e.g. EP 2604625). Material of two mice was pooled for library construction. The resulting PCR products were then cut with the restriction enzymes Sfi1 and BstEII and cloned in frame with the bacteriophage gene III for display on filamentous bacteriophage, essentially as described in [2], only the phagemid vector already contained the Vκ1-39 germline VL gene. Phage library ML1155 was generated from the two mice with the highest α-EGFR serum titer (mice E094 #12 and E094 #18). Library ML1156 was generated from the two mice that received the additional A431 boost (mice E094 #14 and E094 #16). Characteristics of the libraries are depicted in Table 1.

Phage Selections for EGFR Binding Clones

The (Fc-) immune-fusion of the ecto-domain of EGFR (R&D systems) was diluted in PBS (to 5 µg/ml and in two-fold dilutions thereof) and coated to the wells of Maxisorp immune-plates. Phage were then panned for binding as described [3]. Selection of Fc-reactive clones was avoided by stringent counter-selection using (10 µg of) soluble IgG during the incubation of phage with coated antigen. To direct the selections on EGFR towards the ligand binding (L1) domain I, competition with an excess of the EGFR variant III (vIII) immune-fusion was also performed. In order to obtain cLC antibodies with functionality in inhibiting the receptor, phage selections on immobilised antigens were performed in combination with epitope-specific elution [4] using the either the ligand (EGF), or antibodies copied from literature (Matuzumab, Cetuximab). Elutions of EGFR-reactive phage were also performed using the domain I specific antibody ICR10 (Abcam, nr. ab231) and the domain II-specific antibody EGFR.1 (Thermo Scientific, nr. MS-311). As A431 cells [5] have been shown to carry an amplification of the EGFR gene [6] and therefore express high numbers of the EGFR, these were used for selection of EGFR-reactive phage.

Output phage titers were determined and for every selection where the output phage titer was 1.5 times above background (selection on a non antigen-coated well), 48 different clones were picked and phage were screened for binding to the respective antigens in ELISA. All clones were also tested for binding to human IgG in ELISA to identify binders to the Fc-portion of the immune-fusions used for selection. A high percentage of positive clones (defined as clones recognising the respective immune-fusions in ELISA, but not being IgG-reactive) was found in all selection outputs (up to 0.625 µg/ml) of coated immune-fusion. Clones that scored positive in phage ELISA on EGFR-Fc but not on hIgG were then sequenced and sequences were compared. Sequences were analysed as previously described (EP 2604625) and grouped on the basis of their VH gene segment usage and heavy chain CDR3 (HCDR3) sequence. An antibody cluster was defined as all sequences using the same germline VH segment having an HCDR3 with the same length and over 70% sequence identity in that HCDR3. In total, 17 antibody clusters were identified from immunised MeMo mice.

Using large synthetic LC repertoires (synthesised in house) and selections on rhEGFR-Fc (as described above) many EGFR-specific clones were isolated, of which only one (MF3370) was later shown to be able to inhibit EGF-induced A431 cell death. This clone was therefore also analysed in more detail and used in subsequent EGFR× HER3 screening assays.

Testing Selected Anti-EGFR Phage Antibodies for Competitive Binding with Control Antibodies To delineate the epitope recognized by representative anti-EGFR Fabs, they were tested (as Fabs expressed on phage: named 'MF') for binding to EGFR in the presence of an excess of control, literature-derived IgG [7]. Control IgG used for these competition experiments are listed in Table 2.

When phage expressing the selected Fabs were tested for binding to the antigen in ELISA in the presence of an excess of these control antibodies, several were found to be competed for binding by one or more of the control antibodies: FIG. 3. These results show the anti-EGFR panel to be diverse in epitope recognition.

Re-Cloning of Selected Anti-EGFR cLC Fab's, Expression and Purification of cLC IgG1

EGFR specific phage clones (termed 'MF') were re-cloned as mono-specific, bivalent IgG (termed 'PG') by re-cloning the VH-encoding gene fragment (as Sfi1-BstEII fragment) in an expression vector (named 'MG') for the transient expression of IgG in 293F cells. After production by transient transfection of 293F cells, secreted IgG (termed 'PG') was purified from the culture supernatant by prot. A affinity chromatography using standardised procedures.

Testing of Anti-EGFR Antibodies for their Cross-Reactivity with Cynomolgus EGFR and Mouse EGFR To test whether anti-EGFR cLC IgG were reactive with cynomolgus EGFR, the constructs encoding full-length human EGFR, as well as the newly synthesized expression construct encoding the chimeric cynomolgus/human EGFR (FIG. 1) were both transfected in (antigen negative) CHO cells and cells were then stained with the anti-EGFR cLC IgG (PG) at 5 µg/ml and finally analysed by FACS. As a positive control for the staining, the clinically used antibody cetuximab was used, as this antibody is known to cross-react with cynomolgus EGFR [8]. The construct encoding the chimeric cyno-human receptor gave rise to high levels of the chimeric construct being expressed on the surface of transfected cells (as judged by the staining using cetuximab). In addition, all cLC IgG were shown to be reactive with cynomolgus EGFR, as the staining of cells expressing human EGFR was virtually indistinguishable from that of cells expressing the chimeric receptor.

To test anti-EGFR cLC IgG for their cross-reactivity with murine EGFR, an ELISA was performed. Purified protein, composed of the mouse EGFR ECD, fused to human IgG1 Fc was bought from Sino Biologicals (cat. nr. 51091-M02H) and a serial 2-fold dilution of this antigen was used to coat wells of an ELISA plate, starting at 5 µg/ml. Binding of the anti-EGFR cLC IgG to this antigen was then tested at a fixed concentration of 5 µg/ml. As a positive control for the immuno-reactivity of the antibodies, the same ELISA setup was performed using the human EGFR ECD-Fc fusion protein as antigen (R&D systems). From all 17 antibody clusters as described above, at least one representative antibody was tested. In addition, clone MF3370 from the synthetic library was also tested as an IgG (PG3370). All but one of the cLC antibodies were shown not to recognise mouse EGFR, as they failed to react with the fusion protein in ELISA. However, antibody PG3370 was shown to recognise murine EGFR, as well as human EGFR with similar affinity (data not shown): Table 3 summarises the data.

Testing the Domain Specificity of Anti-EGFR Antibodies Using EGFR Swap-Domain Constructs in FACS To unequivocally demonstrate the domain-specificity of the anti-EGFR cLC IgG, they were tested for binding to CHO cells stably expressing 'swap-domain' constructs: i.e. CHO cells expressing mutants of EGFR in which specific domains had been replaced for the corresponding domains of Her3 in FACS (FIG. 2). FIG. 4 gives an example of the FACS data obtained; data are summarized in Table 3.

Testing Anti-EGFR Antibodies for their Effect on Ligand-Induced Signalling

Figure 5:
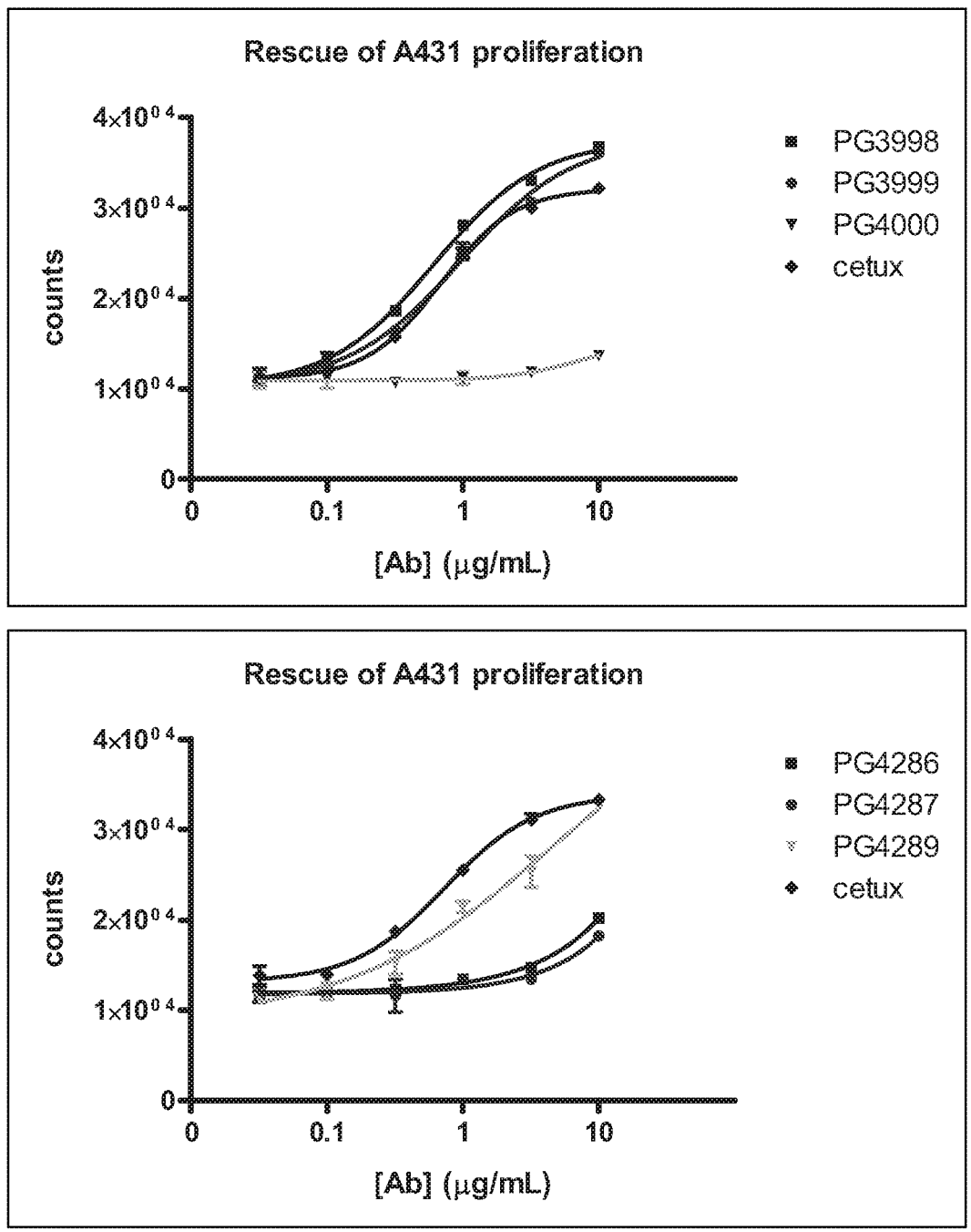
FIG. 5: example of the functionality of anti-EGFR cLC IgG (PG numbers) in inhibiting the EGF-induced death of A431 cells.
Y axis (counts) shows the fluorescence readout of the assay, reminiscent of the number of metabolically active cells, as a function of the concentration of antibody used (X-axis). Antibodies that show functional EGFR blocking activity dose-dependently inhibit the EGF-induced cell death and therefore show enhanced growth of the cells with increasing antibody concentration. The clinically used antibody cetuximab was used in all experiments as an internal standard (diamonds).

To test the selected anti-EGFR cLC IgG for their effects on EGF-induced signalling, they were tested for their ability to prevent the EGF-induced cell death of A431 cells. In brief, high (10 nM) concentrations of EGF induce (apoptotic) cell death in A431 cells [9]. This effect can be dose-dependently reverted by the addition of ligand-blocking anti-EGFR antibodies, such as cetuximab (the murine 225 antibody is the mouse equivalent of cetuximab: [9]) Antibodies were tested in this assay for their effect on receptor inhibition in a serial semi-log dilution from 10 μg/ml onwards. In every assay, the EGFR-blocking and clinically used antibody cetuximab was included as positive control. Anti-EGFR antibodies were found to have varying potencies in inhibiting EGF-induced cell death: some were more potent than cetuximab in rescuing the EGF-induced effect (e.g. PG3998: FIG. 5), some were less potent (e.g. PG4289, FIG. 5) and some had very little to no activity (e.g. PG4000, FIG. 5). Table 3 shows the activity of cLC antibodies directed to EGFR in inhibiting the receptor, compared to that of cetuximab.

Screening of Bispecific Anti-EGFR×HER3 Antibodies for their Capacity to Inhibit BxPC-3 Cell Proliferation VH-encoding cDNA fragments from the EGFR and HER3 antibody panel were re-cloned into vectors encoding charge-engineered CH3 domains that forced the generation of bispecific antibodies (Gunasekaran et al., JBC 2010; PCT/NL2013/050294) after transient transfection into 293F cells (termed 'PB' for bispecific protein). Three different strategies were used in combining EGFR and HER3 arms in bispecific IgG format: I) bispecifics of which both parental antibodies had proven ligand blocking activity for the receptor in respective cellular assays (the A431 assay for EGFR and the MCF-7 assay for Her3) resulting in 120 unique bispecific antibodies (Table 4); II) bispecifics of which only one of the arms (either the anti-Her3 or the anti-EGFR) had functionality in the above-mentioned assays (a total of 440 unique bispecific antibodies, not shown) and III) bispecifics of which both Fab arms had no (or almost no) functionality in these assays (a total of 320 unique bispecific antibodies, not shown). In total, 880 unique bispecific antibodies were tested for their ability to inhibit the growth of BxPC-3 cells.

All 880 bispecific antibodies were produced by co-transfection and transient co-expression in 293F cells; IgG was purified from the culture supernatant and the buffer in which the protein was kept was changed to PBS according to standardised procedures. Purified protein was quantified using Octet analysis. Bispecifics were tested at two concentrations (1 μg/ml and 100 ng/ml) in a ligand- (EGF- and NRG-) dependent assay (addition of 100 ng/ml of EGF, next to 10 ng/ml of NRG), as well as in a ligand-independent assay (no ligand added).

First, antibodies were diluted in chemically defined starvation medium (CDS: RPMI1640 medium, containing 80 U penicillin and 80 μg of streptomycin per ml, 0.05% (w/v) BSA and 10 μg/ml holo-transferrin) and 50 μl of diluted antibody was added to the wells of a 96 wells black well clear bottom plate (Costar). Ligand was added (50 μl per well of a stock solution containing 40 ng/ml NRG and 400 ng/ml of EGF, diluted in CDS: R&D systems, cat. nr. 396-HB and 236-EG). In case of the ligand-independent assay, no ligand was added, instead only 50 μl of CDS. BxPC-3 cells were trypsinised, harvested and counted and 8000 cells in 100 μl of CDS were added to each well of the plate. Plates were left for an hour at rt before being put in a container inside a 37° C. cell culture incubator for three days. On the fourth day, Alamar blue (Invitrogen, #DAL1100) was added (20 μl per well) and the fluorescence was measured after 6 hours of incubation (at 37° C.) with Alamar blue using 560 nm excitation and 590 nm readout on a Biotek Synergy 2 Multi-mode microplate reader. Fluorescence values were normalised to uninhibited growth (no antibody, but both ligands added).

IC50 Determination

Figure 6:
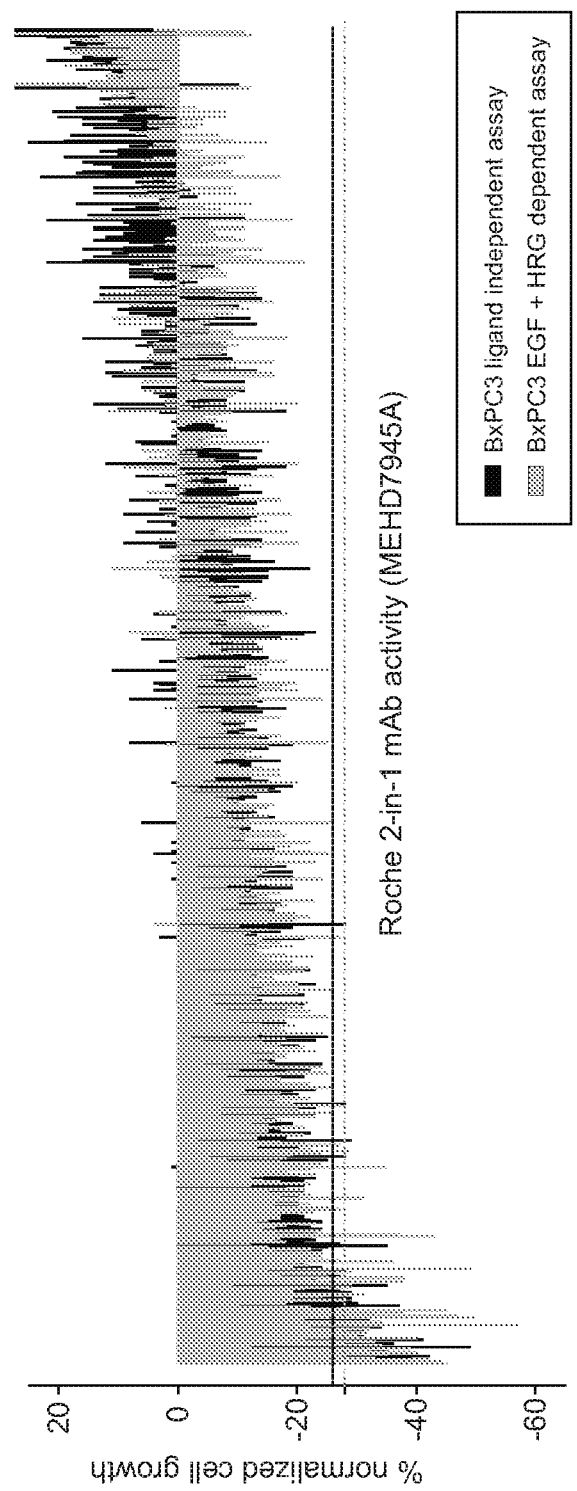
FIG. 6: overview of the screening of anti-EGFR×HER3 bispecifics, compared to the activity of the MEHD7945A antibody. Every bar represents the activity of a bispecific anti-EGFR×HER3 antibody in the BxPC-3 ligand-independent (light bars) and ligand-driven assay (dark bars). The average activity of the MEHD7945A antibody is indicated by a light (upper) and dark (lower) line for the independent and dependent assay respectively. Growth was normalized to untreated controls. Over 800 bispecific anti-EGFR×HER3 antibodies were screened.
Figure 7:
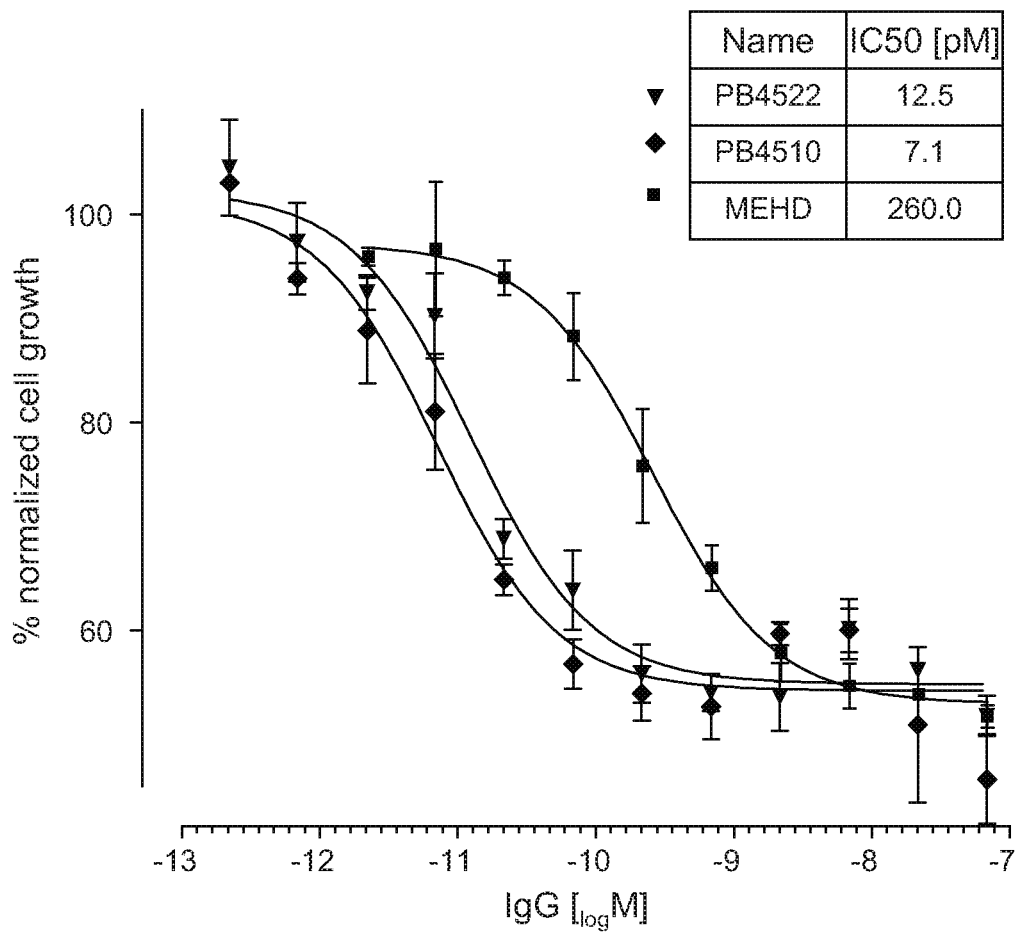
FIG. 7: IC50 determination for BxPC-3 cell proliferation inhibition of the two best performing bispecifics (PB numbers), compared to MEHD7945A. The Y-axis represents the percentage of growth, normalised to the control situation (i.e. uninhibited growth in the presence of both ligands) and the X-axis the antibody concentration used. IC50 values are indicated.

An overview of the screening data of the 880 bispecific antibodies is given in FIG. 6. MEHD7945A served as a benchmark antibody; the upper dotted line in FIG. 5 represents the average activity observed in the ligand-independent assay and the lower dotted line the average activity of that antibody observed in the ligand-dependent assay. Twenty bispecifics that had a potency in both assays that was at least as good as that of the MEHD7945A antibody were then re-produced, re-purified and tested again in the ligand-driven BxPC-3 proliferation assays to determine IC50 values. Antibodies were serially diluted in CDS from 10 μg/ml downward and 50 μl of antibody solution was added per well. Ligands and cells were added as described above and cells were incubated for three days before the addition of Alamar Blue and fluorescence readout. Again, values were normalised to uninhibited growth and IC50 values were calculated using GraphPad Prism software (non-linear curve fitting). The six best performing bispecifics were selected based on their IC50 being lower than that of the comparator antibody MEHD7945A in both assays. FIG. 7 shows the IC50 determination of two of these best performing antibodies; Table 6 summarises the data for these six bispecifics, as compared to the activity of a mixture of each of the parental monoclonal antibodies (see below).

Testing Anti-EGFR×HER3 Bispecifics for their Effect on the Growth of BxPC-3 Tumours Orthotopically Implanted CB17 SCID female mice, 8-10 weeks old at the beginning of the study were engrafted orthotopically in the pancreas with $1 \times 10^6$ tumor cells in 20 μl. Therefore mice were anesthetized and laid on the right side to expose the left side and a 0.5 cm incision is made on the left flank region. The pancreas and spleen were exteriorized and $1 \times 10^6$ tumor cells in 2 0 μl were injected into the sub-capsulary space of the pancreas tail. One week after implantation, bioluminescence (BLI) data were generated. For BLI imaging (once or twice weekly) left side view, all mice received 15 minutes prior to the imaging all of the mice receive i.p. injections of 150 mg/kg Luciferin (D-Luciferin-EF Potassium Salt, Cat. #E6552, Promega). Outlier animals—based on BLI/tumor volume—were removed and the mice were randomly distributed into groups of 7 mice each. On experimental day 8, the treatment was started. The animals in the antibody treatment group were dosed weekly for 3 consecutive weeks (days 0, 7, 14 and 21) with 30 mg/kg of antibody. At day 0 of the treatment the animals receive twice the loading dose, i.e. 60 mg/kg of antibody. The final imaging was carried out at day 31.

Figure 8:
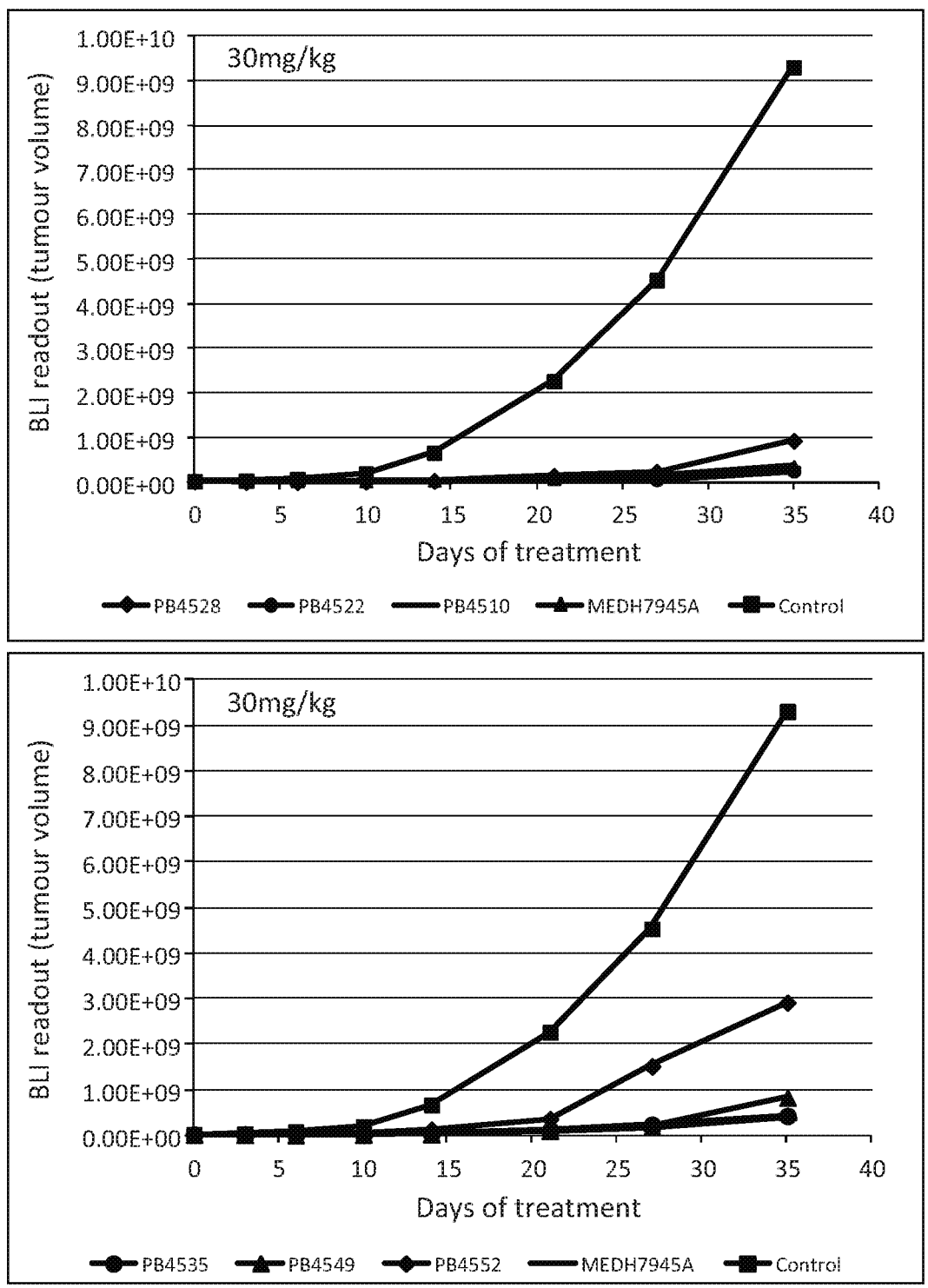
FIG. 8: therapeutic effect of bispecific antibody (PB numbers) treatment on the growth of BxPC-3 cells ortho-topically implanted. The Y-axis shows the bioluminescence (BLI) readout (reminiscent of the number of live tumor cells) after injection of luciferin in the mice as a function of time (X-axis). The MEHD7945A antibody was used as reference and an irrelevant (anti-RSV) antibody as a negative control antibody (squares). For the sake of clarity, error bars have been omitted from the Figure.
Figure 9:
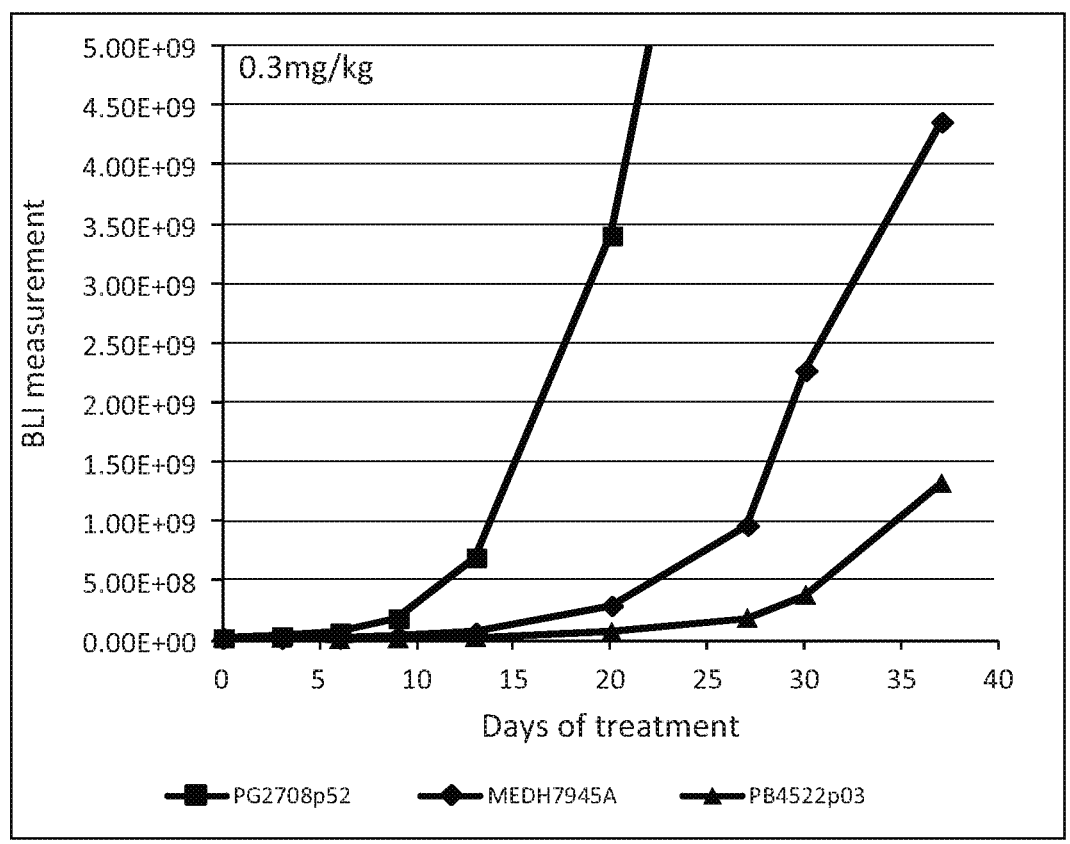
FIG. 9: therapeutic effect of the lead bispecific PB4522 in comparison with that of MEHD7945A at 0.3 mg/kg dose. Y axis shows the in vivo bioluminescence (BLI), reminiscent of the number of live tumor cells as a function of time (X-axis). NC: negative control antibody (anti-RSV, 30 mg/kg dose). For the sake of clarity, error bars have been omitted from the Figure.
Figure 10:
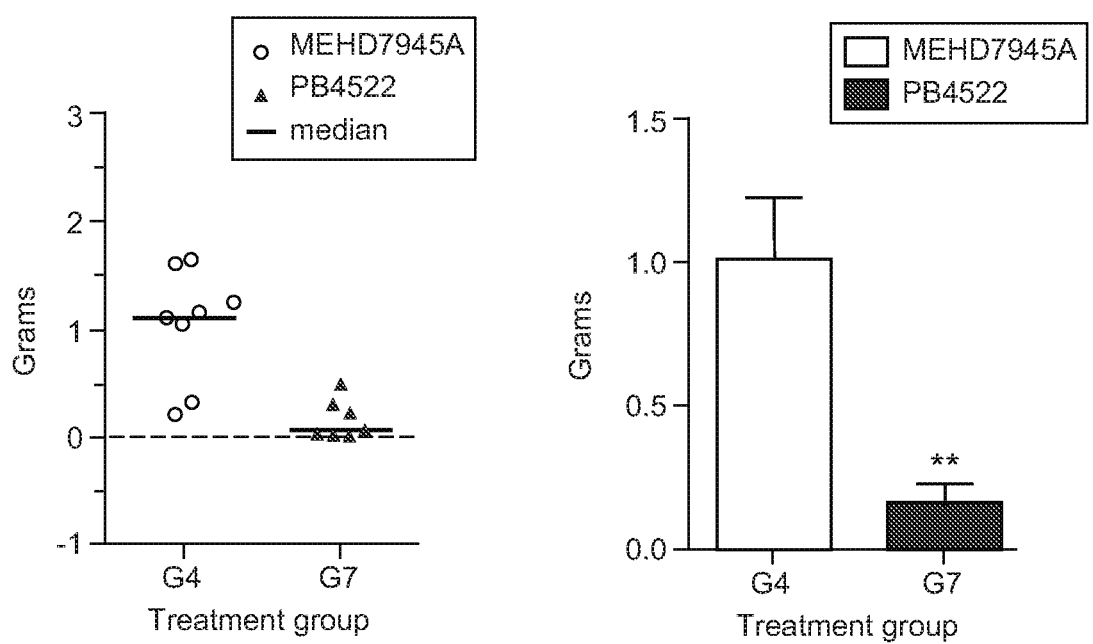
FIG. 10: tumor weights measured ex vivo at day 38 of the study of tumors isolated from mice treated with either MEHD7945A (group G4) or PB4522 (group G7) at 0.3 mg/kg. The left panel shows the weight of the tumor of every individual mouse and the right panel shows the average weight of the 7 mice that were treated. ** $p<0.05$.

All six bispecifics were shown to significantly decrease BxPC-3 tumour outgrowth in the model (p<0.001) (FIG. 8). However, there was no significant difference between the therapeutic effect of the comparator antibody MEHD7945A and two of these six bispecifics, PB4522 and PB4510 (data not shown). Therefore, a dose-escalation study was performed with one of the bispecific antibodies, PB4522, and the comparator antibody MEHD7945A. Using the exact same in vivo model and dosing schedule, different groups of mice were treated with a decreasing antibody dose, lowered from 30 mg/kg to 3 and finally 0.3 mg/kg. FIG. 9 shows the data for the groups treated with 0.3 mg/kg. There was no significant difference in therapeutic effect between all groups treated with either MEHD7945A or PB4522 at 30 and 3 mg/kg (data not shown). However, there was a significant difference in therapeutic effect between treatment with MEHD7945A and PB4522 at the 0.3 mg/kg dose, the latter being more potent in tumour growth reduction. After mice were taken out of the study, the weight of all their tumours was determined ex vivo. FIG. 10 shows that the average weight of tumours taken from mice treated with PB4522 (at 0.3 mg/kg) was significantly lower (P=0.007, unpaired T-Test) than that of mice treated with MEHD7945A (at 0.3 mg/kg).

Comparison of the Potency of Different Antibody Formats in BxPC-3 Cell Proliferation Inhibition To compare the potency of different antibody formats in cell proliferation inhibition, purified bispecific anti-EGFR× HER3 antibodies were tested for their ability to inhibit BxPC-3 cell proliferation in comparison with an equimolar mix of the parental antibodies. In every assay plate, MEHD7945A was used as positive control to be able to compare the IC50 of the antibody being tested directly with the 'two-in-one' MEHD7945A. Titrations were performed starting from 10 µg/ml and in 6 ten-fold dilutions. These serial dilutions of antibodies were tested in duplicate over the whole concentration range. From the obtained sigmoidal curves, IC50 values were calculated using the GraphPad Prism software. Table 6 summarises the data.

As can be seen in Table 6, in all cases the bispecific format was more potent then the mix of the two parental antibodies in inhibiting the proliferation of BxPC-3 tumour cells and this format was therefore the preferred format for co-targeting of EGFR and HER3. When the IC50 value for proliferation inhibition of same bispecific was measured several times, slightly different values were obtained in the different assays. However, these differences were considered to be unavoidable small experimental variations.

Keratinocyte Assay

EGFR blockade has been demonstrated to affect chemokine expression in keratinocytes (Pastore, Mascia et al. 2005). Recent analyses of EGFR-Inhibitor (EGFRI) skin toxicities show that the early inflammatory infiltrate of the rash is dominated by dendritic cells, macrophages, granulocytes, mast cells and T-cells. EGFR inhibition induces the expression of chemokines (CCL2, CCL5, CCL27, CXCL14) in epidermal keratinocytes, while the production of antimicrobial peptides and skin barrier proteins such as Rnase 7 is impaired. The skin toxicity observed in vivo could be translated in vitro using a primary keratinocyte system in combination with Q-PCR analysis. (Lichtenberger, Gerber et al., Science Translational Medicine, 2013). The effect of PB4522 in comparison to MEHD7945A and cetuximab was tested at 10 and 100 nM concentrations on human primary epidermal keratinocytes. Human primary epidermal keratinocytes were isolated and seeded at a density of 100,000 cells per well in 6 well plates in SFM cell growth medium (Invitrogen) at 37° C., 5% CO2. Cells were treated in the absence or presence of 10 ng/ml TNF-α (AbD Serotec, Kidlington, UK) and 5 ng/ml IL-16 (R&D Systems, Inc., Minneapolis, MN) for 24H. Duplicates of each condition were prepared. Twenty-four hours later cells were harvested and RNA was extracted from cells by using the TRIzol® Reagent. cDNA was synthesized from different messenger RNA (mRNA) templates using reverse transcriptase enzyme Superscript II (Invitrogen, Carlsbad, CA). Gene specific oligonucleotides for qPCR were obtained as a TaqMan® Gene Expression Assays by Applied Biosystems. The expression of CXCL14 and Rnase 7 as well as 18S and GAPDH housekeeping genes were determined. PB4522 induces less CXCL14 compared to Cetuximab and MEHD7945A. In contrast Rnase 7 expression was less severe hampered by PB4522 compared to Cetuximab and MEHD7945A.

PB4522 Shows Superior ADCC Activity Compared to MEHD7945A

ADCC activity is an important anti-tumour mechanism of action for therapeutic antibodies in cancer. Human monoclonal antibodies directed to the HER family of receptors like cetuximab and trastuzumab induce ADCC. Multiple strategies have been used to achieve ADCC enhancement including glycoengineering and mutagenesis. All of these seek to improve Fc binding to low-affinity activating FcγRIIIa and/or reducing binding to the low-affinity inhibitory FcγRIIb. One of the methods used in glycoengineering to achieve ADCC enhancement is the removal of fucose. Removal of fucose has resulted in increased anti-tumour activity in several in vivo models [Junttila, 2010]. To maximize PB4522 activity, this afucosylation technology was applied (Liu and Lee. 2009 [13-17]) to remove fucose from the N-linked carbohydrate structure in the Fc region.

To determine ADCC activity of PB4522 in comparison to MEDH7945a and cetuximab the ADCC Reporter Bioassay (Promega) was used. Three different cell lines where tested; the EGFR amplified and high EGFR expressing head and neck cell line A431, the intermediate EGFR expressing lung cancer cell line A549 and the intermediate EGFR expressing pancreatic cancer cell line BxPC3.

Figure 13:
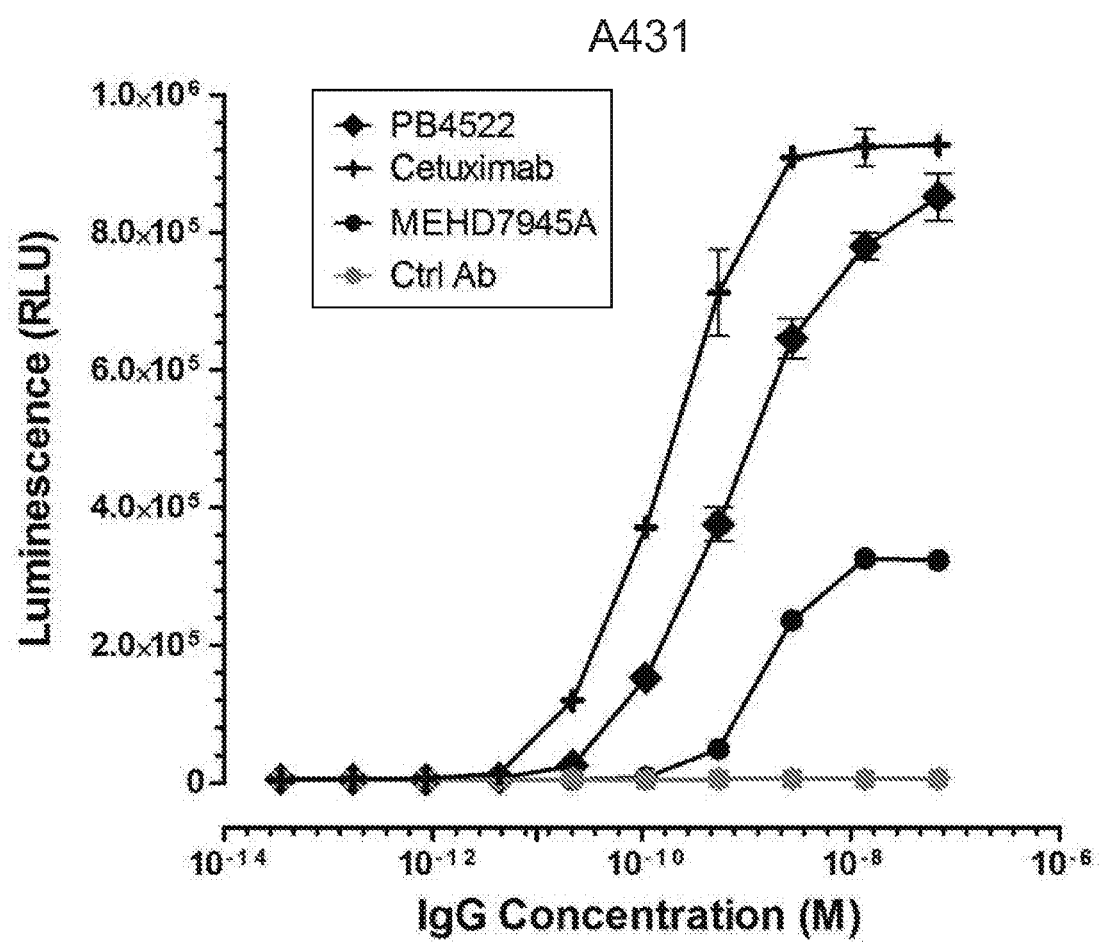
FIG. 13: ADCC activity of afucosylated PB4522 compared to MEHD7945A and cetuximab on high EGFR (A431) and intermediate EGFR (BxPC3 and A549) expressing cells. 'Ctrl Ab' is an IgG directed against Tetanus Toxoid
Figure 14:
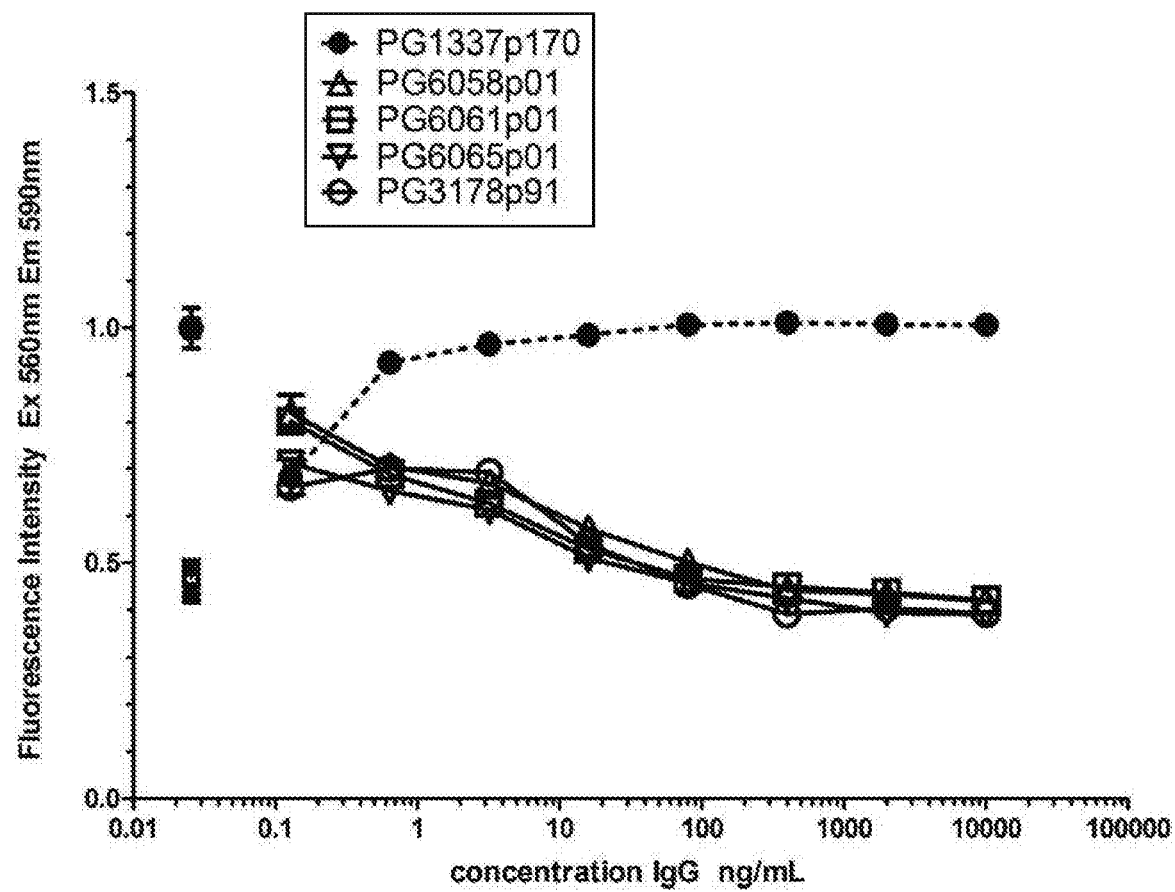
FIG. 14: Titration curves of HER3 monoclonal antibodies in the HRG dependent N87 assay. PG6058, PG6061 and PG6065 are variants of PG3178. PG1337 is a negative control specific for tetanus toxoid. Data were normalized to basal proliferation with ligand present on each plate.
Figure 15:
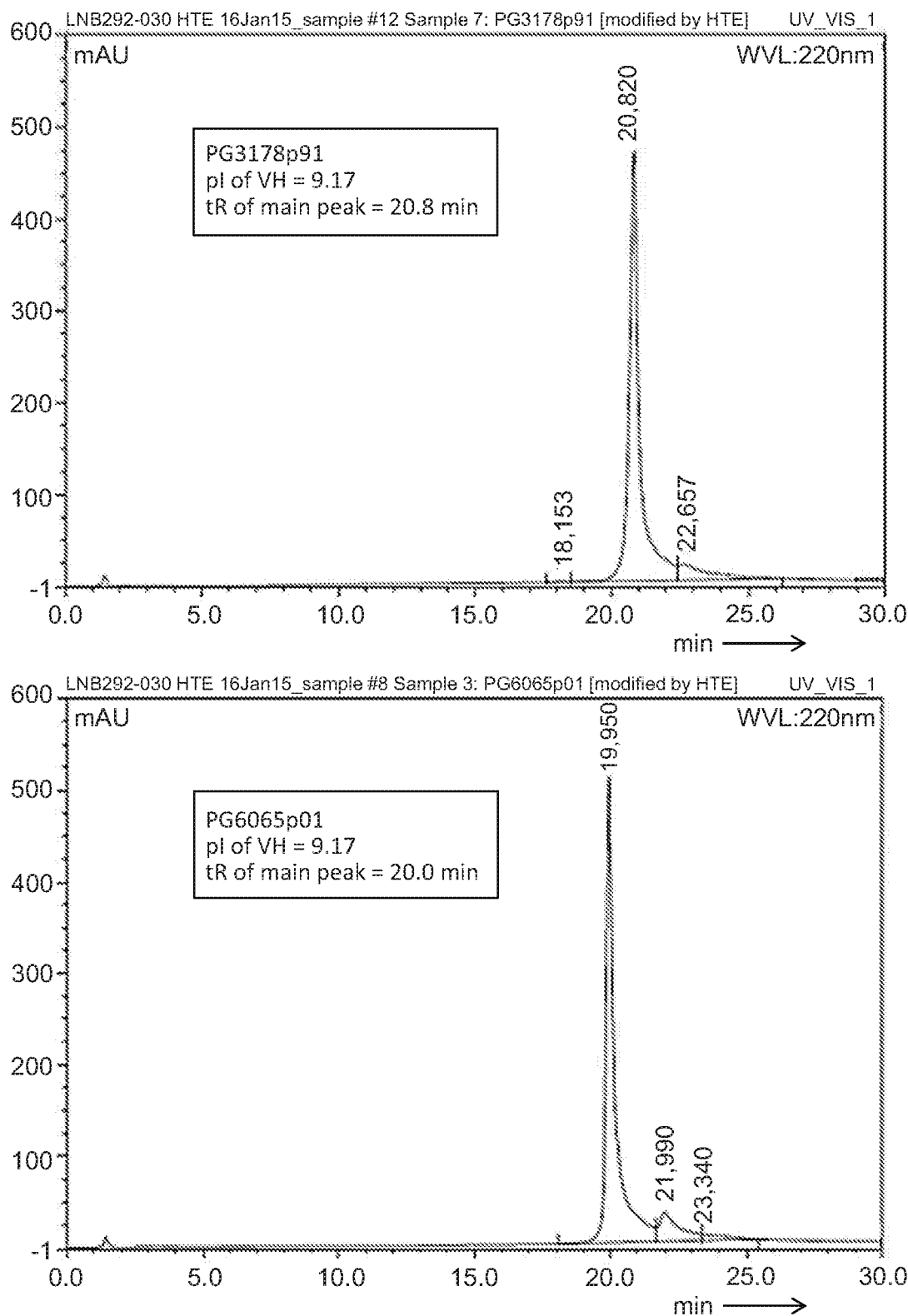
FIG. 15: CIEX-HPLC profiles of HER3 monoclonal antibodies. PG6058, PG6061 and PG6065 are variants of PG3178. The calculated iso-electric point (pI) of the VH region and the retention time (tR) of the main peak are given for each antibody.
Figure 16A:
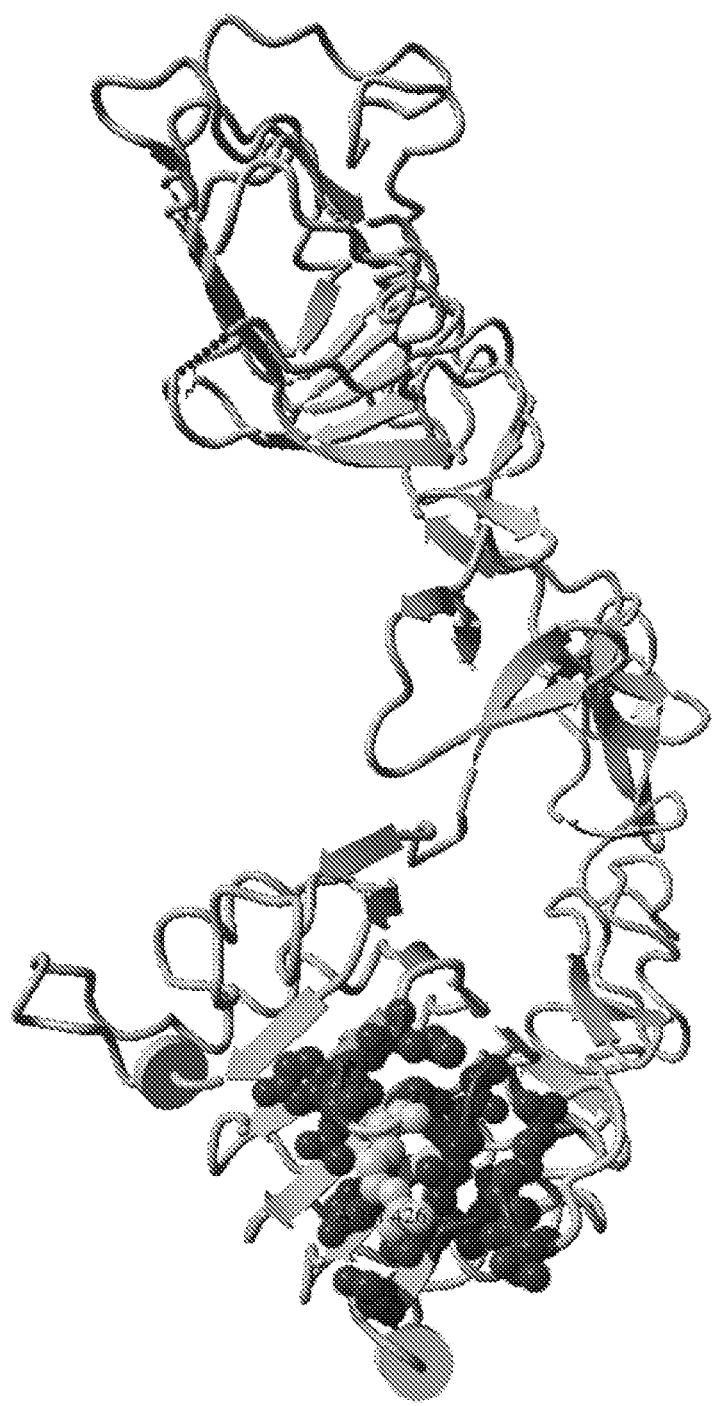
FIGS. 16A-16C.
Figure 16B:
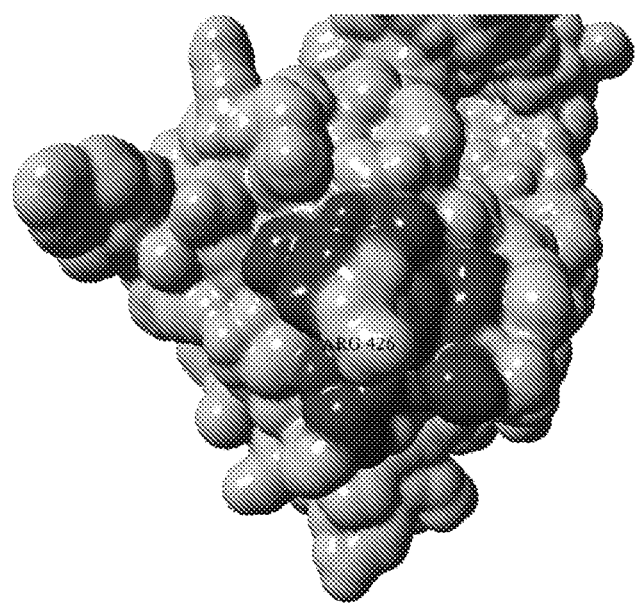
Figure 16C:
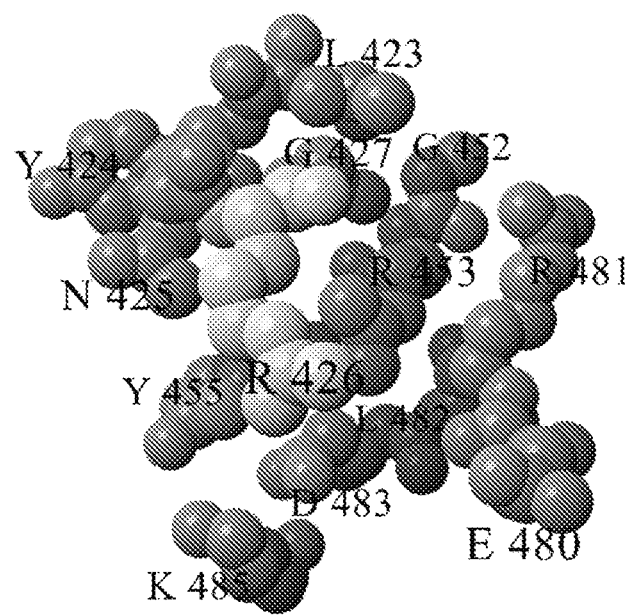

The bioassay uses engineered Jurkat cells stably expressing either the FcγRIIIa receptor V158 (high affinity) or F158 (low affinity) variant, and an NFAT response element driving expression of firefly luciferase which is a measure for FcγR activation. The assay has been validated by comparing data obtained with this ADCC Reporter Bioassay to the classical 51Cr release assay and both assays yield similar results. The ADCC assays were performed using the Promega ADCC Bioassay kit using 384 white well plates. In this experimental setup A431 cells, BxPC3 cells and A549 cells were plated at a density of 1000 cells/well in 30 µl assay medium (RPMI with 4% low IgG serum) 20-24H before the bioassay. The next day, the culture medium was removed. Next, a serial dilution of antibodies, PB4522 and its comparator antibodies cetuximab, MEHD7945A and a Ctrl antibody were prepared in duplicates. 10 µl of these antibody dilutions were added to the wells. The starting concentrations of the antibodies were 10 µg/ml and a 10 points 5-fold serial dilutions were generated to provide full dose-response curves. Finally, 5 µl of ADCC Bioassay effector cells (15000 cells/well, V158)

were added. The cells were incubated for 6H at 37° C. Next, 15 µl BIO-Glo luciferase substrate was added and 5 minutes later luminescence was detected in a plate reader. The obtained data are shown in FIG. 13. Both PB4522 and cetuximab showed ADCC activity towards the medium EGFR expressing cells BxPC3 and A549 whereby the EC50 of cetuximab was lower compared to PB4522. The total ADCC activity—Area Under the Curve (AUC)—and the maximal ADCC activity however of PB4522 were higher compared to cetuximab. All three antibodies showed ADCC activity towards the EGFR amplified cell line A431, whereby cetuximab showed the highest ADCC activity followed by PB4522 and Cetuximab. Of note is that the intermediate EGFR expressing cell lines are representative for the number of EGFR expressed on patient derived tumor cell samples. In all three cell lines the maximal ADCC and the AUC of PB4522 are higher compared to MEHD7945A. In all three cell lines the EC50 of PB4522 is lower compared to MEHD7945A.

HER3

Figure 17:
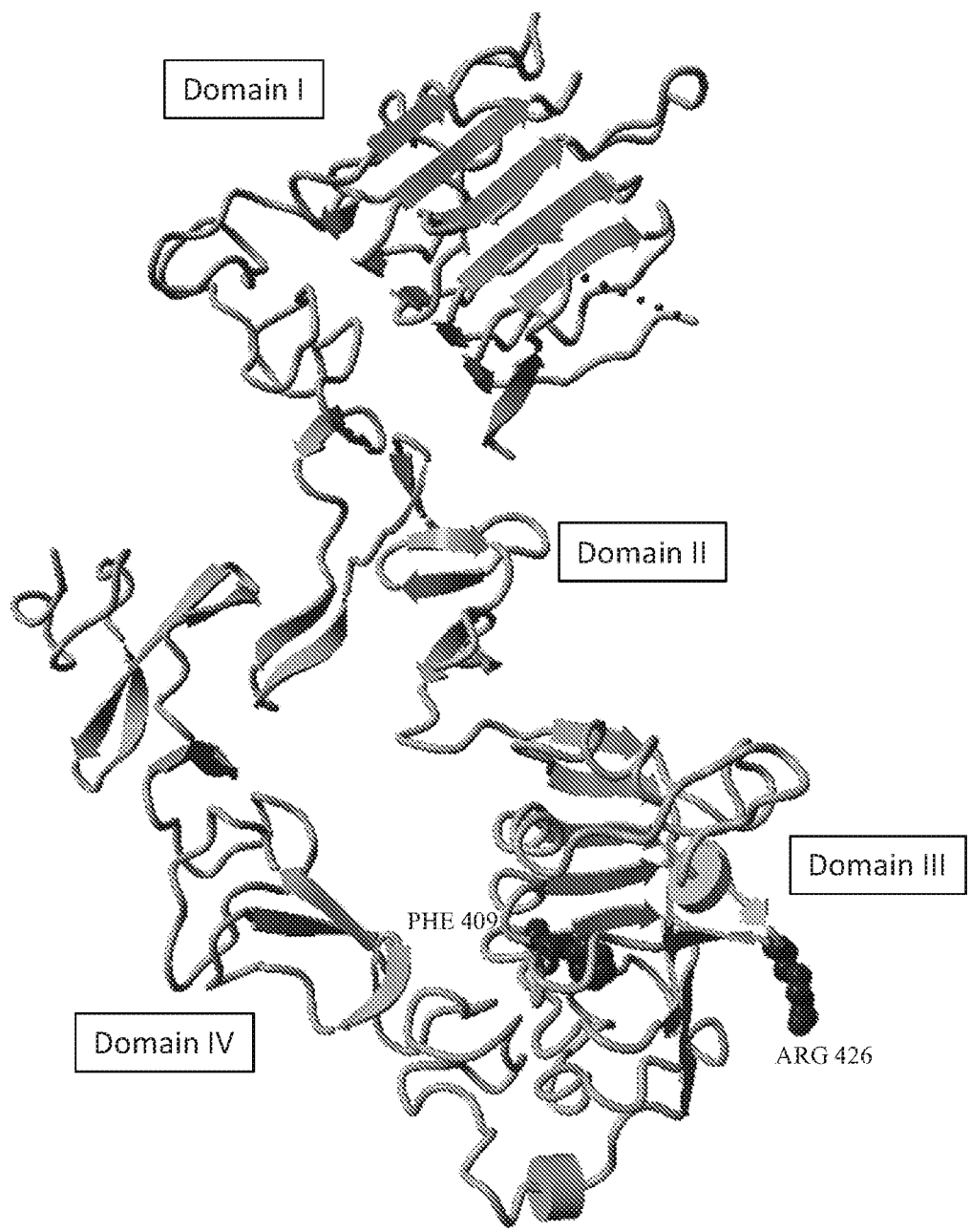
FIG. 17: Critical residues for PG3178 binding represented in the HER3 crystal structure. Critical residues identified for PG3178 binding are represented as black spheres on the HER3 crystal structure (PDB ID #4P59).

Binding analysis of PG3178 IgG at 0.25 µg/ml to HER3 ECD mutants in FACS resulted in the identification of two so-called 'critical' residues (F409, R426) for which mutation to alanine caused substantial loss of binding compared to WT HER3, while binding of the control mAb was retained (Table 7 and FIG. 17). Both residues are located in Domain III of HER3 and spatially distant. Moreover, F409 is buried in the HER3 hydrophobic core, which makes it unlikely to be part of the PG3178 epitope.

Confirmation Experiments HER3 Epitope

Figure 18:
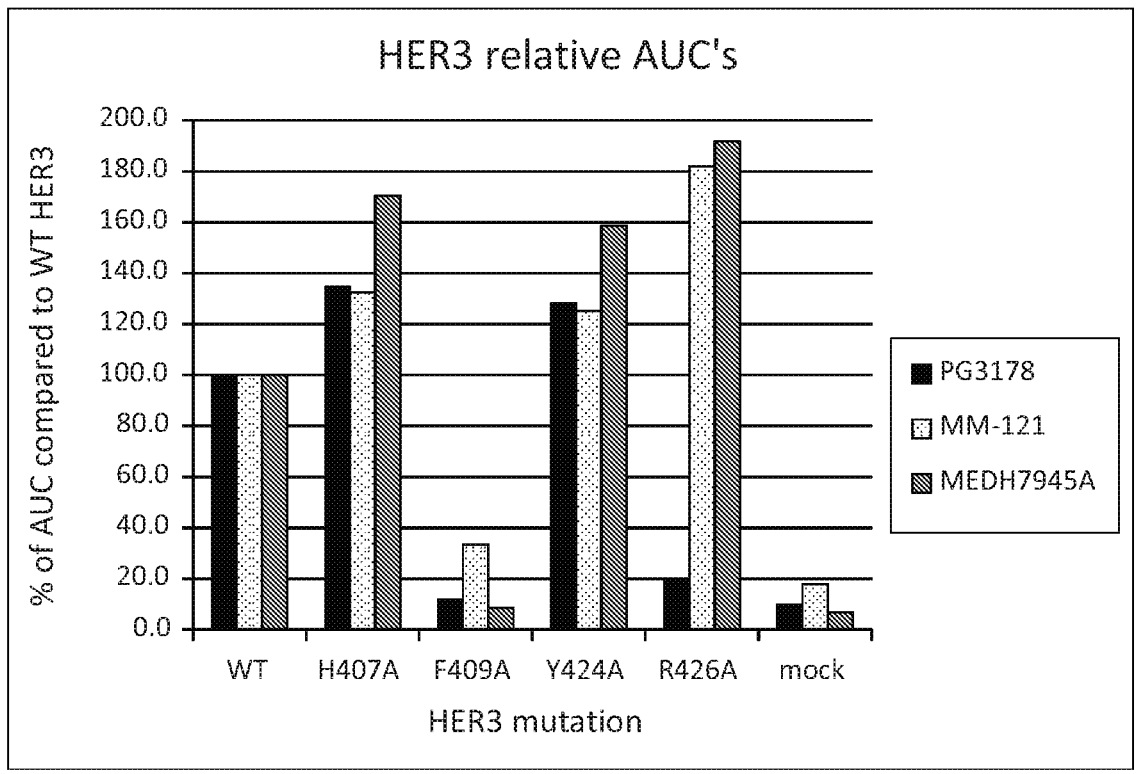
FIG. 18: Confirmation of R426 as a critical binding residue for PG3175 to HER3. Two anti-HER3 antibodies were included as control antibodies. Binding was determined in a FACS titration and binding is expressed as AUC in comparison to binding to WT HER3.

CHO-K1 cells were transfected with HER3 ECD mutation constructs (listed in Table 7), WT HER3 ECD and two control constructs (H407A and Y424A). PG3178 binding to the HER3 ECD variants was tested in a FACS titration experiment. Two control antibodies, binding Domain I (MM-121) and Domain III (MEHD7945A) of HER3 were included to verify HER3 ECD expression on the cell surface. Mean MFI values were plotted and for each curve the AUC was calculated using GraphPad Prism 5 software. WT HER3 binding was used to normalize the data. The R426A mutation was shown to be critical for PG3178 binding whereas the binding to F409A could not be confirmed due to loss of cell surface expression (FIG. 18).

REFERENCES CITED IN THE EXAMPLES

1. Schmitz, K. R. and K. M. Ferguson, *Interaction of antibodies with ErbB receptor extracellular regions*. Exp Cell Res, 2009. 315(4): p. 659-70.
2. de Haard, H. J., et al., *A large non-immunized human Fab fragment phage library that permits rapid isolation and kinetic analysis of high affinity antibodies*. J Biol Chem, 1999. 274(26): p. 18218-30.
3. Marks, J. D., et al., By-passing immunization. *Human antibodies from V-gene libraries displayed on phage*. J Mol Biol, 1991. 222(3): p. 581-97.
4. Meulemans, E. V., et al., *Selection of phage-displayed antibodies specific for a cytoskeletal antigen by competitive elution with a monoclonal antibody*. J Mol Biol, 1994. 244(4): p. 353-60.
5. Giard, D. J., et al., *In vitro cultivation of human tumors: establishment of cell lines derived from a series of solid tumors*. J Natl Cancer Inst, 1973. 51(5): p. 1417-23.
6. Merlino, G. T., et al., *Amplification and enhanced expression of the epidermal growth factor receptor gene in A431 human carcinoma cells*. Science, 1984. 224(4647): p. 417-9.
7. Cochran, J. R., et al., *Domain-level antibody epitope mapping through yeast surface display of epidermal growth factor receptor fragments*. J Immunol Methods, 2004. 287(1-2): p. 147-58.
8. Ledon, N., et al., *Comparative analysis of binding affinities to epidermal growth factor receptor of monoclonal antibodies nimotuzumab and cetuximab using different experimental animal models*. Placenta, 2011. 32(7): p. 531-4.
9. Gulli, L. F., et al., *Epidermal growth factor-induced apoptosis in A431 cells can be reversed by reducing the tyrosine kinase activity*. Cell Growth Differ, 1996. 7(2): p. 173-8.
10. Pastore S, Mascia F, Mariotti F, Dattilo C, Mariani V, Girolomoni G. ERK1/2 regulates epidermal chemokine expression and skin inflammation. *J Immunol.* 2005; 174(8):5047-5056.
11. Lichtenberger B M, Gerber P a., Holcmann M, et al. Epidermal EGFR Controls Cutaneous Host Defense and Prevents Inflammation. *Sci Transl Med.* 2013; 5: 199ra111-199ra111. doi:10.1126/scitranslmed.3005886.
12. PCT/NL2013/050294
13. ADCC Enhancement Technologies for Next Generation Therapeutic Antibody. Cheng Liu and Andreia Lee. Antibody therapeutics—Trends in Bio/Pharmaceutical Industry 2009 [13-17]

TABLE 1

Overview of the phage antibody libraries generated from EGFR immunised mice.

| Library no. | Mouse | Library size | Insert frequency | Unique clones |
|---|---|---|---|---|
| ML1155 | E094#12 and E094#18 | 8.30E+06 | 96% | 97% |
| ML1156 | E094#14 and E094#16 | 8.60E+06 | 100% | 97% |

TABLE 2

Overview of known anti-EGFR antibodies used to epitope map the selected phage antibodies.

| Antibody name | PG nr/supplier: | Cat. Nr. | Domain specificity |
|---|---|---|---|
| ICR10 | Abcam | ab321 | I |
| EGFR.1 | Thermo scientific | MS-311-P | II |
| MatuzuMab | PG2982p02 | n/a | III |
| Cetuximab | Merck (clinical batch) | n/a | III |

N/A: not applicable.

TABLE 3

Overview of the domain specificity (as assessed by FACS using the 'swap domain' mutants and functionality of anti-EGFR antibodies. Functionality was compared to the clinically used antibody cetuximab. Activity of anti-EGFR cLC IgG (PG codes) in inhibiting EGF-induced cell death in A431 cells, compared to the activity of cetuximab in that assay.

| Cluster nr. | Representative antibody tested: | Origen of antibody | EGFR domain specificity | Mouse cross-reactivity | Cynomolgus cross-reactivity | EGFR blocking activity compared to cetuximab |
|---|---|---|---|---|---|---|
| 1 | PG3998 | MeMo | III | No | Yes | >100% |
|   | PG4010 | MeMo |   |   |   |   |
| 2 | PG4289 | MeMo | I | No | Yes | 80% |
|   | PG4003 | MeMo |   |   |   |   |
| 3 | PG4000 | MeMo | IV | No | Yes | <5% |
| 4 | PG4016 | MeMo | I | No | Yes | <5% |
| 5 | PG4033 | MeMo | II | No | Yes | 0% |
| 6 | PG4034 | MeMo | II | No | Yes | 0% |
| 7 | PG4035 | MeMo | IV | No | Yes | 0% |
| 8 | PG4032 | MeMo | III | No | Yes | <5% |
| 9 | PG4284 | MeMo | III | No | Yes | 30% |
| 10 | PG4358 | MeMo | III | No | Yes | ND |
| 11 | PG4280 | MeMo | III | No | Yes | 100% |
| 12 | PG4283 | MeMo | Variant III | No | Yes | 0% |
| 13 | PG4281 | MeMo | III | No | Yes | 70% |
| 14 | PG4286 | MeMo | III/IV | No | Yes | <10% |
| 15 | PG4285 | MeMo | Variant III | No | Yes | 0% |
| 16 | PG4287 | MeMo | III | No | Yes | <10% |
| 17 | PG4359 | MeMo | ND | No | Yes | ND |
| 18 | PG3370 | Synthetic library | III | Yes | Yes | 80% |

ND not determined.
Variant III: EGFR variant III specific.
PG codes represent full length IgG1 monoclonal antibodies.

TABLE 4

List of antagonistic anti-EGFR x anti-HER3 bispecific antibodies (PB codes) tested for BxPC3-Luc2 cell proliferation inhibition. These anti-EGFR and anti-HER3 arms were all shown to be active as mono-specific monoclonal antibody in inhibiting ligand (EGF- or NRG-) driven growth of tumour cells. The table shows the number of the bispecific protein (PB) that is composed of the respective EGFR- and HER3 binding arms (e.g. PB4510 is composed of MG3998 and MG3178). TheVH chain sequence of various MG chains are indicated with MF followed by the number in FIGS. 11A-11D. PB codes represent full length IgG1 bispecific antibodies

| EGFR | HER3 MG3178 | MG3176 | MG3163 | MG3157 | MG3156 | MG3125 |
|---|---|---|---|---|---|---|
| MG3998 | PB4510 | PG4556 | PG4533 | PB4579 | PB4631 | PB4654 |
| MG3999 | PB4511 | PB4557 | PB4534 | PB4580 | PB4616 | PB4639 |
| MG4010 | PB4512 | PB4558 | PB4535 | PB4581 | PB4617 | PB4640 |
| MG4013 | PB4514 | PB4560 | PB4537 | PB4583 | PB4618 | PG4641 |
| MG3751 | PB4518 | PB4564 | PB4541 | PB4587 | PB4620 | PB4643 |
| MG3752 | PB4519 | PB4565 | PB4542 | PB4588 | PB4621 | PB4644 |
| MG4025 | PB4521 | PB4567 | PB4544 | PB4590 | PB4622 | PB4645 |
| MG4280 | PB4522 | PB4568 | PB4545 | PB4591 | PB4623 | PB4646 |
| MG4290 | PB4523 | PB4569 | PB4546 | PB4592 | PB4624 | PB4647 |
| MG4281 | PB4524 | PB4570 | PB4547 | PB4593 | PB4625 | PB4648 |
| MG4284 | PB4525 | PB4571 | PB4548 | PB4594 | PB4626 | PB4649 |
| MG3370 | PB4526 | PB4572 | PB4549 | PB4595 | PB4627 | PB4650 |
| MG4002 | PB4527 | PB4573 | PB4550 | PB4596 | PB4628 | PB4651 |
| MG4003 | PB4528 | PB4574 | PB4551 | PB4597 | PB4629 | PB4652 |
| MG4289 | PB4529 | PB4575 | PB4552 | PB4598 | PB4630 | PB4653 |
| MG4011 | PB4513 | PB4559 | PB4536 | PB4582 | PB4632 | PB4655 |
| MG4014 | PB4515 | PB4561 | PB4538 | PB4584 | PB4633 | PB4656 |
| MG3756 | PB4517 | PB4563 | PB4540 | PB4586 | PB4634 | PB4657 |
| MG4023 | PB4520 | PB4566 | PB4543 | PB4589 | PB4635 | PB4658 |

TABLE 5

List of six anti-EGFR × anti-HER3 bispecific antibodies that were selected for in vivo testing in the BxPC3-Luc2 orthotopic model and their IC50 value for ligand-driven BxPC-3 cell proliferation inhibition.

| PB nr. | HER3 arm | EGFR arm | Domain specificity EGFR arm | IC50 for BxPC-3 ligand-driven cell proliferation inhibition (nM) |
|---|---|---|---|---|
| PB4510 | MG3178 | MG3998 | Domain III | 7 |
| PB4522 | MG3178 | MG4280 | Domain III | 13 |
| PB4528 | MG3178 | MG4003 | Domain I | 29 |
| PB4535 | MG3163 | MG4010 | Domain III | 65 |
| PB4549 | MG3163 | MG3370 | Domain III | 250 |
| PB4552 | MG3163 | MG4289 | Domain I | 62 |
| MEHD7945A | N/A | N/A | Domain III | 260 |

TABLE 6

IC50 values for inhibition of BxPC-3 cell proliferation determined for the different antibody formats tested: the bispecific (PB) anti-EGFR × HER3 leads, or a mix of the mono-specific, bivalent parental (PG) antibodies.

| Antibody tested | HER3 arm | EGFR arm | IC50 for BxPC-3 ligand-driven cell proliferation inhibition (pM) |
|---|---|---|---|
| PB4510 | MG3178 | MG3998 | 13 |
| PG3178 + PG3998 | | | 260 |
| PB4522 | MG3178 | MG4280 | 27 |
| PG3178 + PG4280 | | | 390 |
| PB4528 | MG3178 | MG4003 | 29 |
| PG3178 + PG4003 | | | 80 |
| PB4535 | MG3163 | MG4010 | 65 |
| PG3163 + PG4010 | | | 670 |
| PB4549 | MG3163 | MG3370 | 253 |
| PG3163 + PG3370 | | | 753 |
| PB4552 | MG3163 | MG4289 | 62 |
| PG3163 + PG4289 | | | 767 |
| MEHD7945A | N/A | N/A | 287 |

TABLE 7

The mean binding protein reactivities (and ranges) are listed for both critical residues. Critical residues involved in PG3178 binding were identified as those mutated in clones that were negative for PG3178 mAb binding (<20% WT) but positive for the control mAb 66223 binding (>70% WT). Residue numbering is that of PDB ID #4P59.

| HER3 Residue | Mutation | PG3178 binding % of wt binding (range) | Control of mAB binding % of wt binding (range) | Designation |
|---|---|---|---|---|
| 409 | F409A | 16.74 (8) | 79.63 (0) | Possibly critical |
| 426 | R426A | 3.17 (5) | 93.08 (36) | Critical |

TABLE 8

List of exposed residues within 11.2 Å radius of Arg 426 in HER3:

| | |
|---|---|
| Leu 423 | L423 |
| Tyr 424 | Y424 |
| Asn 425 | N425 |
| Glu 427 | G427 |
| Glu 452 | G452 |
| Arg 453 | R453 |
| Tyr 455 | Y455 |
| Glu 480 | E480 |
| Arg 481 | R481 |
| Leu482 | L482 |
| Asp 483 | D483 |
| Lys 485 | K485 |

REFERENCES CITED IN THE SPECIFICATION

1. Garrett T P, McKern N M, Lou M, Elleman T C, Adams T E, Lovrecz G O, Zhu H J, Walker F, Frenkel M J, Hoyne P A, Jorissen R N, Nice E C, et al. Crystal structure of a truncated epidermal growth factor receptor extracellular domain bound to transforming growth factor alpha. Cell 2002; 110:763-73.
2. Ogiso H, Ishitani R, Nureki O, Fukai S, Yamanaka M, Kim J H, Saito K, Sakamoto A, Inoue M, Shirouzu M, Yokoyama S. Crystal structure of the complex of human epidermal growth factor and receptor extracellular domains. Cell 2002; 110: 775-87.
3. Ferguson K M. Structure-based view of epidermal growth factor receptor regulation. Annu Rev Biophys 2008; 37: 353-73.
4. Yarden Y. The EGFR family and its ligands in human cancer. Signalling mechanisms and therapeutic opportunities. Eur J Cancer 2001; 37 (Suppl 4): S3-S8.
5. Jorissen R N, Walker F, Pouliot N, Garrett T P, Ward C W, Burgess A W. Epidermal growth factor receptor: mechanisms of activation and signalling. Exp Cell Res 2003; 284:31-53.
6. Buday L, Downward J. Epidermal growth factor regulates p21ras through the formation of a complex of receptor, Grb2 adapter protein, and Sos nucleotide exchange factor. Cell 1993; 73: 611-20.
7. Gale N W, Kaplan S, Lowenstein E J, Schlessinger J, Bar-Sagi D. Grb2 mediates the EGF-dependent activation of guanine nucleotide exchange on Ras. Nature 1993; 363:88-92.
8. Soltoff S P, Carraway K L, III, Prigent S A, Gullick W G, Cantley L C. ErbB3 is involved in activation of phosphatidylinositol 3-kinase by epidermal growth factor. Mol Cell Biol 1994; 14:3550-8.
9. Prigent S A, Gullick W J. Identification of cErbB-3 binding sites for phosphatidylinositol 30-kinase and SHC using an EGF receptor/c-ErbB-3 chimera. EMBO J 1994; 13:2831-41.
10. Uberall I, Kolar Z, Trojanec R, Berkovcova J, Hajduch M. The status and role of ErbB receptors in human cancer. Exp Mol Pathol 2008; 84:79-89.
11. Robertson S C, Tynan J, Donoghue D J. RTK mutations and human syndromes: when good receptors turn bad. Trends Genet 2000; 16:368.
12. Patel D K. Clinical use of anti-epidermal growth factor receptor monoclonal antibodies in metastatic colorectal cancer. Pharmacotherapy 2008; 28:31S-41S
13. Merchant et al. Nature Biotechnology, Vol. 16 Jul. 1998 pp 677-681

14. Nissim A, Hoogenboom H R, Tomlinson I M, Flynn G, Midgley C, Lane D, Winter G. 1994. Antibody fragments from a 'single pot' phage display library as immunochemical reagents. EMBO J. 1994 Feb. 1; 13(3):692-8.
15. WO2004/009618
16. WO2009/157771
17. WO 2008/027236
18. WO 2010/108127
19. Schaefer et al. Cancer Cell 20, 472-486, October 2011
20. Olayioye M A et al.; EMBO J (2000) Vol 19: pp 3159-3167)
21. Kubota T, Niwa R, Satoh M, Akinaga S, Shitara K, Hanai N. Engineered therapeutic antibodies with improved effector functions. Cancer Sci. 2009 September; 100(9): 1566-72.
22. US Patent Application 20030078385
23. Gunasekaran (JBC 2010, vol 285, pp 19637-19646)
24. WO 2013/157954 A1

The invention claimed is:

1. A method for the treatment of a subject having a EGFR, ErbB-3 or EGFR/ErbB-3 positive tumor or at risk of having said tumor comprising administering to the subject a bispecific antibody comprising a first variable domain comprising a first antigen-binding site that binds domain III of EGFR, wherein said first variable domain comprises a heavy chain variable region comprising a CDR1 comprising SEO ID NO: 9, a CDR2 comprising SEO ID NO: 11, and a CDR3 comprising SEO ID NO: 13; and a second variable domain comprising a second antigen-binding site that binds domain III of Erb-B3, wherein said second variable domain comprises a heavy chain variable region comprising a CDR1 comprising SEO ID NO: 90, a CDR2 comprising SEO ID NO: 156, and a CDR3 comprising SEO ID NO: 92, wherein said first and said second variable domains each comprise a common light chain comprising a CDR1 sequence of SEO ID NO:157, a CDR2 sequence of AAS, and a CDR3 sequence of SEQ ID NO:158, and wherein the heavy chain variable regions of the bispecific antibody are different from each other.

2. The method according to claim 1, wherein the tumor cell is a breast cancer cell, an ovarian cancer cell, a gastric cancer cell, a colorectal cancer cell, a pancreatic cancer cell or a lung cancer cell.

3. The method of claim 1, wherein said first variable domain comprises a heavy chain variable region at least 90% identical to SEQ ID NO: 7.

4. The method of claim 1, wherein said second variable domain comprises a heavy chain variable region at least 90% identical to SEQ ID NO: 120.

5. The method of claim 1, wherein the antibody is afucosylated in order to enhance ADCC.

6. The method of claim 1, wherein the antibody comprises two different immunoglobulin heavy chains with compatible heterodimerization domains.

7. The method of claim 6, wherein said compatible hetero-dimerization domains are compatible immunoglobulin heavy chain CH3 hetero-dimerization domains.

8. The method of claim 4, wherein a pharmaceutical composition comprises the bispecific antibody.

9. The method of claim 1, wherein the common light chain comprises a light chain variable region IGKV1-39.

10. The method of claim 9, wherein the common light chain comprises a germ-line light chain variable region IGKV1-39.

11. The method of claim 1, wherein said first variable domain comprises a heavy chain variable region comprising SEQ ID NO: 7.

12. The method of claim 11, wherein said second variable domain comprises a heavy chain variable region comprising SEQ ID NO: 120.

* * * * *

SEQUENCE LISTING

```
<160> NUMBER OF SEQ ID NOS: 158

<210> SEQ ID NO 1
<211> LENGTH: 3650
<212> TYPE: DNA
<213> ORGANISM: Artificial Sequence
<220> FEATURE:
<223> OTHER INFORMATION: chimeric cynomolgus-human EGFR encoding
      construct
<220> FEATURE:
<221> NAME/KEY: CDS
<222> LOCATION: (1)..(3639)
<220> FEATURE:
<221> NAME/KEY: mat_peptide
<222> LOCATION: (82)..(3639)

<400> SEQUENCE: 1 gct agc acc atg ggg ccc agc ggc acc gcc ggc gcc gcc ctg ctg gcc        48
Ala Ser Thr Met Gly Pro Ser Gly Thr Ala Gly Ala Ala Leu Leu Ala
        -25             -20                 -15 ctg ctg gcc gcc ctg tgc ccc gcc agc cgg gcc ctg gag gag aag aag        96
Leu Leu Ala Ala Leu Cys Pro Ala Ser Arg Ala Leu Glu Glu Lys Lys
    -10              -5              -1  1                   5 gtg tgc cag ggc acc agc aac aag ctg acc cag ctg ggc acc ttc gag       144
Val Cys Gln Gly Thr Ser Asn Lys Leu Thr Gln Leu Gly Thr Phe Glu
                    10                  15                  20 gac cac ttc ctg agc ctg cag cgg atg ttc aac aac tgc gag gtg gtg       192
Asp His Phe Leu Ser Leu Gln Arg Met Phe Asn Asn Cys Glu Val Val
                25                  30                  35 ctg ggc aac ctg gag atc acc tac gtg cag cgg aac tac gac ctg agc       240
Leu Gly Asn Leu Glu Ile Thr Tyr Val Gln Arg Asn Tyr Asp Leu Ser
            40                  45                  50 ttc ctg aag acc atc cag gag gtg gcc ggc tac gtg ctg atc gcc ctg       288
Phe Leu Lys Thr Ile Gln Glu Val Ala Gly Tyr Val Leu Ile Ala Leu
        55                  60                  65 aac acc gtg gag cgg atc ccc ctg gag aac ctg cag atc atc cgg ggc       336
Asn Thr Val Glu Arg Ile Pro Leu Glu Asn Leu Gln Ile Ile Arg Gly
70                  75                  80                  85 aac atg tac tac gag aac agc tac gcc ctg gcc gtg ctg agc aac tac       384
Asn Met Tyr Tyr Glu Asn Ser Tyr Ala Leu Ala Val Leu Ser Asn Tyr
                    90                  95                 100 gac gcc aac aag acc ggc ctg aag gag ctg ccc atg cgg aac ctg cag       432
Asp Ala Asn Lys Thr Gly Leu Lys Glu Leu Pro Met Arg Asn Leu Gln
                105                 110                 115 gag atc ctg cac ggc gcc gtg cgg ttc agc aac aac ccc gcc ctg tgc       480
Glu Ile Leu His Gly Ala Val Arg Phe Ser Asn Asn Pro Ala Leu Cys
            120                 125                 130 aac gtg gag agc atc cag tgg cgg gac atc gtg agc agc gag ttc ctg       528
Asn Val Glu Ser Ile Gln Trp Arg Asp Ile Val Ser Ser Glu Phe Leu
        135                 140                 145 agc aac atg agc atg gac ttc cag aac cac ctg ggc agc tgc cag aag       576
Ser Asn Met Ser Met Asp Phe Gln Asn His Leu Gly Ser Cys Gln Lys
150                 155                 160                 165
```

-continued

| | |
|---|---|
| tgc gac ccc agc tgc ccc aac ggc agc tgc tgg ggc gcc ggc gag gag<br>Cys Asp Pro Ser Cys Pro Asn Gly Ser Cys Trp Gly Ala Gly Glu Glu<br>               170                                175                     180 | 624 |
| aac tgc cag aag ctg acc aag atc atc tgc gcc cag cag tgc agc ggc<br>Asn Cys Gln Lys Leu Thr Lys Ile Ile Cys Ala Gln Gln Cys Ser Gly<br>               185                               190                        195 | 672 |
| cgg tgc cgg ggc aag agc ccc agc gac tgc tgc cac aac cag tgc gcc<br>Arg Cys Arg Gly Lys Ser Pro Ser Asp Cys Cys His Asn Gln Cys Ala<br>           200                             205                           210 | 720 |
| gcc ggc tgc acc ggc ccc cgg gag agc gac tgc ctg gtg tgc cgg aag<br>Ala Gly Cys Thr Gly Pro Arg Glu Ser Asp Cys Leu Val Cys Arg Lys<br>           215                             220                       225 | 768 |
| ttc cgg gac gag gcc acc tgc aag gac acc tgc ccc ccc ctg atg ctg<br>Phe Arg Asp Glu Ala Thr Cys Lys Asp Thr Cys Pro Pro Leu Met Leu<br>230                           235                         240                       245 | 816 |
| tac aac ccc acc acc tac cag atg gac gtg aac ccc gag ggc aag tac<br>Tyr Asn Pro Thr Thr Tyr Gln Met Asp Val Asn Pro Glu Gly Lys Tyr<br>                    250                               255                       260 | 864 |
| agc ttc ggc gcc acc tgc gtg aag aag tgc ccc cgg aac tac gtg gtg<br>Ser Phe Gly Ala Thr Cys Val Lys Lys Cys Pro Arg Asn Tyr Val Val<br>           265                             270                           275 | 912 |
| acc gac cac ggc agc tgc gtg cgg gcc tgc ggc gcc gac agc tac gag<br>Thr Asp His Gly Ser Cys Val Arg Ala Cys Gly Ala Asp Ser Tyr Glu<br>                    280                               285                       290 | 960 |
| atg gag gag gac ggc gtg cgg aag tgc aag aag tgc gag ggc ccc tgc<br>Met Glu Glu Asp Gly Val Arg Lys Cys Lys Lys Cys Glu Gly Pro Cys<br>           295                             300                           305 | 1008 |
| cgg aag gtg tgc aac ggc atc ggc atc ggc gag ttc aag gac acc ctg<br>Arg Lys Val Cys Asn Gly Ile Gly Ile Gly Glu Phe Lys Asp Thr Leu<br>310                           315                         320                       325 | 1056 |
| agc atc aac gcc acc aac atc aag cac ttc aag aac tgc acc agc atc<br>Ser Ile Asn Ala Thr Asn Ile Lys His Phe Lys Asn Cys Thr Ser Ile<br>                    330                               335                       340 | 1104 |
| agc ggc gac ctg cac atc ctg ccc gtg gcc ttc cgg ggc gac agc ttc<br>Ser Gly Asp Leu His Ile Leu Pro Val Ala Phe Arg Gly Asp Ser Phe<br>           345                             350                           355 | 1152 |
| acc cac acc ccc ccc ctg gac ccc cag gag ctg gac atc ctg aag acc<br>Thr His Thr Pro Pro Leu Asp Pro Gln Glu Leu Asp Ile Leu Lys Thr<br>                    360                               365                       370 | 1200 |
| gtg aag gag atc acc ggc ttc ctg ctg atc cag gcc tgg ccc gag aac<br>Val Lys Glu Ile Thr Gly Phe Leu Leu Ile Gln Ala Trp Pro Glu Asn<br>375                         380                         385 | 1248 |
| cgg acc gac ctg cac gcc ttc gag aac ctg gag atc atc cgg ggc cgg<br>Arg Thr Asp Leu His Ala Phe Glu Asn Leu Glu Ile Ile Arg Gly Arg<br>390                         395                         400                       405 | 1296 |
| acc aag cag cac ggc cag ttc agc ctg gcc gtg gtg agc ctg aac atc<br>Thr Lys Gln His Gly Gln Phe Ser Leu Ala Val Val Ser Leu Asn Ile<br>                    410                               415                       420 | 1344 |
| acc agc ctg ggc ctg cgg agc ctg aag gag atc agc gac ggc gac gtg<br>Thr Ser Leu Gly Leu Arg Ser Leu Lys Glu Ile Ser Asp Gly Asp Val<br>           425                             430                           435 | 1392 |
| atc atc agc ggc aac aag aac ctg tgc tac gcc aac acc atc aac tgg<br>Ile Ile Ser Gly Asn Lys Asn Leu Cys Tyr Ala Asn Thr Ile Asn Trp<br>                    440                               445                       450 | 1440 |
| aag aag ctg ttc ggc acc agc agc cag aag acc aag atc atc agc aac<br>Lys Lys Leu Phe Gly Thr Ser Ser Gln Lys Thr Lys Ile Ile Ser Asn<br>           455                             460                           465 | 1488 |
| cgg ggc gag aac agc tgc aag gcc acc ggc cag gtg tgc cac gcc ctg<br>Arg Gly Glu Asn Ser Cys Lys Ala Thr Gly Gln Val Cys His Ala Leu<br>470                         475                         480                       485 | 1536 |

```
tgc agc ccc gag ggc tgc tgg ggc ccc gag ccc cgg gac tgc gtg agc     1584
Cys Ser Pro Glu Gly Cys Trp Gly Pro Glu Pro Arg Asp Cys Val Ser
            490                 495                 500 tgc cag aac gtg agc cgg ggc cgg gag tgc gtg gac aag tgc aac atc     1632
Cys Gln Asn Val Ser Arg Gly Arg Glu Cys Val Asp Lys Cys Asn Ile
        505                 510                 515 ctg gag ggc gag ccc cgg gag ttc gtg gag aac agc gag tgc atc cag     1680
Leu Glu Gly Glu Pro Arg Glu Phe Val Glu Asn Ser Glu Cys Ile Gln
    520                 525                 530 tgc cac ccc gag tgc ctg ccc cag gtg atg aac atc acc tgc acc ggc     1728
Cys His Pro Glu Cys Leu Pro Gln Val Met Asn Ile Thr Cys Thr Gly
535                 540                 545 cgg ggc ccc gac aac tgc atc cag tgc gcc cac tac atc gac ggc ccc     1776
Arg Gly Pro Asp Asn Cys Ile Gln Cys Ala His Tyr Ile Asp Gly Pro
550                 555                 560                 565 cac tgc gtg aag acc tgc ccc gcc ggc gtg atg ggc gag aac aac acc     1824
His Cys Val Lys Thr Cys Pro Ala Gly Val Met Gly Glu Asn Asn Thr
            570                 575                 580 ctg gtg tgg aag tac gcc gac gcc ggc cac gtg tgc cac ctg tgc cac     1872
Leu Val Trp Lys Tyr Ala Asp Ala Gly His Val Cys His Leu Cys His
        585                 590                 595 ccc aac tgc acc tac ggc tgc acc ggc ccc ggc ctg gag ggc tgc gcc     1920
Pro Asn Cys Thr Tyr Gly Cys Thr Gly Pro Gly Leu Glu Gly Cys Ala
    600                 605                 610 cgg aac ggc ccc aag atc ccc agc atc gcc acc ggc atg ctg ggc gcc     1968
Arg Asn Gly Pro Lys Ile Pro Ser Ile Ala Thr Gly Met Leu Gly Ala
615                 620                 625 ctg ctg ctg ctg ctg gtg gtg gcc ctg ggc atc ggc ctg ttc atg cgg     2016
Leu Leu Leu Leu Leu Val Val Ala Leu Gly Ile Gly Leu Phe Met Arg
630                 635                 640                 645 cgg cgg cac atc gtg cgg aag cgg acc ctg cgg cgg ctg ctg cag gag     2064
Arg Arg His Ile Val Arg Lys Arg Thr Leu Arg Arg Leu Leu Gln Glu
            650                 655                 660 cgg gag ctg gtg gag ccc ctg acc ccc agc ggc gag gcc ccc aac cag     2112
Arg Glu Leu Val Glu Pro Leu Thr Pro Ser Gly Glu Ala Pro Asn Gln
        665                 670                 675 gcc ctg ctg cgg atc ctg aag gag acc gag ttc aag aag atc aag gtg     2160
Ala Leu Leu Arg Ile Leu Lys Glu Thr Glu Phe Lys Lys Ile Lys Val
    680                 685                 690 ctg ggc agc ggc gcc ttc ggc acc gtg tac aag ggc ctg tgg atc ccc     2208
Leu Gly Ser Gly Ala Phe Gly Thr Val Tyr Lys Gly Leu Trp Ile Pro
695                 700                 705 gag ggc gag aag gtg aag atc ccc gtg gcc atc aag gag ctg cgg gag     2256
Glu Gly Glu Lys Val Lys Ile Pro Val Ala Ile Lys Glu Leu Arg Glu
710                 715                 720                 725 gcc acc agc ccc aag gcc aac aag gag atc ctg gac gag gcc tac gtg     2304
Ala Thr Ser Pro Lys Ala Asn Lys Glu Ile Leu Asp Glu Ala Tyr Val
            730                 735                 740 atg gcc agc gtg gac aac ccc cac gtg tgc cgg ctg ctg ggc atc tgc     2352
Met Ala Ser Val Asp Asn Pro His Val Cys Arg Leu Leu Gly Ile Cys
        745                 750                 755 ctg acc agc acc gtg cag ctg atc acc cag ctg atg ccc ttc ggc tgc     2400
Leu Thr Ser Thr Val Gln Leu Ile Thr Gln Leu Met Pro Phe Gly Cys
    760                 765                 770 ctg ctg gac tac gtg cgg gag cac aag gac aac atc ggc agc cag tac     2448
Leu Leu Asp Tyr Val Arg Glu His Lys Asp Asn Ile Gly Ser Gln Tyr
775                 780                 785 ctg ctg aac tgg tgc gtg cag atc gcc aag ggc atg aac tac ctg gag     2496
Leu Leu Asn Trp Cys Val Gln Ile Ala Lys Gly Met Asn Tyr Leu Glu
```

-continued

| | | | | | | | | | | | | | | | |
|---|---|---|---|---|---|---|---|---|---|---|---|---|---|---|---|
| 790 | | | | | 795 | | | | | 800 | | | | | 805 |

```
gac cgg cgg ctg gtg cac cgg gac ctg gcc gcc cgg aac gtg ctg gtg           2544
Asp Arg Arg Leu Val His Arg Asp Leu Ala Ala Arg Asn Val Leu Val
                810                 815                 820 aag acc ccc cag cac gtg aag atc acc gac ttc ggc ctg gcc aag ctg           2592
Lys Thr Pro Gln His Val Lys Ile Thr Asp Phe Gly Leu Ala Lys Leu
            825                 830                 835 ctg ggc gcc gag gag aag gag tac cac gcc gag ggc ggc aag gtg ccc           2640
Leu Gly Ala Glu Glu Lys Glu Tyr His Ala Glu Gly Gly Lys Val Pro
        840                 845                 850 atc aag tgg atg gcc ctg gag agc atc ctg cac cgg atc tac acc cac           2688
Ile Lys Trp Met Ala Leu Glu Ser Ile Leu His Arg Ile Tyr Thr His
    855                 860                 865 cag agc gac gtg tgg agc tac ggc gtg acc gtg tgg gag ctg atg acc           2736
Gln Ser Asp Val Trp Ser Tyr Gly Val Thr Val Trp Glu Leu Met Thr
870                 875                 880                 885 ttc ggc agc aag ccc tac gac ggc atc ccc gcc agc gag atc agc agc           2784
Phe Gly Ser Lys Pro Tyr Asp Gly Ile Pro Ala Ser Glu Ile Ser Ser
                890                 895                 900 atc ctg gag aag ggc gag cgg ctg ccc cag ccc ccc atc tgc acc atc           2832
Ile Leu Glu Lys Gly Glu Arg Leu Pro Gln Pro Pro Ile Cys Thr Ile
            905                 910                 915 gac gtg tac atg atc atg gtg aag tgc tgg atg atc gac gcc gac agc           2880
Asp Val Tyr Met Ile Met Val Lys Cys Trp Met Ile Asp Ala Asp Ser
        920                 925                 930 cgg ccc aag ttc cgg gag ctg atc atc gag ttc agc aag atg gcc cgg           2928
Arg Pro Lys Phe Arg Glu Leu Ile Ile Glu Phe Ser Lys Met Ala Arg
    935                 940                 945 gac ccc cag cgg tac ctg gtg atc cag ggc gac gag cgg atg cac ctg           2976
Asp Pro Gln Arg Tyr Leu Val Ile Gln Gly Asp Glu Arg Met His Leu
950                 955                 960                 965 ccc agc ccc acc gac agc aac ttc tac cgg gcc ctg atg gac gag gag           3024
Pro Ser Pro Thr Asp Ser Asn Phe Tyr Arg Ala Leu Met Asp Glu Glu
                970                 975                 980 gac atg gac gac gtg gtg gac gcc gac gag tac ctg atc ccc cag cag           3072
Asp Met Asp Asp Val Val Asp Ala Asp Glu Tyr Leu Ile Pro Gln Gln
            985                 990                 995 ggc ttc ttc agc agc ccc agc acc  agc cgg acc ccc ctg ctg agc              3117
Gly Phe Phe Ser Ser Pro Ser Thr  Ser Arg Thr Pro Leu Leu Ser
                1000                 1005                1010 agc ctg agc gcc acc agc aac aac  agc acc gtg gcc tgc  atc gac             3162
Ser Leu Ser Ala Thr Ser Asn Asn  Ser Thr Val Ala Cys  Ile Asp
             1015                1020                  1025 cgg aac ggc ctg cag agc tgc ccc  atc aag gag gac agc  ttc ctg             3207
Arg Asn Gly Leu Gln Ser Cys Pro  Ile Lys Glu Asp Ser  Phe Leu
         1030                1035                     1040 cag cgg tac agc agc gac ccc acc  ggc gcc ctg acc gag  gac agc             3252
Gln Arg Tyr Ser Ser Asp Pro Thr  Gly Ala Leu Thr Glu  Asp Ser
     1045                1050                         1055 atc gac gac acc ttc ctg ccc gtg  ccc gag tac atc aac  cag agc             3297
Ile Asp Asp Thr Phe Leu Pro Val  Pro Glu Tyr Ile Asn  Gln Ser
 1060                1065                             1070 gtg ccc aag cgg ccc gcc ggc agc  gtg cag aac ccc gtg  tac cac             3342
Val Pro Lys Arg Pro Ala Gly Ser  Val Gln Asn Pro Val  Tyr His
         1075                1080                     1085 aac cag ccc ctg aac ccc gcc ccc  agc cgg gac ccc cac  tac cag             3387
Asn Gln Pro Leu Asn Pro Ala Pro  Ser Arg Asp Pro His  Tyr Gln
     1090                1095                         1100 gac ccc cac agc acc gcc gtg ggc  aac ccc gag tac ctg  aac acc             3432
Asp Pro His Ser Thr Ala Val Gly  Asn Pro Glu Tyr Leu  Asn Thr
```

-continued

| | | | | | | | | | | | | |
|---|---|---|---|---|---|---|---|---|---|---|---|---|
| Asp | Pro | His | Ser | Thr | Ala | Val | Gly | Asn | Pro | Glu | Tyr | Leu | Asn | Thr |
| | | 1105 | | | | 1110 | | | | 1115 | | |

```
gtg cag ccc acc tgc gtg aac agc acc ttc gac agc ccc gcc cac        3477
Val Gln Pro Thr Cys Val Asn Ser Thr Phe Asp Ser Pro Ala His
    1120                    1125                    1130 tgg gcc cag aag ggc agc cac cag atc agc ctg gac aac ccc gac        3522
Trp Ala Gln Lys Gly Ser His Gln Ile Ser Leu Asp Asn Pro Asp
    1135                    1140                    1145 tac cag cag gac ttc ttc ccc aag gag gcc aag ccc aac ggc atc        3567
Tyr Gln Gln Asp Phe Phe Pro Lys Glu Ala Lys Pro Asn Gly Ile
    1150                    1155                    1160 ttc aag ggc agc acc gcc gag aac gcc gag tac ctg cgg gtg gcc        3612
Phe Lys Gly Ser Thr Ala Glu Asn Ala Glu Tyr Leu Arg Val Ala
    1165                    1170                    1175 ccc cag agc agc gag ttc atc ggc gcc tgagcggccg c                   3650
Pro Gln Ser Ser Glu Phe Ile Gly Ala
    1180                    1185
```

<210> SEQ ID NO 2
<211> LENGTH: 1213
<212> TYPE: PRT
<213> ORGANISM: Artificial Sequence
<220> FEATURE:
<223> OTHER INFORMATION: Synthetic Construct

<400> SEQUENCE: 2

```
Ala Ser Thr Met Gly Pro Ser Gly Thr Ala Gly Ala Ala Leu Leu Ala
            -25                 -20                 -15

Leu Leu Ala Ala Leu Cys Pro Ala Ser Arg Ala Leu Glu Glu Lys Lys
    -10                  -5              -1   1               5

Val Cys Gln Gly Thr Ser Asn Lys Leu Thr Gln Leu Gly Thr Phe Glu
                 10                  15                  20

Asp His Phe Leu Ser Leu Gln Arg Met Phe Asn Asn Cys Glu Val Val
             25                  30                  35

Leu Gly Asn Leu Glu Ile Thr Tyr Val Gln Arg Asn Tyr Asp Leu Ser
         40                  45                  50

Phe Leu Lys Thr Ile Gln Glu Val Ala Gly Tyr Val Leu Ile Ala Leu
     55                  60                  65

Asn Thr Val Glu Arg Ile Pro Leu Glu Asn Leu Gln Ile Ile Arg Gly
 70                  75                  80                  85

Asn Met Tyr Tyr Glu Asn Ser Tyr Ala Leu Ala Val Leu Ser Asn Tyr
                 90                  95                 100

Asp Ala Asn Lys Thr Gly Leu Lys Glu Leu Pro Met Arg Asn Leu Gln
            105                 110                 115

Glu Ile Leu His Gly Ala Val Arg Phe Ser Asn Asn Pro Ala Leu Cys
        120                 125                 130

Asn Val Glu Ser Ile Gln Trp Arg Asp Ile Val Ser Ser Glu Phe Leu
    135                 140                 145

Ser Asn Met Ser Met Asp Phe Gln Asn His Leu Gly Ser Cys Gln Lys
150                 155                 160                 165

Cys Asp Pro Ser Cys Pro Asn Gly Ser Cys Trp Gly Ala Gly Glu Glu
                170                 175                 180

Asn Cys Gln Lys Leu Thr Lys Ile Ile Cys Ala Gln Gln Cys Ser Gly
            185                 190                 195

Arg Cys Arg Gly Lys Ser Pro Ser Asp Cys Cys His Asn Gln Cys Ala
        200                 205                 210

Ala Gly Cys Thr Gly Pro Arg Glu Ser Asp Cys Leu Val Cys Arg Lys
```

```
                215                 220                 225
Phe Arg Asp Glu Ala Thr Cys Lys Asp Thr Cys Pro Pro Leu Met Leu
230                 235                 240                 245

Tyr Asn Pro Thr Thr Tyr Gln Met Asp Val Asn Pro Glu Gly Lys Tyr
                250                 255                 260

Ser Phe Gly Ala Thr Cys Val Lys Lys Cys Pro Arg Asn Tyr Val Val
                265                 270                 275

Thr Asp His Gly Ser Cys Val Arg Ala Cys Gly Ala Asp Ser Tyr Glu
            280                 285                 290

Met Glu Glu Asp Gly Val Arg Lys Cys Lys Lys Cys Glu Gly Pro Cys
295                 300                 305

Arg Lys Val Cys Asn Gly Ile Gly Ile Gly Glu Phe Lys Asp Thr Leu
310                 315                 320                 325

Ser Ile Asn Ala Thr Asn Ile Lys His Phe Lys Asn Cys Thr Ser Ile
                330                 335                 340

Ser Gly Asp Leu His Ile Leu Pro Val Ala Phe Arg Gly Asp Ser Phe
                345                 350                 355

Thr His Thr Pro Pro Leu Asp Pro Gln Glu Leu Asp Ile Leu Lys Thr
            360                 365                 370

Val Lys Glu Ile Thr Gly Phe Leu Leu Ile Gln Ala Trp Pro Glu Asn
375                 380                 385

Arg Thr Asp Leu His Ala Phe Glu Asn Leu Glu Ile Ile Arg Gly Arg
390                 395                 400                 405

Thr Lys Gln His Gly Gln Phe Ser Leu Ala Val Val Ser Leu Asn Ile
                410                 415                 420

Thr Ser Leu Gly Leu Arg Ser Leu Lys Glu Ile Ser Asp Gly Asp Val
                425                 430                 435

Ile Ile Ser Gly Asn Lys Asn Leu Cys Tyr Ala Asn Thr Ile Asn Trp
            440                 445                 450

Lys Lys Leu Phe Gly Thr Ser Ser Gln Lys Thr Lys Ile Ile Ser Asn
455                 460                 465

Arg Gly Glu Asn Ser Cys Lys Ala Thr Gly Gln Val Cys His Ala Leu
470                 475                 480                 485

Cys Ser Pro Glu Gly Cys Trp Gly Pro Glu Pro Arg Asp Cys Val Ser
                490                 495                 500

Cys Gln Asn Val Ser Arg Gly Arg Glu Cys Val Asp Lys Cys Asn Ile
                505                 510                 515

Leu Glu Gly Glu Pro Arg Glu Phe Val Glu Asn Ser Glu Cys Ile Gln
            520                 525                 530

Cys His Pro Glu Cys Leu Pro Gln Val Met Asn Ile Thr Cys Thr Gly
535                 540                 545

Arg Gly Pro Asp Asn Cys Ile Gln Cys Ala His Tyr Ile Asp Gly Pro
550                 555                 560                 565

His Cys Val Lys Thr Cys Pro Ala Gly Val Met Gly Glu Asn Asn Thr
                570                 575                 580

Leu Val Trp Lys Tyr Ala Asp Ala Gly His Val Cys His Leu Cys His
                585                 590                 595

Pro Asn Cys Thr Tyr Gly Cys Thr Gly Pro Gly Leu Glu Gly Cys Ala
            600                 605                 610

Arg Asn Gly Pro Lys Ile Pro Ser Ile Ala Thr Gly Met Leu Gly Ala
615                 620                 625

Leu Leu Leu Leu Leu Val Val Ala Leu Gly Ile Gly Leu Phe Met Arg
630                 635                 640                 645
```

```
Arg Arg His Ile Val Arg Lys Arg Thr Leu Arg Arg Leu Leu Gln Glu
            650                 655                 660

Arg Glu Leu Val Glu Pro Leu Thr Pro Ser Gly Glu Ala Pro Asn Gln
            665                 670                 675

Ala Leu Leu Arg Ile Leu Lys Glu Thr Glu Phe Lys Lys Ile Lys Val
            680                 685                 690

Leu Gly Ser Gly Ala Phe Gly Thr Val Tyr Lys Gly Leu Trp Ile Pro
695                 700                 705

Glu Gly Glu Lys Val Lys Ile Pro Val Ala Ile Lys Glu Leu Arg Glu
710                 715                 720                 725

Ala Thr Ser Pro Lys Ala Asn Lys Glu Ile Leu Asp Glu Ala Tyr Val
            730                 735                 740

Met Ala Ser Val Asp Asn Pro His Val Cys Arg Leu Leu Gly Ile Cys
            745                 750                 755

Leu Thr Ser Thr Val Gln Leu Ile Thr Gln Leu Met Pro Phe Gly Cys
            760                 765                 770

Leu Leu Asp Tyr Val Arg Glu His Lys Asp Asn Ile Gly Ser Gln Tyr
            775                 780                 785

Leu Leu Asn Trp Cys Val Gln Ile Ala Lys Gly Met Asn Tyr Leu Glu
790                 795                 800                 805

Asp Arg Arg Leu Val His Arg Asp Leu Ala Ala Arg Asn Val Leu Val
            810                 815                 820

Lys Thr Pro Gln His Val Lys Ile Thr Asp Phe Gly Leu Ala Lys Leu
            825                 830                 835

Leu Gly Ala Glu Glu Lys Glu Tyr His Ala Glu Gly Gly Lys Val Pro
            840                 845                 850

Ile Lys Trp Met Ala Leu Glu Ser Ile Leu His Arg Ile Tyr Thr His
            855                 860                 865

Gln Ser Asp Val Trp Ser Tyr Gly Val Thr Val Trp Glu Leu Met Thr
870                 875                 880                 885

Phe Gly Ser Lys Pro Tyr Asp Gly Ile Pro Ala Ser Glu Ile Ser Ser
            890                 895                 900

Ile Leu Glu Lys Gly Glu Arg Leu Pro Gln Pro Pro Ile Cys Thr Ile
            905                 910                 915

Asp Val Tyr Met Ile Met Val Lys Cys Trp Met Ile Asp Ala Asp Ser
            920                 925                 930

Arg Pro Lys Phe Arg Glu Leu Ile Ile Glu Phe Ser Lys Met Ala Arg
935                 940                 945

Asp Pro Gln Arg Tyr Leu Val Ile Gln Gly Asp Glu Arg Met His Leu
950                 955                 960                 965

Pro Ser Pro Thr Asp Ser Asn Phe Tyr Arg Ala Leu Met Asp Glu Glu
            970                 975                 980

Asp Met Asp Asp Val Val Asp Ala Asp Glu Tyr Leu Ile Pro Gln Gln
            985                 990                 995

Gly Phe Phe Ser Ser Pro Ser Thr Ser Arg Thr Pro Leu Leu Ser
            1000                1005                1010

Ser Leu Ser Ala Thr Ser Asn Asn Ser Thr Val Ala Cys Ile Asp
            1015                1020                1025

Arg Asn Gly Leu Gln Ser Cys Pro Ile Lys Glu Asp Ser Phe Leu
            1030                1035                1040

Gln Arg Tyr Ser Ser Asp Pro Thr Gly Ala Leu Thr Glu Asp Ser
            1045                1050                1055
```

```
Ile Asp Asp Thr Phe Leu Pro Val Pro Glu Tyr Ile Asn Gln Ser
        1060                1065                1070

Val Pro Lys Arg Pro Ala Gly Ser Val Gln Asn Pro Val Tyr His
        1075                1080                1085

Asn Gln Pro Leu Asn Pro Ala Pro Ser Arg Asp Pro His Tyr Gln
        1090                1095                1100

Asp Pro His Ser Thr Ala Val Gly Asn Pro Glu Tyr Leu Asn Thr
        1105                1110                1115

Val Gln Pro Thr Cys Val Asn Ser Thr Phe Asp Ser Pro Ala His
        1120                1125                1130

Trp Ala Gln Lys Gly Ser His Gln Ile Ser Leu Asp Asn Pro Asp
        1135                1140                1145

Tyr Gln Gln Asp Phe Phe Pro Lys Glu Ala Lys Pro Asn Gly Ile
        1150                1155                1160

Phe Lys Gly Ser Thr Ala Glu Asn Ala Glu Tyr Leu Arg Val Ala
        1165                1170                1175

Pro Gln Ser Ser Glu Phe Ile Gly Ala
        1180                1185

<210> SEQ ID NO 3
<211> LENGTH: 617
<212> TYPE: PRT
<213> ORGANISM: Artificial Sequence
<220> FEATURE:
<223> OTHER INFORMATION: EGFR HER3 swap varII ECD

<400> SEQUENCE: 3

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Cys Pro Pro Cys His Glu Val Cys Lys Gly Arg Cys Trp Gly Pro Gly
                165                 170                 175

Ser Glu Asp Cys Gln Thr Leu Thr Lys Thr Ile Cys Ala Pro Gln Cys
            180                 185                 190

Asn Gly His Cys Phe Gly Pro Asn Pro Asn Gln Cys Cys His Asp Glu
        195                 200                 205

Cys Ala Gly Gly Cys Ser Gly Pro Gln Asp Thr Asp Cys Phe Ala Cys
    210                 215                 220
```

Arg His Phe Asn Asp Ser Gly Ala Cys Val Pro Arg Cys Pro Gln Pro
225                 230                 235                 240

Leu Val Tyr Asn Lys Leu Thr Phe Gln Leu Glu Pro Asn Pro His Thr
            245                 250                 255

Lys Tyr Gln Tyr Gly Gly Val Cys Val Ala Ser Cys Pro His Asn Phe
                260                 265                 270

Val Val Asp Gln Thr Ser Cys Val Arg Ala Cys Pro Pro Asp Lys Met
            275                 280                 285

Glu Val Asp Lys Asn Gly Leu Lys Met Cys Glu Pro Cys Gly Gly Leu
            290                 295                 300

Cys Pro Lys Ala Cys Glu Gly Ile Gly Ile Gly Glu Phe Lys Asp Ser
305                 310                 315                 320

Leu Ser Ile Asn Ala Thr Asn Ile Lys His Phe Lys Asn Cys Thr Ser
                325                 330                 335

Ile Ser Gly Asp Leu His Ile Leu Pro Val Ala Phe Arg Gly Asp Ser
                340                 345                 350

Phe Thr His Thr Pro Pro Leu Asp Pro Gln Glu Leu Asp Ile Leu Lys
            355                 360                 365

Thr Val Lys Glu Ile Thr Gly Phe Leu Leu Ile Gln Ala Trp Pro Glu
370                 375                 380

Asn Arg Thr Asp Leu His Ala Phe Glu Asn Leu Glu Ile Ile Arg Gly
385                 390                 395                 400

Arg Thr Lys Gln His Gly Gln Phe Ser Leu Ala Val Val Ser Leu Asn
                405                 410                 415

Ile Thr Ser Leu Gly Leu Arg Ser Leu Lys Glu Ile Ser Asp Gly Asp
            420                 425                 430

Val Ile Ile Ser Gly Asn Lys Asn Leu Cys Tyr Ala Asn Thr Ile Asn
            435                 440                 445

Trp Lys Lys Leu Phe Gly Thr Ser Gly Gln Lys Thr Lys Ile Ile Ser
450                 455                 460

Asn Arg Gly Glu Asn Ser Cys Lys Ala Thr Gly Gln Val Cys His Ala
465                 470                 475                 480

Leu Cys Ser Pro Glu Gly Cys Trp Gly Pro Glu Pro Arg Asp Cys Val
            485                 490                 495

Ser Cys Arg Asn Val Ser Arg Gly Arg Glu Cys Val Asp Lys Cys Asn
            500                 505                 510

Leu Leu Glu Gly Glu Pro Arg Glu Phe Val Glu Asn Ser Glu Cys Ile
            515                 520                 525

Gln Cys His Pro Glu Cys Leu Pro Gln Ala Met Asn Ile Thr Cys Thr
            530                 535                 540

Gly Arg Gly Pro Asp Asn Cys Ile Gln Cys Ala His Tyr Ile Asp Gly
545                 550                 555                 560

Pro His Cys Val Lys Thr Cys Pro Ala Gly Val Met Gly Glu Asn Asn
            565                 570                 575

Thr Leu Val Trp Lys Tyr Ala Asp Ala Gly His Val Cys His Leu Cys
            580                 585                 590

His Pro Asn Cys Thr Tyr Gly Cys Thr Gly Pro Gly Leu Glu Gly Cys
            595                 600                 605

Pro Thr Asn Gly Pro Lys Ile Pro Ser
610                 615

<210> SEQ ID NO 4
<211> LENGTH: 622
<212> TYPE: PRT

<213> ORGANISM: Artificial Sequence
<220> FEATURE:
<223> OTHER INFORMATION: EGFR HER3 swap varIII ECD

<400> SEQUENCE: 4

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Lys Ile Leu Gly Asn Leu Asp Phe Leu Ile Thr Gly Leu
            340                 345                 350

Asn Gly Asp Pro Trp His Lys Ile Pro Ala Leu Asp Pro Glu Lys Leu
        355                 360                 365

Asn Val Phe Arg Thr Val Arg Glu Ile Thr Gly Tyr Leu Asn Ile Gln
    370                 375                 380

Ser Trp Pro Pro His Met His Asn Phe Ser Val Phe Ser Asn Leu Thr
```

```
                385                 390                 395                 400
        Thr Ile Gly Gly Arg Ser Leu Tyr Asn Arg Gly Phe Ser Leu Leu Ile
                        405                 410                 415

Met Lys Asn Leu Asn Val Thr Ser Leu Gly Phe Arg Ser Leu Lys Glu
                        420                 425                 430

Ile Ser Ala Gly Arg Ile Tyr Ile Ser Ala Asn Arg Gln Leu Cys Tyr
                        435                 440                 445

His His Ser Leu Asn Trp Thr Lys Val Leu Gly Thr Ser Gly Gln Lys
                        450                 455                 460

Thr Lys Ile Ile Ser Asn Arg Gly Glu Asn Ser Cys Lys Ala Thr Gly
        465                 470                 475                 480

Gln Val Cys His Ala Leu Cys Ser Pro Glu Gly Cys Trp Gly Pro Glu
                        485                 490                 495

Pro Arg Asp Cys Val Ser Cys Arg Asn Val Ser Arg Gly Arg Glu Cys
                        500                 505                 510

Val Asp Lys Cys Asn Leu Leu Glu Gly Glu Pro Arg Glu Phe Val Glu
                        515                 520                 525

Asn Ser Glu Cys Ile Gln Cys His Pro Glu Cys Leu Pro Gln Ala Met
                        530                 535                 540

Asn Ile Thr Cys Thr Gly Arg Gly Pro Asp Asn Cys Ile Gln Cys Ala
        545                 550                 555                 560

His Tyr Ile Asp Gly Pro His Cys Val Lys Thr Cys Pro Ala Gly Val
                        565                 570                 575

Met Gly Glu Asn Asn Thr Leu Val Trp Lys Tyr Ala Asp Ala Gly His
                        580                 585                 590

Val Cys His Leu Cys His Pro Asn Cys Thr Tyr Gly Cys Thr Gly Pro
                        595                 600                 605

Gly Leu Glu Gly Cys Pro Thr Asn Gly Pro Lys Ile Pro Ser
                        610                 615                 620

<210> SEQ ID NO 5
<211> LENGTH: 619
<212> TYPE: PRT
<213> ORGANISM: Artificial Sequence
<220> FEATURE:
<223> OTHER INFORMATION: EGFR HER3 swap varIV ECD

<400> SEQUENCE: 5

Leu Glu Glu Lys Lys Val Cys Gln Gly Thr Ser Asn Lys Leu Thr Gln
        1               5                   10                  15

Leu Gly Thr Phe Glu Asp His Phe Leu Ser Leu Gln Arg Met Phe Asn
                        20                  25                  30

Asn Cys Glu Val Val Leu Gly Asn Leu Glu Ile Thr Tyr Val Gln Arg
                        35                  40                  45

Asn Tyr Asp Leu Ser Phe Leu Lys Thr Ile Gln Glu Val Ala Gly Tyr
                        50                  55                  60

Val Leu Ile Ala Leu Asn Thr Val Glu Arg Ile Pro Leu Glu Asn Leu
        65                  70                  75                  80

Gln Ile Ile Arg Gly Asn Met Tyr Tyr Glu Asn Ser Tyr Ala Leu Ala
                        85                  90                  95

Val Leu Ser Asn Tyr Asp Ala Asn Lys Thr Gly Leu Lys Glu Leu Pro
                        100                 105                 110

Met Arg Asn Leu Gln Glu Ile Leu His Gly Ala Val Arg Phe Ser Asn
                        115                 120                 125

Asn Pro Ala Leu Cys Asn Val Glu Ser Ile Gln Trp Arg Asp Ile Val
```

```
              130                 135                 140
Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
                195                 200                 205

His Asn Gln Cys Ala Ala Gly Cys Thr Gly Pro Arg Glu Ser Asp Cys
210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
                275                 280                 285

Ala Asp Ser Tyr Glu Met Glu Glu Asp Gly Val Arg Lys Cys Lys Lys
                290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
                355                 360                 365

Asp Ile Leu Lys Thr Val Lys Glu Ile Thr Gly Phe Leu Leu Ile Gln
                370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
                420                 425                 430

Ser Asp Gly Asp Val Ile Ile Ser Gly Asn Lys Asn Leu Cys Tyr Ala
                435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
                500                 505                 510

Asp Lys Cys Asn Leu Leu Glu Gly Glu Pro Arg Glu Phe Val Glu Glu
                515                 520                 525

Cys Phe Ser Cys His Pro Glu Cys Gln Pro Met Glu Gly Thr Ala Thr
                530                 535                 540

Cys Asn Gly Ser Gly Ser Asp Thr Cys Ala Gln Cys Ala His Phe Arg
545                 550                 555                 560
```

```
Asp Gly Pro His Cys Val Ser Ser Cys Pro His Gly Val Met Gly Glu
            565                 570                 575

Asn Asn Thr Leu Val Trp Lys Tyr Ala Asp Ala Gly His Val Cys His
        580                 585                 590

Leu Cys His Pro Asn Cys Thr Tyr Gly Cys Thr Gly Pro Gly Leu Glu
    595                 600                 605

Gly Cys Pro Thr Asn Gly Pro Lys Ile Pro Ser
610                 615
```

<210> SEQ ID NO 6
<211> LENGTH: 375
<212> TYPE: DNA
<213> ORGANISM: Artificial Sequence
<220> FEATURE:
<223> OTHER INFORMATION: MF4280: heavy chain variable region sequence of
      an EGFR binding antibody
<220> FEATURE:
<221> NAME/KEY: CDS
<222> LOCATION: (1)..(375)

<400> SEQUENCE: 6

```
cag gtg cag ctg gtg cag tct ggg gct gag gtg aag aag cct ggg gcc     48
Gln Val Gln Leu Val Gln Ser Gly Ala Glu Val Lys Lys Pro Gly Ala
1               5                   10                  15 tca gtg aag gtc tcc tgc aag gtt tcc gga tac acc ctc act gaa tta    96
Ser Val Lys Val Ser Cys Lys Val Ser Gly Tyr Thr Leu Thr Glu Leu
            20                  25                  30 tcc atg cac tgg gtg cga cag gct cct ggt aaa ggg ctt gaa tgg atg   144
Ser Met His Trp Val Arg Gln Ala Pro Gly Lys Gly Leu Glu Trp Met
        35                  40                  45 gga ggc ttt gat cct gag tat ggt aaa aca ttc ttc gca cag aac ttc   192
Gly Gly Phe Asp Pro Glu Tyr Gly Lys Thr Phe Phe Ala Gln Asn Phe
    50                  55                  60 cag ggc aga gtc acc atg acc gag gac aca tct gca gac aca gcc tac   240
Gln Gly Arg Val Thr Met Thr Glu Asp Thr Ser Ala Asp Thr Ala Tyr
65                  70                  75                  80 atg gag cta agc agc ctg aga tct gag gac acg gcc gtg tat tac tgt   288
Met Glu Leu Ser Ser Leu Arg Ser Glu Asp Thr Ala Val Tyr Tyr Cys
                85                  90                  95 gca aca gag ggg tat tat gag act act act tat tac tac aac ctt ttt   336
Ala Thr Glu Gly Tyr Tyr Glu Thr Thr Thr Tyr Tyr Tyr Asn Leu Phe
            100                 105                 110 gac tcc tgg ggc cag gga acc ctg gtc acc gtc tca agc                375
Asp Ser Trp Gly Gln Gly Thr Leu Val Thr Val Ser Ser
        115                 120                 125
```

<210> SEQ ID NO 7
<211> LENGTH: 125
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Tyr Gly Lys Thr Phe Phe Ala Gln Asn Phe
```

```
                    50                  55                  60

Gln Gly Arg Val Thr Met Thr Glu Asp Thr Ser Ala Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Glu Gly Tyr Tyr Glu Thr Thr Tyr Tyr Tyr Asn Leu Phe
            100                 105                 110

Asp Ser Trp Gly Gln Gly Thr Leu Val Thr Val Ser Ser
        115                 120                 125

<210> SEQ ID NO 8
<211> LENGTH: 30
<212> TYPE: PRT
<213> ORGANISM: Artificial Sequence
<220> FEATURE:
<223> OTHER INFORMATION: MF4280 FR1

<400> SEQUENCE: 8

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr
             20                  25                  30

<210> SEQ ID NO 9
<211> LENGTH: 5
<212> TYPE: PRT
<213> ORGANISM: Artificial Sequence
<220> FEATURE:
<223> OTHER INFORMATION: MF4280 CDR1

<400> SEQUENCE: 9

Glu Leu Ser Met His
 1               5

<210> SEQ ID NO 10
<211> LENGTH: 14
<212> TYPE: PRT
<213> ORGANISM: Artificial Sequence
<220> FEATURE:
<223> OTHER INFORMATION: MF4280 FR2

<400> SEQUENCE: 10

Trp Val Arg Gln Ala Pro Gly Lys Gly Leu Glu Trp Met Gly
 1               5                  10

<210> SEQ ID NO 11
<211> LENGTH: 17
<212> TYPE: PRT
<213> ORGANISM: Artificial Sequence
<220> FEATURE:
<223> OTHER INFORMATION: MF4280 CDR2

<400> SEQUENCE: 11

Gly Phe Asp Pro Glu Tyr Gly Lys Thr Phe Phe Ala Gln Asn Phe Gln
 1               5                  10                  15

Gly

<210> SEQ ID NO 12
<211> LENGTH: 32
<212> TYPE: PRT
<213> ORGANISM: Artificial Sequence
<220> FEATURE:
<223> OTHER INFORMATION: MF4280 FR3
```

<400> SEQUENCE: 12

Arg Val Thr Met Thr Glu Asp Thr Ser Ala Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 13
<211> LENGTH: 16
<212> TYPE: PRT
<213> ORGANISM: Artificial Sequence
<220> FEATURE:
<223> OTHER INFORMATION: MF4280 CDR3

<400> SEQUENCE: 13

Glu Gly Tyr Tyr Glu Thr Thr Thr Tyr Tyr Tyr Asn Leu Phe Asp Ser
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: MF4280 FR4

<400> SEQUENCE: 14

Trp Gly Gln Gly Thr Leu Val Thr Val Ser Ser
1               5                   10

<210> SEQ ID NO 15
<211> LENGTH: 360
<212> TYPE: DNA
<213> ORGANISM: Artificial Sequence
<220> FEATURE:
<223> OTHER INFORMATION: MF3998: heavy chain variable region sequence of
      an EGFR binding antibody
<220> FEATURE:
<221> NAME/KEY: CDS
<222> LOCATION: (1)..(360)

<400> SEQUENCE: 15 cag gtg cag ctg gtg cag tct ggg tct gag ttg aag aag cct ggg gcc     48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aac aat     96
Ser Val Lys Val Ser Cys Lys Ala Ser Gly Tyr Thr Phe Thr Asn Asn
            20                  25                  30 gcc ata aat tgg gtg cga cag gcc cct gga caa ggg ctt gag tgg atg    144
Ala Ile Asn Trp Val Arg Gln Ala Pro Gly Gln Gly Leu Glu Trp Met
        35                  40                  45 gga tgg atc aac acc atc act ggg gac cca acg tat gcc cag ggc ttc    192
Gly Trp Ile Asn Thr Ile Thr Gly Asp Pro Thr Tyr Ala Gln Gly Phe
    50                  55                  60 aca gga cgg ttt gtc ttc tcc ttg gac acc tct gtc agc acg gca tat    240
Thr Gly Arg Phe Val Phe Ser Leu Asp Thr Ser Val Ser Thr Ala Tyr
65                  70                  75                  80 ctg cag atc agc agc ctg aag gct gag gac act ggc gtg tat tac tgt    288
Leu Gln Ile Ser Ser Leu Lys Ala Glu Asp Thr Gly Val Tyr Tyr Cys
                85                  90                  95 gcg aga gag gaa ttt ttg gag tgg tta ttc ttt gac tac tgg ggc cag    336
Ala Arg Glu Glu Phe Leu Glu Trp Leu Phe Phe Asp Tyr Trp Gly Gln
            100                 105                 110 gga acc ctg gtc acc gtc tca agc                                    360
Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
            20                  25                  30

Ala Ile Asn Trp Val Arg Gln Ala Pro Gly Gln Gly Leu Glu Trp Met
        35                  40                  45

Gly Trp Ile Asn Thr Ile Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Gly Val Tyr Tyr Cys
                85                  90                  95

Ala Arg Glu Glu Phe Leu Glu Trp Leu Phe Phe Asp Tyr Trp Gly Gln
            100                 105                 110

Gly Thr Leu Val Thr Val Ser Ser
        115                 120

<210> SEQ ID NO 17
<211> LENGTH: 30
<212> TYPE: PRT
<213> ORGANISM: Artificial Sequence
<220> FEATURE:
<223> OTHER INFORMATION: MF3998 FR1

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 18
<211> LENGTH: 5
<212> TYPE: PRT
<213> ORGANISM: Artificial Sequence
<220> FEATURE:
<223> OTHER INFORMATION: MF3998 CDR1

<400> SEQUENCE: 18

Asn Asn Ala Ile Asn
1               5

<210> SEQ ID NO 19
<211> LENGTH: 14
<212> TYPE: PRT
<213> ORGANISM: Artificial Sequence
<220> FEATURE:
<223> OTHER INFORMATION: MF3998 FR2

<400> SEQUENCE: 19

Trp Val Arg Gln Ala Pro Gly Gln Gly Leu Glu Trp Met Gly
1               5                   10

<210> SEQ ID NO 20

```
<211> LENGTH: 17
<212> TYPE: PRT
<213> ORGANISM: Artificial Sequence
<220> FEATURE:
<223> OTHER INFORMATION: MF3998 CDR2

<400> SEQUENCE: 20

Trp Ile Asn Thr Ile Thr Gly Asp Pro Thr Tyr Ala Gln Gly Phe Thr
1               5                   10                  15

Gly

<210> SEQ ID NO 21
<211> LENGTH: 32
<212> TYPE: PRT
<213> ORGANISM: Artificial Sequence
<220> FEATURE:
<223> OTHER INFORMATION: MF3998 FR3

<400> SEQUENCE: 21

Arg Phe Val Phe Ser Leu Asp Thr Ser Val Ser Thr Ala Tyr Leu Gln
1               5                   10                  15

Ile Ser Ser Leu Lys Ala Glu Asp Thr Gly Val Tyr Tyr Cys Ala Arg
            20                  25                  30

<210> SEQ ID NO 22
<211> LENGTH: 11
<212> TYPE: PRT
<213> ORGANISM: Artificial Sequence
<220> FEATURE:
<223> OTHER INFORMATION: MF3998 CDR3

<400> SEQUENCE: 22

Glu Glu Phe Leu Glu Trp Leu Phe Phe Asp Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: MF3998 FR4

<400> SEQUENCE: 23

Trp Gly Gln Gly Thr Leu Val Thr Val Ser Ser
1               5                   10

<210> SEQ ID NO 24
<211> LENGTH: 369
<212> TYPE: DNA
<213> ORGANISM: Artificial Sequence
<220> FEATURE:
<223> OTHER INFORMATION: MF4010: heavy chain variable region sequence of
      an EGFR binding antibody:
<220> FEATURE:
<221> NAME/KEY: CDS
<222> LOCATION: (1)..(369)

<400> SEQUENCE: 24 cag gtg cag ctg gtg cag tct ggg tct gag ttg aag aag cct ggg gcc      48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc act aac aat      96
Ser Val Lys Val Ser Cys Lys Ala Ser Gly Tyr Thr Phe Thr Asn Asn
            20                  25                  30 gcc atg aat tgg gtg cga cag gcc cct gga caa ggg ctt gag tgg atg     144
Ala Met Asn Trp Val Arg Gln Ala Pro Gly Gln Gly Leu Glu Trp Met
```

```
                      35                  40                  45
gga tgg atc aac acc atc act ggg gac cca tcg tat gcc cag ggc ttc     192
Gly Trp Ile Asn Thr Ile Thr Gly Asp Pro Ser Tyr Ala Gln Gly Phe
         50                  55                  60 aca gga cgg ttt gtc ttc tcc ctg gac acc tct gtc aac acg gca tat     240
Thr Gly Arg Phe Val Phe Ser Leu Asp Thr Ser Val Asn Thr Ala Tyr
 65                  70                  75                  80 ctg cag atc agc agc ctg aag gct gag gac act gcc gta tat tac tgt     288
Leu Gln Ile Ser Ser Leu Lys Ala Glu Asp Thr Ala Val Tyr Tyr Cys
                 85                  90                  95 gcg aga gag gaa ttt ttg gag tgg tta ttc ttt gac tac tgg ggc cag     336
Ala Arg Glu Glu Phe Leu Glu Trp Leu Phe Phe Asp Tyr Trp Gly Gln
            100                 105                 110 gga acc ctg gtc acc gtc tca agc gtc tcc agt                         369
Gly Thr Leu Val Thr Val Ser Ser Val Ser Ser
            115                 120

<210> SEQ ID NO 25
<211> LENGTH: 123
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Asn
             20                  25                  30

Ala Met Asn Trp Val Arg Gln Ala Pro Gly Gln Gly Leu Glu Trp Met
         35                  40                  45

Gly Trp Ile Asn Thr Ile Thr Gly Asp Pro Ser Tyr Ala Gln Gly Phe
     50                  55                  60

Thr Gly Arg Phe Val Phe Ser Leu Asp Thr Ser Val Asn Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Glu Glu Phe Leu Glu Trp Leu Phe Phe Asp Tyr Trp Gly Gln
            100                 105                 110

Gly Thr Leu Val Thr Val Ser Ser Val Ser Ser
            115                 120

<210> SEQ ID NO 26
<211> LENGTH: 30
<212> TYPE: PRT
<213> ORGANISM: Artificial Sequence
<220> FEATURE:
<223> OTHER INFORMATION: MF4010 FR1

<400> SEQUENCE: 26

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr
             20                  25                  30

<210> SEQ ID NO 27
<211> LENGTH: 5
<212> TYPE: PRT
<213> ORGANISM: Artificial Sequence
<220> FEATURE:
<223> OTHER INFORMATION: MF40101 FR1
```

```
<400> SEQUENCE: 27

Asn Asn Ala Met Asn
1               5

<210> SEQ ID NO 28
<211> LENGTH: 14
<212> TYPE: PRT
<213> ORGANISM: Artificial Sequence
<220> FEATURE:
<223> OTHER INFORMATION: MF4010 FR2

<400> SEQUENCE: 28

Trp Val Arg Gln Ala Pro Gly Gln Gly Leu Glu Trp Met Gly
1               5                   10

<210> SEQ ID NO 29
<211> LENGTH: 17
<212> TYPE: PRT
<213> ORGANISM: Artificial Sequence
<220> FEATURE:
<223> OTHER INFORMATION: MF4010 CDR2

<400> SEQUENCE: 29

Trp Ile Asn Thr Ile Thr Gly Asp Pro Ser Tyr Ala Gln Gly Phe Thr
1               5                   10                  15

Gly

<210> SEQ ID NO 30
<211> LENGTH: 32
<212> TYPE: PRT
<213> ORGANISM: Artificial Sequence
<220> FEATURE:
<223> OTHER INFORMATION: MF4010 FR3

<400> SEQUENCE: 30

Arg Phe Val Phe Ser Leu Asp Thr Ser Val Asn Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 31
<211> LENGTH: 11
<212> TYPE: PRT
<213> ORGANISM: Artificial Sequence
<220> FEATURE:
<223> OTHER INFORMATION: MF40101 CDR3

<400> SEQUENCE: 31

Glu Glu Phe Leu Glu Trp Leu Phe Phe Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: MF4010 FR4

<400> SEQUENCE: 32

Trp Gly Gln Gly Thr Leu Val Thr Val Ser Ser
1               5                   10

<210> SEQ ID NO 33
<211> LENGTH: 366
```

<212> TYPE: DNA
<213> ORGANISM: Artificial Sequence
<220> FEATURE:
<223> OTHER INFORMATION: MF4003: heavy chain variable region sequence of
    an EGFR binding antibody:
<220> FEATURE:
<221> NAME/KEY: CDS
<222> LOCATION: (1)..(366)

<400> SEQUENCE: 33

```
cag gtg cag ctg gtg caa tct ggg tct gag ttg aag aag cct ggg gcc      48
Gln Val Gln Leu Val Gln Ser Gly Ser Glu Leu Lys Lys Pro Gly Ala
1               5                   10                  15 tca gtg aag gtt tcc tgc aag gct tct gga tac acc ttc cct agt ttt      96
Ser Val Lys Val Ser Cys Lys Ala Ser Gly Tyr Thr Phe Pro Ser Phe
            20                  25                  30 gct atg aat tgg ctt cga cag gcc cct gga caa ggg ctt gag tgg atg     144
Ala Met Asn Trp Leu Arg Gln Ala Pro Gly Gln Gly Leu Glu Trp Met
        35                  40                  45 gga tgg atc acc acc aac act ggg gac cca acg tat gcc cag ggc ttc     192
Gly Trp Ile Thr Thr Asn Thr Gly Asp Pro Thr Tyr Ala Gln Gly Phe
    50                  55                  60 tca gga cgg ttt gtg ttc tcc ctg gac acc tct gtc agc acg gca tat     240
Ser Gly Arg Phe Val Phe Ser Leu Asp Thr Ser Val Ser Thr Ala Tyr
65                  70                  75                  80 ctg cag atc agc agc cta aag gct gag gac act gcc gtg tat tac tgt     288
Leu Gln Ile Ser Ser Leu Lys Ala Glu Asp Thr Ala Val Tyr Tyr Cys
                85                  90                  95 gcg aga gtt tat aac tgg ata agg gga ttt gac tac tgg ggc cag gga     336
Ala Arg Val Tyr Asn Trp Ile Arg Gly Phe Asp Tyr Trp Gly Gln Gly
            100                 105                 110 acc ctg gtc acc gtc tca agc gtc tcc agt                             366
Thr Leu Val Thr Val Ser Ser Val Ser Ser
        115                 120
```

<210> SEQ ID NO 34
<211> LENGTH: 122
<212> TYPE: PRT
<213> ORGANISM: Artificial Sequence
<220> FEATURE:
<223> OTHER INFORMATION: Synthetic Construct

<400> SEQUENCE: 34

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Pro Ser Phe
            20                  25                  30

Ala Met Asn Trp Leu Arg Gln Ala Pro Gly Gln Gly Leu Glu Trp Met
        35                  40                  45

Gly Trp Ile Thr Thr Asn Thr Gly Asp Pro Thr Tyr Ala Gln Gly Phe
    50                  55                  60

Ser Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Val Tyr Asn Trp Ile Arg Gly Phe Asp Tyr Trp Gly Gln Gly
            100                 105                 110

Thr Leu Val Thr Val Ser Ser Val Ser Ser
        115                 120
```

<210> SEQ ID NO 35

```
<211> LENGTH: 30
<212> TYPE: PRT
<213> ORGANISM: Artificial Sequence
<220> FEATURE:
<223> OTHER INFORMATION: MF4003 FR1

<400> SEQUENCE: 35

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Pro
            20                  25                  30

<210> SEQ ID NO 36
<211> LENGTH: 5
<212> TYPE: PRT
<213> ORGANISM: Artificial Sequence
<220> FEATURE:
<223> OTHER INFORMATION: MF4003 CDR1

<400> SEQUENCE: 36

Ser Phe Ala Met Asn
1               5

<210> SEQ ID NO 37
<211> LENGTH: 14
<212> TYPE: PRT
<213> ORGANISM: Artificial Sequence
<220> FEATURE:
<223> OTHER INFORMATION: MF4003 FR2

<400> SEQUENCE: 37

Trp Leu Arg Gln Ala Pro Gly Gln Gly Leu Glu Trp Met Gly
1               5                   10

<210> SEQ ID NO 38
<211> LENGTH: 17
<212> TYPE: PRT
<213> ORGANISM: Artificial Sequence
<220> FEATURE:
<223> OTHER INFORMATION: MF4003 CDR2

<400> SEQUENCE: 38

Trp Ile Thr Thr Asn Thr Gly Asp Pro Thr Tyr Ala Gln Gly Phe Ser
1               5                   10                  15
Gly

<210> SEQ ID NO 39
<211> LENGTH: 32
<212> TYPE: PRT
<213> ORGANISM: Artificial Sequence
<220> FEATURE:
<223> OTHER INFORMATION: MF4003 FR3

<400> SEQUENCE: 39

Arg Phe Val Phe Ser Leu Asp Thr Ser Val Ser Thr Ala Tyr Leu Gln
1               5                   10                  15
Ile Ser Ser Leu Lys Ala Glu Asp Thr Ala Val Tyr Tyr Cys Ala Arg
            20                  25                  30

<210> SEQ ID NO 40
<211> LENGTH: 10
<212> TYPE: PRT
<213> ORGANISM: Artificial Sequence
<220> FEATURE:
<223> OTHER INFORMATION: MF4003 CDR3
```

```
<400> SEQUENCE: 40

Val Tyr Asn Trp Ile Arg Gly Phe Asp Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: MF4003 FR4

<400> SEQUENCE: 41

Trp Gly Gln Gly Thr Leu Val Thr Val Ser Ser
1               5                   10

<210> SEQ ID NO 42
<211> LENGTH: 385
<212> TYPE: DNA
<213> ORGANISM: Artificial Sequence
<220> FEATURE:
<223> OTHER INFORMATION: MF4289: heavy chain variable region sequence of
      an EGFR binding antibody:
<220> FEATURE:
<221> NAME/KEY: CDS
<222> LOCATION: (2)..(385)

<400> SEQUENCE: 42 g gcc cag ccg gcc atg gcc cag gtg cag ctg gtg caa tct ggg tct gaa      49
  Ala Gln Pro Ala Met Ala Gln Val Gln Leu Val Gln Ser Gly Ser Glu
  1               5                   10                  15 ttg aag aag cct ggg gcc tca gtg aag gtt tcc tgc aag act tct gga        97
Leu Lys Lys Pro Gly Ala Ser Val Lys Val Ser Cys Lys Thr Ser Gly
                20                  25                  30 tac acc ttc act gac tat gct atg act tgg gtg cga cag gcc cct gga       145
Tyr Thr Phe Thr Asp Tyr Ala Met Thr Trp Val Arg Gln Ala Pro Gly
            35                  40                  45 caa ggg ctt gaa tgg atg gga tgg atc acc acc aac act ggg gac cca       193
Gln Gly Leu Glu Trp Met Gly Trp Ile Thr Thr Asn Thr Gly Asp Pro
        50                  55                  60 acg tat gcc ccg ggc ttc aca gga cgg ttt gtc ttc tcc ttg gac acc       241
Thr Tyr Ala Pro Gly Phe Thr Gly Arg Phe Val Phe Ser Leu Asp Thr
65                  70                  75                  80 tct gtc agc acg gca tat ctg cag atc agc agc cta aag gcc gag gac       289
Ser Val Ser Thr Ala Tyr Leu Gln Ile Ser Ser Leu Lys Ala Glu Asp
                85                  90                  95 act gcc gta tat tac tgt gcg aga gtg tat cat tgg ata cgg gga ttt       337
Thr Ala Val Tyr Tyr Cys Ala Arg Val Tyr His Trp Ile Arg Gly Phe
            100                 105                 110 gag ttt tgg ggc cag gga acc ctg gtc acc gtc tca agc gtc tcc agt       385
Glu Phe Trp Gly Gln Gly Thr Leu Val Thr Val Ser Ser Val Ser Ser
        115                 120                 125

<210> SEQ ID NO 43
<211> LENGTH: 128
<212> TYPE: PRT
<213> ORGANISM: Artificial Sequence
<220> FEATURE:
<223> OTHER INFORMATION: Synthetic Construct

<400> SEQUENCE: 43

Ala Gln Pro Ala Met Ala Gln Val Gln Leu Val Gln Ser Gly Ser Glu
1               5                   10                  15

Leu Lys Lys Pro Gly Ala Ser Val Lys Val Ser Cys Lys Thr Ser Gly
                20                  25                  30
```

```
Tyr Thr Phe Thr Asp Tyr Ala Met Thr Trp Val Arg Gln Ala Pro Gly
            35                  40                  45

Gln Gly Leu Glu Trp Met Gly Trp Ile Thr Thr Asn Thr Gly Asp Pro
 50                  55                  60

Thr Tyr Ala Pro Gly Phe Thr Gly Arg Phe Val Phe Ser Leu Asp Thr
 65                  70                  75                  80

Ser Val Ser Thr Ala Tyr Leu Gln Ile Ser Ser Leu Lys Ala Glu Asp
                 85                  90                  95

Thr Ala Val Tyr Tyr Cys Ala Arg Val Tyr His Trp Ile Arg Gly Phe
                100                 105                 110

Glu Phe Trp Gly Gln Gly Thr Leu Val Thr Val Ser Ser Val Ser Ser
            115                 120                 125

<210> SEQ ID NO 44
<211> LENGTH: 119
<212> TYPE: PRT
<213> ORGANISM: Artificial Sequence
<220> FEATURE:
<223> OTHER INFORMATION: MF4289 complete VH sequence

<400> SEQUENCE: 44

Gln Val Gln Leu Val Gln Ser Gly Ser Glu Leu Lys Lys Pro Gly Ala
 1               5                  10                  15

Ser Val Lys Val Ser Cys Lys Thr Ser Gly Tyr Thr Phe Thr Asp Tyr
                 20                  25                  30

Ala Met Thr Trp Val Arg Gln Ala Pro Gly Gln Gly Leu Glu Trp Met
            35                  40                  45

Gly Trp Ile Thr Thr Asn Thr Gly Asp Pro Thr Tyr Ala Pro Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Val Tyr His Trp Ile Arg Gly Phe Glu Phe Trp Gly Gln Gly
                100                 105                 110

Thr Leu Val Thr Val Ser Ser
            115

<210> SEQ ID NO 45
<211> LENGTH: 30
<212> TYPE: PRT
<213> ORGANISM: Artificial Sequence
<220> FEATURE:
<223> OTHER INFORMATION: MF4289 FR1

<400> SEQUENCE: 45

Gln Val Gln Leu Val Gln Ser Gly Ser Glu Leu Lys Lys Pro Gly Ala
 1               5                  10                  15

Ser Val Lys Val Ser Cys Lys Thr Ser Gly Tyr Thr Phe Thr
                 20                  25                  30

<210> SEQ ID NO 46
<211> LENGTH: 5
<212> TYPE: PRT
<213> ORGANISM: Artificial Sequence
<220> FEATURE:
<223> OTHER INFORMATION: MF4289 CDR1

<400> SEQUENCE: 46
```

Asp Tyr Ala Met Thr
1               5

<210> SEQ ID NO 47
<211> LENGTH: 14
<212> TYPE: PRT
<213> ORGANISM: Artificial Sequence
<220> FEATURE:
<223> OTHER INFORMATION: MF4289 FR2

<400> SEQUENCE: 47

Trp Val Arg Gln Ala Pro Gly Gln Gly Leu Glu Trp Met Gly
1               5                   10

<210> SEQ ID NO 48
<211> LENGTH: 17
<212> TYPE: PRT
<213> ORGANISM: Artificial Sequence
<220> FEATURE:
<223> OTHER INFORMATION: MF4289 CDR2

<400> SEQUENCE: 48

Trp Ile Thr Thr Asn Thr Gly Asp Pro Thr Tyr Ala Pro Gly Phe Thr
1               5                   10                  15

Gly

<210> SEQ ID NO 49
<211> LENGTH: 32
<212> TYPE: PRT
<213> ORGANISM: Artificial Sequence
<220> FEATURE:
<223> OTHER INFORMATION: MF4289 FR3

<400> SEQUENCE: 49

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 50
<211> LENGTH: 10
<212> TYPE: PRT
<213> ORGANISM: Artificial Sequence
<220> FEATURE:
<223> OTHER INFORMATION: MF4289 CDR3

<400> SEQUENCE: 50

Val Tyr His Trp Ile Arg Gly Phe Glu Phe
1               5                   10

<210> SEQ ID NO 51
<211> LENGTH: 11
<212> TYPE: PRT
<213> ORGANISM: Artificial Sequence
<220> FEATURE:
<223> OTHER INFORMATION: MF4289 FR4

<400> SEQUENCE: 51

Trp Gly Gln Gly Thr Leu Val Thr Val Ser Ser
1               5                   10

<210> SEQ ID NO 52
<211> LENGTH: 366
<212> TYPE: DNA
<213> ORGANISM: Artificial Sequence
<220> FEATURE:

<223> OTHER INFORMATION: MF3370: heavy chain variable region sequence of
      an EGFR binding antibody:
<220> FEATURE:
<221> NAME/KEY: CDS
<222> LOCATION: (1)..(366)

<400> SEQUENCE: 52

| cag gtt cag ctg gtg cag tct gga gct gag gtg aag aag cct ggg gcc | 48 |
| Gln Val Gln Leu Val Gln Ser Gly Ala Glu Val Lys Lys Pro Gly Ala | |
| 1               5                  10                 15        | |

| tca gtg aag gtc tcc tgc aag gct tct ggt tac acc ttt acc agc tat | 96 |
| Ser Val Lys Val Ser Cys Lys Ala Ser Gly Tyr Thr Phe Thr Ser Tyr | |
|             20                 25                  30           | |

| ggt atc agc tgg gtg cga cag gcc cct gga caa ggg ctt gag tgg atg | 144 |
| Gly Ile Ser Trp Val Arg Gln Ala Pro Gly Gln Gly Leu Glu Trp Met | |
|         35                  40                 45               | |

| gga tgg atc agc gct tac aat ggt aac aca aac tat gca cag aag ctc | 192 |
| Gly Trp Ile Ser Ala Tyr Asn Gly Asn Thr Asn Tyr Ala Gln Lys Leu | |
|     50                  55                  60                  | |

| cag ggc aga gtc acc atg acc aca gac aca tcc acg agc aca gcc tac | 240 |
| Gln Gly Arg Val Thr Met Thr Thr Asp Thr Ser Thr Ser Thr Ala Tyr | |
| 65                  70                  75                  80  | |

| atg gag ctg agg agc ctg aga tct gac gac acg gct gtg tat tac tgt | 288 |
| Met Glu Leu Arg Ser Leu Arg Ser Asp Asp Thr Ala Val Tyr Tyr Cys | |
|                 85                  90                  95      | |

| gca aaa gat cgt cat tgg cat tgg tgg ctg gac gcc ttt gat tat tgg | 336 |
| Ala Lys Asp Arg His Trp His Trp Trp Leu Asp Ala Phe Asp Tyr Trp | |
|             100                 105                 110         | |

| ggc caa ggt acc ctg gtc acc gtc tcc agt | 366 |
| Gly Gln Gly Thr Leu Val Thr Val Ser Ser | |
|         115                 120         | |

<210> SEQ ID NO 53
<211> LENGTH: 122
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 54
<211> LENGTH: 30
<212> TYPE: PRT
<213> ORGANISM: Artificial Sequence

<220> FEATURE:
<223> OTHER INFORMATION: MF3370 FR1

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 55
<211> LENGTH: 5
<212> TYPE: PRT
<213> ORGANISM: Artificial Sequence
<220> FEATURE:
<223> OTHER INFORMATION: MF3370 CDR1

<400> SEQUENCE: 55

Ser Tyr Gly Ile Ser
1               5

<210> SEQ ID NO 56
<211> LENGTH: 14
<212> TYPE: PRT
<213> ORGANISM: Artificial Sequence
<220> FEATURE:
<223> OTHER INFORMATION: MF3370 FR2

<400> SEQUENCE: 56

Trp Val Arg Gln Ala Pro Gly Gln Gly Leu Glu Trp Met Gly
1               5                   10

<210> SEQ ID NO 57
<211> LENGTH: 17
<212> TYPE: PRT
<213> ORGANISM: Artificial Sequence
<220> FEATURE:
<223> OTHER INFORMATION: MF3370 CDR2

<400> SEQUENCE: 57

Trp Ile Ser Ala Tyr Asn Gly Asn Thr Asn Tyr Ala Gln Lys Leu Gln
1               5                   10                  15

Gly

<210> SEQ ID NO 58
<211> LENGTH: 32
<212> TYPE: PRT
<213> ORGANISM: Artificial Sequence
<220> FEATURE:
<223> OTHER INFORMATION: MF3370 FR3

<400> SEQUENCE: 58

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30

<210> SEQ ID NO 59
<211> LENGTH: 13
<212> TYPE: PRT
<213> ORGANISM: Artificial Sequence
<220> FEATURE:
<223> OTHER INFORMATION: MF3370 CDR3

<400> SEQUENCE: 59

Asp Arg His Trp His Trp Trp Leu Asp Ala Phe Asp Tyr

<210> SEQ ID NO 60
<211> LENGTH: 11
<212> TYPE: PRT
<213> ORGANISM: Artificial Sequence
<220> FEATURE:
<223> OTHER INFORMATION: MF3370 FR4

<400> SEQUENCE: 60

```
Trp Gly Gln Gly Thr Leu Val Thr Val Ser Ser
1               5                   10
```

<210> SEQ ID NO 61
<211> LENGTH: 366
<212> TYPE: DNA
<213> ORGANISM: Artificial Sequence
<220> FEATURE:
<223> OTHER INFORMATION: MF4002: heavy chain variable region sequence of
      an EGFR binding antibody:
<220> FEATURE:
<221> NAME/KEY: CDS
<222> LOCATION: (1)..(366)

<400> SEQUENCE: 61

```
cag gtg cag ctg gtg caa tct ggg tct gag ttg aag aag cct ggg tcc       48
Gln Val Gln Leu Val Gln Ser Gly Ser Glu Leu Lys Lys Pro Gly Ser
1               5                   10                  15 tca gtg aag gtt tcc tgc aag gct tct gga tac acc ttc act aac tat       96
Ser Val Lys Val Ser Cys Lys Ala Ser Gly Tyr Thr Phe Thr Asn Tyr
                20                  25                  30 gct atg aat tgg gtg cga cag gcc cct gga caa ggg ctt gag tgg atg      144
Ala Met Asn Trp Val Arg Gln Ala Pro Gly Gln Gly Leu Glu Trp Met
            35                  40                  45 gga tgg atc acc acc aac act ggg gac cca acg tat gcc cag ggc ttc      192
Gly Trp Ile Thr Thr Asn Thr Gly Asp Pro Thr Tyr Ala Gln Gly Phe
        50                  55                  60 aca gga cgt ttt gtc ttc tcc ttg gac acc tct gtc agt acg gca tat      240
Thr Gly Arg Phe Val Phe Ser Leu Asp Thr Ser Val Ser Thr Ala Tyr
65                  70                  75                  80 ctg cag atc agc agc cta aag gct gag gac act gcc gta tat tac tgt      288
Leu Gln Ile Ser Ser Leu Lys Ala Glu Asp Thr Ala Val Tyr Tyr Cys
                85                  90                  95 gtg aga gtg tat aac tgg ata agg gga ttt gac tac tgg ggc cag gga      336
Val Arg Val Tyr Asn Trp Ile Arg Gly Phe Asp Tyr Trp Gly Gln Gly
            100                 105                 110 acc ctg gtc acc gtc tca agc gtc tcc agt                              366
Thr Leu Val Thr Val Ser Ser Val Ser Ser
        115                 120
```

<210> SEQ ID NO 62
<211> LENGTH: 122
<212> TYPE: PRT
<213> ORGANISM: Artificial Sequence
<220> FEATURE:
<223> OTHER INFORMATION: Synthetic Construct

<400> SEQUENCE: 62

```
Gln Val Gln Leu Val Gln Ser Gly Ser Glu Leu Lys Lys Pro Gly Ser
1               5                   10                  15

Ser Val Lys Val Ser Cys Lys Ala Ser Gly Tyr Thr Phe Thr Asn Tyr
                20                  25                  30

Ala Met Asn Trp Val Arg Gln Ala Pro Gly Gln Gly Leu Glu Trp Met
            35                  40                  45
```

Gly Trp Ile Thr Thr Asn Thr Gly Asp Pro Thr Tyr Ala Gln Gly Phe
            50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Val Arg Val Tyr Asn Trp Ile Arg Gly Phe Asp Tyr Trp Gly Gln Gly
            100                 105                 110

Thr Leu Val Thr Val Ser Ser Val Ser Ser
            115                 120

<210> SEQ ID NO 63
<211> LENGTH: 30
<212> TYPE: PRT
<213> ORGANISM: Artificial Sequence
<220> FEATURE:
<223> OTHER INFORMATION: MF4002 FR1

<400> SEQUENCE: 63

Gln Val Gln Leu Val Gln Ser Gly Ser Glu Leu Lys Lys Pro Gly Ser
1               5                   10                  15

Ser Val Lys Val Ser Cys Lys Ala Ser Gly Tyr Thr Phe Thr
            20                  25                  30

<210> SEQ ID NO 64
<211> LENGTH: 5
<212> TYPE: PRT
<213> ORGANISM: Artificial Sequence
<220> FEATURE:
<223> OTHER INFORMATION: MF4002 CDR1

<400> SEQUENCE: 64

Asn Tyr Ala Met Asn
1               5

<210> SEQ ID NO 65
<211> LENGTH: 14
<212> TYPE: PRT
<213> ORGANISM: Artificial Sequence
<220> FEATURE:
<223> OTHER INFORMATION: MF4002 FR2

<400> SEQUENCE: 65

Trp Val Arg Gln Ala Pro Gly Gln Gly Leu Glu Trp Met Gly
1               5                   10

<210> SEQ ID NO 66
<211> LENGTH: 17
<212> TYPE: PRT
<213> ORGANISM: Artificial Sequence
<220> FEATURE:
<223> OTHER INFORMATION: MF4002 CDR2

<400> SEQUENCE: 66

Trp Ile Thr Thr Asn Thr Gly Asp Pro Thr Tyr Ala Gln Gly Phe Thr
1               5                   10                  15

Gly

<210> SEQ ID NO 67
<211> LENGTH: 32
<212> TYPE: PRT
<213> ORGANISM: Artificial Sequence
<220> FEATURE:

<223> OTHER INFORMATION: MF4002 FR3

<400> SEQUENCE: 67

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Val Arg
            20                  25                  30

<210> SEQ ID NO 68
<211> LENGTH: 10
<212> TYPE: PRT
<213> ORGANISM: Artificial Sequence
<220> FEATURE:
<223> OTHER INFORMATION: MF4002 CDR3

<400> SEQUENCE: 68

Val Tyr Asn Trp Ile Arg Gly Phe Asp Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: MF4002 FR4

<400> SEQUENCE: 69

Trp Gly Gln Gly Thr Leu Val Thr Val Ser Ser
1               5                   10

<210> SEQ ID NO 70
<211> LENGTH: 357
<212> TYPE: DNA
<213> ORGANISM: Artificial Sequence
<220> FEATURE:
<223> OTHER INFORMATION: MF3751: heavy chain variable region sequence of
      an EGFR binding antibody:
<220> FEATURE:
<221> NAME/KEY: CDS
<222> LOCATION: (1)..(357)

<400> SEQUENCE: 70 cag gtg cag ctg gta cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtt tcc tgc aag gca tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga aca atc aac cct agt ggt ggt agc aca tac tac gca cag aag ttc       192
Gly Thr Ile Asn Pro Ser Gly Gly Ser Thr Tyr Tyr Ala Gln Lys Phe
    50                  55                  60 cag ggc aga gtc acc atg acc agg gac acg tcc acg agc aca gtc tac       240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                85                  90                  95 gcg aga gat cgg aac tgg gga tgg gac ttt gac tac tgg ggc cag gga       336
Ala Arg Asp Arg Asn Trp Gly Trp Asp Phe Asp Tyr Trp Gly Gln Gly
            100                 105                 110 acc ctg gtc acc gtc tcc agt                                           357

Thr Leu Val Thr Val Ser Ser
        115

<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Thr Ile Asn Pro Ser Gly Gly Ser Thr Tyr Ala Gln Lys Phe
        50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Asn Trp Gly Trp Asp Phe Asp Tyr Trp Gly Gln Gly
            100                 105                 110

Thr Leu Val Thr Val Ser Ser
        115

<210> SEQ ID NO 72
<211> LENGTH: 30
<212> TYPE: PRT
<213> ORGANISM: Artificial Sequence
<220> FEATURE:
<223> OTHER INFORMATION: MF3751 FR1

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
                20                  25                  30

<210> SEQ ID NO 73
<211> LENGTH: 5
<212> TYPE: PRT
<213> ORGANISM: Artificial Sequence
<220> FEATURE:
<223> OTHER INFORMATION: MF3751 CDR1

<400> SEQUENCE: 73

Gly Tyr Tyr Met His
1               5

<210> SEQ ID NO 74
<211> LENGTH: 14
<212> TYPE: PRT
<213> ORGANISM: Artificial Sequence
<220> FEATURE:
<223> OTHER INFORMATION: MF3751 FR2

<400> SEQUENCE: 74

Trp Val Arg Gln Ala Pro Gly Gln Gly Leu Glu Trp Met Gly
1               5                   10

<210> SEQ ID NO 75
<211> LENGTH: 17
<212> TYPE: PRT
<213> ORGANISM: Artificial Sequence
<220> FEATURE:
<223> OTHER INFORMATION: MF3751 CDR2

<400> SEQUENCE: 75

```
Thr Ile Asn Pro Ser Gly Gly Ser Thr Tyr Tyr Ala Gln Lys Phe Gln
1               5                   10                  15

Gly
```

<210> SEQ ID NO 76
<211> LENGTH: 32
<212> TYPE: PRT
<213> ORGANISM: Artificial Sequence
<220> FEATURE:
<223> OTHER INFORMATION: MF3751 FR3

<400> SEQUENCE: 76

```
Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 77
<211> LENGTH: 10
<212> TYPE: PRT
<213> ORGANISM: Artificial Sequence
<220> FEATURE:
<223> OTHER INFORMATION: MF3751 CDR3

<400> SEQUENCE: 77

```
Asp Arg Asn Trp Gly Trp Asp Phe Asp Tyr
1               5                   10
```

<210> SEQ ID NO 78
<211> LENGTH: 11
<212> TYPE: PRT
<213> ORGANISM: Artificial Sequence
<220> FEATURE:
<223> OTHER INFORMATION: MF3751 FR4

<400> SEQUENCE: 78

```
Trp Gly Gln Gly Thr Leu Val Thr Val Ser Ser
1               5                   10
```

<210> SEQ ID NO 79
<211> LENGTH: 366
<212> TYPE: DNA
<213> ORGANISM: Artificial Sequence
<220> FEATURE:
<223> OTHER INFORMATION: MF3752: heavy chain variable region sequence of
      an EGFR binding antibody:
<220> FEATURE:
<221> NAME/KEY: CDS
<222> LOCATION: (1)..(366)

<400> SEQUENCE: 79

```
gag gtg cag ctg gtg gag tct ggg cct gag gtg aag aag cct ggg gcc      48
Glu Val Gln Leu Val Glu Ser Gly Pro Glu Val Lys Lys Pro Gly Ala
1               5                   10                  15 tca gtg aag gtt tcc tgc aag gca tct gga tac acc ttc acc agc tac      96
Ser Val Lys Val Ser Cys Lys Ala Ser Gly Tyr Thr Phe Thr Ser Tyr
            20                  25                  30
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga aca atc aac cct agt ggt ggt agc aca tac tac gca cag aag ttc      192
Gly Thr Ile Asn Pro Ser Gly Gly Ser Thr Tyr Tyr Ala Gln Lys Phe
 50                  55                  60 cag ggc aga gtc acc ctg acc agg gac acg tcc acg agc aca gtc tac      240
Gln Gly Arg Val Thr Leu Thr Arg Asp Thr Ser Thr Ser Thr Val Tyr
 65                  70                  75                  80 atg gtg ctg agc agc ctg aga tct gag gac acg gcc gtg tat tac tgt      288
Met Val Leu Ser Ser Leu Arg Ser Glu Asp Thr Ala Val Tyr Tyr Cys
                 85                  90                  95 gcg aga gat cgg aac tgg gga tgg gac ttt gac tac tgg ggc cag gga      336
Ala Arg Asp Arg Asn Trp Gly Trp Asp Phe Asp Tyr Trp Gly Gln Gly
            100                 105                 110 acc ctg gtc acc gtc tca agc gtc tcc agt                              366
Thr Leu Val Thr Val Ser Ser Val Ser Ser
            115                 120
```

<210> SEQ ID NO 80
<211> LENGTH: 122
<212> TYPE: PRT
<213> ORGANISM: Artificial Sequence
<220> FEATURE:
<223> OTHER INFORMATION: Synthetic Construct

<400> SEQUENCE: 80

```
Glu Val Gln Leu Val Glu Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Thr Ile Asn Pro Ser Gly Gly Ser Thr Tyr Tyr Ala Gln Lys Phe
 50                  55                  60

Gln Gly Arg Val Thr Leu Thr Arg Asp Thr Ser Thr Ser Thr Val Tyr
 65                  70                  75                  80

Met Val Leu Ser Ser Leu Arg Ser Glu Asp Thr Ala Val Tyr Tyr Cys
                 85                  90                  95

Ala Arg Asp Arg Asn Trp Gly Trp Asp Phe Asp Tyr Trp Gly Gln Gly
            100                 105                 110

Thr Leu Val Thr Val Ser Ser Val Ser Ser
            115                 120
```

<210> SEQ ID NO 81
<211> LENGTH: 30
<212> TYPE: PRT
<213> ORGANISM: Artificial Sequence
<220> FEATURE:
<223> OTHER INFORMATION: MF3752 FR1

<400> SEQUENCE: 81

```
Glu Val Gln Leu Val Glu Ser Gly Pro Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 82
<211> LENGTH: 5
<212> TYPE: PRT
<213> ORGANISM: Artificial Sequence

<220> FEATURE:
<223> OTHER INFORMATION: FR3752 CDR1

<400> SEQUENCE: 82

Ser Tyr Tyr Met His
1               5

<210> SEQ ID NO 83
<211> LENGTH: 14
<212> TYPE: PRT
<213> ORGANISM: Artificial Sequence
<220> FEATURE:
<223> OTHER INFORMATION: MF3752 FR2

<400> SEQUENCE: 83

Trp Val Arg Gln Ala Pro Gly Gln Gly Leu Glu Trp Met Gly
1               5                   10

<210> SEQ ID NO 84
<211> LENGTH: 17
<212> TYPE: PRT
<213> ORGANISM: Artificial Sequence
<220> FEATURE:
<223> OTHER INFORMATION: MF3752 CDR2

<400> SEQUENCE: 84

Thr Ile Asn Pro Ser Gly Gly Ser Thr Tyr Tyr Ala Gln Lys Phe Gln
1               5                   10                  15

Gly

<210> SEQ ID NO 85
<211> LENGTH: 32
<212> TYPE: PRT
<213> ORGANISM: Artificial Sequence
<220> FEATURE:
<223> OTHER INFORMATION: MF3752 FR3

<400> SEQUENCE: 85

Arg Val Thr Leu Thr Arg Asp Thr Ser Thr Ser Thr Val Tyr Met Val
1               5                   10                  15

Leu Ser Ser Leu Arg Ser Glu Asp Thr Ala Val Tyr Tyr Cys Ala Arg
                20                  25                  30

<210> SEQ ID NO 86
<211> LENGTH: 10
<212> TYPE: PRT
<213> ORGANISM: Artificial Sequence
<220> FEATURE:
<223> OTHER INFORMATION: MF3752 CDR3

<400> SEQUENCE: 86

Asp Arg Asn Trp Gly Trp Asp Phe Asp Tyr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: MF3752 FR4

<400> SEQUENCE: 87

Trp Gly Gln Gly Thr Leu Val Thr Val Ser Ser
1               5                   10

<210> SEQ ID NO 88
<211> LENGTH: 391
<212> TYPE: DNA
<213> ORGANISM: Artificial Sequence
<220> FEATURE:
<223> OTHER INFORMATION: MF3178: heavy chain variable region sequence of an erbB-3 binding antibody
<220> FEATURE:
<221> NAME/KEY: CDS
<222> LOCATION: (20)..(391)

<400> SEQUENCE: 88

```
ggcccagccg gccatggcc cag gtg cag ctg gtg cag tct ggg gct gag gtg      52
                     Gln Val Gln Leu Val Gln Ser Gly Ala Glu Val
                       1               5                  10 aag aag cct ggg gcc tca gtg aag gtc tcc tgc aag gct tct gga tac     100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa     148
Thr Phe Thr Gly Tyr Tyr Met His Trp Val Arg Gln Ala Pro Gly Gln
         30                  35                  40 ggg ctt gag tgg atg gga tgg atc aac cct aac agt ggt ggc aca aac     196
Gly Leu Glu Trp Met Gly Trp Ile Asn Pro Asn Ser Gly Gly Thr Asn
     45                  50                  55 tat gca cag aag ttt cag ggc agg gtc acg atg acc agg gac acg tcc     244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg     292
Ile Ser Thr Ala Tyr Met Glu Leu Ser Arg Leu Arg Ser Asp Asp Thr
                 80                  85                  90 gct gtg tat tac tgt gca aga gat cat ggt tct cgt cat ttc tgg tct     340
Ala Val Tyr Tyr Cys Ala Arg Asp His Gly Ser Arg His Phe Trp Ser
             95                 100                 105 tac tgg ggc ttt gat tat tgg ggc caa ggt acc ctg gtc acc gtc tcc     388
Tyr Trp Gly Phe Asp Tyr Trp Gly Gln Gly Thr Leu Val Thr Val Ser
         110                 115                 120 agt                                                                  391
Ser
```

<210> SEQ ID NO 89
<211> LENGTH: 124
<212> TYPE: PRT
<213> ORGANISM: Artificial Sequence
<220> FEATURE:
<223> OTHER INFORMATION: Synthetic Construct

<400> SEQUENCE: 89

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 90
<211> LENGTH: 5
<212> TYPE: PRT
<213> ORGANISM: Artificial Sequence
<220> FEATURE:
<223> OTHER INFORMATION: MF3178 CDR1

<400> SEQUENCE: 90

Gly Tyr Tyr Met His
1               5

<210> SEQ ID NO 91
<211> LENGTH: 17
<212> TYPE: PRT
<213> ORGANISM: Artificial Sequence
<220> FEATURE:
<223> OTHER INFORMATION: MF3178 CDR2

<400> SEQUENCE: 91

Trp Ile Asn Pro Asn Ser Gly Gly Thr Asn Tyr Ala Gln Lys Phe Gln
1               5                   10                  15

Gly

<210> SEQ ID NO 92
<211> LENGTH: 15
<212> TYPE: PRT
<213> ORGANISM: Artificial Sequence
<220> FEATURE:
<223> OTHER INFORMATION: MF3178 CDR3

<400> SEQUENCE: 92

Asp His Gly Ser Arg His Phe Trp Ser Tyr Trp Gly Phe Asp Tyr
1               5                   10                  15

<210> SEQ ID NO 93
<211> LENGTH: 385
<212> TYPE: DNA
<213> ORGANISM: Artificial Sequence
<220> FEATURE:
<223> OTHER INFORMATION: MF3176: heavy chain variable region sequence of
      an erbB-3 binding antibody
<220> FEATURE:
<221> NAME/KEY: CDS
<222> LOCATION: (20)..(385)

<400> SEQUENCE: 93
ggcccagccg gccatggcc gag gtg cag ctg ttg gag tct ggg gga ggc ttg      52
                     Glu Val Gln Leu Leu Glu Ser Gly Gly Gly Leu
                      1               5                   10 gta cag cct ggg ggg tcc ctg aga ctc tcc tgt gca gcc tct gga ttc      100
Val Gln Pro Gly Gly Ser Leu Arg Leu Ser Cys Ala Ala Ser Gly Phe
            15                  20                  25 acc ttt agc agc tat gcc atg agc tgg gtc cgc cag gct cca ggg aag      148
Thr Phe Ser Ser Tyr Ala Met Ser Trp Val Arg Gln Ala Pro Gly Lys
        30                  35                  40 ggg ctg gag tgg gtc tca gct att agt ggt agt ggt ggt agc aca tac      196
Gly Leu Glu Trp Val Ser Ala Ile Ser Gly Ser Gly Gly Ser Thr Tyr
    45                  50                  55 tac gca gac tcc gtg aag ggc cgg ttc acc atc tcc aga gac aat tcc      244
Tyr Ala Asp Ser Val Lys Gly Arg Phe Thr Ile Ser Arg Asp Asn Ser
60                  65                  70                  75 aag aac acg ctg tat ctg caa atg aac agc ctg aga gcc gag gac acg      292

```
                Lys Asn Thr Leu Tyr Leu Gln Met Asn Ser Leu Arg Ala Glu Asp Thr
                                 80                  85                  90 gct gtg tat tac tgt gca aga gat tgg tgg tac ccg ccg tac tac tgg            340
Ala Val Tyr Tyr Cys Ala Arg Asp Trp Trp Tyr Pro Pro Tyr Tyr Trp
         95                 100                 105 ggc ttt gat tat tgg ggc caa ggt acc ctg gtc acc gtc tcc agt                385
Gly Phe Asp Tyr Trp Gly Gln Gly Thr Leu Val Thr Val Ser Ser
    110                 115                 120
```

<210> SEQ ID NO 94
<211> LENGTH: 122
<212> TYPE: PRT
<213> ORGANISM: Artificial Sequence
<220> FEATURE:
<223> OTHER INFORMATION: Synthetic Construct

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Trp Trp Tyr Pro Pro Tyr Tyr Trp Gly Phe Asp Tyr Trp
        100                 105                 110

Gly Gln Gly Thr Leu Val Thr Val Ser Ser
    115                 120
```

<210> SEQ ID NO 95
<211> LENGTH: 5
<212> TYPE: PRT
<213> ORGANISM: Artificial Sequence
<220> FEATURE:
<223> OTHER INFORMATION: MF3176 CDR1

<400> SEQUENCE: 95

```
Ser Tyr Ala Met Ser
1               5
```

<210> SEQ ID NO 96
<211> LENGTH: 17
<212> TYPE: PRT
<213> ORGANISM: Artificial Sequence
<220> FEATURE:
<223> OTHER INFORMATION: MF3176 CDR2

<400> SEQUENCE: 96

```
Ala Ile Ser Gly Ser Gly Gly Ser Thr Tyr Tyr Ala Asp Ser Val Lys
1               5                   10                  15

Gly
```

<210> SEQ ID NO 97
<211> LENGTH: 13
<212> TYPE: PRT
<213> ORGANISM: Artificial Sequence
<220> FEATURE:

<223> OTHER INFORMATION: MF3176 CDR3

<400> SEQUENCE: 97

Asp Trp Trp Tyr Pro Pro Tyr Tyr Trp Gly Phe Asp Tyr
1               5                   10

<210> SEQ ID NO 98
<211> LENGTH: 391
<212> TYPE: DNA
<213> ORGANISM: Artificial Sequence
<220> FEATURE:
<223> OTHER INFORMATION: MF3163: heavy chain variable region sequence of an erbB-3 binding antibody
<220> FEATURE:
<221> NAME/KEY: CDS
<222> LOCATION: (20)..(391)

<400> SEQUENCE: 98

```
ggcccagccg gccatggcc cag gtg cag ctg gtg cag tct ggg gct gag gtg        52
                     Gln Val Gln Leu Val Gln Ser Gly Ala Glu Val
                      1               5                  10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
         15                  20                  25 acc ttc acc ggc tac tat atg cac tgg gtg cga cag gcc cct gga caa        148
Thr Phe Thr Gly Tyr Tyr Met His Trp Val Arg Gln Ala Pro Gly Gln
     30                  35                  40 ggg ctt gag tgg atg gga tgg atc aac cct aac agt ggt ggc aca aac        196
Gly Leu Glu Trp Met Gly Trp Ile Asn Pro Asn Ser Gly Gly Thr Asn
 45                  50                  55 tat gca cag aag ttt cag ggc agg gtc acg atg acc agg gac acg tcc        244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg        292
Ile Ser Thr Ala Tyr Met Glu Leu Ser Arg Leu Arg Ser Asp Asp Thr
                 80                  85                  90 gcc gtg tat tac tgt gca aaa gat tct tac tct cgt cat ttc tac tct        340
Ala Val Tyr Tyr Cys Ala Lys Asp Ser Tyr Ser Arg His Phe Tyr Ser
             95                 100                 105 tgg tgg gcc ttt gat tat tgg ggc caa ggt acc ctg gtc acc gtc tcc        388
Trp Trp Ala Phe Asp Tyr Trp Gly Gln Gly Thr Leu Val Thr Val Ser
            110                 115                 120 agt                                                                     391
Ser
```

<210> SEQ ID NO 99
<211> LENGTH: 124
<212> TYPE: PRT
<213> ORGANISM: Artificial Sequence
<220> FEATURE:
<223> OTHER INFORMATION: Synthetic Construct

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr

```
                65                  70                  75                  80
Met Glu Leu Ser Arg Leu Arg Ser Asp Asp Thr Ala Val Tyr Tyr Cys
                        85                  90                  95
Ala Lys Asp Ser Tyr Ser Arg His Phe Tyr Ser Trp Trp Ala Phe Asp
                    100                 105                 110
Tyr Trp Gly Gln Gly Thr Leu Val Thr Val Ser Ser
        115                 120
```

<210> SEQ ID NO 100
<211> LENGTH: 5
<212> TYPE: PRT
<213> ORGANISM: Artificial Sequence
<220> FEATURE:
<223> OTHER INFORMATION: MF3163 CDR1

<400> SEQUENCE: 100

```
Gly Tyr Tyr Met His
1               5
```

<210> SEQ ID NO 101
<211> LENGTH: 17
<212> TYPE: PRT
<213> ORGANISM: Artificial Sequence
<220> FEATURE:
<223> OTHER INFORMATION: MF3163 CDR2

<400> SEQUENCE: 101

```
Trp Ile Asn Pro Asn Ser Gly Gly Thr Asn Tyr Ala Gln Lys Phe Gln
1               5                   10                  15
Gly
```

<210> SEQ ID NO 102
<211> LENGTH: 15
<212> TYPE: PRT
<213> ORGANISM: Artificial Sequence
<220> FEATURE:
<223> OTHER INFORMATION: MF3163 CDR3

<400> SEQUENCE: 102

```
Asp Ser Tyr Ser Arg His Phe Tyr Ser Trp Trp Ala Phe Asp Tyr
1               5                   10                  15
```

<210> SEQ ID NO 103
<211> LENGTH: 382
<212> TYPE: DNA
<213> ORGANISM: Artificial Sequence
<220> FEATURE:
<223> OTHER INFORMATION: MF3099: heavy chain variable region sequence of
      an erbB-3 binding antibody
<220> FEATURE:
<221> NAME/KEY: CDS
<222> LOCATION: (20)..(382)

<400> SEQUENCE: 103

```
ggcccagccg gccatggcc gag gtc cag ctg cag cag cct ggg gct gag ctg        52
                     Glu Val Gln Leu Gln Gln Pro Gly Ala Glu Leu
                      1               5                  10 gtg agg cct ggg act tca gtg aag ttg tcc tgc aag gct tct ggc tac       100
Val Arg Pro Gly Thr Ser Val Lys Leu Ser Cys Lys Ala Ser Gly Tyr
             15                  20                  25 acc ttc acc agc tac tgg atg cac tgg gta aag cag agg cct gga caa       148
Thr Phe Thr Ser Tyr Trp Met His Trp Val Lys Gln Arg Pro Gly Gln
         30                  35                  40 ggc ctt gag tgg atc gga att ctt gat cct tct gat agt tat act acc       196
```

```
Gly Leu Glu Trp Ile Gly Ile Leu Asp Pro Ser Asp Ser Tyr Thr Thr
        45              50              55 tac aat caa aag ttc aag ggc aag gcc aca tta aca gta gac aca tcc    244
Tyr Asn Gln Lys Phe Lys Gly Lys Ala Thr Leu Thr Val Asp Thr Ser
 60              65              70              75 tcc agc ata gcc tac atg cag ctc agc agc ctg aca tct gag gac tct    292
Ser Ser Ile Ala Tyr Met Gln Leu Ser Ser Leu Thr Ser Glu Asp Ser
                 80              85              90 gcg ctc tat tac tgt gca aga ggg gga gat tac gac gag gga ggt gct    340
Ala Leu Tyr Tyr Cys Ala Arg Gly Gly Asp Tyr Asp Glu Gly Gly Ala
             95             100             105 atg gac tac tgg ggt caa gga acc tcg gtc acc gtc tcc agt            382
Met Asp Tyr Trp Gly Gln Gly Thr Ser Val Thr Val Ser Ser
        110             115             120

<210> SEQ ID NO 104
<211> LENGTH: 121
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ile Leu Asp Pro Ser Asp Ser Tyr Thr Thr Tyr Asn Gln Lys Phe
    50                  55                  60

Lys Gly Lys Ala Thr Leu Thr Val Asp Thr Ser Ser Ser Ile Ala Tyr
65                  70                  75                  80

Met Gln Leu Ser Ser Leu Thr Ser Glu Asp Ser Ala Leu Tyr Tyr Cys
                85                  90                  95

Ala Arg Gly Gly Asp Tyr Asp Glu Gly Gly Ala Met Asp Tyr Trp Gly
            100                 105                 110

Gln Gly Thr Ser Val Thr Val Ser Ser
        115                 120

<210> SEQ ID NO 105
<211> LENGTH: 5
<212> TYPE: PRT
<213> ORGANISM: Artificial Sequence
<220> FEATURE:
<223> OTHER INFORMATION: MF3099 CDR1

<400> SEQUENCE: 105

Ser Tyr Trp Met His
1               5

<210> SEQ ID NO 106
<211> LENGTH: 17
<212> TYPE: PRT
<213> ORGANISM: Artificial Sequence
<220> FEATURE:
<223> OTHER INFORMATION: MF3099 CDR2

<400> SEQUENCE: 106

Ile Leu Asp Pro Ser Asp Ser Tyr Thr Thr Tyr Asn Gln Lys Phe Lys
1               5                   10                  15
```

<210> SEQ ID NO 107
<211> LENGTH: 12
<212> TYPE: PRT
<213> ORGANISM: Artificial Sequence
<220> FEATURE:
<223> OTHER INFORMATION: MF3099 CDR3

<400> SEQUENCE: 107

Gly Gly Asp Tyr Asp Glu Gly Gly Ala Met Asp Tyr
1               5                   10

<210> SEQ ID NO 108
<211> LENGTH: 391
<212> TYPE: DNA
<213> ORGANISM: Artificial Sequence
<220> FEATURE:
<223> OTHER INFORMATION: MF3307: heavy chain variable region sequence of
      an erbB-3 binding antibody
<220> FEATURE:
<221> NAME/KEY: CDS
<222> LOCATION: (20)..(391)

<400> SEQUENCE: 108

```
ggcccagccg gccatggcc cag gtg cag ctg gtg cag tct ggg gct gag gtg       52
                     Gln Val Gln Leu Val Gln Ser Gly Ala Glu Val
                      1               5                  10 aag aag cct ggg gcc tca gtg aag gtc tcc tgc aag gct tct gga tac       100
Lys Lys Pro Gly Ala Ser Val Lys Val Ser Cys Lys Ala Ser Gly Tyr
             15                  20                  25 acc ttc acc ggc tac tat atg cac tgg gtg cga cag gcc cct gga caa       148
Thr Phe Thr Gly Tyr Tyr Met His Trp Val Arg Gln Ala Pro Gly Gln
         30                  35                  40 ggg ctt gag tgg atg gga tgg atc aac cct aac agt ggt ggc aca aac       196
Gly Leu Glu Trp Met Gly Trp Ile Asn Pro Asn Ser Gly Gly Thr Asn
     45                  50                  55 tat gca cag aag ttt cag ggc agg gtc acg atg acc agg gac acg tcc       244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg       292
Ile Ser Thr Ala Tyr Met Glu Leu Ser Arg Leu Arg Ser Asp Asp Thr
                 80                  85                  90 gcc gtg tat tac tgt gca aga ggt tct cgt aaa cgt ctg tct aac tac       340
Ala Val Tyr Tyr Cys Ala Arg Gly Ser Arg Lys Arg Leu Ser Asn Tyr
             95                 100                 105 ttc aac gcc ttt gat tat tgg ggc caa ggt acc ctg gtc acc gtc tcc       388
Phe Asn Ala Phe Asp Tyr Trp Gly Gln Gly Thr Leu Val Thr Val Ser
        110                 115                 120 agt                                                                    391
Ser
```

<210> SEQ ID NO 109
<211> LENGTH: 124
<212> TYPE: PRT
<213> ORGANISM: Artificial Sequence
<220> FEATURE:
<223> OTHER INFORMATION: Synthetic Construct

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

```
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Gly Ser Arg Lys Arg Leu Ser Asn Tyr Phe Asn Ala Phe Asp
            100                 105                 110
Tyr Trp Gly Gln Gly Thr Leu Val Thr Val Ser Ser
        115                 120
```

```
<210> SEQ ID NO 110
<211> LENGTH: 5
<212> TYPE: PRT
<213> ORGANISM: Artificial Sequence
<220> FEATURE:
<223> OTHER INFORMATION: MF3307 CDR1

<400> SEQUENCE: 110

Gly Tyr Tyr Met His
1               5

<210> SEQ ID NO 111
<211> LENGTH: 17
<212> TYPE: PRT
<213> ORGANISM: Artificial Sequence
<220> FEATURE:
<223> OTHER INFORMATION: MF3307 CDR2

<400> SEQUENCE: 111

Trp Ile Asn Pro Asn Ser Gly Gly Thr Asn Tyr Ala Gln Lys Phe Gln
1               5                   10                  15
Gly

<210> SEQ ID NO 112
<211> LENGTH: 15
<212> TYPE: PRT
<213> ORGANISM: Artificial Sequence
<220> FEATURE:
<223> OTHER INFORMATION: MF3307 CDR3

<400> SEQUENCE: 112

Gly Ser Arg Lys Arg Leu Ser Asn Tyr Phe Asn Ala Phe Asp Tyr
1               5                   10                  15

<210> SEQ ID NO 113
<211> LENGTH: 372
<212> TYPE: DNA
<213> ORGANISM: Artificial Sequence
<220> FEATURE:
<223> OTHER INFORMATION: MF6055_VH
<220> FEATURE:
<221> NAME/KEY: CDS
<222> LOCATION: (1)..(372)

<400> SEQUENCE: 113
```

```
cag gtg cag ctg gtg cag tct ggg gct gac gtg aag aag cct ggg gcc        48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
```

```
                 20                  25                  30
tat atg cac tgg gtg cga cag gcc cct gga caa gct ctt gag tgg atg     144
Tyr Met His Trp Val Arg Gln Ala Pro Gly Gln Ala Leu Glu Trp Met
         35                  40                  45 gga tgg atc aac cct tct agt ggt ggc aca aac tat gca aag aag ttt     192
Gly Trp Ile Asn Pro Ser Ser Gly Gly Thr Asn Tyr Ala Lys Lys Phe
 50                  55                  60 cag ggc agg gtc acg atg acc agg gag acg tcc aca agc aca gcc tac     240
Gln Gly Arg Val Thr Met Thr Arg Glu Thr Ser Thr Ser Thr Ala Tyr
 65                  70                  75                  80 atg gag ctg agc agg ctg aga tct gac gac acg gct acg tat tac tgt     288
Met Glu Leu Ser Arg Leu Arg Ser Asp Asp Thr Ala Thr Tyr Tyr Cys
                 85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
                100                 105                 110 tat tgg ggc caa ggt acc ctg gtc acc gtc tcc agt                     372
Tyr Trp Gly Gln Gly Thr Leu Val Thr Val Ser Ser
        115                 120

<210> SEQ ID NO 114
<211> LENGTH: 124
<212> TYPE: PRT
<213> ORGANISM: Artificial Sequence
<220> FEATURE:
<223> OTHER INFORMATION: Synthetic Construct

<400> SEQUENCE: 114

Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Ser Ser Gly Gly Thr Asn Tyr Ala Lys Lys Phe
    50                  55                  60

Gln Gly Arg Val Thr Met Thr Arg Glu Thr Ser Thr Ser Thr Ala Tyr
65                  70                  75                  80

Met Glu Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 115
<211> LENGTH: 372
<212> TYPE: DNA
<213> ORGANISM: Artificial Sequence
<220> FEATURE:
<223> OTHER INFORMATION: MF6056_VH
<220> FEATURE:
<221> NAME/KEY: CDS
<222> LOCATION: (1)..(372)

<400> SEQUENCE: 115 cag gtg cag ctg gtg cag tct ggg gct gac gtg aag aag cct ggg gcc     48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac     96
Ser Val Lys Val Thr Cys Lys Ala Ser Gly Tyr Thr Phe Thr Gly Tyr
```

```
              20                  25                  30
tat atg cac tgg gtg cga cag gcc cct gga caa gct ctt gag tgg atg    144
Tyr Met His Trp Val Arg Gln Ala Pro Gly Gln Ala Leu Glu Trp Met
         35                  40                  45 gga tgg atc aac cct tct agt ggt ggc aca aac tat gca aag aag ttt    192
Gly Trp Ile Asn Pro Ser Ser Gly Gly Thr Asn Tyr Ala Lys Lys Phe
 50                  55                  60 cag ggc agg gtc tct atg acc agg gag acg tcc aca agc aca gcc tac    240
Gln Gly Arg Val Ser Met Thr Arg Glu Thr Ser Thr Ser Thr Ala Tyr
 65                  70                  75                  80 atg cag ctg agc agg ctg aga tct gac gac acg gct acg tat tac tgt    288
Met Gln Leu Ser Arg Leu Arg Ser Asp Asp Thr Ala Thr Tyr Tyr Cys
                 85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
                100                 105                 110 tat tgg ggc caa ggt acc ctg gtc acc gtc tcc agt                    372
Tyr Trp Gly Gln Gly Thr Leu Val Thr Val Ser Ser
        115                 120
```

<210> SEQ ID NO 116
<211> LENGTH: 124
<212> TYPE: PRT
<213> ORGANISM: Artificial Sequence
<220> FEATURE:
<223> OTHER INFORMATION: Synthetic Construct

<400> SEQUENCE: 116

```
Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
         35                  40                  45

Gly Trp Ile Asn Pro Ser Ser Gly Gly Thr Asn Tyr Ala Lys Lys Phe
 50                  55                  60

Gln Gly Arg Val Ser Met Thr Arg Glu Thr Ser Thr Ser Thr Ala Tyr
 65                  70                  75                  80

Met Gln Leu Ser Arg Leu Arg Ser Asp Asp Thr Ala Thr Tyr Tyr Cys
                 85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
        115                 120
```

<210> SEQ ID NO 117
<211> LENGTH: 372
<212> TYPE: DNA
<213> ORGANISM: Artificial Sequence
<220> FEATURE:
<223> OTHER INFORMATION: MF6057_VH
<220> FEATURE:
<221> NAME/KEY: CDS
<222> LOCATION: (1)..(372)

<400> SEQUENCE: 117

```
cag gtg cag ctg gtg cag tct ggg gct gat gtg aag aag cct ggg gcc    48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac    96
Ser Val Lys Val Thr Cys Lys Ala Ser Gly Tyr Thr Phe Thr Gly Tyr
            20                  25                  30
```

```
                   20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
 50                  55                  60 cag ggc agg gtc acg atg acc agg gac acg tcc atc agc aca gcc tac      240
Gln Gly Arg Val Thr Met Thr Arg Asp Thr Ser Ile Ser Thr Ala Tyr
 65                  70                  75                  80 atg cag ctg agc agg ctg aga tct gac gac acg gct gtg tat tac tgt      288
Met Gln Leu Ser Arg Leu Arg Ser Asp Asp Thr Ala Val Tyr Tyr Cys
             85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 118
<211> LENGTH: 124
<212> TYPE: PRT
<213> ORGANISM: Artificial Sequence
<220> FEATURE:
<223> OTHER INFORMATION: Synthetic Construct

<400> SEQUENCE: 118

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 119
<211> LENGTH: 372
<212> TYPE: DNA
<213> ORGANISM: Artificial Sequence
<220> FEATURE:
<223> OTHER INFORMATION: MF6058_VH
<220> FEATURE:
<221> NAME/KEY: CDS
<222> LOCATION: (1)..(372)

<400> SEQUENCE: 119 cag gtg cag ctg gtg cag tct ggg gct gac gtg aag aag cct ggg gcc       48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac       96
Ser Val Lys Val Thr Cys Lys Ala Ser Gly Tyr Thr Phe Thr Gly Tyr
            20                  25                  30
```

```
tat atg cac tgg gtg cga cag gcc cct gga caa gct ctt gag tgg atg      144
Tyr Met His Trp Val Arg Gln Ala Pro Gly Gln Ala Leu Glu Trp Met
        35                  40                  45 gga tgg atc aac cct caa agt ggt ggc aca aac tat gca aag aag ttt      192
Gly Trp Ile Asn Pro Gln Ser Gly Gly Thr Asn Tyr Ala Lys Lys Phe
 50                  55                  60 cag ggc agg gtc tct atg acc agg gag acg tcc aca agc aca gcc tac      240
Gln Gly Arg Val Ser Met Thr Arg Glu Thr Ser Thr Ser Thr Ala Tyr
65                  70                  75                  80 atg cag ctg agc agg ctg aga tct gac gac acg gct acg tat tac tgt      288
Met Gln Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 120
<211> LENGTH: 124
<212> TYPE: PRT
<213> ORGANISM: Artificial Sequence
<220> FEATURE:
<223> OTHER INFORMATION: Synthetic Construct

<400> SEQUENCE: 120

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Ser Met Thr Arg Glu Thr Ser Thr Ser Thr Ala Tyr
65                  70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 121
<211> LENGTH: 372
<212> TYPE: DNA
<213> ORGANISM: Artificial Sequence
<220> FEATURE:
<223> OTHER INFORMATION: MF6059_VH
<220> FEATURE:
<221> NAME/KEY: CDS
<222> LOCATION: (1)..(372)

<400> SEQUENCE: 121 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
              20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct ggc agt ggt tct aca aac tat gca cag aag ttt      192
Gly Trp Ile Asn Pro Gly Ser Gly Ser Thr Asn Tyr Ala Gln Lys Phe
 50                  55                  60 cag ggc agg gtc acg atg acc agg gac acg tcc atc agc aca gcc tac      240
Gln Gly Arg Val Thr Met Thr Arg Asp Thr Ser Ile Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 122
<211> LENGTH: 124
<212> TYPE: PRT
<213> ORGANISM: Artificial Sequence
<220> FEATURE:
<223> OTHER INFORMATION: Synthetic Construct

<400> SEQUENCE: 122

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 123
<211> LENGTH: 372
<212> TYPE: DNA
<213> ORGANISM: Artificial Sequence
<220> FEATURE:
<223> OTHER INFORMATION: MF6060_VH
<220> FEATURE:
<221> NAME/KEY: CDS
<222> LOCATION: (1)..(372)

<400> SEQUENCE: 123

```
cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
                20                  25                  30
tat atg cac tgg gtg cga cag gcc cct gga caa gct ctt gag tgg atg      144
Tyr Met His Trp Val Arg Gln Ala Pro Gly Gln Ala Leu Glu Trp Met
         35                  40                  45 gga tgg atc aac cct caa agt ggt ggc aca aac tat gca aag aag ttt      192
Gly Trp Ile Asn Pro Gln Ser Gly Gly Thr Asn Tyr Ala Lys Lys Phe
 50                  55                  60 cag ggc agg gtc acg atg acc agg gag acg tcc aca agc aca gcc tac      240
Gln Gly Arg Val Thr Met Thr Arg Glu Thr Ser Thr Ser Thr Ala Tyr
 65                  70                  75                  80 atg gag ctg agc agg ctg aga tct gac gac acg gct acg tat tac tgt      288
Met Glu Leu Ser Arg Leu Arg Ser Asp Asp Thr Ala Thr Tyr Tyr Cys
             85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 124
<211> LENGTH: 124
<212> TYPE: PRT
<213> ORGANISM: Artificial Sequence
<220> FEATURE:
<223> OTHER INFORMATION: Synthetic Construct

<400> SEQUENCE: 124

Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Thr Met Thr Arg Glu Thr Ser Thr Ser Thr Ala Tyr
65                  70                  75                  80

Met Glu Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 125
<211> LENGTH: 372
<212> TYPE: DNA
<213> ORGANISM: Artificial Sequence
<220> FEATURE:
<223> OTHER INFORMATION: MF6061_VH
<220> FEATURE:
<221> NAME/KEY: CDS
<222> LOCATION: (1)..(372)

<400> SEQUENCE: 125 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg         144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt         192
Gly Trp Ile Asn Pro Gln Ser Gly Gly Thr Asn Tyr Ala Gln Lys Phe
 50                  55                  60 aag ggc agg gtc acg atg acc agg gac acg tcc acc agc aca gcc tac         240
Lys Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt         288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat         336
Ala Arg Asp His Gly Ser Arg His Phe Trp Ser Tyr Trp Gly Phe Asp
                100                 105                 110 tat tgg ggc caa ggt acc ctg gtc acc gtc tcc agt                         372
Tyr Trp Gly Gln Gly Thr Leu Val Thr Val Ser Ser
        115                 120

<210> SEQ ID NO 126
<211> LENGTH: 124
<212> TYPE: PRT
<213> ORGANISM: Artificial Sequence
<220> FEATURE:
<223> OTHER INFORMATION: Synthetic Construct

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
 50                  55                  60

Lys Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
        115                 120

<210> SEQ ID NO 127
<211> LENGTH: 372
<212> TYPE: DNA
<213> ORGANISM: Artificial Sequence
<220> FEATURE:
<223> OTHER INFORMATION: MF6062_VH
<220> FEATURE:
<221> NAME/KEY: CDS
<222> LOCATION: (1)..(372)

<400> SEQUENCE: 127 cag gtg cag ctg gtg cag tct ggg gct gag gtg aag aag cct ggg gcc          48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac          96
Ser Val Lys Val Ser Cys Lys Ala Ser Gly Tyr Thr Phe Thr Gly Tyr
```

-continued

```
                   20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct ggc agt ggt tct aca aac tat gca cag aag ttt      192
Gly Trp Ile Asn Pro Gly Ser Gly Ser Thr Asn Tyr Ala Gln Lys Phe
 50                  55                  60 cag ggc agg gtc acg atg acc agg gac acg tcc aca agc aca gcc tac      240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120

<210> SEQ ID NO 128
<211> LENGTH: 124
<212> TYPE: PRT
<213> ORGANISM: Artificial Sequence
<220> FEATURE:
<223> OTHER INFORMATION: Synthetic Construct

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 129
<211> LENGTH: 372
<212> TYPE: DNA
<213> ORGANISM: Artificial Sequence
<220> FEATURE:
<223> OTHER INFORMATION: MF6063_VH
<220> FEATURE:
<221> NAME/KEY: CDS
<222> LOCATION: (1)..(372)

<400> SEQUENCE: 129 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
                 20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct cag agt ggt ggc aca aac tat gca aag aag ttt      192
Gly Trp Ile Asn Pro Gln Ser Gly Gly Thr Asn Tyr Ala Lys Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                100                 105                 110 tat tgg ggc caa ggt acc ctg gtc acc gtc tcc agt                      372
Tyr Trp Gly Gln Gly Thr Leu Val Thr Val Ser Ser
        115                 120

<210> SEQ ID NO 130
<211> LENGTH: 124
<212> TYPE: PRT
<213> ORGANISM: Artificial Sequence
<220> FEATURE:
<223> OTHER INFORMATION: Synthetic Construct

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Gln Ser Gly Gly Thr Asn Tyr Ala Lys Lys Phe
        50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
        115                 120

<210> SEQ ID NO 131
<211> LENGTH: 372
<212> TYPE: DNA
<213> ORGANISM: Artificial Sequence
<220> FEATURE:
<223> OTHER INFORMATION: MF6064_VH
<220> FEATURE:
<221> NAME/KEY: CDS
<222> LOCATION: (1)..(372)

<400> SEQUENCE: 131 cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
            20                  25                  30
tat atg cac tgg gtg cga cag gcc cct gga aag ggg ctt gag tgg atg      144
Tyr Met His Trp Val Arg Gln Ala Pro Gly Lys Gly Leu Glu Trp Met
        35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
 50                  55                  60 cag ggc agg gtc acg atg acc agg gac acg tcc acg agc aca gcc tac      240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
                100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 132
<211> LENGTH: 124
<212> TYPE: PRT
<213> ORGANISM: Artificial Sequence
<220> FEATURE:
<223> OTHER INFORMATION: Synthetic Construct

<400> SEQUENCE: 132

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Lys Gly Leu Glu Trp Met
        35                  40                  45

Gly Trp Ile Asn Pro Gln Ser Gly Gly Thr Asn Tyr Ala Gln Lys Phe
 50                  55                  60

Gln Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
                100                 105                 110

Tyr Trp Gly Gln Gly Thr Leu Val Thr Val Ser Ser
        115                 120
```

<210> SEQ ID NO 133
<211> LENGTH: 372
<212> TYPE: DNA
<213> ORGANISM: Artificial Sequence
<220> FEATURE:
<223> OTHER INFORMATION: MF6065_VH
<220> FEATURE:
<221> NAME/KEY: CDS
<222> LOCATION: (1)..(372)

<400> SEQUENCE: 133

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac      96
Ser Val Lys Val Ser Cys Lys Ala Ser Gly Tyr Thr Phe Thr Ser Tyr
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct cag ggg ggt tct aca aac tat gca cag aag ttt      192
Gly Trp Ile Asn Pro Gln Gly Gly Ser Thr Asn Tyr Ala Gln Lys Phe
 50                  55                  60 cag ggc agg gtc acg atg acc agg gac acg tcc acc agc aca gtg tac      240
Gln Gly Arg Val Thr Met Thr Arg Asp Thr Ser Thr Ser Thr Val Tyr
65                  70                  75                  80 atg gag ctg agc agg ctg aga tct gag gac acg gct gtg tat tac tgt      288
Met Glu Leu Ser Arg Leu Arg Ser Glu Asp Thr Ala Val Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 134
<211> LENGTH: 124
<212> TYPE: PRT
<213> ORGANISM: Artificial Sequence
<220> FEATURE:
<223> OTHER INFORMATION: Synthetic Construct

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Gln Gly Gly Ser Thr Asn Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 135
<211> LENGTH: 372
<212> TYPE: DNA
<213> ORGANISM: Artificial Sequence
<220> FEATURE:
<223> OTHER INFORMATION: MF6066_VH
<220> FEATURE:
<221> NAME/KEY: CDS
<222> LOCATION: (1)..(372)

<400> SEQUENCE: 135

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct cag agt ggt tct aca aac tat gca cag aag ttt      192
Gly Trp Ile Asn Pro Gln Ser Gly Ser Thr Asn Tyr Ala Gln Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
 65                  70                  75                  80 atg gag ctg agc tct ctg aga tct gag gac acg gct gtg tat tac tgt      288
Met Glu Leu Ser Ser Leu Arg Ser Glu Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120

<210> SEQ ID NO 136
<211> LENGTH: 124
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
         35                  40                  45

Gly Trp Ile Asn Pro Gln Ser Gly Ser Thr Asn Tyr Ala Gln Lys Phe
 50                  55                  60

Gln Gly Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120

<210> SEQ ID NO 137
<211> LENGTH: 372
<212> TYPE: DNA
<213> ORGANISM: Artificial Sequence
<220> FEATURE:
<223> OTHER INFORMATION: MF6067_VH
<220> FEATURE:
<221> NAME/KEY: CDS
<222> LOCATION: (1)..(372)

<400> SEQUENCE: 137 cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                  10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
 50                  55                  60 cag ggc agg gtc acg atg acc agg gac acg tcc acc agc aca gtc tac      240
Gln Gly Arg Val Thr Met Thr Arg Asp Thr Ser Thr Ser Thr Val Tyr
 65                  70                  75                  80 atg gag ctg agc tct ctg aga tct gac gac acg gct gtg tat tac tgt      288
Met Glu Leu Ser Ser Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120
```

<210> SEQ ID NO 138
<211> LENGTH: 124
<212> TYPE: PRT
<213> ORGANISM: Artificial Sequence
<220> FEATURE:
<223> OTHER INFORMATION: Synthetic Construct

<400> SEQUENCE: 138

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120
```

<210> SEQ ID NO 139
<211> LENGTH: 372
<212> TYPE: DNA
<213> ORGANISM: Artificial Sequence
<220> FEATURE:
<223> OTHER INFORMATION: MF6068_VH
<220> FEATURE:
<221> NAME/KEY: CDS
<222> LOCATION: (1)..(372)

<400> SEQUENCE: 139

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt      192
Gly Trp Ile Asn Pro Gln Ser Gly Gly Thr Asn Tyr Ala Gln Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 140
<211> LENGTH: 124
<212> TYPE: PRT
<213> ORGANISM: Artificial Sequence
<220> FEATURE:
<223> OTHER INFORMATION: Synthetic Construct

<400> SEQUENCE: 140

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
 50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 141
<211> LENGTH: 372
<212> TYPE: DNA
<213> ORGANISM: Artificial Sequence
<220> FEATURE:
<223> OTHER INFORMATION: MF6069_VH
<220> FEATURE:
<221> NAME/KEY: CDS
<222> LOCATION: (1)..(372)

<400> SEQUENCE: 141

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30
```

```
                   20                  25                  30
tat atg cac tgg gtg cga cag gcc cct gga caa ggg ctt gag tgg atg        144
Tyr Met His Trp Val Arg Gln Ala Pro Gly Gln Gly Leu Glu Trp Met
         35                  40                  45 gga tgg atc aac cct cag agt ggt ggc aca aac tat gca cag aag ttt        192
Gly Trp Ile Asn Pro Gln Ser Gly Gly Thr Asn Tyr Ala Gln Lys Phe
 50                  55                  60 cag ggc agg gtc acg atg acc agg gac acg tcc atc agc aca gcc tac        240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt        288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
            100                 105                 110 tat tgg ggc caa ggt acc ctg gtc acc gtc tcc agt                        372
Tyr Trp Gly Gln Gly Thr Leu Val Thr Val Ser Ser
        115                 120
```

<210> SEQ ID NO 142
<211> LENGTH: 124
<212> TYPE: PRT
<213> ORGANISM: Artificial Sequence
<220> FEATURE:
<223> OTHER INFORMATION: Synthetic Construct

<400> SEQUENCE: 142

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 143
<211> LENGTH: 372
<212> TYPE: DNA
<213> ORGANISM: Artificial Sequence
<220> FEATURE:
<223> OTHER INFORMATION: MF6070_VH
<220> FEATURE:
<221> NAME/KEY: CDS
<222> LOCATION: (1)..(372)

<400> SEQUENCE: 143

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac        96
Ser Val Lys Val Ser Cys Lys Ala Ser Gly Tyr Thr Phe Thr Ser Tyr
            20                  25                  30
```

```
                    20                  25                  30
tat atg cac tgg gtg cga cag gcc cct gga caa ggg ctt gag tgg atg    144
Tyr Met His Trp Val Arg Gln Ala Pro Gly Gln Gly Leu Glu Trp Met
         35                  40                  45 gga tgg atc aac cct tct ggg ggt tct aca aac tat gca cag aag ttt    192
Gly Trp Ile Asn Pro Ser Gly Gly Ser Thr Asn Tyr Ala Gln Lys Phe
 50                  55                  60 cag ggc agg gtc acg atg acc agg gac acg tcc acc agc aca gtg tac    240
Gln Gly Arg Val Thr Met Thr Arg Asp Thr Ser Thr Ser Thr Val Tyr
 65                  70                  75                  80 atg gag ctg agc agg ctg aga tct gag gac acg gct gtg tat tac tgt    288
Met Glu Leu Ser Arg Leu Arg Ser Glu Asp Thr Ala Val Tyr Tyr Cys
                 85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
            100                 105                 110 tat tgg ggc caa ggt acc ctg gtc acc gtc tcc agt                    372
Tyr Trp Gly Gln Gly Thr Leu Val Thr Val Ser Ser
        115                 120

<210> SEQ ID NO 144
<211> LENGTH: 124
<212> TYPE: PRT
<213> ORGANISM: Artificial Sequence
<220> FEATURE:
<223> OTHER INFORMATION: Synthetic Construct

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Ser Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 145
<211> LENGTH: 372
<212> TYPE: DNA
<213> ORGANISM: Artificial Sequence
<220> FEATURE:
<223> OTHER INFORMATION: MF6071_VH
<220> FEATURE:
<221> NAME/KEY: CDS
<222> LOCATION: (1)..(372)

<400> SEQUENCE: 145 cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac    96
Ser Val Lys Val Ser Cys Lys Ala Ser Gly Tyr Thr Phe Thr Gly Tyr
```

```
          20                  25                  30
tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct tct agt ggt tct aca aac tat gca cag aag ttt     192
Gly Trp Ile Asn Pro Ser Ser Gly Ser Thr Asn Tyr Ala Gln Lys Phe
 50                  55                  60 cag ggc agg gtc acg atg acc agg gac acg tcc acc agc aca gcc tac     240
Gln Gly Arg Val Thr Met Thr Arg Asp Thr Ser Thr Ser Thr Ala Tyr
 65                  70                  75                  80 atg gag ctg agc tct ctg aga tct gag gac acg gct gtg tat tac tgt     288
Met Glu Leu Ser Ser Leu Arg Ser Glu Asp Thr Ala Val Tyr Tyr Cys
                 85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc gtc tcc agt                     372
Tyr Trp Gly Gln Gly Thr Leu Val Thr Val Ser Ser
        115                 120
```

<210> SEQ ID NO 146
<211> LENGTH: 124
<212> TYPE: PRT
<213> ORGANISM: Artificial Sequence
<220> FEATURE:
<223> OTHER INFORMATION: Synthetic Construct

<400> SEQUENCE: 146

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Ser Thr Asn Tyr Ala Gln Lys Phe
 50                  55                  60

Gln Gly Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 147
<211> LENGTH: 372
<212> TYPE: DNA
<213> ORGANISM: Artificial Sequence
<220> FEATURE:
<223> OTHER INFORMATION: MF6072_VH
<220> FEATURE:
<221> NAME/KEY: CDS
<222> LOCATION: (1)..(372)

<400> SEQUENCE: 147

```
cag gtg cag ctg gtg cag tct ggg gct gag gtg aag aag cct ggg gcc     48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac     96
Ser Val Lys Val Ser Cys Lys Ala Ser Gly Tyr Thr Phe Thr Gly Tyr
```

```
                  20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt      192
Gly Trp Ile Asn Pro Ser Ser Gly Gly Thr Asn Tyr Ala Gln Lys Phe
 50                  55                  60 cag ggc agg gtc acg atg acc agg gac acg tcc acc agc aca gtc tac      240
Gln Gly Arg Val Thr Met Thr Arg Asp Thr Ser Thr Ser Thr Val Tyr
 65                  70                  75                  80 atg gag ctg agc tct ctg aga tct gac gac acg gct gtg tat tac tgt      288
Met Glu Leu Ser Ser Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc gtc tcc agt                      372
Tyr Trp Gly Gln Gly Thr Leu Val Thr Val Ser Ser
        115                 120
```

<210> SEQ ID NO 148
<211> LENGTH: 124
<212> TYPE: PRT
<213> ORGANISM: Artificial Sequence
<220> FEATURE:
<223> OTHER INFORMATION: Synthetic Construct

<400> SEQUENCE: 148

```
Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 149
<211> LENGTH: 372
<212> TYPE: DNA
<213> ORGANISM: Artificial Sequence
<220> FEATURE:
<223> OTHER INFORMATION: MF6073_VH
<220> FEATURE:
<221> NAME/KEY: CDS
<222> LOCATION: (1)..(372)

<400> SEQUENCE: 149

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
 1               5                   10                  15 tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
```

```
                20                  25                  30
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct tct agt ggt ggc aca aac tat gca cag aag ttt      192
Gly Trp Ile Asn Pro Ser Ser Gly Gly Thr Asn Tyr Ala Gln Lys Phe
 50                  55                  60 cag ggc agg gtc acg atg acc agg gac acg tcc acc agc aca gcc tac      240
Gln Gly Arg Val Thr Met Thr Arg Asp Thr Ser Thr Ser Thr Ala Tyr
 65                  70                  75                  80 atg gag ctg agc agg ctg aga tct gac gac acg gct gtg tat tac tgt      288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
             100                 105                 110 tat tgg ggc caa ggt acc ctg gtc acc gtc tcc agt                      372
Tyr Trp Gly Gln Gly Thr Leu Val Thr Val Ser Ser
         115                 120

<210> SEQ ID NO 150
<211> LENGTH: 124
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
         35                  40                  45

Gly Trp Ile Asn Pro Ser Ser Gly Gly Thr Asn Tyr Ala Gln Lys Phe
 50                  55                  60

Gln Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
             100                 105                 110

Tyr Trp Gly Gln Gly Thr Leu Val Thr Val Ser Ser
         115                 120

<210> SEQ ID NO 151
<211> LENGTH: 372
<212> TYPE: DNA
<213> ORGANISM: Artificial Sequence
<220> FEATURE:
<223> OTHER INFORMATION: MF6074_VH
<220> FEATURE:
<221> NAME/KEY: CDS
<222> LOCATION: (1)..(372)

<400> SEQUENCE: 151 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
```

```
                    20                  25                  30
tat atg cac tgg gtg cga cag gcc cct gga caa ggg ctt gag tgg atg        144
Tyr Met His Trp Val Arg Gln Ala Pro Gly Gln Gly Leu Glu Trp Met
         35                  40                  45 gga tgg atc aac cct tct agt ggt ggc aca aac tat gca cag aag ttt        192
Gly Trp Ile Asn Pro Ser Ser Gly Gly Thr Asn Tyr Ala Gln Lys Phe
 50                  55                  60 cag ggc agg gtc acg atg acc agg gac acg tcc atc agc aca gcc tac        240
Gln Gly Arg Val Thr Met Thr Arg Asp Thr Ser Ile Ser Thr Ala Tyr
 65                  70                  75                  80 atg gag ctg agc agg ctg aga tct gac gac acg gct gtg tat tac tgt        288
Met Glu Leu Ser Arg Leu Arg Ser Asp Asp Thr Ala Val Tyr Tyr Cys
                 85                  90                  95 gca aga gat cat ggt tct cgt cat ttc tgg tct tac tgg ggc ttt gat        336
Ala Arg Asp His Gly Ser Arg His Phe Trp Ser Tyr Trp Gly Phe Asp
                 100                 105                 110 tat tgg ggc caa ggt acc ctg gtc acc gtc tcc agt                        372
Tyr Trp Gly Gln Gly Thr Leu Val Thr Val Ser Ser
             115                 120

<210> SEQ ID NO 152
<211> LENGTH: 124
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Ser Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
                 100                 105                 110

Tyr Trp Gly Gln Gly Thr Leu Val Thr Val Ser Ser
             115                 120

<210> SEQ ID NO 153
<211> LENGTH: 214
<212> TYPE: PRT
<213> ORGANISM: Artificial Sequence
<220> FEATURE:
<223> OTHER INFORMATION: Common Light Chain

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 154
<211> LENGTH: 454
<212> TYPE: PRT
<213> ORGANISM: Artificial Sequence
<220> FEATURE:
<223> OTHER INFORMATION: heavy chain for EGFR binding

<400> SEQUENCE: 154

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
             35                  40                  45

Gly Gly Phe Asp Pro Glu Tyr Gly Lys Thr Phe Phe Ala Gln Asn Phe
         50                  55                  60

Gln Gly Arg Val Thr Met Thr Glu Asp Thr Ser Ala Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Glu Gly Tyr Tyr Glu Thr Thr Thr Tyr Tyr Asn Leu Phe
                100                 105                 110

Asp Ser Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190
```

```
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Asp Pro Pro Ser Arg Glu Glu Met Thr Lys
        355                 360                 365

Asn Gln Val Ser Leu Thr Cys Glu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450

<210> SEQ ID NO 155
<211> LENGTH: 453
<212> TYPE: PRT
<213> ORGANISM: Artificial Sequence
<220> FEATURE:
<223> OTHER INFORMATION: heavy chain for erbB-3 binding

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Lys Pro Pro Ser Arg Glu Glu Met Thr Lys Asn
        355                 360                 365

Gln Val Ser Leu Lys Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 156
<211> LENGTH: 17
<212> TYPE: PRT
<213> ORGANISM: Artificial Sequence
<220> FEATURE:
<223> OTHER INFORMATION: MF6058 CDR2

<400> SEQUENCE: 156

```
Trp Ile Asn Pro Gln Ser Gly Gly Thr Asn Tyr Ala Lys Lys Phe Gln
1               5                   10                  15
Gly

<210> SEQ ID NO 157
<211> LENGTH: 6
<212> TYPE: PRT
<213> ORGANISM: Artificial Sequence
<220> FEATURE:
<223> OTHER INFORMATION: Common Light Chain CDR1

<400> SEQUENCE: 157

Gln Ser Ile Ser Ser Tyr
1               5

<210> SEQ ID NO 158
<211> LENGTH: 9
<212> TYPE: PRT
<213> ORGANISM: Artificial Sequence
<220> FEATURE:
<223> OTHER INFORMATION: Common Light Chain CDR3

<400> SEQUENCE: 158

Gln Gln Ser Tyr Ser Thr Pro Pro Thr
1               5
```